United States Patent [19]
Cochran et al.

[11] Patent Number: 5,910,139
[45] Date of Patent: Jun. 8, 1999

[54] NUMERIC KEYPAD SIMULATED ON TOUCHSCREEN

[75] Inventors: Bruce Robert Cochran, St. Charles, Mo.; Christopher Michael Eberhardt, Fort Worth, Tex.; John A. Painter, Bridgeton, Mo.

[73] Assignee: Storz Instrument Co., St. Louis, Mo.

[21] Appl. No.: 08/919,607

[22] Filed: Aug. 28, 1997

Related U.S. Application Data

[60] Provisional application No. 60/025,498, Aug. 29, 1996.

[51] Int. Cl.[6] .................................................. A61B 17/00
[52] U.S. Cl. ................................................................ 606/1
[58] Field of Search ........................... 606/1, 4; 600/103; 345/10; 604/65

[56] References Cited

U.S. PATENT DOCUMENTS

| | | | |
|---|---|---|---|
| 3,693,613 | 9/1972 | Kelman | 128/24 |
| 3,812,855 | 5/1974 | Banko | 128/276 |

(List continued on next page.)

FOREIGN PATENT DOCUMENTS

| | | |
|---|---|---|
| WO 8903230 | 4/1989 | WIPO . |
| WO 9408518 | 4/1994 | WIPO . |

OTHER PUBLICATIONS

Signals, "Smart Cards–The New Bank Cards", MacMillian Publishing Co., 1985, pp. 5–7 & 101–104.
Site TXR Product Catalog (twenty–one pages, Copyright 1985.
Surgical Design Corp. Product Brochure, "The Standard In Intraocular Microsurgery" (16 pages, 1986).
"A linear Suction Control for Vitreous Cutter (Ocutome)" Arch Ophthalmol, vol. 99, p. 1613, Sep. 1981. By Steve Charles and Carl Wang.
"Fresh Idea Your Custom Surgical Center CooperVisision System VI" 6–page brochure, 1983.
Cavitron/Kelman Model 6500 A.L.s & Model 7500 I/A System, 6 pages 1983.
Grieshaber & Co., "MPC Membrane Peeler Cutter" product brochure (2 pages, 1980).
CooperVision Brochure "The Cutting Edge of Ultrasonic Technology" (2 pages, 1986).
Brochure: Cavitron/Kelman Phaco–Emulsifier Aspirator Model 8001 (2–pages, 1985).
Brochure: Cavitron/Kelman Phaco–Emulsifier Aspirator Model 9001 (2–pages, 1985).
Brochure: "Storz Irrigation Aspiration system" (12–pages, 1983) and Instruction Manual (9 pages).

(List continued on next page.)

*Primary Examiner*—Michael Buiz
*Assistant Examiner*—Julian W. Woo
*Attorney, Agent, or Firm*—Grant D. Kang

[57] ABSTRACT

A system for controlling a plurality of ophthalmic microsurgical instruments connected thereto. The microsurgical instruments are for use by a user such as a surgeon in performing ophthalmic surgical procedures. The system includes a data communications bus and a user interface connected to the data communications bus. The user interface provides information to the user and receives information from the user which is representative of operating parameters of the microsurgical instruments. The system also includes surgical modules connected to and controlling the microsurgical instruments as a function of at least one of the operating parameters. The surgical modules are also connected to the data communications bus. The data communications bus provides communication of data representative of the operating parameters between the user interface and the surgical modules. Other features are also disclosed including a main control, an endo-illuminator system, a phacoemulsification handpiece, surgical scissors, a vitrectomy cutter, a surgical foot control, a remote control, a cart.

2 Claims, 137 Drawing Sheets

Microfiche Appendix Included
(32 Microfiche, 6294 Pages)

U.S. PATENT DOCUMENTS

| | | | |
|---|---|---|---|
| 3,920,014 | 11/1975 | Banko | 128/230 |
| 4,007,742 | 2/1977 | Banko | 128/230 |
| 4,024,866 | 5/1977 | Wallach | 128/276 |
| 4,117,843 | 10/1978 | Banko | 128/230 |
| 4,168,707 | 9/1979 | Douvas et al. | 128/276 |
| 4,180,074 | 12/1979 | Murry et al. | 128/276 |
| 4,188,927 | 2/1980 | Harris | 128/303 |
| 4,314,560 | 2/1982 | Helfgott et al. | 128/305 |
| 4,395,258 | 7/1983 | Wang et al. | 128/276 |
| 4,428,748 | 1/1984 | Peyman et al. | 604/22 |
| 4,432,360 | 2/1984 | Mumford et al. | 128/419 |
| 4,457,750 | 7/1984 | Hill | 604/65 |
| 4,496,342 | 1/1985 | Banko | 604/27 |
| 4,525,775 | 6/1985 | Eydelman | 364/148 |
| 4,529,401 | 7/1985 | Leslie et al. | 604/131 |
| 4,542,740 | 9/1985 | Kleinschmidt et al. | 128/204 |
| 4,553,958 | 11/1985 | LeCocq | 604/67 |
| 4,557,270 | 12/1985 | John | 128/731 |
| 4,580,557 | 4/1986 | Hertzmann | 128/303 |
| 4,622,503 | 11/1986 | Sundblom et al. | 318/645 |
| 4,642,769 | 2/1987 | Petrofsky | 364/415 |
| 4,650,460 | 3/1987 | Roizenblatt | 60/22 |
| 4,669,466 | 6/1987 | L'Esperance | 128/303 |
| 4,676,776 | 6/1987 | Howson | 604/31 |
| 4,686,980 | 8/1987 | Williams et al. | 128/303 |
| 4,688,574 | 8/1987 | Dufresne et al. | 128/421 |
| 4,695,954 | 9/1987 | Rose et al. | 364/413 |
| 4,705,038 | 11/1987 | Sjostrom et al. | 128/305 |
| 4,705,067 | 11/1987 | Coffee | 137/487 |
| 4,706,687 | 11/1987 | Rogers | 128/752 |
| 4,713,051 | 12/1987 | Steppe et al. | 604/30 |
| 4,758,220 | 7/1988 | Sundblom et al. | 604/65 |
| 4,758,238 | 7/1988 | Sundblom et al. | 604/310 |
| 4,787,889 | 11/1988 | Steppe et al. | 604/22 |
| 4,790,816 | 12/1988 | Sundblom et al. | 604/31 |
| 4,810,242 | 3/1989 | Sundblom et al. | 604/28 |
| 4,813,927 | 3/1989 | Morris et al. | 604/23 |
| 4,838,281 | 6/1989 | Rogers et al. | 604/65 |
| 4,900,301 | 2/1990 | Morris et al. | 604/23 |
| 4,902,276 | 2/1990 | Zakko | 604/28 |
| 4,950,224 | 8/1990 | Fellingham et al. | 604/118 |
| 4,983,160 | 1/1991 | Steppe et al. | 604/22 |
| 5,011,483 | 4/1991 | Sleister | 606/37 |
| 5,020,535 | 6/1991 | Parker et al. | 606/174 |
| 5,024,654 | 6/1991 | Tyler | 604/43 |
| 5,032,111 | 7/1991 | Morris et al. | 604/23 |
| 5,033,496 | 7/1991 | Reid | 137/85 |
| 5,041,096 | 8/1991 | Beuchat et al. | 604/118 |
| 5,047,009 | 9/1991 | Morris et al. | 604/23 |
| 5,091,656 | 2/1992 | Gahn | 307/119 |
| 5,094,260 | 3/1992 | Stuart et al. | 137/102 |
| 5,112,300 | 5/1992 | Ureche | 604/22 |
| 5,157,603 | 10/1992 | Scheller et al. | 364/413 |
| 5,158,108 | 10/1992 | Semaan et al. | 137/487 |
| 5,163,900 | 11/1992 | Wortrich | 604/30 |
| 5,176,628 | 1/1993 | Charles et al. | 604/22 |
| 5,178,605 | 1/1993 | Imonti | 604/22 |
| 5,185,002 | 2/1993 | Venturini | 604/30 |
| 5,188,589 | 2/1993 | Wypych et al. | 604/22 |
| 5,197,981 | 3/1993 | Southard | 623/6 |
| 5,199,943 | 4/1993 | Wypych | 604/22 |
| 5,213,569 | 5/1993 | Davis | 604/22 |
| 5,220,940 | 6/1993 | Palmer | 137/487 |
| 5,242,404 | 9/1993 | Conley et al. | 604/119 |
| 5,249,121 | 9/1993 | Baum et al. | 364/413 |
| 5,267,956 | 12/1993 | Beuchat | 604/30 |
| 5,268,624 | 12/1993 | Zanger | 318/551 |
| 5,275,607 | 1/1994 | Lo et al. | 606/169 |
| 5,282,786 | 2/1994 | Ureche | 604/22 |
| 5,282,787 | 2/1994 | Wortrich | 604/30 |
| 5,288,290 | 2/1994 | Brody | 604/32 |
| 5,300,926 | 4/1994 | Stoeckl | 364/157 |
| 5,336,222 | 8/1994 | Durgin, Jr. et al. | 606/50 |
| 5,360,398 | 11/1994 | Grieshaber et al. | 604/30 |
| 5,364,342 | 11/1994 | Beuchat et al. | 604/30 |
| 5,409,457 | 4/1995 | del Cerro et al. | 604/51 |
| 5,417,246 | 5/1995 | Perkins et al. | 137/870 |
| 5,449,356 | 9/1995 | Walbrink et al. | 606/49 |
| 5,455,766 | 10/1995 | Scheller et al. | 364/413 |
| 5,456,684 | 10/1995 | Schmidt et al. | 606/41 |
| 5,474,532 | 12/1995 | Steppe | 604/22 |
| 5,549,139 | 8/1996 | Perkins et al. | 137/884 |

OTHER PUBLICATIONS

Brochure: Storz Micro Vit Vetrectomy System (4–pages with flap, 1983) and Instruction Manual (18 pages).

Article: Wang and Charles, "Microsurgical Instrumentation for Virectomy: Part 1", Journal of Clinical Engineering (8–pages, 1983).

Cavitron/Kelman Phaco–Emulsifier Aspirator, Model 9001 Service Manual, Sections 2, 3 and 7 (43–pages, 1985).

MVX XX Opthalmic surgical system Manufal by MID Labs (43–pages, Revised Apr. 18, 1985).

CooperVision Surgical Brochure, A Cataract Instrument That Does Phaco and More, (2 pages, 1986).

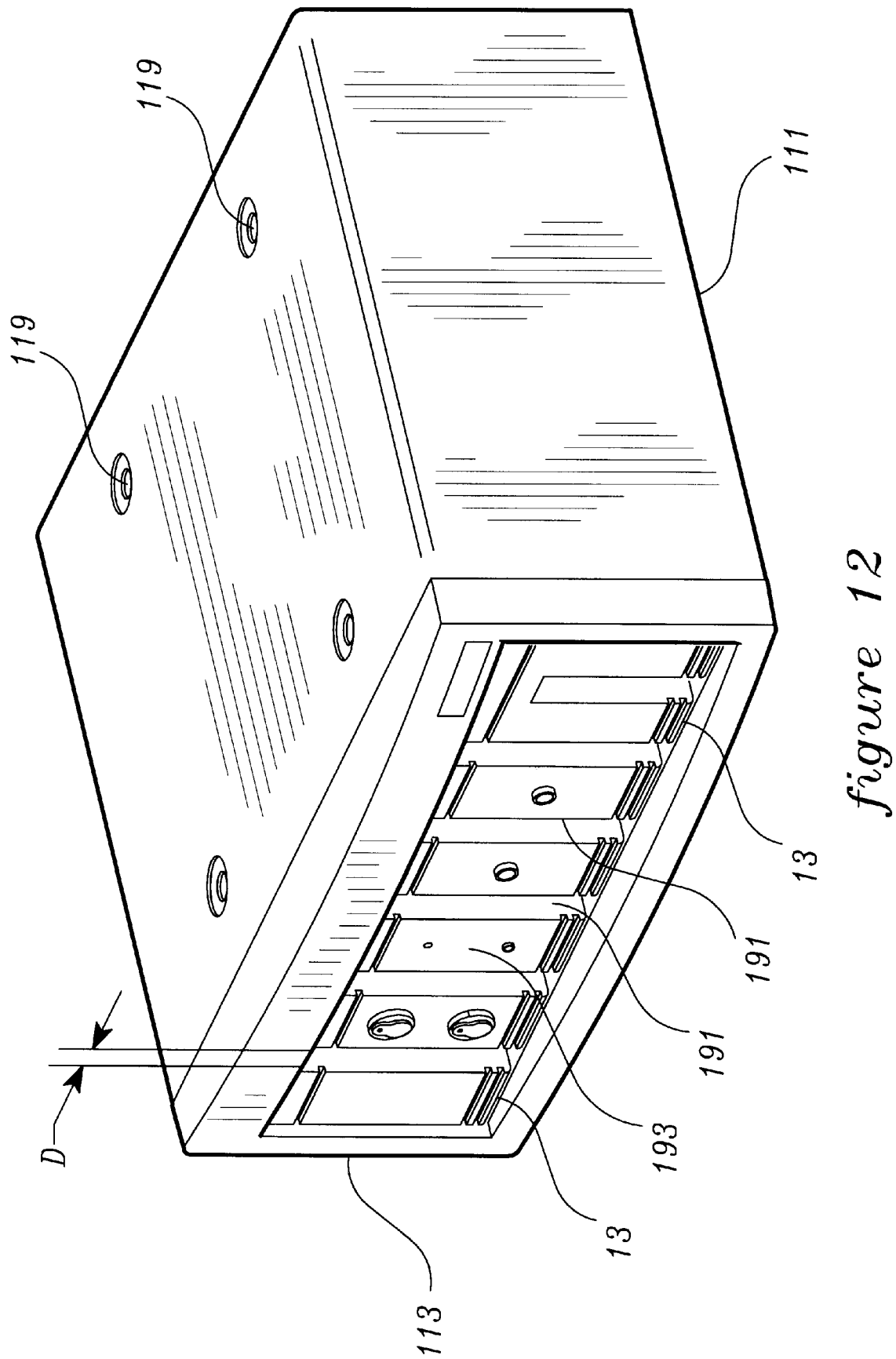

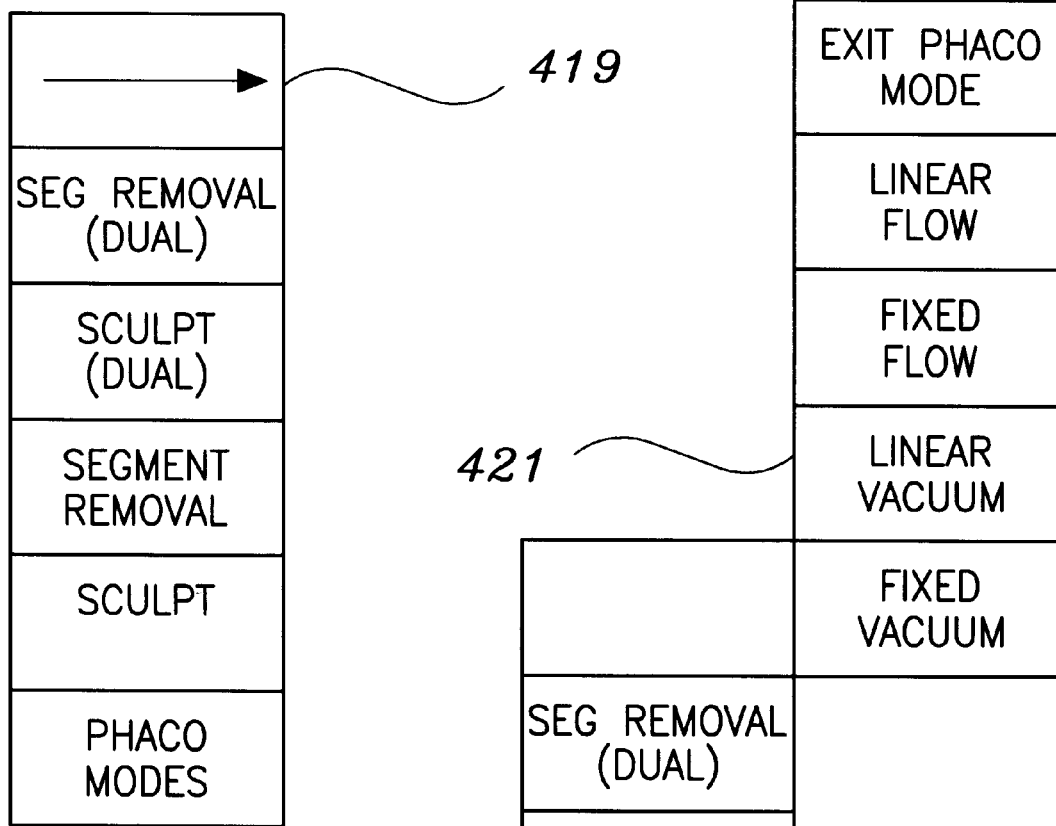
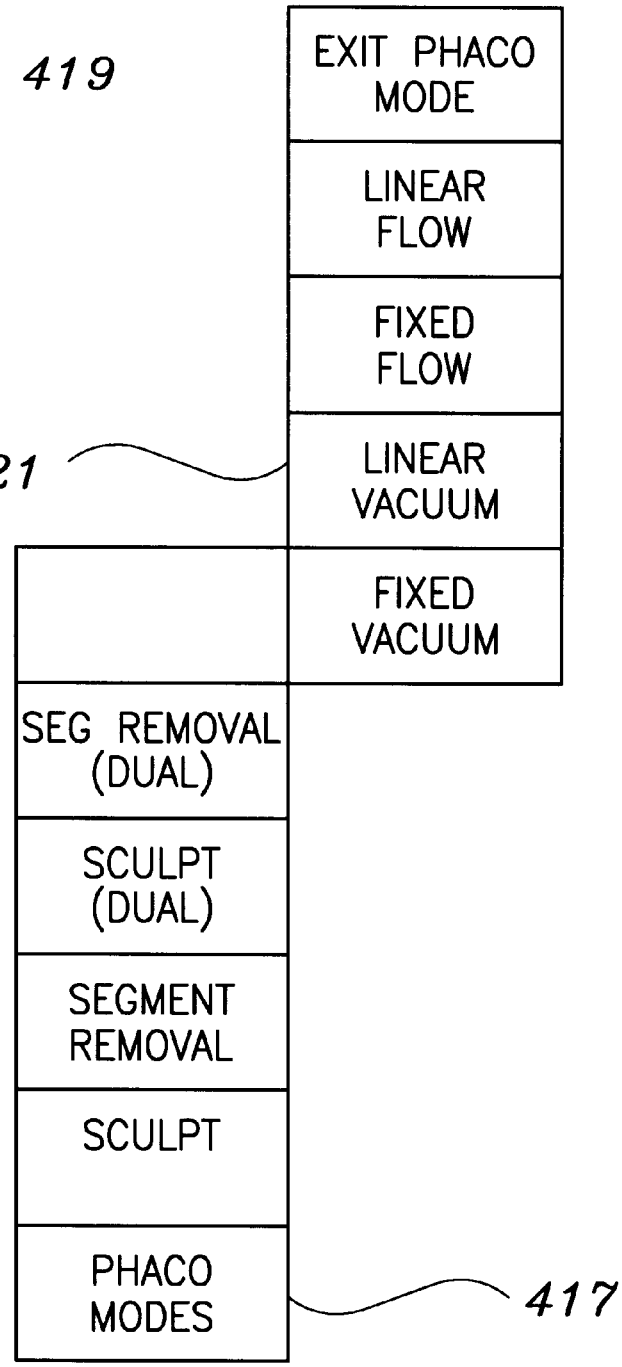
figure 28
figure 29

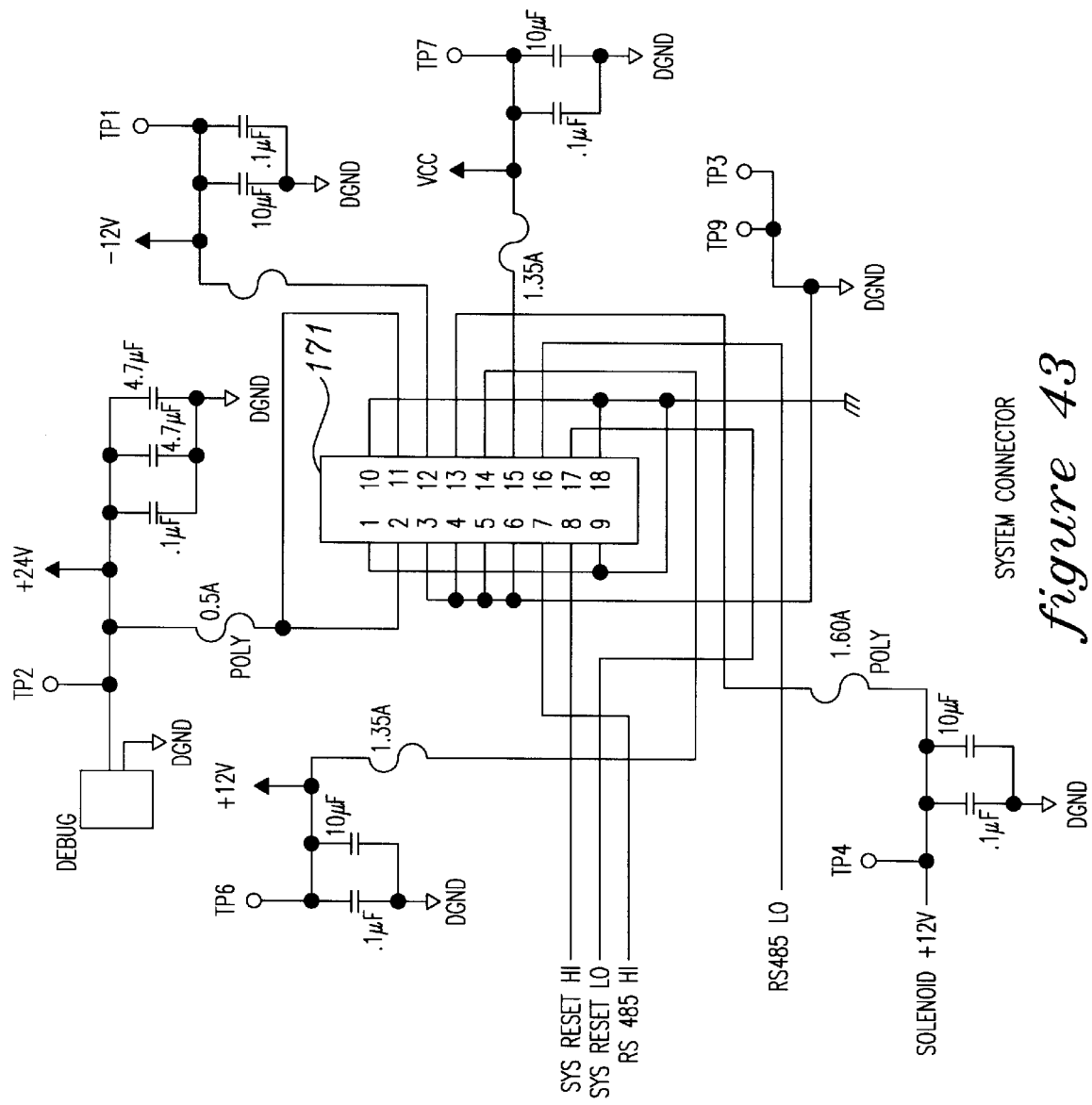

RESET CIRCUIT

FROM FIG 91

FROM FIG 91 { CP0, CP1, CP2 } FROM FIG 90

| 10 | 224P | CHIP SELECT |
| 9 | 211P | SERIAL DATA OUT |
| 8 | 209P | SERIAL CLOCK |
| 7 | 207P | CHIP SELECT2 |
| 6 | 212P | WATCHDOG |
| 5 | 217P | SERIAL DATA OUT |
| 4 | 215P | SERIAL CLOCK |
| 3 | 219P | DATA STROB2 |
| 2 | 221P | DC HP PRESENT |
| 1 | 229P | SOLENOID HP PRESENT |
| 0 | 200P | FRONT PANEL LED |

NUMERIC KEYPAD SIMULATED ON TOUCHSCREEN

This application claims benefit under 35 U.S.C. Section 119(e) of U.S. Provisional application Ser. No. 60/025,498, filed Aug. 29, 1996.

MICROFICHE APPENDIX

This application contains a microfiche appendix, which contains 6,294 microfiche and 32 pages.

BACKGROUND OF THE INVENTION

This invention relates generally to microsurgical and ophthalmic systems and, particularly, to a control system for operating microsurgical instruments.

Present day ophthalmic microsurgical systems provide one or more surgical instruments connected to a control console. The instruments are often electrically or pneumatically operated and the control console provides electrical or fluid pressure control signals for operating the instruments. The control console usually includes several different types of human actuable controllers for generating the control signals supplied to the surgical instruments. Often, the surgeon uses a foot pedal controller to remotely control the surgical instruments.

The conventional console has push-button switches and adjustable knobs for setting the desired operating characteristics of the system. The conventional control system usually serves several different functions. For example, the typical ophthalmic microsurgical system has anterior and/or posterior segment capabilities and may include a variety of functions, such as irrigation/aspiration, vitrectomy, microscissor cutting, fiber optic illumination, and fragmentation/emulsification.

While conventional microsurgical systems and ophthalmic systems have helped to make microsurgery and ophthalmic surgery possible, these systems are not without drawbacks. Microsurgical and ophthalmic systems are relatively costly and are often purchased by hospitals and clinics for sharing among many surgeons with different specialties. In eye surgery, for example, some surgeons may specialize in anterior segment procedures, while other surgeons may specialize in posterior segment procedures. Due to differences in these procedures, the control system will not be set up with the same operating characteristics for both procedures. Also, due to the delicate nature of eye surgery, the response characteristics or "feel" of the system can be a concern to surgeons who practice in several different hospitals, using different makes and models of equipment.

U.S. Pat. Nos. 4,933,843, 5,157,603, 5,417,246 and 5,455,766, all of which are commonly assigned and the entire disclosures of which are incorporated herein by reference, disclose improved microsurgical control systems. For example, such systems provide improved uniformity of performance characteristics, while at the same time providing enough flexibility in the system to accommodate a variety of different procedures. The systems shown in these patents improve upon the prior art by providing a programmable and universal microsurgical control system, which can be readily programmed to perform a variety of different surgical procedures and which may be programmed to provide the response characteristics which any given surgeon may require. The control system is preprogrammed to perform a variety of different functions to provide a variety of different procedures. These preprogrammed functions can be selected by pressing front panel buttons.

In addition to the preprogrammed functions, these patents disclose providing each surgeon with a programming key, which includes a digital memory circuit loaded with particular response characteristic parameters and particular surgical procedure parameters selected by that surgeon. By inserting the key into the system console jack, the system is automatically set up to respond in a familiar way to each surgeon.

For maximum versatility, the console push buttons and potentiometer knobs are programmable. Their functions and response characteristics can be changed to suit the surgeons' needs. An electronic display screen on the console displays the current function of each programmable button and knob as well as other pertinent information. The display screen is self-illuminating so that it can be read easily in darkened operating rooms.

Although the above-described systems provide improvements over the prior art, further improvements are needed to improve performance, simplify operation, simplify repair and replacement, reduce the time and cost of repairs, and so forth.

SUMMARY OF THE INVENTION

Among the several objects of this invention may be noted the provision of an improved system which permits network communications between its components; the provision of such a system which is modular; the provision of such a system which permits distributed control of its components; the provision of such a system which reconfigures itself automatically at power-up; the provision of such a system which permits operation in a number of different modes; the provision of such a system which operates in the different modes in a predefined sequence; the provision of such a system which permits adaptation to different configurations; the provision of such a system which is easily reprogrammable; and the provision of such a system circuit which is economically feasible and commercially practical.

Briefly described, a system embodying aspects of the invention controls a plurality of ophthalmic microsurgical instruments connected thereto. A user, such as a surgeon, uses the microsurgical instruments in performing ophthalmic surgical procedures. The system includes a data communications bus and a user interface connected to the data communications bus. The user interface provides information to the user and receives information from the user which is representative of operating parameters of the microsurgical instruments. The system also includes first and second surgical modules. Each surgical module is connected to and controls one of the microsurgical instruments as a function of at least one of the operating parameters. The surgical modules are also connected to the data communications bus which provides communication of data representative of the operating parameters between the user interface and the first and second surgical modules. In particular, data may be transmitted between the surgical modules and/or between the user interface and one or more of the surgical modules.

Another embodiment of the invention is a system for controlling a plurality of ophthalmic microsurgical instruments connected thereto. A user, such as a surgeon, uses the microsurgical instruments in performing ophthalmic surgical procedures. The system includes a data communications bus and a user interface connected to the data communications bus. The user interface provides information to the user and receives information from the user which is representative of operating parameters of the microsurgical instruments. The system also includes a surgical module and a remote control circuit. The surgical module is connected to and controls one of the microsurgical instruments as a function of at least one of the operating parameters. The remote control circuit is connected to and controls a remote control unit as a function of at least one of the operating parameters. The remote control unit operates to change the operating parameters of the microsurgical instruments during performance of the surgical procedures. Both the surgical module and the control circuit are also connected to the data communications bus which provides communication of data representative of the operating parameters between the user interface and the surgical module and the remote control circuit. In particular, data may be transmitted between the surgical module and the control circuit and/or between the user interface and either or both of the surgical module and control circuit.

Yet another embodiment of the invention is a system for controlling a plurality of ophthalmic microsurgical instruments connected thereto. A user, such as a surgeon, uses the microsurgical instruments in performing ophthalmic surgical procedures. The system includes a user interface providing information to the user and receives information from the user which is representative of operating parameters of the microsurgical instruments. The system also includes a memory storing a plurality of operating parameters. A central processor retrieves a set of the operating parameters from the memory for the microsurgical instruments. The set of operating parameters retrieved by the central processor approximate an individualized set of surgeon-selected operating parameters provided by the user via the user interface. The system further includes a surgical module connected to and controlling one of the microsurgical instruments as a function of the set of operating parameters retrieved from the memory.

Yet another embodiment of the invention is a system for controlling a plurality of ophthalmic microsurgical instruments connected thereto. A user, such as a surgeon, uses the microsurgical instruments in performing ophthalmic surgical procedures. The system includes a user interface providing information to the user and receives information from the user which is representative of operating parameters of the microsurgical instruments. The system also includes a memory storing a plurality of operating parameters which are retrievable from the memory as a function of user-selected modes. Each mode is representative of one or more surgical procedures to be performed and is defined by operation of at least one of the microsurgical instruments. A central processor retrieves a set of the operating parameters from the memory for the microsurgical instruments to be used in a selected one of the modes. The system further includes a surgical module connected to and controlling one of the microsurgical instruments as a function of the set of operating parameters retrieved from the memory.

Another system embodying aspects of the invention controls a plurality of ophthalmic microsurgical instruments connected thereto. A user, such as a surgeon, uses the microsurgical instruments in performing ophthalmic surgical procedures. The system includes a data communications bus and a user interface connected to the data communications bus. The user interface, including a central processor, provides information to the user and receives information from the user which is representative of operating parameters of the microsurgical instruments. The system also includes a surgical module which is connected to and controls one of the microsurgical instruments as a function of at least one of the operating parameters. The surgical module has a flash EEPROM storing executable routines for controlling the corresponding microsurgical instrument connected to it during performance of the surgical procedures and is connected to the data communications bus. The data communications bus provides communication of data representative of the operating parameters between the user interface and the module and the central processor reprograms the flash EEPROM via the data communications bus in response to the information provided by the user.

In another embodiment, the invention is a system for controlling a plurality of ophthalmic microsurgical instruments connected thereto. A user, such as a surgeon, uses the microsurgical instruments in performing ophthalmic surgical procedures. The system includes a data communications bus and a user interface connected to the data communications bus. The user interface, including a central processor, provides information to the user and receives information from the user which is representative of operating parameters of the microsurgical instruments. The system also includes a surgical module which is connected to and controls one of the microsurgical instruments as a function of at least one of the operating parameters. The surgical module is connected to the data communications bus which provides communication of data representative of the operating parameters between the user interface and the module. In this instance, the central processor executes routines to identify and initialize the module communicating via the data communications bus.

Yet another embodiment of the invention is a system for controlling a plurality of ophthalmic microsurgical instruments connected thereto. A user, such as a surgeon, uses the microsurgical instruments in performing ophthalmic surgical procedures. The system includes a user interface which provides and displays information to the user and receives information from the user which is representative of operating parameters of the ophthalmic procedures and operating parameters of the microsurgical instruments to be used by the surgeon in performing the ophthalmic procedure. The user selects a particular procedure via the user interface. An aspiration module of the system is adapted to receive different microsurgical cassettes, each having different color-bearing insert. Each color indicates the procedure for which the cassette is to be used. The system also includes a sensor for sensing the color of the color-bearing insert when the cassettes are received in the system and for providing information to the user interface when the color of the color-bearing insert of the cassette received by the system does not correspond to the particular procedure selected.

Alternatively, the invention may comprise various other systems and methods.

Other objects and features will be in part apparent and in part pointed out hereinafter.

BRIEF DESCRIPTION OF THE DRAWINGS

FIG. 12 is a perspective of a typical base unit and module assembly;

FIGS. 27–30 are exemplary screen displays generated by the user interface computer for selecting an operating mode according to the invention;

FIGS. 43–60 are schematic diagrams illustrating the irrigation, aspiration and/or vitrectomy module of FIG. 32;

FIGS. 89–103 are schematic diagrams illustrating the air/fluid exchange, electric scissors and/or forceps module of FIG. 34;

DETAILED DESCRIPTION OF PREFERRED EMBODIMENTS

Figure 1:
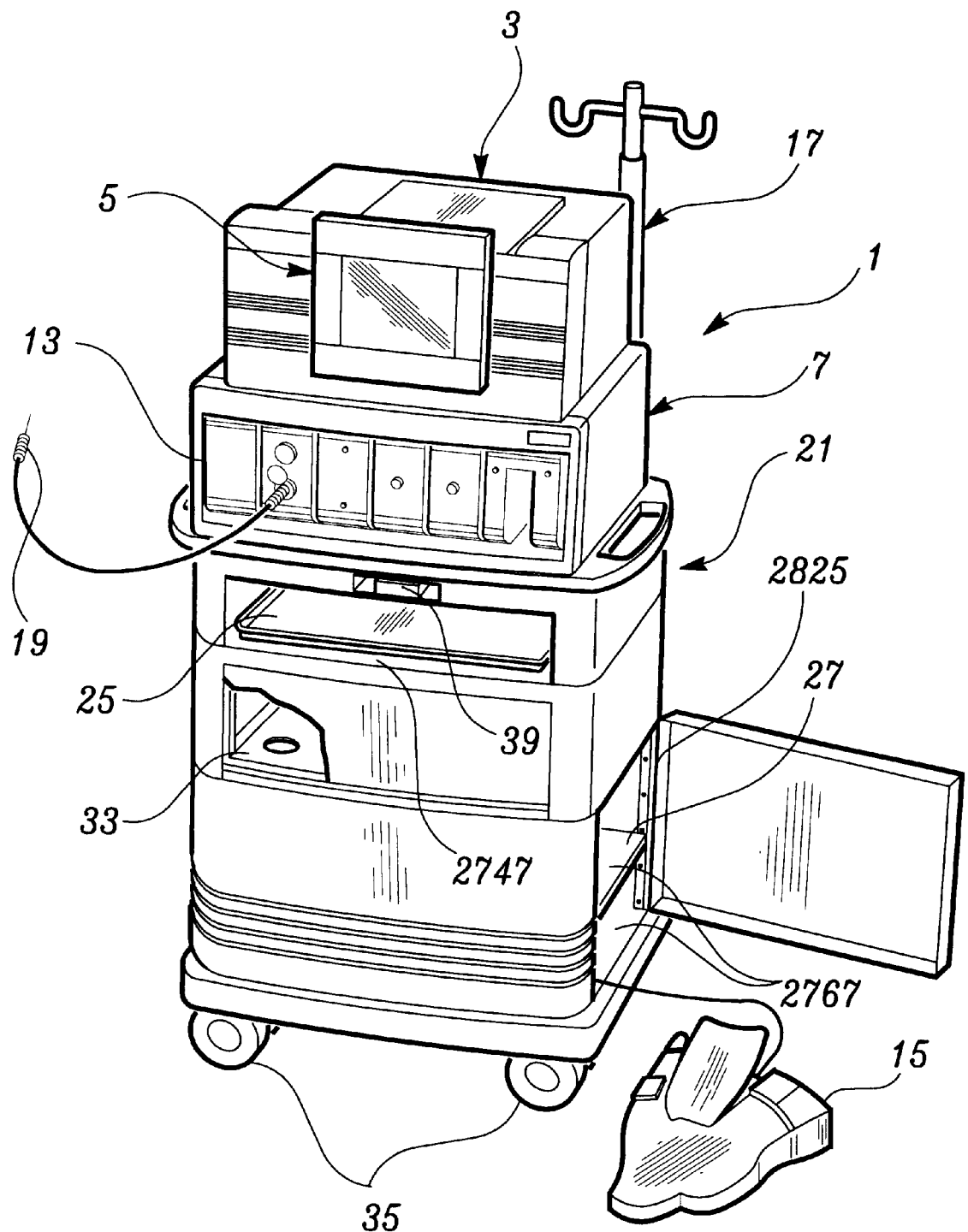
FIG. 1 is a perspective of a microsurgical control system according to the invention for use with ophthalmic microsurgical instruments and having a plurality of modules.

FIG. 1 illustrates a microsurgical control system, generally designated 1, according to a preferred embodiment of the present invention. As shown, the system 1 includes a computer unit 3 having a flat panel display 5, a base unit 7 housing a plurality of modules 13, and peripherals such as a foot control assembly 15 and a motorized intravenous (IV) pole assembly 17 (each of which is generally indicated by its respective reference numeral). Each of the modules 13 housed in the base unit 7 controls at least one ophthalmic microsurgical instrument 19 for use by a surgeon in performing various ophthalmic surgical procedures. As is well known in the art, ophthalmic microsurgery involves the use of a number of different instruments 19 for performing different functions. These instruments 19 include vitrectomy cutters, phacoemulsification or phacofragmentation handpieces, electric microscissors, fiber optic illumination instruments, coagulation handpieces and other microsurgical instruments known in the art. To optimize performance of instruments 19 during surgery, their operating parameters differ according to, for example, the particular procedure being performed, the different stages of the procedure, the surgeon's personal preferences, whether the procedure is being performed in the anterior or posterior portion of the patient's eye, and so on.

As shown in FIG. 1, an instrumentation cart, generally designated 21, supports system 1. Preferably, the cart 21 includes a surgical, or Mayo, tray 25, the automated IV pole assembly 17, a storage compartment 27 for stowing the foot control assembly 15, disposable packs and other items, an opening 33 to house an expansion base unit (not shown in FIG. 1), and rotating casters 35. Base unit 7 and computer unit 3 preferably sit on top of instrumentation cart 21 as shown in FIG. 1 and the Mayo tray 25 is mounted on an articulating arm (not shown) preferably attached to the top of instrumentation cart 21, directly beneath base unit 7. Instrumentation cart 21 also holds a remote control transmitter, generally indicated 39, for use in remotely controlling system 1.

According to the invention, the modules 13 in base unit 7 house control circuits for the various microsurgical instruments 19 so that the system's user is able to configure system 1 for optimizing its use by the surgeon. As will be described in detail below, modules 13 include connections or ports by which one or more microsurgical instruments 19 connect to each module 13 and house the necessary control circuitry for controlling operation of the particular instrument or instruments 19 connected thereto. Thus, the user, by inserting the desired modules 13 in base unit 7, configures system 1 to meet a particular surgeon's preference, to control each of the instruments 19 needed for a particular surgical procedure, or to otherwise optimize system 1 for use by the surgeon.

As will be described in detail below, foot control assembly 15 and IV pole assembly 17 include electronic control circuits for controlling their operation.

To support user-configurability, computer unit 3, each of the modules 13, and the control circuits for each of the peripherals, namely, foot control assembly 15 and IV pole assembly 17, constitute nodes on a computer network. The computer network provides power distribution and peer-to-peer data communication between the nodes.

Figure 2:
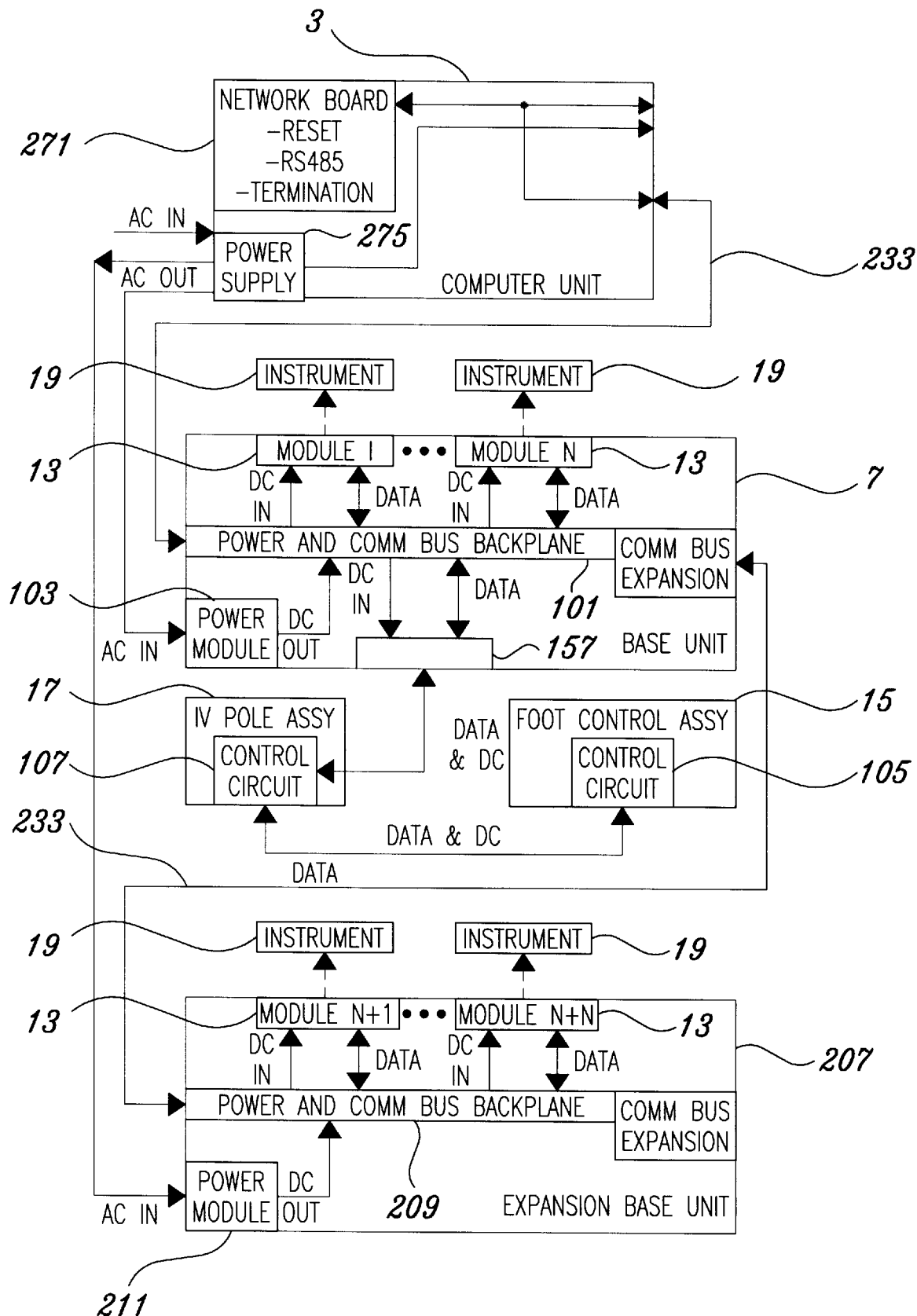
FIG. 2 is a block diagram of the system of FIG. 1.

Referring now to the block diagram of FIG. 2, base unit 7 includes a number of modules 13 which control various microsurgical instruments 19 typically used in performing ophthalmic surgical procedures. In a preferred embodiment, each module 13 controls one or more surgical instruments 19 connected to it. A power bus and a data communications bus, each positioned on a backplane 101 (shown in detail in FIGS. 5 and 40–42), connect modules 13 to each other. When received by base unit 7, modules 13 engage the backplane 101 via a connector (e.g., connector 171 in FIG. 10) at the rear of each module 13. When engaged, backplane 101 provides power distribution between modules 13 as well as data communication between modules 13 and between modules 13 and computer unit 3. According to the invention, modules 13 also include a power module 103 housed by base unit 7 which is connected to both an external AC power source and backplane 101. The power module 103 provides power to backplane 101 and, thus, provides power to system 1.

According to the invention, a control circuit 105 (see FIGS. 37, 126–136) controls foot control assembly 15 and a control circuit 107 (see FIGS. 38 and 137–146) controls IV pole assembly 17. As described above, computer unit 3, each module 13 and the control circuits 105, 107 for the peripherals constitute nodes on a computer network. The computer network provides peer-to-peer data communication between the nodes. In other words, each module 13 is able to communicate directly with the other modules 13, the peripherals and computer unit 3. As such, system 1 provides modular control of several different instruments 19 as well as user-configurability.

Figure 3:
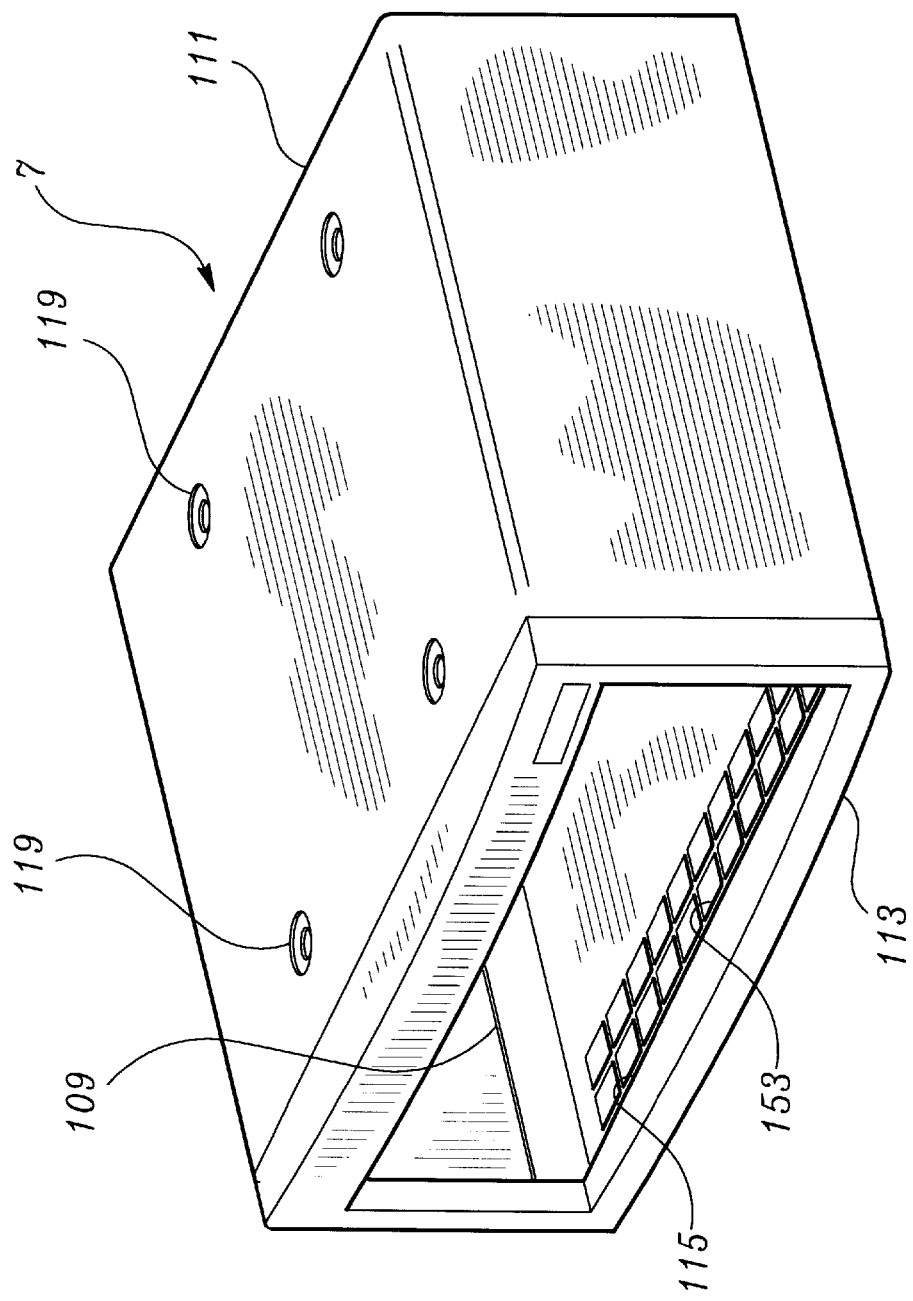
FIG. 3 is a perspective of a base unit of the system of FIG. 1.
Figure 4:
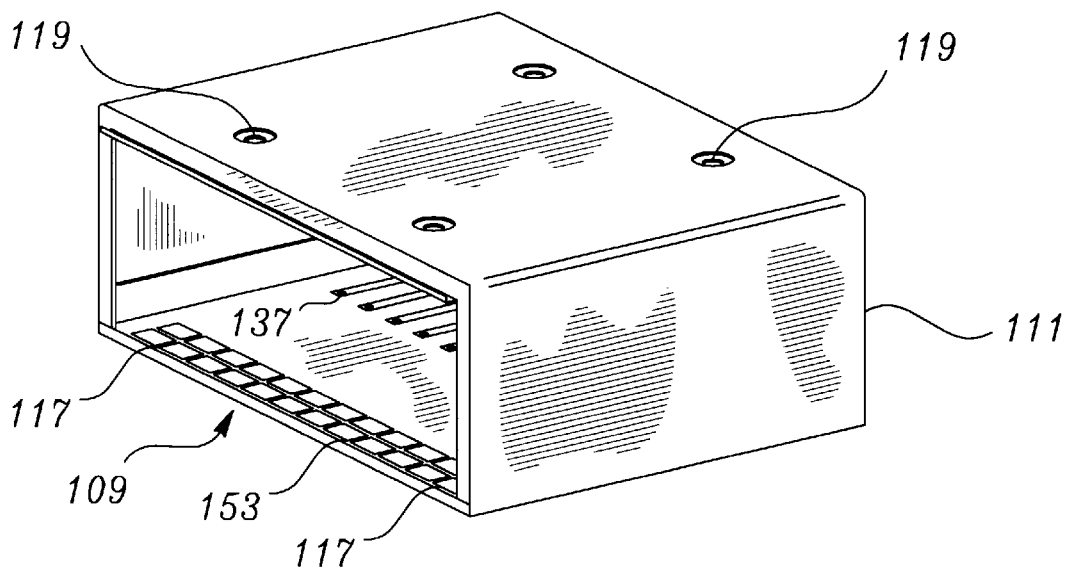
FIG. 4 is a perspective of the base unit shown without a front cover.

Referring now to FIG. 3, the base unit 7 forms a rack having positions or slots for receiving a plurality of modules 13 which electronically control the operation of surgical instruments 19 used by a surgeon in performing ophthalmic surgical procedures. Preferably, the base unit 7 includes a chassis (generally designated 109), a top cover 111 having the shape of an inverted channel, and a front cover or bezel 113 which may be removed as shown in FIG. 4 for inserting and removing modules 13. When the front cover 113 is fastened in place, the rearward wall 115 of the cover holds the modules in place within the base unit 7 thereby forming a retainer for retaining the modules in the rack. The front cover 113 is held in place by two fasteners (not shown) screwed into threaded holes 117 in the front of the chassis 109. In the alternative, front cover 113 clips in place. The top cover 111 includes four circular receptacles 119 for receiving feet on the bottom of computer unit 3. Each of these receptacles 119 is tapered to conform to the shape of the computer unit feet and to center the feet in the receptacles.

Figure 5:
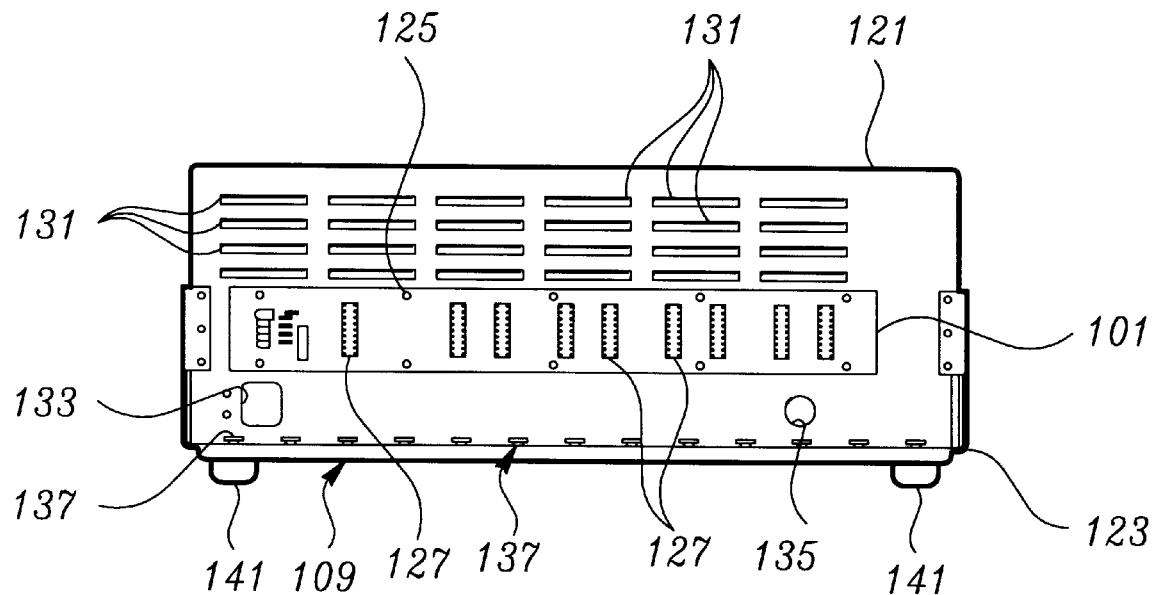
FIG. 5 is a front elevation of a base unit chassis.
Figure 6:
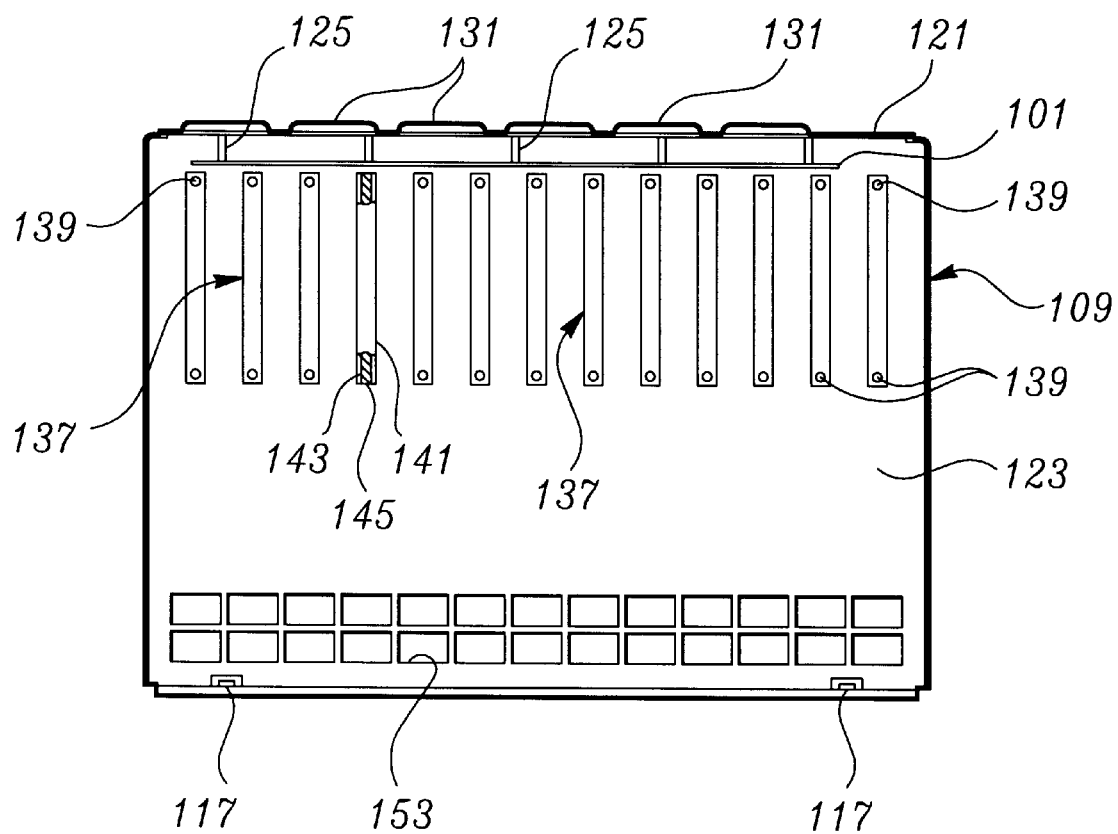
FIG. 6 is a top plan of the base unit chassis.
Figure 14:
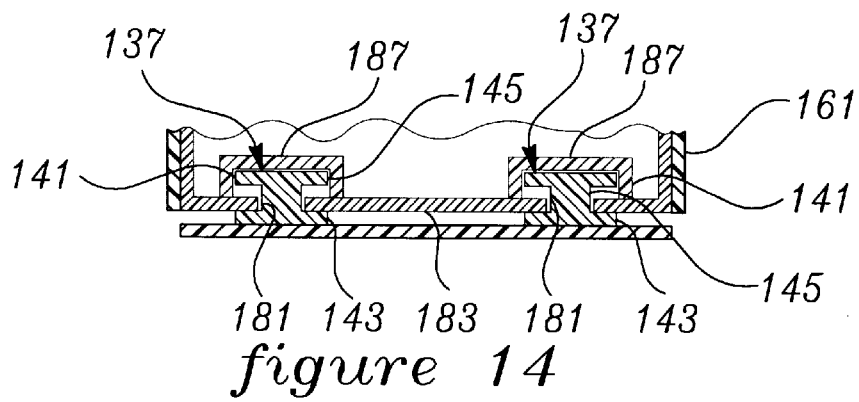
FIG. 14 is a fragmentary cross-section taken in the plane of line 5C—5C of FIG. 13.

As illustrated in FIGS. 5 and 6, the chassis 109 comprises a rear panel 121 integrally formed with a bottom panel 123. The bottom panel 123 extends perpendicular to the front plane (i.e., the front surface) of the backplane 101 which is fastened to the rear panel 121 with fasteners 125. Ten 18-pin female electrical connectors 127 are provided on the front surface of the backplane 101. The three left-most connectors 127 as shown in FIG. 5 are spaced at three inch intervals, and the remaining connectors 127 are spaced at 1.5 inch intervals. Each socket of each connector 127 is connected in parallel to the similarly positioned sockets of the other connectors thereby forming the aforementioned power and data communications buses. Louvers 131 are provided in the rear panel 121 above the backplane 101 for permitting air to escape from the base unit 7 (FIG. 5). A generally rectangular opening 133 extends through the rear panel 121 below the backplane 101 to provide access for a 3-prong connector on the back of the power module 103 as will be explained below. Similarly, a circular opening 135 is provided in the rear panel 121 for accepting a pneumatic quick disconnect coupling (not shown) on the back of an irrigation/aspiration/vitrectomy (IAV) (e.g., module 321 in FIGS. 32 and 43–60). Thirteen parallel rails, each generally designated by 137, are attached to the bottom panel 123 by fasteners 139 (FIG. 6). The rails 137 are evenly spaced at 1.5 inch intervals and extend perpendicular to the front of the backplane 101. One or more of the rails 137 is used to guide the modules 13 into position in the base unit 7 so they are properly aligned for connection with the backplane 101. As shown in FIG. 14, each of the rails 137 has an I-shaped cross-section comprising upper and lower horizontal flanges (141, 143, respectively) joined by a vertical web 145.

Figure 7:
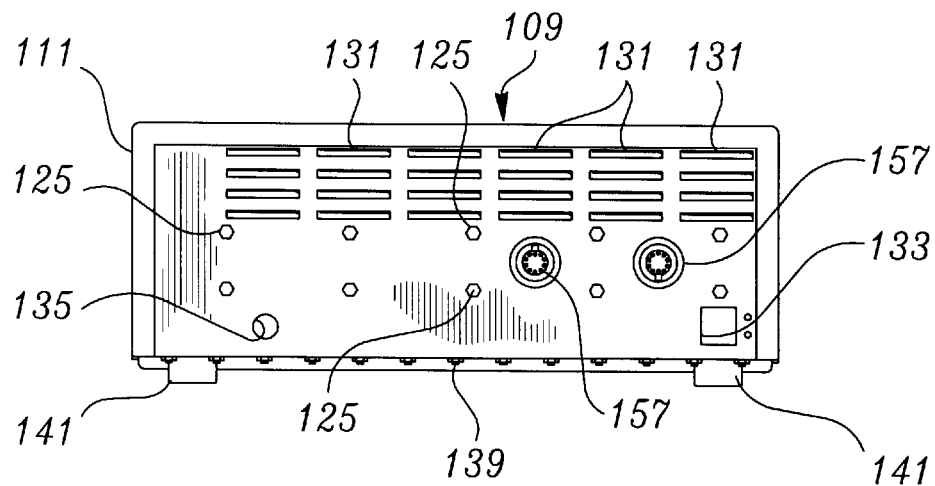
FIG. 7 is a rear elevation of the base unit.

Turning to FIG. 5, four feet 141 extend down from the bottom panel 123 and are sized to seat in depressions (not shown) molded in the cart 21. As shown in FIG. 6, an intake grating 153 is provided in the bottom panel 123 for permitting air to enter the base unit 7 to cool the modules 13. FIG. 7 shows two circular 9-pin female electrical connectors 157 mounted on the back face of the rear panel 121. Each of these connectors 157 is connected in parallel to the data communications bus on the backplane 101 to communicate with peripherals such as the cart 21 (including IV pole assembly 17), the computer unit 3 or the foot control assembly 15. The connectors 157 may also be used to connect base unit 7 to a separate expansion base unit as will be explained in detail below. Although other connectors are envisioned as being within the scope of the present invention, the connectors of the preferred embodiment are Series 703 electrical connectors sold by Amphenol Corporation of Wallingford, Conn.

Figure 9:
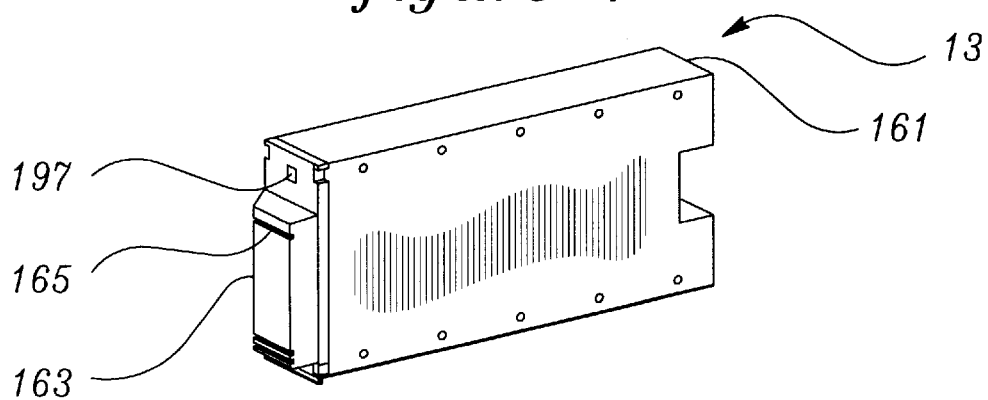
FIG. 9 is a perspective of a typical module of the system of FIG. 1.
Figure 11:
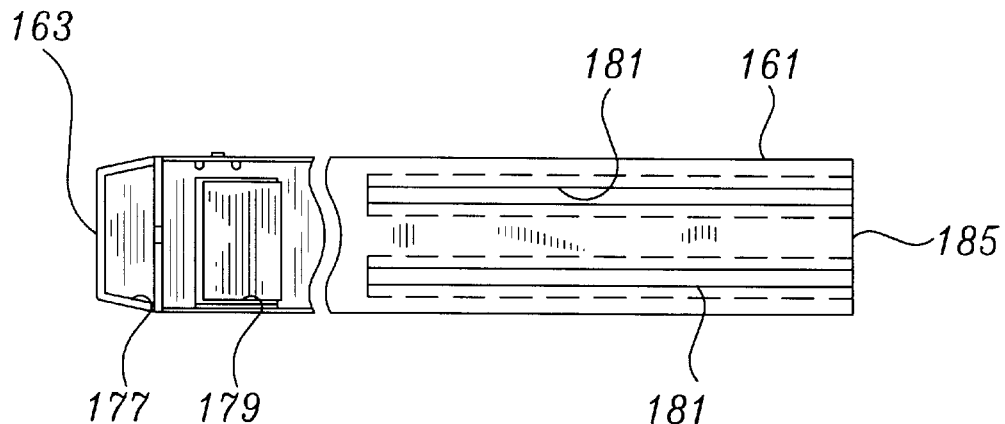
FIG. 11 is a fragmentary bottom plan of the module.
Figure 10:
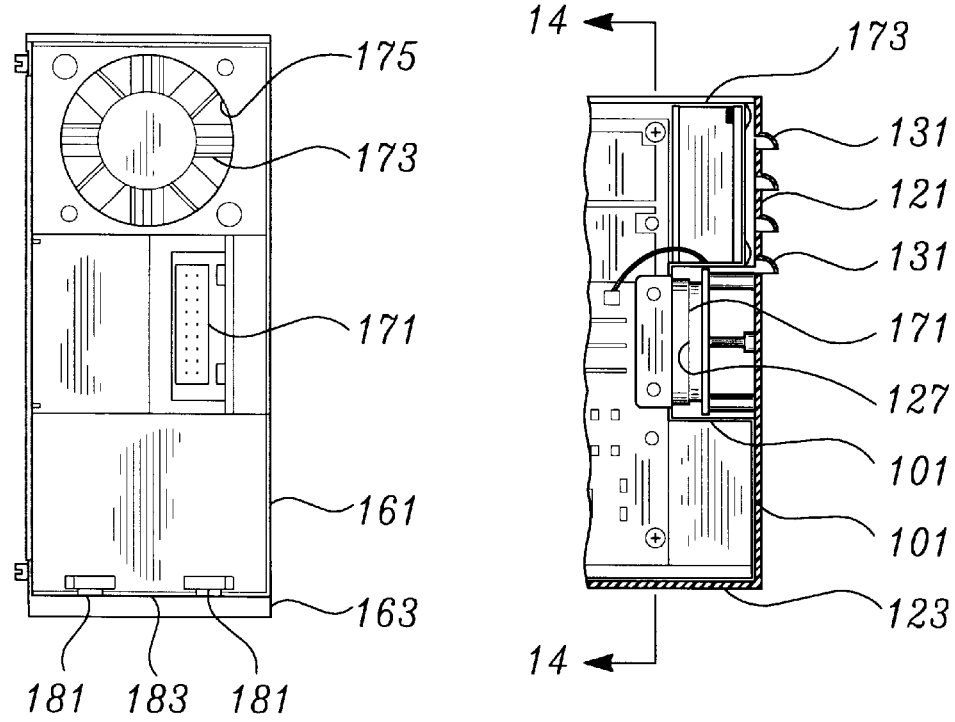
FIG. 10 is a rear elevation of the module.

FIGS. 9–11 illustrate exemplary modules 13 for electronically controlling the operation of surgical instruments 19 used by a surgeon in performing ophthalmic surgical procedures. The exemplary module shown in FIG. 9 is the power module 103 for supplying power to the power bus of the backplane 101. Each of the modules 13 comprises a case 161 formed from aluminum sheet and a molded plastic front cover 163. As shown in FIG. 12, certain modules 13 have one or more ports provided in their front covers 163 for connecting various surgical instruments (not shown) to the modules. The power module 103 illustrated in FIG. 9 is three inches wide. Other modules have other widths which are multiples of 1.5 inches (e.g., 1.5 inches or 4.5 inches). Each of the modules 13 has a green light emitting diode (LED) 165, or other visual indicator, mounted on the front cover 163 to indicate when the module is active.

Turning to FIG. 10, each module 13 includes an 18-pin male electrical connector 171 adapted to connect to any of the female connectors 127 mounted on the backplane 101. The connector 171 is recessed in the case 161 to protect the connector and to maximize the space provided within the base unit 7. A cooling fan 173 is positioned adjacent an exhaust port 175 provided in the rearward face of the module case 161 above the 18-pin connector 171 for exhausting air from the case 161 to cool components within the module 13.

Referring to FIG. 11, a recess 177 is formed in the bottom of the front cover 163 for gripping the module 13 to slide it into and out of the base unit 7. An opening 179 is provided in the bottom of the module case 161 to permit air to enter the module when the fan 173 is energized to cool components housed within the module 13. One or more slots 181 are formed in the bottom wall 183 of each module case 161. Each of these slots 181 extends from a rear wall 185 of the case 161 and is configured to receive one of the guide rails 139 on the bottom panel 123 of the base unit chassis 109 to guide the module 13 and align its connector 171 with the corresponding connector 127 on the backplane 101. Thus, the rails 137 and slots 181 form a guide for guiding each of the modules 13 into the rack so the respective module connector 127 is aligned for connection to the bus.

As illustrated in FIG. 14, a channel 187 is tack welded to the bottom wall 183 of the module case 161 above each slot 181 to prevent debris from entering the case through the slots 181 and to shield the electronic components housed within the case from electromagnetic interference. When the modules 13 are introduced into the base unit 7, each of the base unit rails 137 is received in a respective slot 181 and channel 187 in the manner shown in FIG. 14, that is, with the upper horizontal flange 141 slidable in the channel 187 and the web 145 slidable in the slot 181 therebelow. The interengagement between the web 145 and the slot 181 and between the upper flange 141 and the case bottom wall 183 holds the module 13 in position in the base unit 7 and prevents the module from substantially moving perpendicular to the rails 137 in either the vertical or horizontal directions.

However, the rails 137 and slots 181 are sized to permit some movement (e.g. 1/16 inch) between the module 13 and base unit 7 so the pins of the module connector 171 can properly align with the sockets of the backplane connector 127. The connectors 127, 171 are tapered to guide the pins into the sockets even though the connectors are initially out of alignment by some amount (e.g., 0.1 inch). Even though the rails and slots are dimensioned to allow some movement, they do not permit any more misalignment than the connectors will tolerate. Therefore, the rails 137 and slots 181 adequately provide for piece-part tolerances, but guide each of the modules 13 into the rack so the respective module connector 127 is aligned for connection to the bus.

Portions of the bottom wall 183 of the module case 161 adjacent each slot are engageable with the top of the lower flange 143 of a respective rail 137 to space the case 161 from the base unit chassis 109 and minimize metal-to-metal contact between the modules 13 and base unit 7. Although two slots 181 are present in the exemplary module 13 shown in FIG. 11, one or more slots may be present in other modules depending upon their widths. For instance, 1.5 inch wide modules 13 have one slot 181 and 4.5 inch wide modules have three slots.

Figure 13:
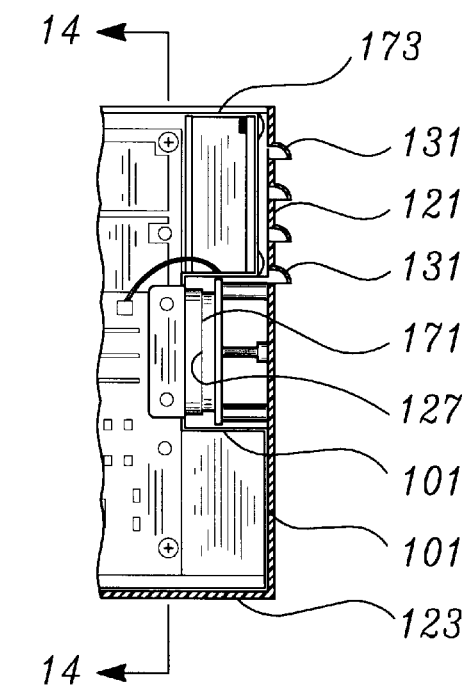
FIG. 13 is a fragmentary cross-section taken in the plane of line 5B—5B of FIG. 7 but with a module installed in the base unit.

When the module 13 is installed in the base unit 7, the exhaust port 175 and fan 173 align with the louvers 131 in the base unit rear panel 121 as shown in FIG. 13 to freely vent air from the module when the cooling fan is energized. Similarly, the intake opening 179 of the module aligns with the grating 153 in the base unit bottom panel 123 to allow air to enter the module 13 from outside the base unit 7.

Each module 13 also provides overcurrent protection to ensure that a single module failure does not damage other parts of the system 1.

As shown in FIGS. 9 and 12, the front cover 163 of each module 13 includes beveled surfaces 191 extending rearwardly from the front surface 193 along opposite sides of the front surface. The bevelled surfaces 191 are convergent with respect to one another toward the front surface 193 so that when the module 13 is placed in the base unit 7 beside another module, with a bevelled surface of one module adjacent a bevelled surface of the other module, the generally planar front surfaces of the adjacent modules are laterally spaced from one another by a distance D. The lateral spacing between the module front surfaces reduces the "noticeability" of any misalignment between the front surfaces 193 of adjacent modules. Thus, greater piece part tolerances are permitted without detracting from the appearance of the system 1.

As previously explained, the module connectors 171 connect to the connectors 127 on the backplane 101 when the modules 13 are installed in the base unit 7. When the male and female connectors are connected, appropriate circuits within the module 13 are connected to the power and data communications buses in the backplane 101. Regardless of the position of the module 13 within the base unit 7, the same module circuits connect to the same circuits of the power and data communications buses. Thus, the modules 13 are generally interchangeable and may be ordered in any sequence within the base unit 7. Further, because each module 13 is separately controlled, only those modules which control instruments necessary for a particular surgical procedure need be installed in the base unit 7. Therefore, the previously described rack is configured to receive the modules 13 in a plurality of different positions along the power and data communications buses so that they are selectively organizable in a plurality of different sequences in the rack.

However, the power module 103 has a dedicated location within the base unit 7 so it may be conveniently connected to the external power source through the rectangular opening 133 in the base unit rear panel 121. Because the power module 103 is 3 inches wide, the spacing between the two left-most connectors 127 as shown in FIG. 5 is three inches. The spacing between the second and third connectors from the left as shown in FIG. 5 permit either a three or 4.5 inch wide module to be inserted next to the power module 103. If an IAV (e.g., module 321 in FIGS. 32 and 43–60) is used, it must be installed over the three right-most rails 137 as shown in FIG. 5. As previously mentioned, a pneumatic quick disconnect coupling protrudes from the back of the IAV module 321. The IAV module 321 can only be installed in the right-most position because the coupling must extend through the circular opening 135 in the rear panel 121 of the base unit 7. If an IAV module is not being used, any other module (besides a power module) may be installed in the right-most position. With the exceptions noted above, the modules 13 are fully interchangeable and may be installed in any order as desired. Thus, the base unit 7 is configured so the modules 13 may be received in a plurality of different positions within the rack and so they are selectively organizable in a plurality of different sequences in the rack. All the modules 13 are capable of being installed into or removed from base unit 7 quickly from the front without the aid of any tools due to their modular construction and the releasable engagement of the backplane 101. This quick installation and removal facilitates convenient maintenance or replacement of modules. For example, if a particular module 13 needs repair, it can be easily removed and shipped to a repair facility. During repair, another module may be used in its place or the system 1 can be operated without the particular module 13.

Figure 8:
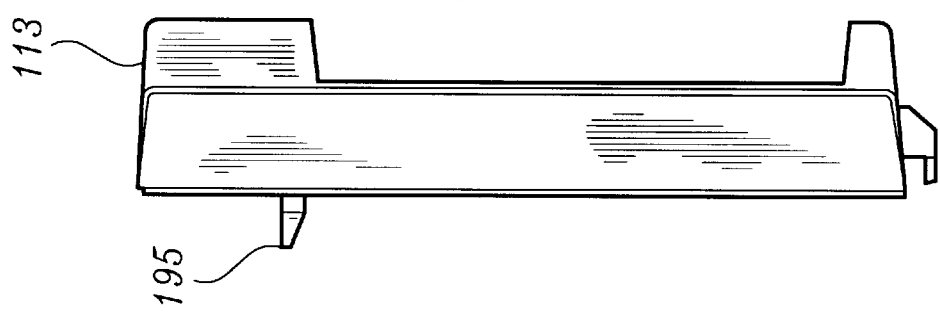
FIG. 8 is a left side elevation of the base unit front cover.

Additionally, as shown in FIG. 8, a post 195 extends from the rear face of the front cover 113 of the base unit 7. The post 195 is positioned on the front cover so it engages a opening 197 (FIG. 9) in the power module 103 when the cover is installed on the base unit with the modules 13 installed. An interlock switch (e.g., interlock switch 783 in FIG. 39) located behind the opening 197 in the power supply module 103 interrupts power to each of modules 13 upon removal of the base unit front cover 113. Thus, users cannot contact the backplane 101 when it is energized. Further, the particular configuration of modules in the rack is checked during each start-up (as explained below with respect to FIG. 31), and cannot be changed without removing the front cover 113. By interrupting power when the cover 113 is removed, the configuration of the modules 13 cannot be changed without being detected.

Referring to FIG. 2, the system 1 may further include an expansion connector 203 (see FIG. 16) for connecting the base unit 7 to an optional expansion base unit 207 thereby to expand the network. Physically and functionally, the expansion base unit 207 is substantially identical to base unit 7. In a preferred embodiment of the invention, the user can expand the network and, thus, expand the operating capabilities of the system 1, by connecting either 9-pin connector 157 on the rear panel 121 of the base unit 7 to the similar connector on the expansion base unit 207 with the expansion connector 203. The expansion base unit 207 of the preferred embodiment includes its own power module 211. Therefore, the expansion connector 203 connects the data communication buses of the units, but not the power buses. However, it is envisioned that a single power module could supply both units without departing from the scope of the present invention. When a single power module is used, power is provided to the expansion base unit 207 via the expansion connector 203 by connecting the power bus on the backplane 101 of the base unit 7 to the power bus on the backplane 209 of the expansion base unit 207.

Figure 15:
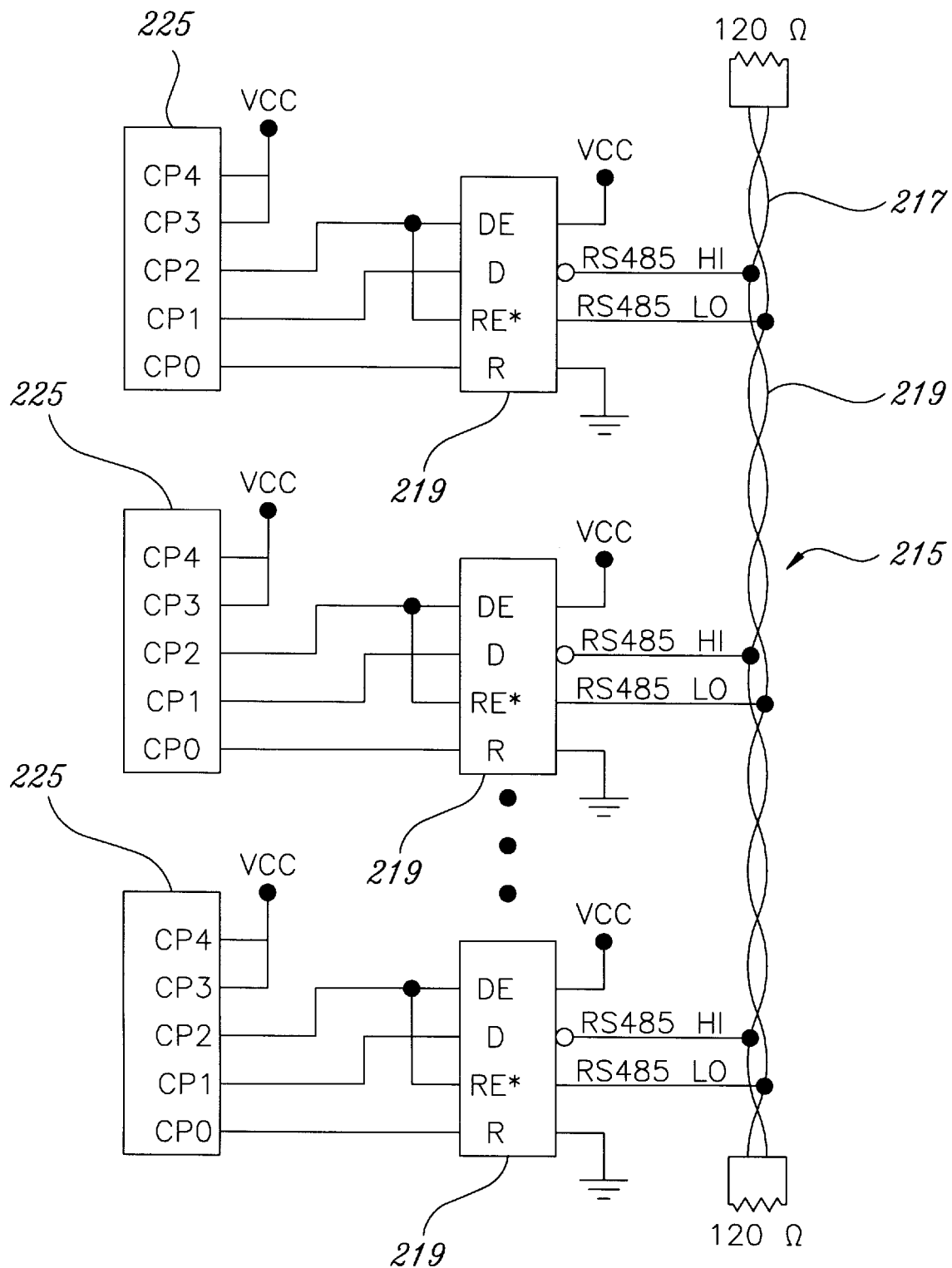
FIG. 15 is a schematic diagram of a communications network according to the invention.

Referring now to FIG. 15, the data communications bus preferably comprises a twisted pair cable 215 having a first wire 217 and a second wire 219. In one preferred embodiment, the computer network linking each of the components of system 1 is of the type sold by Echelon Corporation under the trademark LONTALK® utilizing an RS485 communications protocol. The RS485 standard provides a platform for multi-point data transmission over a balanced twisted pair transmission line. Each module 13 includes an RS485 transceiver 223 for receiving data from and transmitting data to the data communications bus and a processor 225 coupled to the transceiver 223. Motorola manufactures a suitable processor 225 designated NEURON® chip Model No. MC143150 and National Semiconductor manufactures a suitable transceiver 223 designated chip Model No. 75156.

The data communications bus, the transceivers 223 and the processors 225 together form the communications network by which modules 13, computer unit 3, the control circuit 105 of foot control assembly 15 and the control circuit 107 of IV pole assembly 17 communicate with each other. Through the use of the network, system 1 provides peer-to-peer communication between its components.

In such a network, processor 225 is also referred to herein as a "neuron" or "neuron processor" (NEURON® is a registered trademark of Echelon Corporation). Each neuron processor 225 preferably comprises three 8-bit on-board processors. Two of the three on-board processors implement a communication subsystem, enabling the transfer of information from node to node on the network. The third on-board processor executes an embedded application program. Thus, in addition to functioning as communication processors, neuron processors 225 control microsurgical instruments 19 connected thereto. Preferably, the neuron processors 225 of modules 13 receive the data communicated via the data communications bus and, in response to the data, generate control signals to control microsurgical instruments 19.

As shown, transceivers 223 tap into the first and second wires 217, 219 of twisted pair cable 215. In one preferred embodiment of the invention, twisted pair cable 215 is positioned on backplane 101 (i.e., as traces on backplane 101). Thus, when the connectors 171 at the rear of modules 13 engage backplane 101, they tap into twisted pair cable 215. As described above in reference to FIG. 5, backplane 101 also includes a pair of additional data cable connectors 157 for connecting data cables to backplane 101. The data cables include twisted pair cable and extend the data communications bus from backplane 101 to computer unit 3 and to the peripherals. For example, one data cable runs from one data cable connector 157 to computer unit 3 and another data cable runs from the other data cable connectors 157 to either foot control assembly 15 directly or to IV pole assembly 17 and foot control assembly 17 via instrumentation cart 21.

According to the RS485 protocol, each end of twisted pair cable 215 must be terminated by a resistance, such as a 120Ω resistor. However, the need for a termination makes it difficult to expand the network. Advantageously, the present invention provides a termination circuit 229, shown in FIG. 16, located at one end of twisted pair cable 215 for selectively terminating the network by a 120 ohm resistor and allowing for easy expansion of the network.

Figure 16:
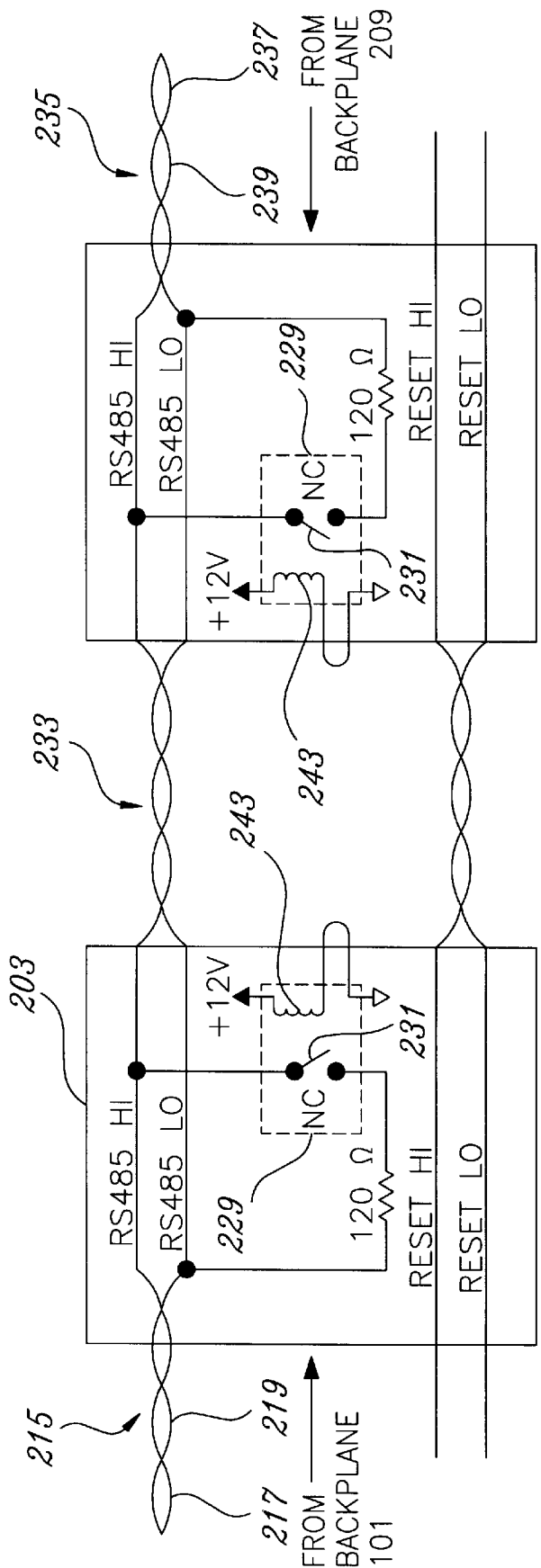
FIG. 16 is a schematic diagram of a termination circuit for selectively terminating the network of FIG. 15.

FIG. 16 illustrates the termination circuit 229 for selectively terminating the data communications bus. As shown, the data communications bus (i.e., twisted pair cable 215) is represented by RS485-HI and RS485-LO lines. Preferably, termination circuit 229 is part of expansion connector 203 and is connected in series between the ends of the first and second wires 217, 219 of the first twisted pair cable 215. In one embodiment, termination circuit 229 comprises a normally closed switch 231 connected in series with the 120 ohm resistance for terminating the data communications bus. In order to expand the network, the user connects an expansion cable 233 having a second twisted pair cable 235 associated with expansion base unit 207 to expansion connector 203. As with the first twisted pair cable 215, the second twisted pair cable 235 has a first wire 237 and a second wire 239 provided for connection to termination circuit 229. According to the invention, second twisted pair 235 is positioned on backplane 209 and constitutes the data communications bus for expansion unit 207.

Termination circuit 229 also includes a coil 243 connected to a positive voltage supply. When the user connects expansion cable 233 associated with expansion base unit 207 to expansion connector 203, the coil 243 is shorted to ground. As a result, the positive voltage energizes coil 243 which in turn opens the normally closed switch 231. Thus, when the ends of the first and second wires 217, 219 of first twisted pair cable 215 are connected to the ends of the first and second wires 237, 239 of second twisted pair cable 235, respectively, switch 231 opens to remove the termination. The termination is then found at the other end of expansion base unit 207. In a preferred embodiment, either the expansion cable 233 or the backplane 209 of expansion base unit 207 also includes termination circuit 229.

FIG. 16 also shows lines labeled RESET-HI and RESET-LO. Preferably, computer unit 3 communicates a reset signal via the data communications bus to the modules 13 installed in base unit 7 via backplane 101 and to the modules 13 installed in expansion base unit 207 via backplane 209.

According to a preferred embodiment of the invention, expansion base unit 207 includes its own power module 211. As such, power is not distributed between base unit 7 and expansion base unit 207. In the alternative, the power bus may also be positioned on backplanes 101, 209 for distributing power from power module 103 to each of the modules 13 of system 1 which are located in either base unit 7 or expansion base unit 207.

Figure 17:
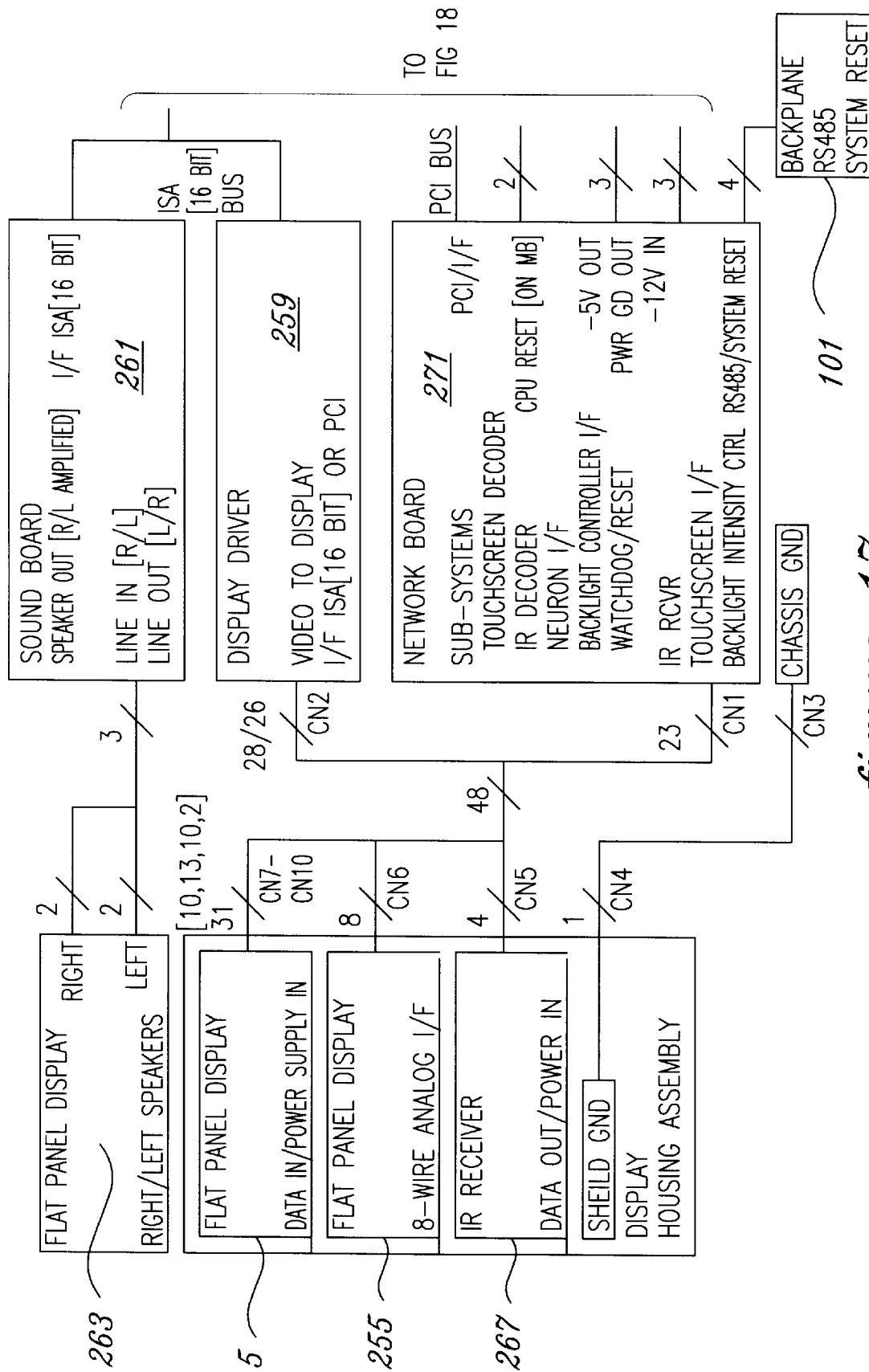
FIGS. 17 and 18 are a block diagram of a user interface computer according to a preferred embodiment of the system of FIG. 1.
Figure 18:
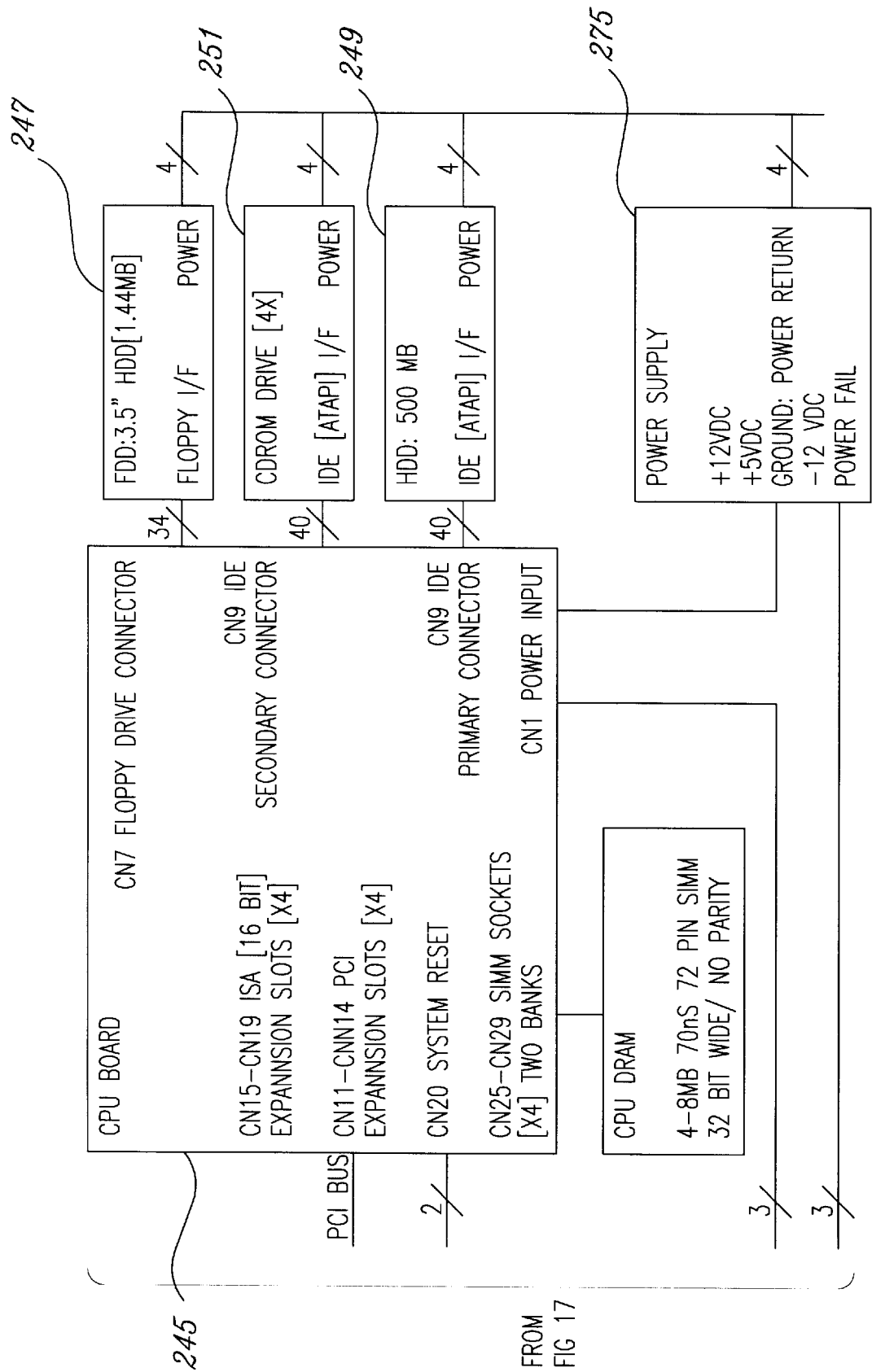

Referring now to the block diagram of FIGS. 17–18, computer unit 3 comprises an embedded central processing computer 245, at least one disk drive 247 and an internal hard drive 249. In a preferred embodiment of the invention, the central processor 245 of computer unit 3 is an IBM compatible microprocessor-based board including, for example, an Intel 486® or Pentium® processor, and having an industry standard AT motherboard. The disk drive 247 is a conventional 3.5 inch, 1.44 MB floppy drive and the hard drive 249 is a conventional IDE 3.5 inch internal hard drive having at least 250 MB of memory. In an alternative embodiment, computer unit 3 includes a CD-ROM drive 251 in addition to floppy drive 247. Computer unit 3 also includes the flat panel display 5, a touch-responsive screen 255 for use with flat panel display 5 and various multimedia hardware accessories such as a video board, or display driver 259, a sound board 261 and speakers 263. Advantageously, each of the various expansion boards of computer unit 3 are compatible with standard PC architectures.

Computer unit 3 constitutes a user interface by which the user (such as a surgeon, medical technician or assistant) receives information representative of the various operating parameters of microsurgical instruments 19 and peripherals which provide the different functions needed to perform the surgical procedures. The user also provides information to system 1 via a graphical user interface provided by computer unit 3. Advantageously, the hard drive 249 of computer unit 3 stores programmable operating parameters for each of the microsurgical instruments 19 and peripherals. By providing information to central processor 245 via the user interface, the user is able to reprogram or select from the operating parameters stored in hard drive 249. Computer unit 3 then communicates the operating parameters to modules 13 as well as to foot assembly 15 and IV pole assembly 17 via the backplane 101 and external data cables and its network. In this manner, the user is able to optimize the performance of instruments 19 during surgery.

In one embodiment, the user stores data representative of a plurality of operating parameters on a removable memory, such as a floppy disk, for use with the disk drive 247 of computer unit 3. In this embodiment, the central processor 245 of computer unit 3 defines a set of operating parameters for the microsurgical instruments 19 and peripherals based on the data stored in the removable memory. For example, the set of operating parameters defined by central processor 245 comprise an individualized set of surgeon-selected operating parameters. Similarly, the hard drive 249 of computer unit 3 stores default operating parameters which may be adapted to approximate the individualized set of parameters provided by the user.

As an example, operating parameters define one or more of the following for use in controlling the various instruments 19: a linearly variable scissors cut rate; a fixed scissors cut rate; a single actuation scissors cut; a proportional actuation scissors closure level; an air/fluid pressure; an air/fluid flow rate; a linearly variable bipolar power level; a fixed bipolar power level; an illumination intensity level; an aspiration vacuum pressure level; an aspiration flow rate; a linearly variable vitrectomy cut rate; a fixed vitrectomy cut rate; a single actuation vitrectomy cut; a phacoemulsification power level; a phacofragmentation power level; a phacoemulsification pulse rate; and a phacofragmentation pulse rate.

The control circuits 105, 107 of the peripherals also form nodes on the computer network and operate as a function of at least one operating parameter. In the above example, the operating parameters also define one or more of following for the peripherals: a plurality of foot control pitch detent levels; and an intravenous pole height.

Referring further to FIGS. 17–18, computer unit 3 also includes an infrared (IR) receiver circuit 267 for receiving IR signals from the hand-held remote control 39. The IR signals preferably represent commands for controlling operation of system 1. As an example, remote control 39 is a wireless infrared transmitter similar in size and appearance to a standard television or video cassette recorder remote. The unit provides line of sight operation and preferably uses a transmitter/receiver encoding scheme to minimize the risk of interference from other infrared transmitters and/or receivers. In terms of function, the keypad of remote control 39 preferably includes control buttons for varying the levels of aspiration, bipolar coagulation power and ultrasound power (for phacoemulsification and phacofragmentation) as well as for varying the IV pole height, turning on and off the illumination instrument and varying the intensity level of the light provided by the illumination instrument. In one preferred embodiment, remote control 39 also includes control buttons for proceeding to the next mode and for returning to the previous mode in a predefined sequence of operational modes.

In addition, computer unit 3 includes a network board 271 designed specifically for use in microsurgical system 1. This application specific network board 271 includes transceiver 223 and neuron processor 225 for connecting computer unit 3 to the network. Preferably, network board 271 is used to interface central processor 245 with the touch-responsive screen 255 and the IR receiver 267 as well as surgical modules 13, foot control assembly 15 and IV pole assembly 17.

In one preferred embodiment, the central processor 245 of computer unit 3 cooperates with each of the neuron processors 225 of the individual control circuits of modules 13, foot control assembly 15 and/or IV pole assembly 17 to execute software in a two-tier software hierarchy. The first tier of the software hierarchy is the user interface which provides an interface between the user (i.e., the surgical team) and microsurgical system 1 of the invention. As used herein, the term "user interface" refers generally to computer unit 3 and specifically to the routines executed by computer unit 3 to generate a series of functional screen displays which enable the user to interface with system 1.

The user interface displays operating parameters and their settings as well as other conditions on flat panel display 5. The user interface also receives input from touch-responsive screen 255, foot control assembly 15 or IR remote control 39 to tailor the operation of system 1 to the surgeon's current surgical procedure. Preferably, the user interface is a Microsoft® Windows '95 based environment providing a highly graphical, user friendly operating environment which generates icons, symbols, and the like. As a result, the user interface simplifies the use of system 1 and is particularly well-suited for use with touch-responsive screen 255.

The second tier of the system software is an embedded control environment used by modules 13, control circuit 105 and control circuit 107. As described above, each component of system 1 forms part of a computer network such that the user interface communicates with the embedded software via a predetermined communication architecture such as the communication architecture Echelon LONTALK®.

The use of embedded software programs by modules 13 and the peripherals provides distributed control of system 1. In other words, each of the modules 13 and peripherals operate independently of the other modules 13 and peripherals while still being linked by the network. Thus, the failure of one component will not affect the functionality of the other components of system 1. In addition to embedded control software, each module 13 and peripheral incorporates built-in-tests so that specific failures can be identified and reported to computer unit 3 and, thus, be reported to the user. The operational status of each module 13 and peripheral is continually checked during operation through the use of a software watchdog timer (e.g., see watchdog timer 475 in FIG. 32).

According to the invention, computer unit 3 is especially well-suited for use in a modular system such as system 1. Hard drive 249 stores the various programs for operating system 1, including the programs normally resident in modules 13. In the event that a program resident in one of modules 13 becomes corrupted or in need of an update, the user may download the appropriate resident program from hard drive 249 to module 13 via the network thereby facilitating its reprogramming. Floppy drive 247 also allows the user to install software updates or application specific software for use with new modules based on this product. In this manner, the software of system 1 follows a modular approach which parallels the modular design of the hardware. Additionally, the user may save, load and transport user settings from system 1 to another like microsurgical system at a different location through the use of floppy drive 247.

Computer unit 3 employs sound board 261 and speakers 263 to generate audio signals for warning messages, alarms or other audible indications. In addition, sound board 261 and speakers 263 cooperate with the video board 259 and the CD-ROM drive 251 to provide audio/visual, or multimedia, presentations such as animated on-line service and instruction manuals, operational demonstrations, and the like in a number of different languages.

Flat panel display 5 and touch-responsive screen 255 are the primary means of interface between system 1 and the user. In one embodiment, flat panel display 5 is an active matrix liquid crystal display (LCD) (10.4" diagonal, VGA resolution, active matrix LCD, 256 colors) overlaid by touch-responsive screen 255. Preferably, touch-responsive screen 255 is an analog resistive touch screen which is chemically resistant to common sterilizing solutions and housed in a watertight bezel.

Preferably, computer unit 3 also includes a separate power supply 275. In the alternative, the power module 103 of base unit 7 provides power to computer unit 3.

Figure 19:
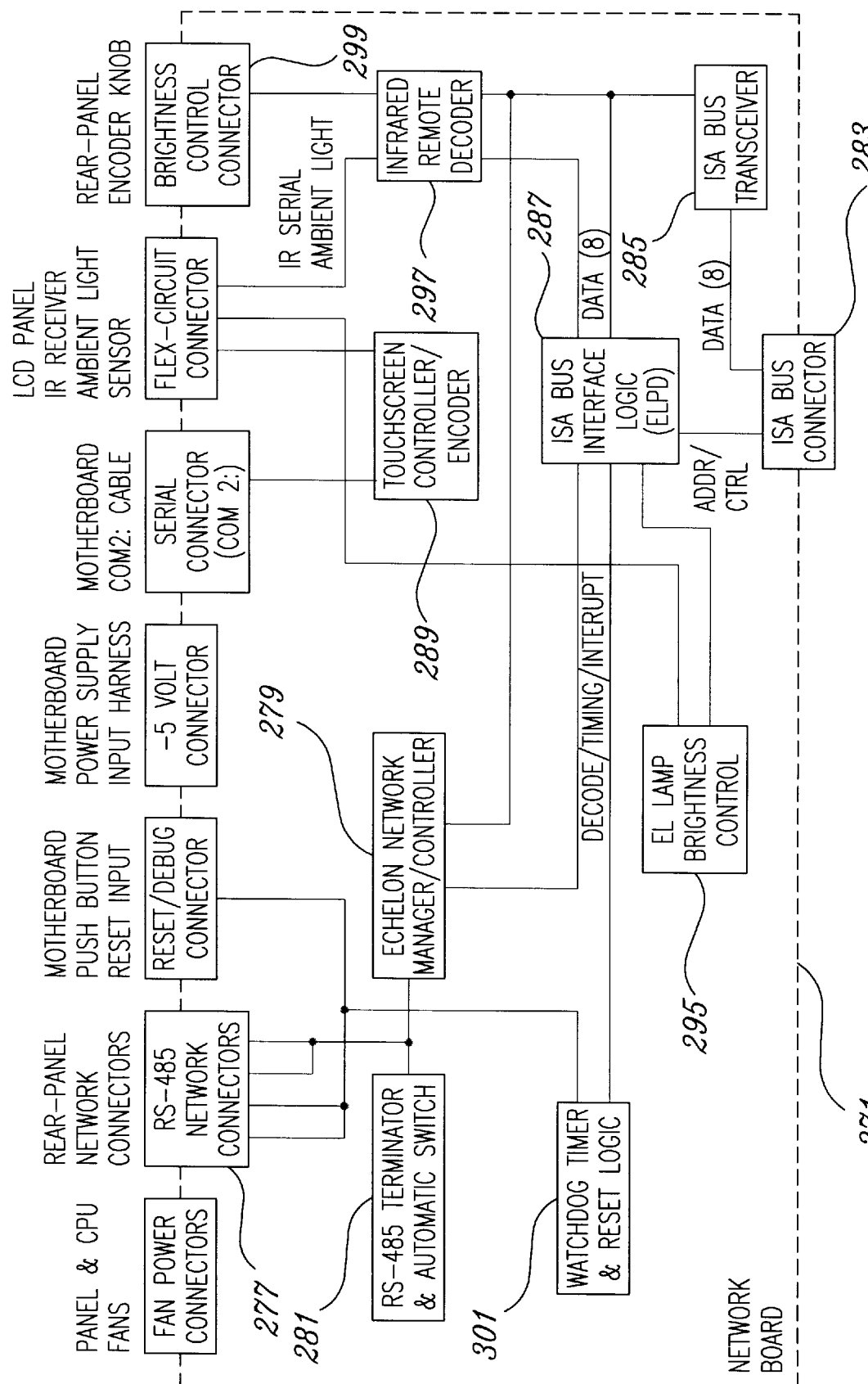
FIG. 19 is a block diagram of a communications network circuit for the user interface computer of FIGS. 17–18.

FIG. 19 illustrates the application specific network board 271 of computer unit 3. As illustrated, network board 271 includes an RS485 network connector circuit 277 as well as a network manager/controller circuit 279 and an RS485 termination circuit 281. Advantageously, the circuits 277, 279, 281 provide a network interface for computer unit 3 to communicate via the data communications bus. Network board 271 further includes an ISA bus connector 283, an ISA bus transceiver 285 and an ISA bus interface circuit 287, such as an electronically programmable logic device (EPLD). The circuit 283, 285, 287 provide an interface between network board 271 and central processor 245.

In addition, network board 271 provides circuit connections and interfaces for touch-responsive screen 255, flat panel display 5 and IR remote control 39. In this instance, network board 271 includes a touchscreen controller/encoder 289 connected to central processor 245 via a serial connector 291 and connected to flat panel display 5 via a flex-circuit connector 293. The flex-circuit connector 293 also connects a backlight brightness control 295 to flat panel display 5 and connects the IR receiver 267 to an IR remote decoder circuit 297. Network board 271 also includes a brightness control connector 299 for use with an encoder knob (not shown) on computer unit 3 by which the user controls the intensity of flat panel display 5. In this instance, remote control 39 also provides a means for varying the display intensity so the input received at the brightness control connector is routed through the IR remote decoder 297 to the bus interface circuit 287. In turn, bus interface circuit 287 provides the necessary control signals to the brightness control 295 for varying the intensity of flat panel display 5.

As shown in FIG. 19, network board 271 further includes a watchdog timer and reset circuit 301 in a preferred embodiment of the invention.

Figure 20:
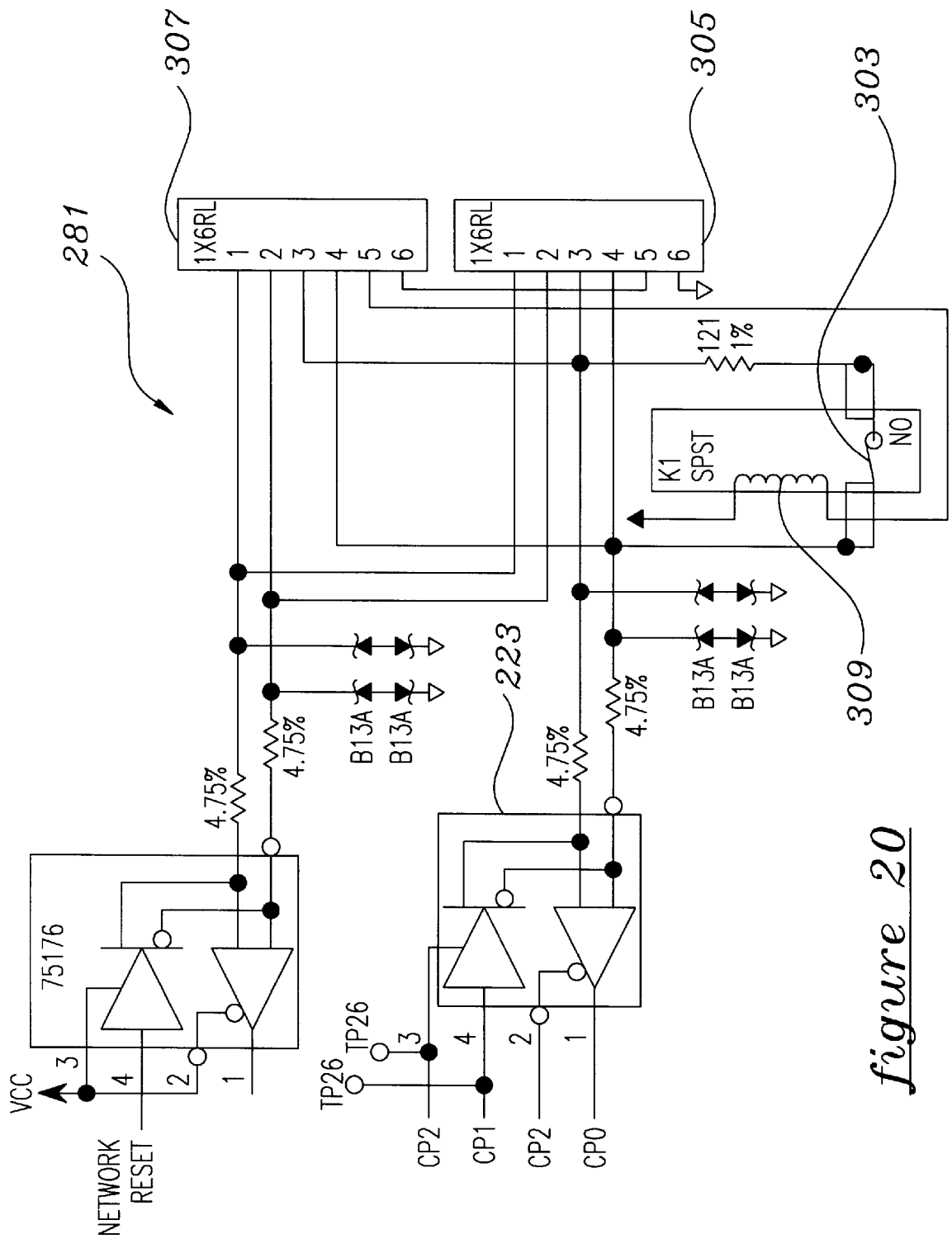
FIG. 20 is a schematic diagram of a termination circuit of the network circuit of FIG. 19 for selectively terminating the network.

Referring now to FIG. 20, the termination circuit 281 is shown in schematic diagram form. In addition to termination circuit 229 associated with the expansion connector 203 of base unit 7, network board 271 provides termination circuit 281 for selectively terminating the computer unit end of the data communications bus. In this instance, termination circuit 281 comprises a normally closed switch 303 connected in series with an approximately 120 ohm resistance. In order to expand the network at this end (as opposed to the end of expansion connector 203), the user connects an expansion cable (not shown) from a peripheral to either a first jumper 305 or a second jumper 307. The jumpers 303, 305 preferably provide means for connecting additional peripherals to the network of system 1. For example, the user can connect foot control assembly 15 or some other peripheral to the network via a connector (not shown) associated with either jumper 305, 307 instead of via connector 157.

According to a preferred embodiment of the invention, the expansion cables from the peripherals that are to be connected to the network short a pair of termination switch pins on jumpers 305, 307. In this instance, a peripheral expansion cable connected to jumper 305 causes a short circuit between TERM SWITCH 1A and TERM SWITCH 1B. Likewise, a peripheral expansion cable connected to jumper 307 causes a short circuit between TERM SWITCH 2A and TERM SWITCH 2B. As shown in FIG. 20, termination circuit 281 also includes a coil 309 connected to a positive voltage supply. In a preferred embodiment, the coil 309 is shorted to ground and, thus, energized when both TERM SWITCH 1A and 1B and TERM SWITCH 2A and 2B are shorted. As a result of coil 309 being energized, the normally closed switch 303 opens to remove the termination. The termination is then found at the peripheral end of the data communications bus.

Figure 21:
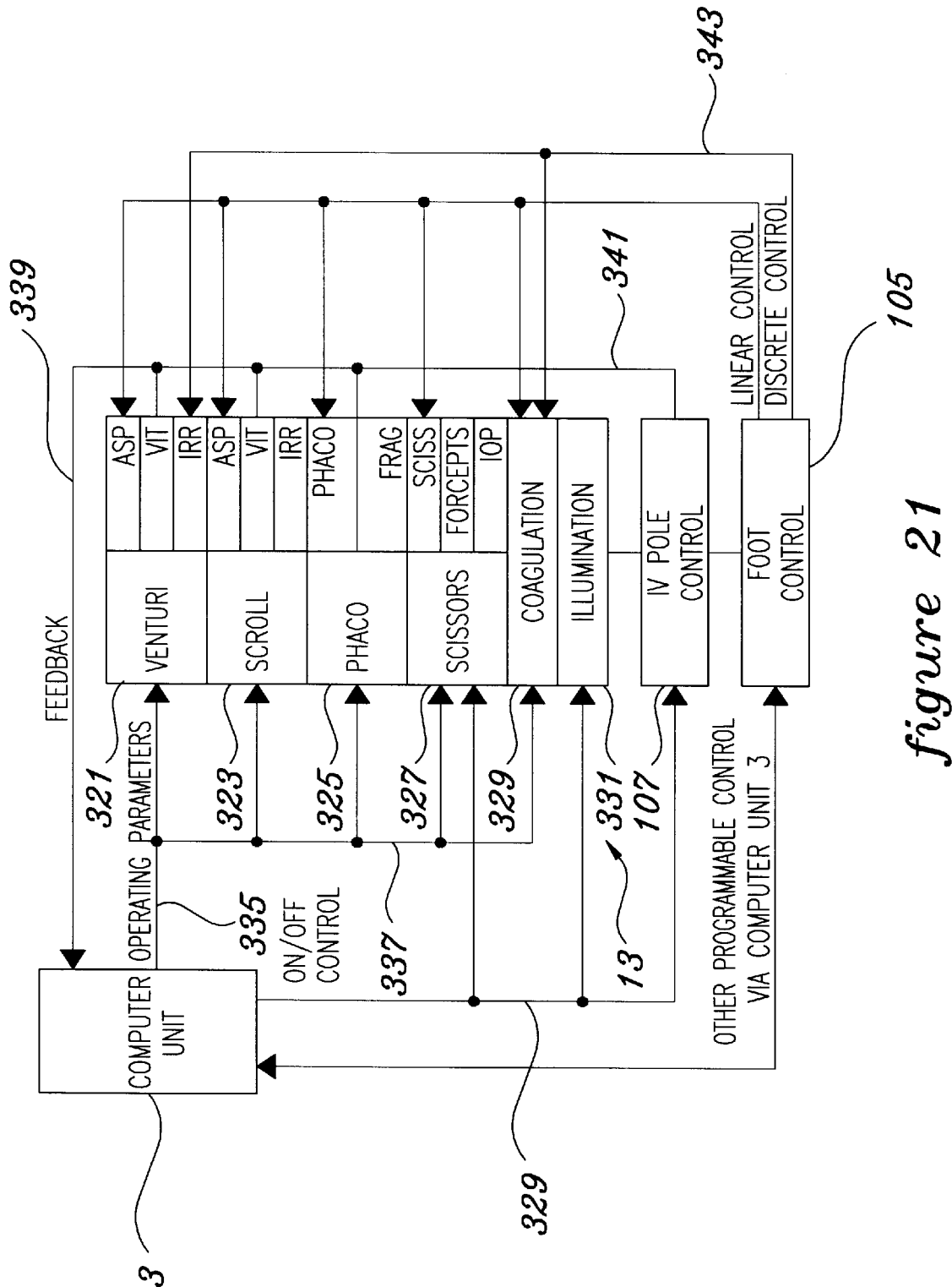
FIG. 21 is a block diagram of the system of FIG. 1 illustrating data flow in the system according to the invention.

FIG. 21 illustrates data flow in system 1 according to one preferred embodiment of the invention. Preferably, each module 13 installed in base unit 7 controls one or more microsurgical instruments 19 for providing several different surgical functions. For example, instruments 19 provide intraocular pressure (IOP), scissors cutting, forceps control, ultrasound (e.g., for phacoemulsification or phacofragmentation), irrigation, aspiration, vitrectomy cutting, bipolar coagulation and/or illumination. In an exemplary setup of system 1, modules 13 include a venturi IAV module 321 and a scroll IAV module 323, both of which control irrigation, aspiration and vitrectomy functions of system 1. The venturi IAV module 321 is for use with a venturi pump whereas the scroll IAV module 323 is for use with a scroll pump. Modules 13 also include a phaco module 325 controlling phacoemulsification and phacofragmentation functions and a scissors module 327 controlling a scissors cutting function. In addition, the scissors module 327 also controls a forceps function and includes air/fluid exchange control circuitry for controlling an IOP function. As shown in FIG. 21, modules 13 further include a coagulation module 329 controlling a bipolar coagulation function and an illumination module 331 controlling an illumination function.

This embodiment of the invention also includes foot control circuit 105 and IV pole control circuit 107 as peripherals connected to the network of system 1. Advantageously, venturi IAV module 321, scroll IAV module 323, phaco module 325, scissors module 327, coagulation module 329 and illumination module 331 as well as the control circuits 105, 107 for foot control assembly 15 and IV pole assembly 17, respectively, each constitute nodes on the network.

As described above, the user either programs the operating parameters, selects them from a set of default operating parameters or inputs them directly from the user interface to optimize performance of the surgery. As shown in the exemplary system setup of FIG. 21, computer unit 3 in turn communicates the operating parameters to modules 13 via line 335. Each active module 13 then provides control signals as a function of at least one of the user-entered or default operating parameters for controlling the microsurgical instrument or instruments 19 connected thereto. In addition, computer unit 3 provides on/off control of a number of instruments 19 and IV pole assembly 17 via line 337 and receives feedback regarding their operational status via line 339. The control circuit 105 of foot control assembly 15 provides both linear control (e.g., by its foot pedal) via line 341 and discrete control (e.g., by its push-buttons) via line 343 of the various modules 13. Further, with its programmable function button, foot control assembly 15 also provides control of system 1 based on instructions from computer unit 3. It is to be understood that the data communications bus of the invention carries the data communicated by lines 335, 337, 339, 341 and 343. Preferably, the data communications bus is a bi-directional serial bus which carries all types of signals. Thus, the lines 335, 337, 339, 341, 343 represent data flow in system 1 but do not represent the data communications bus.

In addition, the network of system 1 provides peer-to-peer communication between its nodes. For example, it may be desirable to disable the user interface when foot control assembly 15 is engaged. In other words, the user is prevented from changing the operating parameters of instruments 19 when the surgeon is using foot control assembly 15 to remotely control instruments 19. In this instance, foot control assembly 15 communicates via the network directly with the user interface and the other modules 13 to provide peer-to-peer communication. Similarly, it may be desirable to prevent certain instruments 19 from operating simultaneously for safety reasons. For example, the phacoemulsification instrument is disabled by the bipolar coagulation instrument when the latter is being used and vice-versa. In contrast, the aspiration function is needed during phacoemulsification or phacofragmentation. Thus, information regarding both functions is communicated via the network between the phaco module 325 and either venturi IAV module 321 or scroll IAV module 323.

Referring now to an example of the user interface's operation, an opening screen display at start-up allows the user to select the various surgical functions available for either the anterior or posterior portions of the patient's eye or to select a utilities program for programming system 1 or for performing other setup functions. When the user selects either the anterior portion or the posterior portion, computer unit 3 preferably displays a surgeon selection menu on flat panel display 5. According to the invention, hard drive 249 stores an individualized set of initial operating parameters for each surgeon listed on the menu. In response to the user's selections, computer unit 3 sets the operating portion to either anterior or posterior with the appropriate set of initial operating parameters depending on the user's selections. If a particular surgeon is not listed on the menu, computer unit 3 sets the operating portion to either anterior or posterior with the default operating parameters. If desired, the surgeon may then change the operating parameters from their default values.

Further to the example, computer unit 3 displays a utilities screen on flat panel display 5 when the user selects the utilities option from the opening screen. In this instance, computer unit 3 sets the operating mode to "none". The utilities program allows the user to modify the various system settings (e.g., modify or add new surgeons to the surgeon selection menu, modify initial operating parameters previously saved or add new initial operating parameters, and access user help information).

In a preferred embodiment of the invention, the user interface establishes dedicated portions of touch-responsive screen 255 for different selection or information windows. For example, primary windows are generated for displaying aspiration, phacoemulsification, phacofragmentation, vitrectomy, scissors and linear coagulation functions. Secondary windows are then available to the user for displaying non-linear coagulation, IOP, illumination, IV pole and the foot control configuration functions. Preferably, the user interface also employs a series of selection tabs (see FIG. 27) which allow the user to select the current operating mode of system 1, activate or deactivate surgical functions (e.g., coagulation), display on-line help and to exit system 1. If needed, the user selection tabs also include multiple choices for one or more of the selections and expand to display these additional selections.

During operation, the user may customize the different operating parameters to meet a surgeon's particular preferences through the use of a surgical function interface of the user interface. In general, the surgical function interface uses a number of displays to represent the various microsurgical system functions (e.g., venturi vacuum, scroll vacuum, vitrectomy, ultrasound, coagulation, scissors cutting, illumination and so forth) which are active. In a preferred embodiment, the surgical function interface displays current operating parameters numerically or graphically, displays operating set points and/or displays the on or off status of the various functions. The central processor 245 of computer unit 3 also executes routines to generate various control icons for use in adjusting the different operating parameters and/or for use in turning the functions on or off. For example, during performance of the venturi vacuum function, the interface provides a spin button, or up/down, control for incrementing or decrementing the current vacuum operating parameter. The interface also uses push-button controls for commanding a number of functions. For example, during performance of the aspiration function, the surgeon typically primes the aspiration line before proceeding to first remove any air in the line. The priming function is preferably indicated on the screen by a push-button. In addition to spin button and push-button controls, the interface also utilizes progress bars for showing current operating parameters with respect to their preset minimum and maximum values. For example, if the ultrasound power level is at 20% of the maximum power level during phacofragmentation, a progress bar covers 20% of a window labeled 0% on its left edge and 100% on its right edge.

Figure 22:
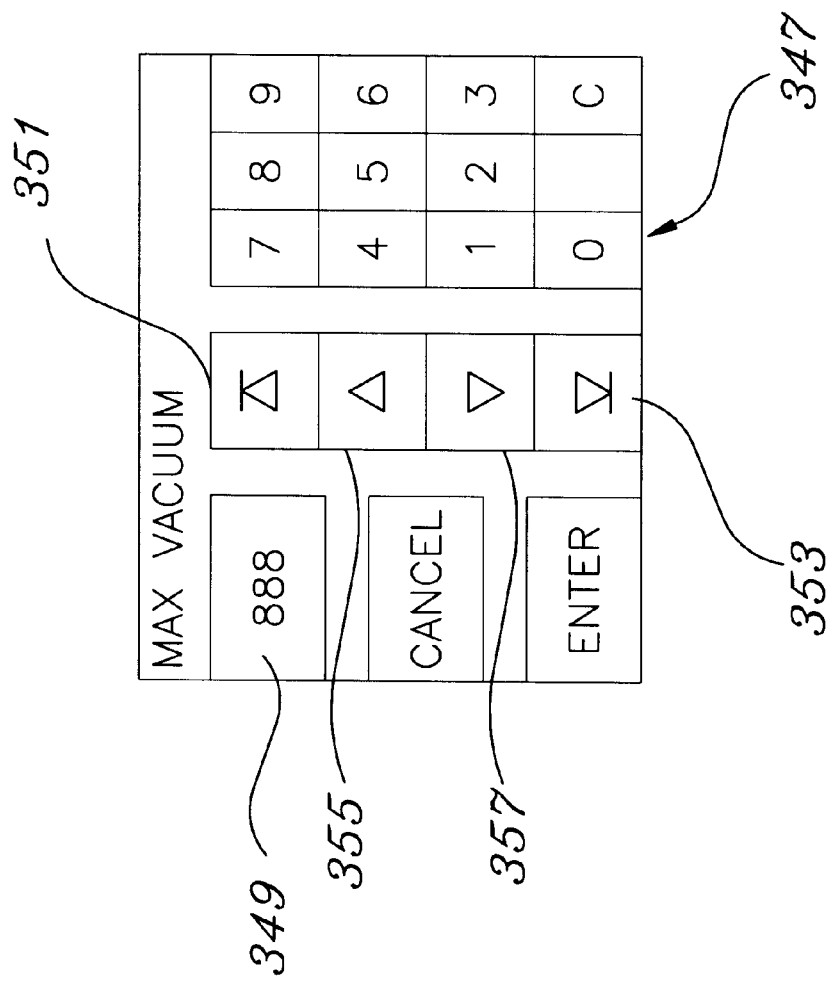
FIG. 22 is an exemplary screen display of a numeric keypad according to the invention.

Referring now to FIG. 22, central processor 245 preferably executes a calculator function interface in response to the user touching the portion of touch-responsive screen 255 corresponding to the numerical display of one of the operating parameter values. The calculator function interface preferably causes flat panel display 5 to display a numeric keypad, generally indicated 347, as part of the touch-responsive screen 255 for use in entering a desired value of the selected operating parameter rather than incrementing or decrementing the value via a spin button control. As such, the user may quickly and easily change the numerical surgical settings without repeatedly or continuously pressing the up or down arrow of the spin button control.

As shown in FIG. 22, the interface displays the particular value entered via the keypad 347 in a window 349 with a legend indicating the operating parameter being modified (e.g., the maximum vacuum setting). Keypad 347 further includes a push-button 351 for entering the default or programmed maximum value, a push-button 353 for entering the default or programmed minimum value and push-buttons 355, 357 for incrementing or decrementing the value, respectively. Preferably, the calculator function interface is disabled during operation of foot control assembly 15 when performing an active operation.

In addition to the surgical function interfaces, the user interface provides programming function interfaces to represent the microsurgical system functions for use in programming mode settings. In the present embodiment, the user accesses the programming function interfaces via the utilities menu described above. The programming interfaces display operating set points and provide means for modifying the operating set points for a given operating mode, changing the functions from linear to fixed, or vice-versa, turning the functions on/off for a given operating mode and so forth.

According to the present invention, system 1 is a mode-based surgical system. A mode is defined to be a surgical setup that includes the use of one or more surgical instruments 19 having specified initial operating parameters. Each of the surgical instruments 19 which are active in a particular mode perform one or more surgical functions. Although the terms "mode" and "function" are sometimes used interchangeably in commonly assigned patents, for example, U.S. Pat. Nos. 4,933,843, 5,157,603, 5,417,246 and 5,455,766, it is to be understood that these terms are distinct as used herein. For example, one phacoemulsification mode is defined such that an aspiration instrument provides the vacuum function and a phacoemulsification handpiece provides the ultrasound, or phacoemulsification, function and both of these instruments have specific initial operating parameters.

As described above, the flat panel display 5 of computer unit 3 displays information to the user. In a preferred embodiment, flat panel display 5 displays this information in the form of various on-screen menus of options available to the user. The menus may be in the form of lists, labeled push-buttons, user-selectable tabs and the like. The user selects one or more of the available options from the on-screen menu by touching a corresponding portion of touch-responsive screen 255. One such display includes a menu of the selectable modes. Preferably, the hard drive 249 of computer unit 3 stores operating parameters according to predefined surgical operating modes in the form of a collection of setup files. As described above, each mode is representative of one or more surgical procedures to be performed and defined by operation of at least one of the microsurgical instruments 19. Each mode determines which instruments 19 are to be used in the particular mode as well as the operating parameters associated with those instruments. Advantageously, the user can modify or define the modes via the user interface.

Figure 23:
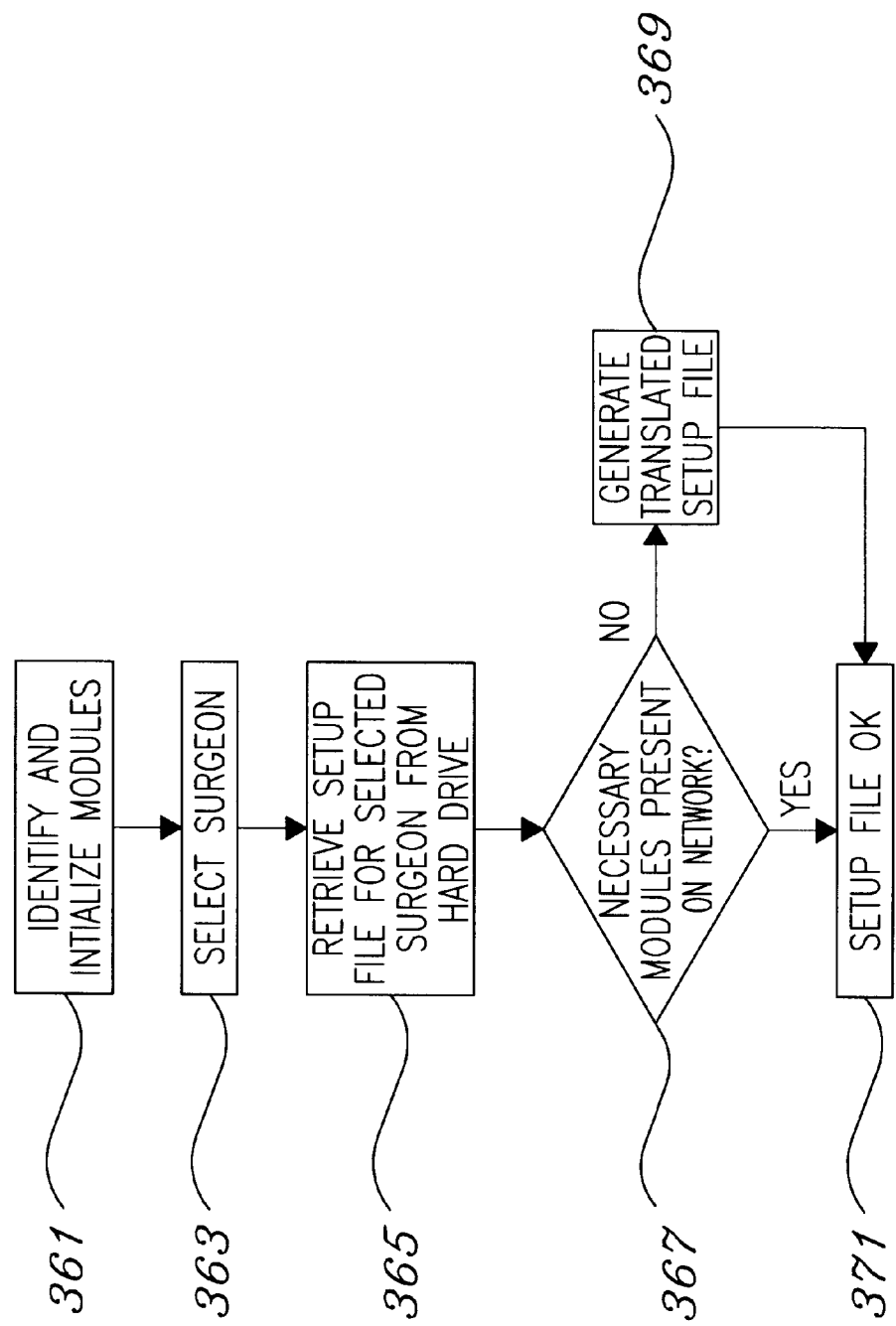
FIGS. 23 and 24 are exemplary flow diagrams illustrating the operation of the central processor in the user interface computer for defining operating modes and mode sequences for the system.

FIG. 23 is a flow diagram illustrating the operation of computer unit 3 for providing operating modes according to the invention. Beginning at step 361, system 1 first identifies and initializes each of the modules 13 installed in base unit 7 at power-up. When the user makes an initial surgeon selection at step 363, central processor 245 retrieves a particular setup file corresponding to the selected surgeon at step 365. According to one embodiment of the invention, the retrieved setup file comprises a mode database having a number of mode records, each being representative of a different mode and the operating parameters for the various surgical functions to be performed by system 1 operating in that mode. The setup file may also include initial values for other operating parameters which are not part of the mode records such as audio levels or other mode-independent settings. The retrieved setup file also includes a mode sequence database which defines a sequence in which certain of the modes are to be provided. At step 367, computer unit 3 compares the identification information to the retrieved setup file to verify that the necessary modules 13 are present in system 1 for performing the desired surgical functions specified in the mode records of the mode database. If not, computer unit 3 generates a translated setup file at step 369 by translating or substituting operating parameters for the operating parameters in the retrieved setup file so that it corresponds to the actual modules 13 in base unit 7. If the necessary modules 13 are present in system 1, or if computer unit 3 has generated a translated setup file, computer unit 3 determines that the setup file is acceptable at step 371.

In this manner, central processor 245 retrieves a set of the operating parameters from hard drive 249 for the microsurgical instrument or instruments 19 to be used in a selected mode and surgical modules 13 control the microsurgical instruments 19 connected thereto as a function of the operating parameters retrieved from memory.

According to the invention, the mode interface also defines a sequence in which the modes are to be active. To simplify mode sequence operation, the on-screen menu also includes an option for either proceeding to the next mode in the sequence defined in the mode sequence database or returning to the previous mode in the sequence. This enables the surgeon to proceed from mode to mode by touching a single push-button on touch-responsive screen 255. In the alternative, the surgeon can also proceed from mode to mode by depressing a particular button on foot control assembly 15 or by depressing a particular button on the hand-held remote control 39. In response to the user's instructions, central processor 245 retrieves in sequence the set of operating parameters from hard drive 249 for the microsurgical instruments 19 to be used in the selected mode and then retrieves another set of the operating parameters from hard drive 249 for the microsurgical instruments 19 to be used in either the next or the previous mode in the predefined sequence depending on the user's instructions.

For example, if the mode database of a particular surgeon's setup file has records for several modes, the mode sequence database may only define a sequence for some of those modes. In particular, the mode sequence database may define a sequence in which the first mode defined in the mode database is to be followed by the third mode, then the ninth mode and then the seventh mode. In other words, there need not be a one-to-one correspondence between the mode records in the mode database and the modes listed in the mode sequence database.

Figure 24:
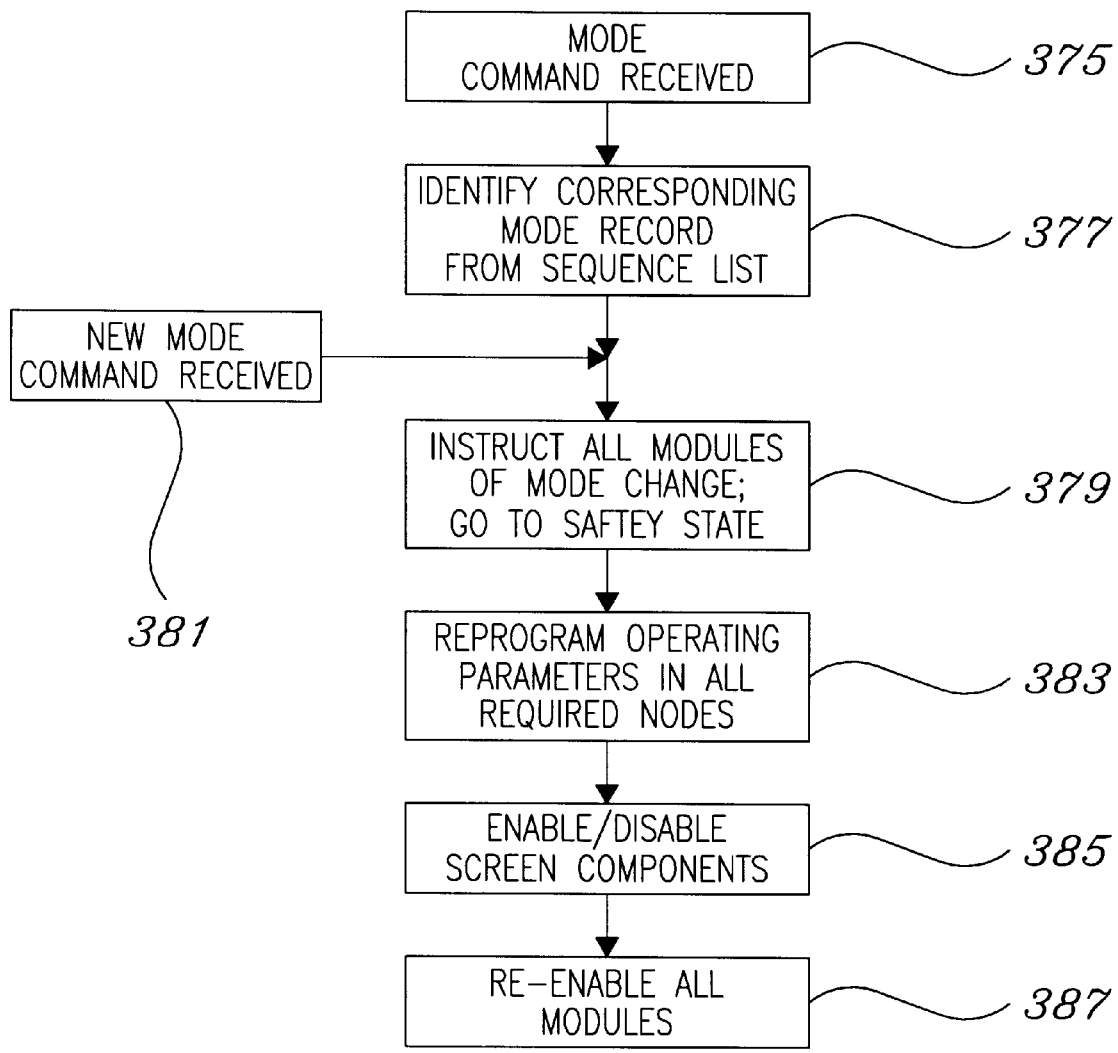

FIG. 24 illustrates the mode sequencing operation of computer unit 3 in flow diagram form. Beginning at step 375, the user enters a mode sequence command via the user interface. As an example, the mode sequence command may be a command to proceed to the next mode in the sequence, to return to the preceding mode in the sequence or to return to the last mode performed. In response to the command, at step 377, computer unit 3 identifies the mode record from the mode database which corresponds to the mode in the predefined sequence. Following step 377, computer unit 3 proceeds to step 379 for instructing each module 13 and peripheral of system 1 of the user's desired mode change. Also at step 379, computer unit 3 executes certain safety routines. For example, the surgeon is only permitted to change from mode to mode when the foot pedal of foot control assembly 15 is inactive. An exception is made for the phacofragmentation, scissors and other modes which may be selected when the foot pedal of foot assembly 15 is active if the irrigation function is operating to provide continuous irrigation.

Referring further to FIG. 24, computer unit also proceeds to step 379 after receiving a new mode selection command at step 381. Following step 379, computer unit 3 reprograms the operating parameters of the microsurgical instruments 19 to be used in the selected operating mode at step 383. At step 385, computer unit 3 enables or disables the various display components so that the display on flat panel display 5 corresponds to the surgical functions available in the selected mode. Following step 385, computer unit 3 enables each of the modules 13 or peripherals to be used in the selected operating mode at step 387.

As an example, Table I, below, lists exemplary modes and the operating parameters associated with the instruments 19 to be used in each of the modes. In other words, Table I lists the mode records of an exemplary mode database.

TABLE I

Operating Modes Database

| # | Mode | Aspiration Function | Max Vacuum (mmHg) | Phaco Function | Max U/S Power (%) | IV Pole Height (cm) |
|---|---|---|---|---|---|---|
| 1 | Open | linear | 400 | off | 0 | 80 |
| 2 | Emulsification-Soft | fixed | 75 | linear | 20 | 30 |
| 3 | Emulsification-Med | fixed | 100 | linear | 30 | 35 |
| 4 | Emulsification-Hard | fixed | 125 | linear | 50 | 40 |
| 5 | Clean | linear | 200 | off | 0 | 55 |
| 6 | Vitreous Removal | linear | 300 | off | 0 | 65 |
| 7 | Clean II | linear | 300 | off | 0 | 65 |
| 8 | Emulsification-High Vac | fixed | 200 | linear | 20 | 50 |
| 9 | Dual | linear | 100 | linear | 30 | 50 |

Further to the example of Table I, the surgeon may define a mode sequence database via the user interface which includes only some of the nine modes. For example, the mode sequence database defines a sequence beginning with mode 1 (open), followed by mode 3 (emulsification-medium), followed by mode 9 (dual) and ending with mode 7 (clean II).

Figure 25:
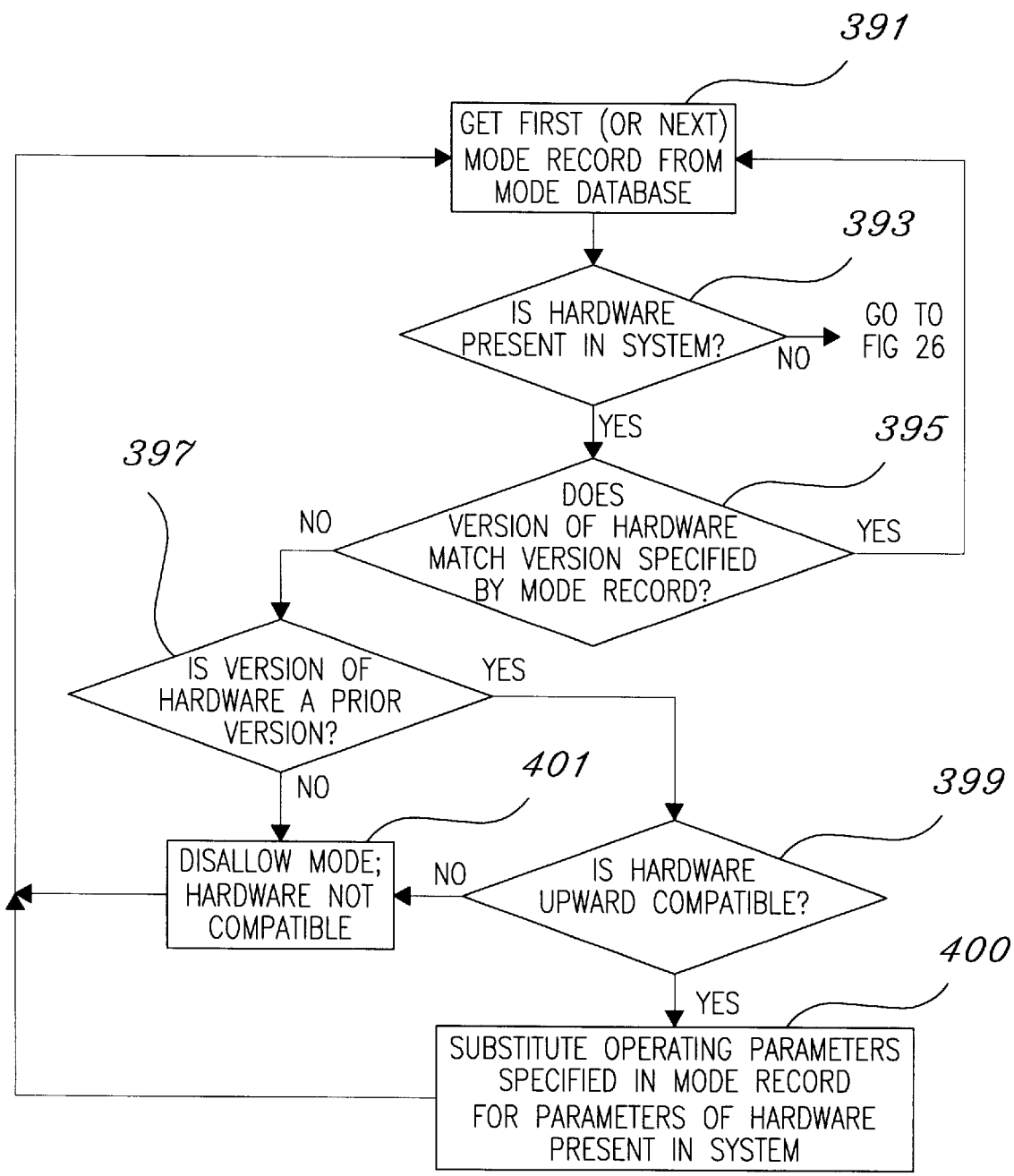
FIGS. 25 and 26 are exemplary flow diagrams illustrating the operation of the central processor in the user interface computer for adapting setup files for the system.
Figure 26:
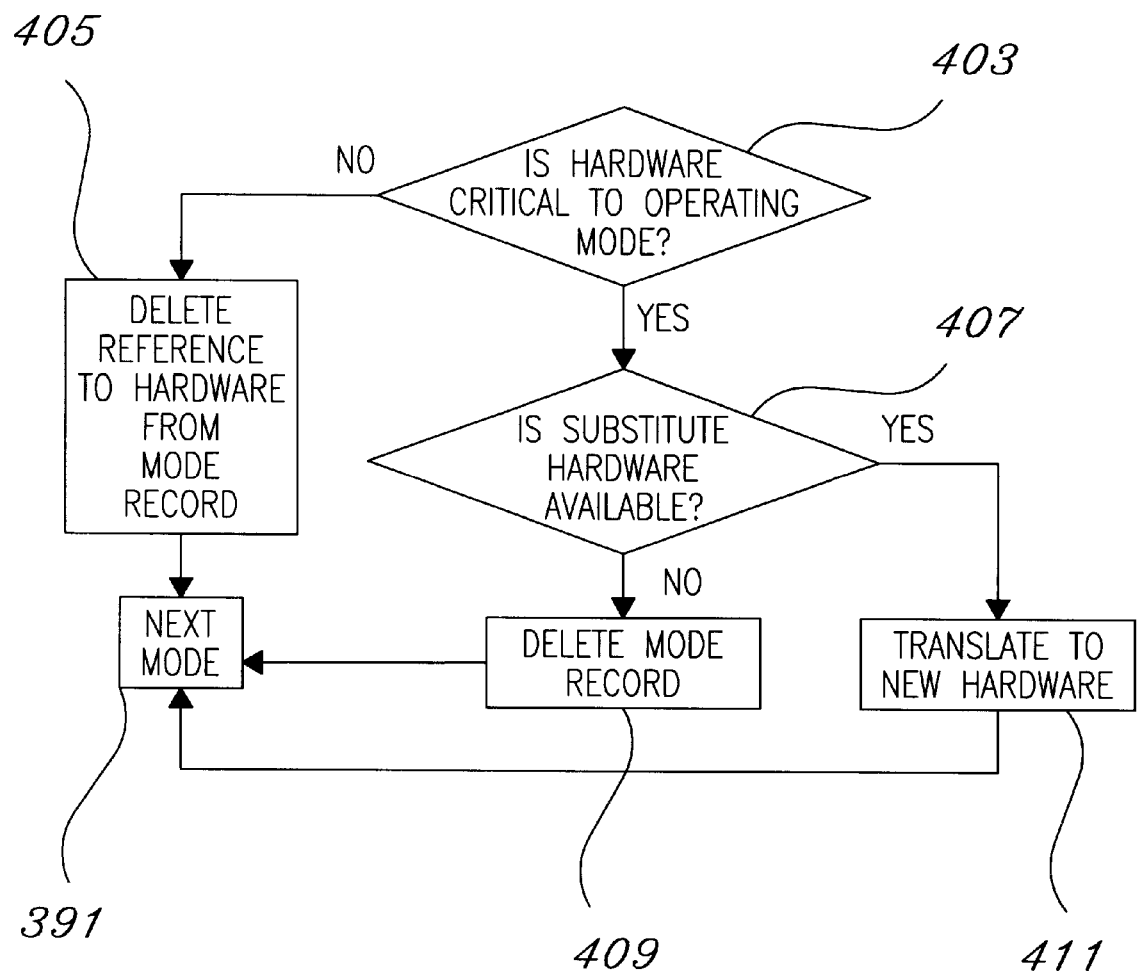

As described above in connection with FIG. 23, computer unit 3 compares the system identification information, built at power-up in the form of a hardware database, to the retrieved setup file. By doing so, computer unit 3 is able to verify that the necessary modules 13 are present in system 1 for performing the desired surgical functions of the modes in the mode database. If not, computer unit 3 generates a translated setup file by translating or substituting operating parameters for the operating parameters in the retrieved setup file so that it corresponds to the actual modules 13 in base unit 7. FIGS. 25 and 26 illustrate a preferred means for adapting the setup files according to the invention.

As shown in FIG. 25, computer unit 3 first examines each mode record in the mode database at step 391. During initialization of system 1, described in detail below, computer unit 3 reads a set of communications parameters corresponding to the hardware (i.e., the different modules 13 and control circuits 105, 107) on the network. As described above, each neuron processor 225 of the various nodes on the network executes embedded programs for controlling the different microsurgical instruments 19 and peripherals. The communications parameters represent a unique identification label specific to each processor 225 which includes information regarding the type of device being controlled (e.g., vitrectomy handpiece or ultrasound device) and the version of module 13 or peripheral in which the processor 225 is located. The identification label also includes a specific identifier (e.g., a serial number) which is unique to the particular module 13 or control circuit 105, 107. As an example, the version of a particular module 13 may change as either the hardware or software is updated. According to the invention, the mode records in the mode database each represent a different operating mode and the operating parameters for the various surgical functions to be provided by system 1 operating in that mode. As such, the operating parameters correspond to specific nodes on the network by both function and version.

At step 393, computer unit 3 determines if the type of hardware needed for each instrument or peripheral to used in the operating mode defined by the mode record is present in system 1. If so, at step 395, computer unit 3 determines if the version information for each module 13 and peripheral control circuit 105, 107 matches the version information specified by the mode record. If the version information is correct, computer unit 3 returns to step 391 for examining the next mode record in the mode database. On the other hand, if the version information is incorrect, computer unit 3 determines at step 397 if the version information for the installed hardware is compatible with the version information specified by the mode record. If compatible, computer unit proceeds to step 399 in which it substitutes the operating parameters associated with the actual hardware of system 1 for the operating parameters set forth in the mode record. If the versions are not compatible, computer unit 3 disallows the particular mode at step 401. Following either step 399 or step 401, computer unit 3 returns to step 391 for examining the next mode record in the mode database.

At step 393, computer unit 3 determines if hardware is present in system 1 for each instrument or peripheral to used in the operating mode defined by the mode record. If not, computer unit 3 proceeds to step 403 shown in the flow diagram of FIG. 26. At step 403, computer unit 3 determines if the absent hardware is necessary to the operation of system 1 in the particular mode. If the absent hardware is not needed, computer unit 3 deletes the reference to the absent hardware from the mode record at step 405 and then returns to step 391 of FIG. 25 for proceeding to the next mode record. On the other hand, if the absent hardware is needed, computer unit 3 determines at step 407 if substitute hardware is available. If not, computer unit 3 deletes the mode record from the mode database at step 409 and then returns to step 391 for proceeding to the next mode record. If substitute hardware is available, computer unit 3 proceeds to step 411. At step 411, computer unit 3 translates the operating parameters in the mode record to correspond to the substitute hardware. As an example, a particular setup of system 1 may include venturi IAV module 321 but not scroll IAV module 323. In this instance, if a mode record specifies an operating mode providing the flow aspiration function, which is not available with venturi IAV module 321, computer unit 3 would substitute the flow aspiration operating parameters for vacuum operating parameters which would approximate a flow aspiration response.

Following step 411, computer unit 3 returns to step 391. After adapting the mode records of the setup file, computer unit 3 examines the mode sequence database of the retrieved setup file. If a mode in the mode sequence is no longer available (i.e., it was deleted at step 409), computer unit 3 also deletes the mode from the mode sequence database. In this manner, computer unit 3 adapts the retrieved setup file for use with the particular configuration of system 1. In other words, computer unit 3 generates a translated setup file.

The mode records shown above in Table I define particular modes in terms of the various procedures performed by the surgeon. For example, the surgeon selects the "open" mode when performing the procedure of opening the patient's eye. It is also contemplated that the operating modes of system 1 are defined in terms of the different surgical functions performed during these procedures. Tables II and III, below, list exemplary modes in the anterior and posterior portions in terms of the different surgical functions.

TABLE II

Anterior Operating Modes

| I/A Modes | Phaco Modes | Vitrectomy Modes | Other Modes |
|---|---|---|---|
| IRR/ASP | Sculpt | Fixed Cut/Linear Vacuum | Linear Coagulation Mode Sequence |
| Capsule Polish | Segment Removal | Fixed Cut/Fixed Flow | |
| Viscoelastic Removal | Dual Linear Sculpt | Linear Cut/Linear Vacuum | |
| Linear Vacuum | Dual Linear Segment Removal | Linear Cut/Fixed Flow | |
| Linear Flow | Fixed Vacuum | | |
| Fixed Flow | Linear Vacuum | | |
| | Fixed Flow | | |
| | Linear Flow | | |

TABLE III

Posterior Operation Modes

| Frag Modes | Vitrectomy Modes | Scissor Modes | Other Modes |
|---|---|---|---|
| Fixed Vacuum | Single Cut/Linear Vacuum | Single Cut | Linear Coagulation Mode Sequence |
| Linear Vacuum | Fixed Cut/Linear Vacuum | Fixed Cut | |
| Fixed Flow | Fixed Cut/Fixed Flow | Linear Cut | |
| Linear Flow | Linear Cut/Linear Vacuum | Proportional Actuation | |

Tables IV–IX, below list exemplary initial operating parameters for the various modes shown in Tables II and III.

TABLE IVa

Default Operating Parameters for Irrigation/Aspiration Modes
IRRIGATION/ASPIRATION MODES

| Parameter | Irr/Asp & Lin Vac | Cap Polish | Vis Rem |
|---|---|---|---|
| Vacuum | linear | linear | linear |
| Min Vac | 100 mmHg | 1 mmHg | 50 mmHg |
| Max Vac | 550 mmHg | 100 mmHg | 200 mmHg |
| Flow | | | |
| Min Flow | | | |
| Max Flow | | | |
| Foot Rocker Sw | max vac | max vac | max vac |
| Foot Pitch | lin vac 30–100% travel | lin vac 30–100% travel | lin vac 30–100% travel |

TABLE IVb

Default Operating Parameters for Irrigation/Aspiration Modes
IRRIGATION/ASPIRATION MODES

| Parameter | Fixed Flow | Lin Flow |
|---|---|---|
| Vacuum | | |
| Min Vac | | |
| Max Vac | linear (25–550 mmHg) | 400 mmHg |
| Flow | fixed (25 cc/min) | linear |
| Min Flow | | 1 cc/min |
| Max Flow | | 35 cc/min |
| Foot Rocker Sw | fixed flow | max vac |
| Foot Pitch | lin max vac 30–100% travel fixed flow 30% travel | lin flow 30–100% travel |

TABLE IVb-continued

Default Operating Parameters for
Irrigation/Aspiration Modes
IRRIGATION/ASPIRATION MODES

| Parameter | Fixed Flow | Lin Flow |
|---|---|---|

The following foot control operating parameters apply to each of the irrigation/aspiration modes:
Coagulation switch—controls coagulation on/off
Programmable function switch—no function
Pitch—irrigation control for pedal travel 1–100%
Yaw left—reflux
Yaw right—none
The operating parameters for the following functions (which are initially disabled in each of the irrigation/aspiration modes) are:
Coagulation power—12%
IV pole height—60 cm (40 cm in capsule polish mode; 50 cm in viscoelastic removal mode)
IOP—40 mmHg
Lamp 1—off
Lamp 2—off

TABLE Va

Default Operating Parameters for Phacoemulsification Modes
PHACOEMULSIFICATION MODES

| Parameter | Sculpt | Mode 2 | Mode 3 & Lin Vac | Mode 4 |
|---|---|---|---|---|
| Vacuum | fixed (30 mm Hg) | fixed (80 mm Hg) | linear | linear |
| Min Vac | | | 5 mm Hg | 30 mm Hg |
| Max Vac | | | 100 mm Hg | 120 mm Hg |
| Flow | | | | |
| Min Flow | | | | |
| Max Flow | | | | |
| PPS | 6 | 6 | 0 | 0 |
| Foot Rocker Sw | fixed vac | fixed vac | max vac | max vac |
| Foot Pitch | fixed vac 30% travel | fixed vac 30% travel | lin vac 30–100% travel | lin vac 30–100% travel |
| | lin U/S 50–100% travel | lin U/S 50–100% travel | | |
| Foot Yaw R | none | enable/disable PPS | lin U/S | lin U/S |

TABLE Vb

Default Operating Parameters for
Phacoemulsification Modes
PHACOEMULSIFICATION MODES

| Parameter | Fixed Vac | Fixed Flow | Lin Flow |
|---|---|---|---|
| Vacuum | fixed (50 mmHg) | | |
| Min Vac | | | |
| Max Vac | | 30 mmHg | 50 mmHg |
| Flow | | fixed (18 cc/min) | linear |
| Min Flow | | | 1 cc/min |
| Max Flow | | | 20 cc/min |
| PPS | 6 | 6 | 0 |
| Foot Rocker Sw | fixed vac | fixed flow | max vac |
| Foot Pitch | fixed vac 30% travel | fixed flow 30% travel | lin flow 30–100% travel |
| | lin U/S 5–100% travel | lin U/S 5–100% travel | |
| Foot Yaw R | enable/disable PPS | PPS on/off | lin U/S |

The following operating parameters apply to each of the phacoemulsification modes:
Ultrasound power—linear
Minimum ultrasound power level—0%

TABLE Vb-continued

Default Operating Parameters for
Phacoemulsification Modes
PHACOEMULSIFICATION MODES

| Parameter | Fixed Vac | Fixed Flow | Lin Flow |
|---|---|---|---|

Maximum ultrasound power level—35%
The following foot control operating parameters apply to each of the phacoemulsification modes:
Coagulation switch—controls coagulation on/off
Programmable function switch—no function
Pitch—irrigation control for pedal travel 1–100%
Yaw left—reflux
The operating parameters for the following functions (which are initially disabled in each of the phacoemulsification modes) are:
Coagulation power—12%
IV pole height—75 cm (80 cm in mode 2 and mode 4)
IOP—40 mmHg
Lamp 1—off
Lamp 2—off

TABLE VIa

Default Operating Parameters
for Phacofragmentation Modes
PHACOFRAGMENTATION MODES

| Parameter | Fixed Vac | Lin Vac |
|---|---|---|
| Vacuum | fixed (150 mmHg) | linear |
| Min Vac | | 5 mmHg |
| Max Vac | | 150 mmHg |
| Flow | | |
| Min Flow | | |
| Max Flow | | |
| PPS | 6 | 0 |
| Foot Rocker Sw | fixed vac | max vac |
| Foot Pitch | fixed vac 5% travel | lin vac 5–100% travel |
| | lin U/S 30–100% travel | |
| Foot Yaw R | enable/disable PPS | lin U/S |

TABLE VIb

Default Operating Parameters
for Phacofragmentation Modes
PHACOFRAGMENTATION MODES

| Parameter | Fixed Flow | Lin Flow |
|---|---|---|
| Vacuum | | |
| Min Vac | | |
| Max Vac | 200 mmHg | 150 mmHg |
| Flow | fixed (15 cc/min) | linear |
| Min Flow | | 1 cc/min |
| Max Flow | | 20 cc/min |
| PPS | 6 | 0 |
| Foot Rocker Sw | fixed flow | max vac |
| Foot Pitch | fixed flow 5% travel lin U/S 30–100% travel | lin flow 5–100% travel |
| Foot Yaw R | PPS on/off | lin U/S |

The following operating parameters apply to each of the phacofragmentation modes:
Ultrasound power—linear
Minimum ultrasound power level—0%
Maximum ultrasound power level—25%
The following foot control operating parameters apply to each of the phacofragmentation modes:
Coagulation switch—controls coagulation on/off
Programmable function switch—no function
Yaw left—reflux
The operating parameters for the following functions (which are initially disabled in each of the phacofragmentation modes) are:
Coagulation power—12%
IV pole height—75 cm
IOP—30 mmHg
Lamp 1—off
Lamp 2—off

TABLE VIIa

Default Operating Parameters for
Vitrectomy (Anterior) Modes
VITRECTOMY (ANTERIOR) MODES

| | Fixed Cut | |
|---|---|---|
| Parameter | Lin Vac | Fixed Flow |
| Vacuum | linear | |
| Min Vac | 0 mmHg | |
| Max Vac | 200 mmHg | linear (0–200 mmHg) |
| Flow | | fixed (15 cc/min) |
| Min Flow | | |
| Max Flow | | |
| Cut Rate | fixed (300 CPM) | fixed (300 CPM) |
| Min Cut Rate | | |
| Max Cut Rate | | |
| Foot Rocker Sw | fixed cut rate | fixed cut rate |
| Foot Pitch | lin vac 30–100% travel | fixed flow 30% travel lin max vac 30–100% travel |
| Foot Yaw R | cutter on/off | cutter on/off |

TABLE VIIb

Default Operating Parameters for
Vitrectomy (Anterior) Modes
VITRECTOMY ANTERIOR MODES

| | Linear Cut | |
|---|---|---|
| Parameter | Lin Vac | Fixed Flow |
| Vacuum | linear | |
| Min Vac | 0 mmHg | |
| Max Vac | 200 mmHg | linear (0–200 mmHg) |
| Flow | | fixed (15 cc/min) |
| Min Flow | | |

TABLE VIIb-continued

Default Operating Parameters for
Vitrectomy (Anterior) Modes
VITRECTOMY ANTERIOR MODES

| | Linear Cut | |
|---|---|---|
| Parameter | Lin Vac | Fixed Flow |
| Max Flow | | |
| Cut Rate | linear | linear |
| Min Cut Rate | 30 CPM | 30 CPM |
| Max Cut Rate | 300 CPM | 300 CPM |
| Foot Rocker Sw | max cut rate | max cut rate |
| Foot Pitch | lin vac 30–100% travel | fixed flow 30% travel lin max vac 30–100% travel |
| Foot Yaw R | linear cut | linear cut |

The following foot control operating parameters apply to each of the vitrectomy (anterior) modes:
Coagulation switch—controls coagulation on/off
Programmable function switch—no function
Pitch—irrigation control for pedal travel 1–100%
Yaw left—reflux
The operating parameters for the following functions (which are initially disabled in each of the vitrectomy (anterior) modes) are:
Coagulation power—12%
IV pole height—40 cm
IOP—40 mmHg
Lamp 1—off
Lamp 2—off

TABLE VIIIa

Default Operating Parameters for
Vitrectomy Posterior Modes
VITRECTOMY POSTERIOR MODES

| | | | Fixed Cut |
|---|---|---|---|
| Parameter | Single | Lin Vac | Fixed Flow |
| Vacuum | linear | linear | |
| Min Vac | 0 mmHg | 0 mmHg | |
| Max Vac | 200 mmHg | 200 mmHg | linear (0–200 mmHg) |
| Flow | | | fixed (15 cc/min) |
| Min Flow | | | |
| Max Flow | | | |
| Cut Rate | single | fixed (600 CPM) | fixed (600 CPM) |
| Min Cut Rate | | | |
| Max Cut Rate | | | |
| Foot Rocker Sw | max vac | fixed cut rate | fixed cut rate |
| Foot Pitch | lin vac 5–100% travel | lin vac 5–100% travel | fixed flow 5% travel lin max vac 5–100% travel |
| Foot Yaw R | linear cut | cutter on/off | cutter on/off |

TABLE VIIIb

Default Operating Parameters for
Vitrectomy Posterior Modes
VITRECTOMY POSTERIOR MODES

| | Linear Cut | |
|---|---|---|
| Parameter | Lin Vac | Fixed Flow |
| Vacuum | linear | |
| Min Vac | 0 mmHg | |
| Max Vac | 200 mmHg | linear (0–200 mmHg) |
| Flow | | fixed (15 cc/min) |
| Min Flow | | |

TABLE VIIIb-continued

Default Operating Parameters for
Vitrectomy Posterior Modes
VITRECTOMY POSTERIOR MODES Linear Cut

| Parameter | Lin Vac | Fixed Flow |
|---|---|---|
| Max Flow | | |
| Cut Rate | linear | linear |
| Min Cut Rate | 30 CPM | 30 CPM |
| Max Cut Rate | 600 CPM | 600 CPM |
| Foot Rocker Sw | max cut rate | max cut rate |
| Foot Pitch | lin vac 5–100% travel | fixed flow 5% travel |
| | | lin max vac 5–100% travel |
| Foot Yaw R | linear cut | linear cut |

The following foot control operating parameters apply to each of the vitrectomy (posterior) modes:
Coagulation switch—controls coagulation on/off
Programmable function switch—no function
Yaw left—reflux
The operating parameters for the following functions (which are initially disabled in each of the vitrectomy (posterior) modes) are:
Coagulation power—12%
IV pole height—75 cm (40 cm for single cut)
IOP—30 mmHg (40 mmHg for single cut)
Lamp 1—off
Lamp 2—off

TABLE IXa

Default Operating Parameters for Scissors Modes
SCISSORS MODES

| Parameter | Single | Fixed Cut |
|---|---|---|
| Cut Rate | single | fixed (60 CPM) |
| Min Cut Rate | | |
| Max Cut Rate | | |
| Min Closure | | |
| Max Closure | | |
| Foot Rocker Sw | none | fixed cut rate |
| Foot Pitch | single cut 5% travel | fixed cut 5% travel |

TABLE IXb

Default Operating Parameters for Scissors Modes
SCISSORS MODES

| Parameter | Linear Cut | Proportional Cut |
|---|---|---|
| Cut Rate | linear | proportional |
| Min Cut Rate | 0 CPM | |
| Max Cut Rate | 100 CPM | |
| Min Closure | | 1% |
| Max Closure | | 100% |
| Foot Rocker Sw | max cut rate | max actuation |
| Foot Pitch | linear cut 5–100% travel | proportional 5–100% travel |

Figure 27:
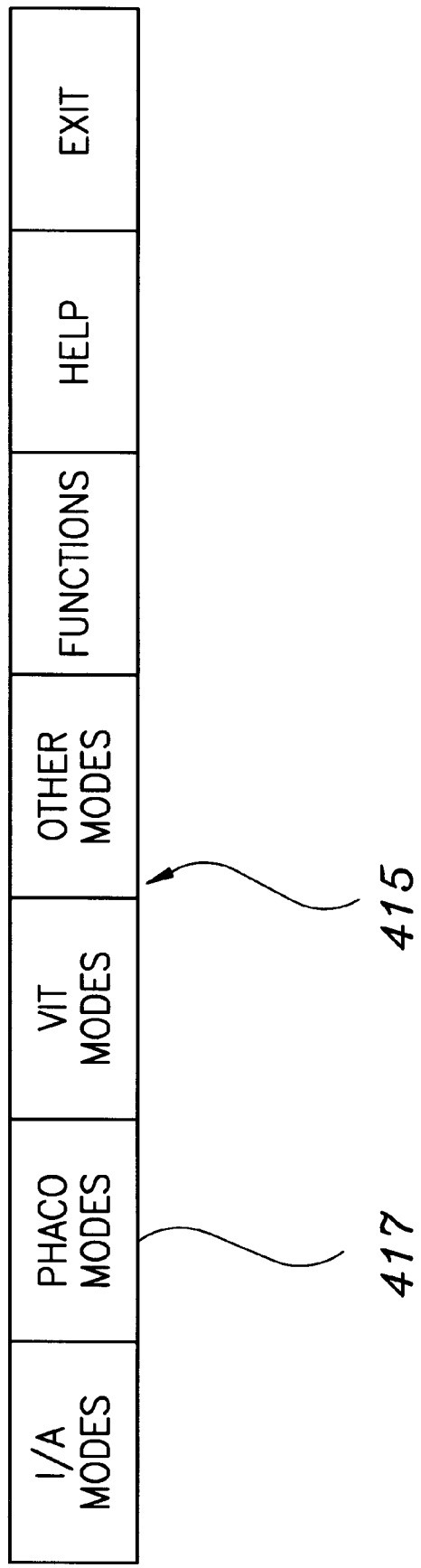
Figure 30:
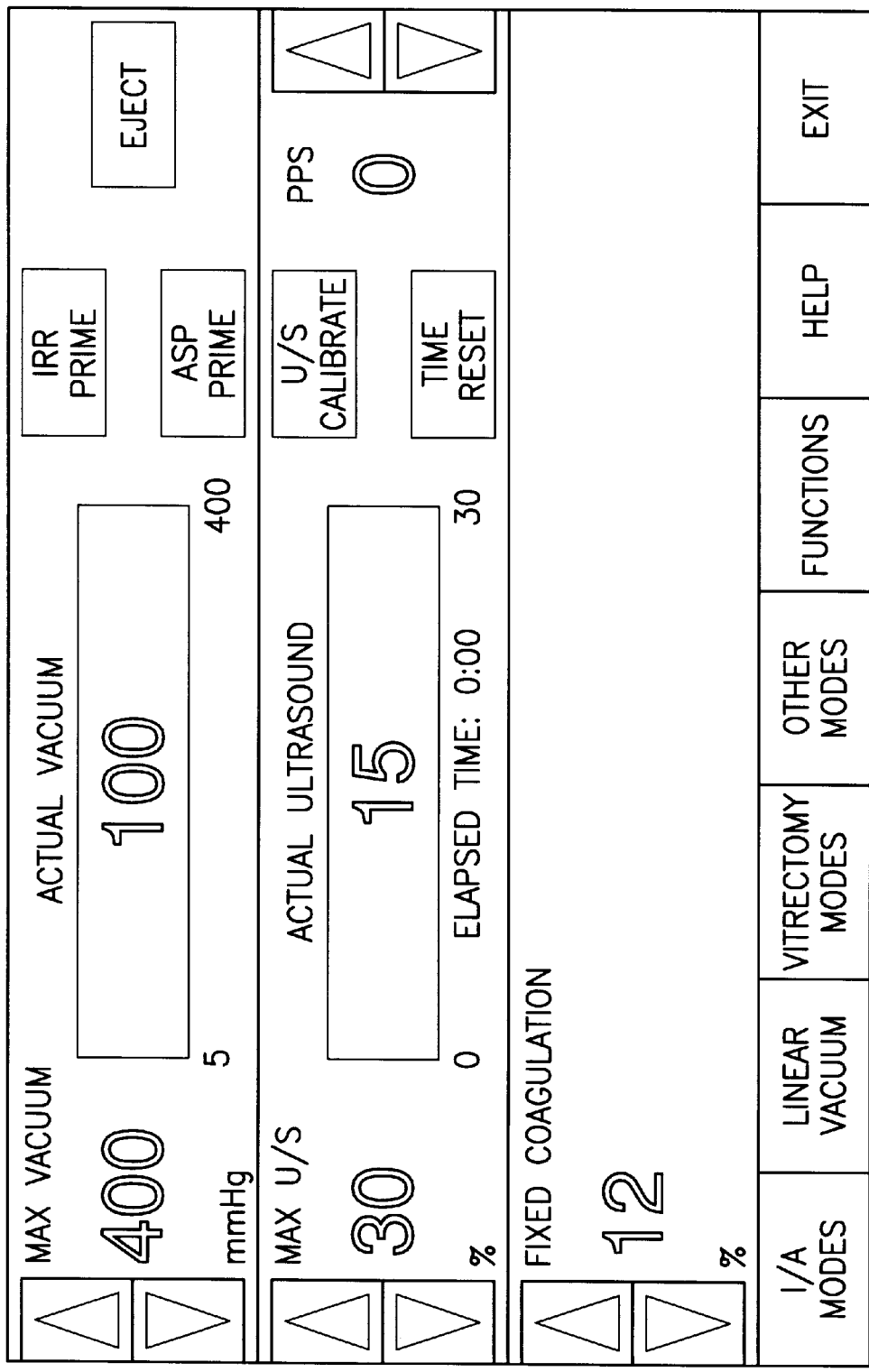

The following foot control operating parameters apply to each of the scissors modes:
Coagulation switch—controls coagulation on/off
Programmable function switch—no function
Yaw left—none
Yaw right—none
The operating parameters for the following functions (which are initially disabled in each of the scissors modes) are:
Coagulation power—12%
IV pole height—75 cm
IOP—30 mmHg
Lamp 1—off
Lamp 2—off With respect to the function-based modes shown in Tables II–IX, in general, the user selects one of the various predefined modes described above from top level user selection tabs 415, an example of which is shown in FIG. 27 for anterior portion operations. Preferably, the tabs 415 are positioned at the bottom of touch-responsive screen 255. Only one mode may be active at a time so computer unit 3 automatically deselects the current operating modes when the user selects one of the user selection tabs. In an example of mode selection, the user touches a phaco mode tab 417 for the available phacoemulsification modes. Referring now to FIGS. 28 and 29, flat panel display 5 initially only displays the first four modes (i.e., sculpt, segment removal, sculpt (dual) and seg removal (dual)) when the user touches the phaco modes user selection tab 417. In response to the user touching a tab 419 containing the arrow symbol, computer unit 3 generates an additional menu of available phaco modes (i.e., fixed vacuum, linear vacuum, fixed flow and linear flow) for display on flat panel display 5. For example, the user touches a tab 421 to select the linear vacuum phaco mode from the menu. FIG. 30 illustrates an exemplary screen display for the linear vacuum phaco mode. As shown, the vacuum, ultrasound (i.e., phacoemulsification) and coagulation functions are available and active in this mode.

As described above, to operate according to the microsurgical system's various operating modes, computer unit 3 first identifies and initializes each of the nodes on the network (i.e., modules 13 installed in base unit 7 and control circuits 105, 107 for foot control assembly 15 and IV pole assembly 17, respectively). In a preferred embodiment, the central processor 245 of computer unit 3 executes software which constitutes a system engine having three operational components: power-up initialization, network management and network liaison. The initialization component of the system engine creates and starts the network. The network management component provides binding/unbinding of network variables for modules 13 on the network to implement user-selected modes, monitors modules 13 for functionality and processes incoming messages from the network. The network liaison component processes the configuration file and mode changes and notifies the user interface of display changes and error occurrences.

Figure 31:
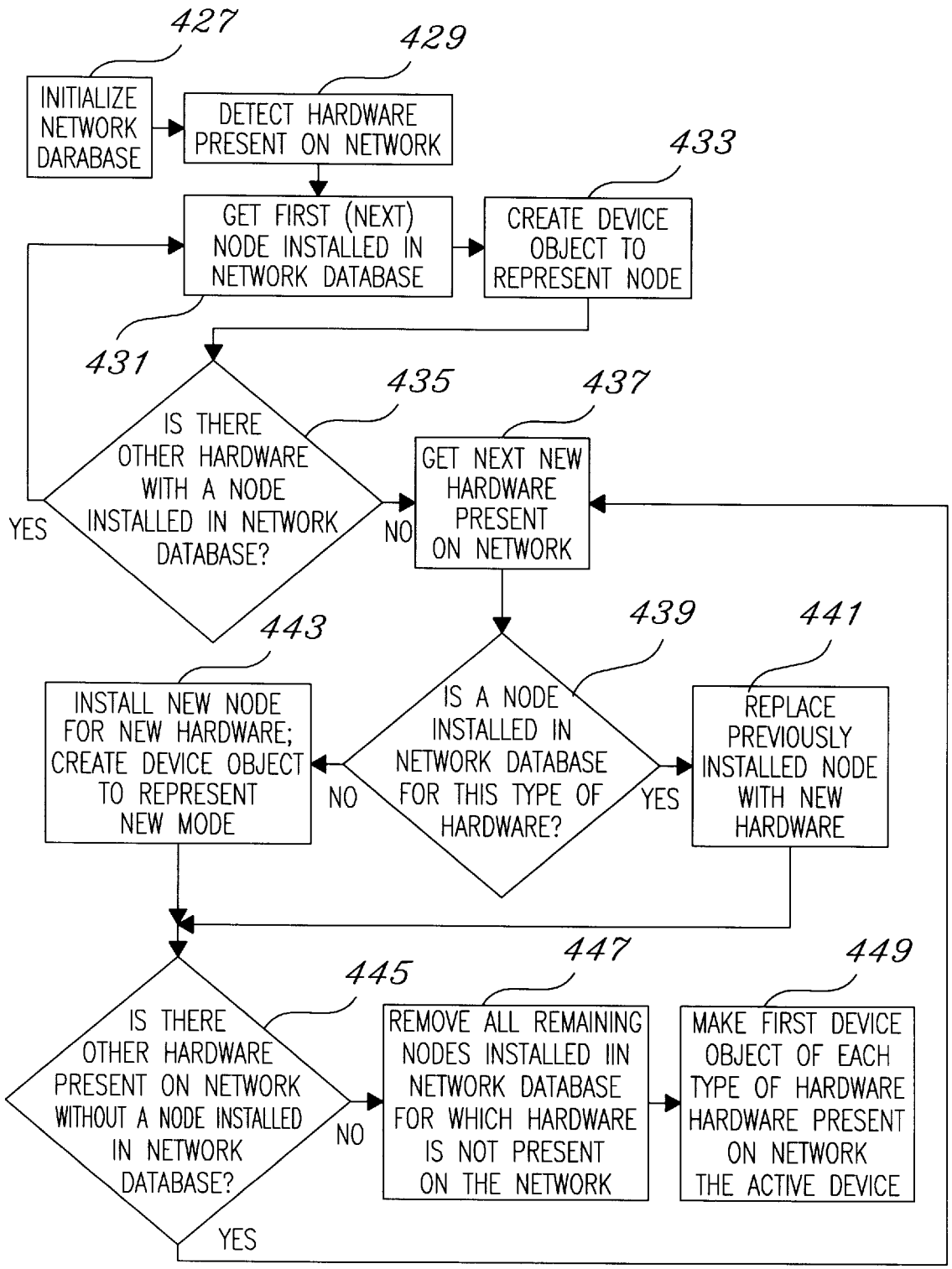
FIG. 31 is an exemplary flow diagram illustrating the operation of a central processor in the user interface computer for automatically configuring the system.

FIG. 31 illustrates the operation of computer unit 3 executing the initialization component of the system engine at power-up of system 1. In general, the system engine identifies each of the nodes on the network and creates a programming object for each node's neuron processor 225 that contains local network variables by which the user interface accesses the node. Beginning at step 427, the system engine initializes a network database stored in the hard drive 249 of computer unit 3. As described above, each neuron processor 225 of the various nodes on the network executes embedded programs for controlling the different microsurgical instruments 19 and peripherals. Communications parameters represent a unique identification label specific to each processor 225 which includes information regarding the type of device being controlled (e.g., vitrectomy handpiece or ultrasound device) as well as information regarding the version of module 13 or peripheral in which the processor 225 is located. The identification label also includes a specific identifier (e.g., a serial number) which is unique to the particular module 13 or control circuit 105, 107. As an example, the version of a particular module 13 may change as either the hardware or software is updated. The network database includes previously installed nodes in the form of specific module 13 or control circuit 105, 107 identifiers, names for the nodes which correspond to the different types of devices and names for the different programs which correspond to those nodes. In other words, the network database may include information regarding a system that has each of the different types of modules 13 and peripherals which are available already installed on the network.

At step 429, the system engine reads a set of communications parameters corresponding to the hardware (i.e., the different modules 13 and control circuits 105, 107) actually present on the network and creates a node object in software to provide access to the particular module 13 or peripheral. Proceeding to step 431, the system engine begins with the first module 13 or peripheral control circuit 105, 107 for which a node is already installed in the network database and, at step 433, creates a device object in software to represent this node. Preferably, the system engine derives the device object from the node object providing access to the hardware. If the system engine determines at step 435 that other modules 13 or peripheral control circuits 105, 107 already have installed nodes in the network database, it returns to step 431 and proceeds to the next module 13 or peripheral control circuit 105, 107. In this manner, the system engine creates device objects for the hardware already installed in the network database. These device objects created by the system engine contain the local network variables by which the user interface accesses the nodes.

After creating device objects to represent the nodes already installed in the network database, the system engine proceeds to step 437 for examining the modules 13 or peripheral control circuits 105, 107 present on the network as compared to the previously installed nodes. Proceeding to step 439, the system engine determines if there is a node installed in the network database (that is no longer present on the network) that corresponds to the same type of module 13 or peripheral control circuit 105, 107 being examined. If so, the system engine replaces the communications parameters for the previously installed node with the communication parameters for the particular module 13 or peripheral control circuit 105, 107 at step 441. When a replacement operation is performed, any network variable bindings are transferred to the new node. Further, the network database as well as other nodes involved in the network variable binding need not be modified. On the other hand, if a node has not been installed in the network database that corresponds to the same type of module 13 or peripheral control circuit 105, 107 being examined, then the system engine proceeds to step 443. At step 443, the system engine installs a new node with the communication parameters for the new module 13 or peripheral control circuit 105, 107 and creates a device object to represent this new node. Following either step 441 or 443, the system engine proceeds to step 445 to determine if other modules 13 or peripheral control circuits 105, 107 are present on the network that do not already have installed nodes in the network database. If so, the system engine returns to step 437. Otherwise, the system engine proceeds to step 447.

At step 447, the system engine removes all of the remaining nodes installed in the network database for which hardware is not present on the network. Proceeding to step 449, in the event that more than one module 13 or peripheral control circuit 105, 107 of the same type are present on the network, the system engine makes the first device object for each type active. In other words, the system engine gives priority to one of the multiple, or duplicative, modules 13 or peripheral control circuits 105, 107.

Thus, if a new module 13 has been added to the configuration since the previous power-up sequence, whether it be the same type or a different type of module 13 compared to those modules 13 previously installed, system 1 automatically detects and initializes the new module 13 and reconfigures both the communication parameters and user interface. By doing so, the user now has access to the new module 13 and can control any surgical instruments 19 associated with it. Similarly, if a particular module 13 has been removed from the network since the previous power-up sequence, system 1 automatically senses the absence of module 13 and removes any associated communication parameters and user interface functions. Further, computer unit 3, in executing the automatic network reconfiguration, allows more than one of the same type of module 13 to be installed in system 1. Computer unit 3 determines primary and secondary priorities as required for identification and control via the user interface. Computer unit 3 also determines disallowed system configurations and instructs the user via the user interface to take appropriate action.

In this manner, computer unit 3 initializes system 1 at power-up by configuring neuron processors 225 and creating the necessary local network variables for use by the user interface to access the network, verifying that system 1 meets certain minimum operational requirements and performing all constant network bindings. Computer unit 3 also notifies the user interface of any configuration changes from the last configuration including the addition/removal of modules 13 or peripherals from system 1. After power-up initialization, control of system 1 passes to the user interface. In an alternative embodiment, computer unit 3 additionally identifies the position of the particular modules 13 within base unit 7 at power-up.

Referring now to the individual components shown generally in the exemplary system configuration of FIG. 21, each module 13 installed in base unit 7 controls one or more microsurgical instruments 19 for providing several different surgical functions. For example, modules 13 include venturi IAV module 321, scroll IAV module 323, phaco module 325, scissors module 327, coagulation module 329 and illumination module 331 (also referred to as illumination module 13A with respect to FIGS. 4A–4D). System 1 also includes foot control assembly 15 and IV pole assembly 17 as peripherals connected to the network of system 1.

Figure 32:
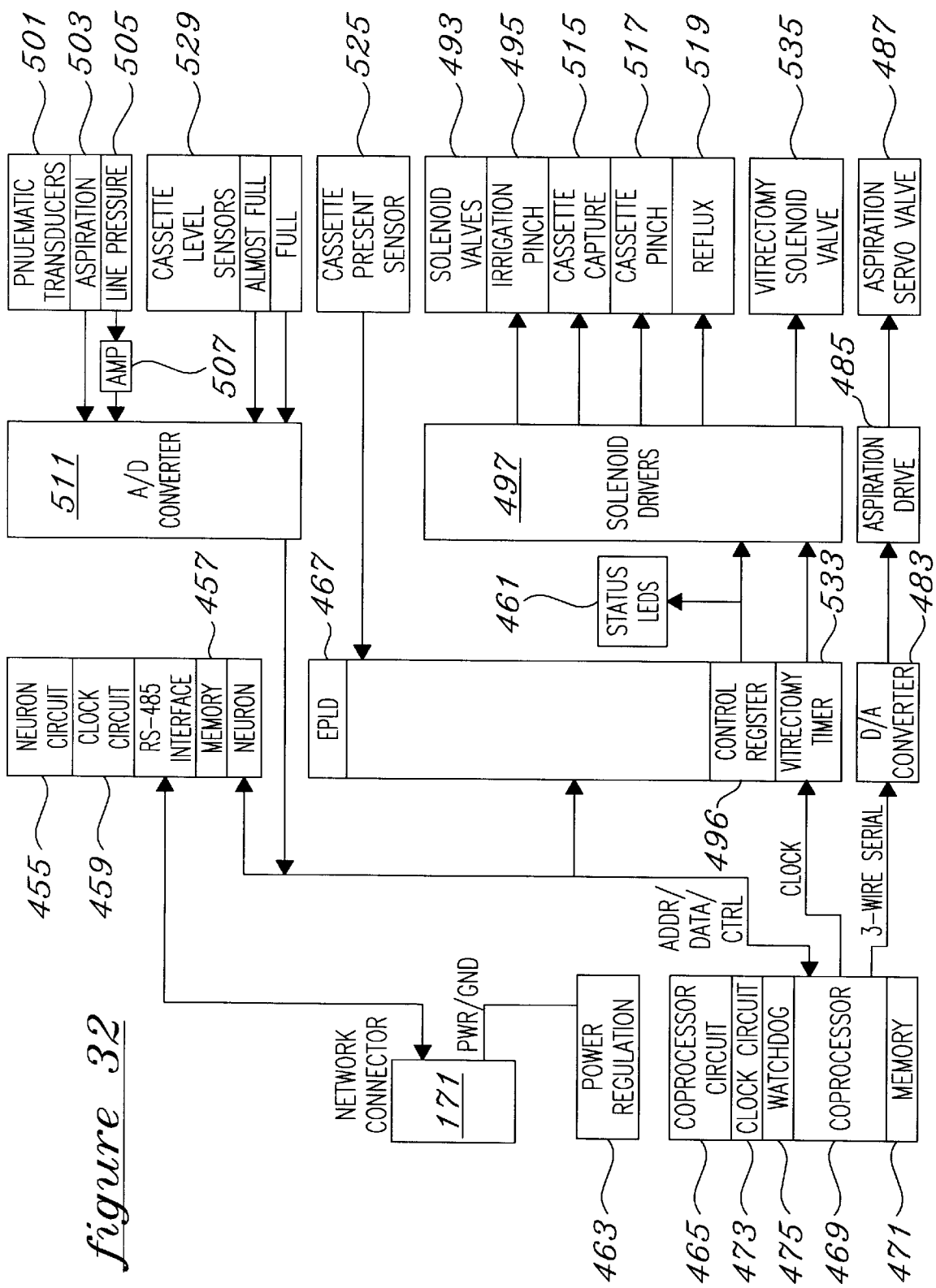
FIG. 32 is a block diagram of an irrigation, aspiration and/or vitrectomy module according to a preferred embodiment of the system of FIG. 1.

FIG. 32 shows venturi IAV module 321 in block diagram form (shown in detail in FIGS. 43–60). As shown in FIG. 32, module 321 has a neuron circuit 455 connected to the network via the network connector 171 at the rear of module 321 which connects to backplane 101. The neuron circuit 455 includes RS485 transceiver 223 for receiving and transmitting data over the data communications bus. Neuron processor 225, coupled to transceiver 223, provides network communications control for module 321. Neuron processor 225 also executes embedded application programs for controlling the irrigation, aspiration and vitrectomy functions of system 1. In this instance, neuron circuit 455 includes a memory 457 (e.g., a flash EEPROM), for storing the application programs for IAV module 321. In addition, the memory 457 stores the configuration and identification data for use in initializing module 321 on the network. Advantageously, central processor 245 is able to reprogram memory 457 via the data communications bus in response to the information provided by the user. Neuron circuit 455 also includes a clock circuit 459 (e.g., a crystal oscillator) providing a time base for neuron 225 to operate. Venturi IAV module 321 further includes a status LED 461, such as a green LED on the front panel of module 321, for indicating that the module is active, and a power regulation circuit 463 for generating a −5 volts supply for use by the circuitry. Although not shown in FIG. 32, neuron circuit 455 also includes another RS485 transceiver for receiving a reset signal from computer unit 3.

In general, neuron processors 225 may be used with coprocessors if greater processing capability is required than that provided by processor 225. In those instances, the particular modules 13 may include a coprocessor receiving and responsive to the control signals generated by neuron processor 225 for generating additional control signals to provide closed loop control during performance of the surgical procedures. In a preferred embodiment of the invention, IAV module 321 includes a coprocessor circuit 465 which cooperates with a programmable logic circuit, such as an electronically programmable logic device (EPLD) 467. The coprocessor circuit 465 preferably includes a coprocessor 469 (e.g., an Intel 386EX processor) and an associated memory 471 (e.g., a flash EEPROM and a static RAM), a clock circuit 473 (e.g., a crystal oscillator) for providing the clock signals used by coprocessor circuit 465, and a watchdog timer 475.

Referring further to FIG. 32, the coprocessor 469 of coprocessor circuit 465 generates an aspiration control signal as a function of an aspiration level operating parameter and provides it to a digital-to-analog (D/A) converter 483. In the illustrated embodiment, the D/A converter 483 provides a parallel interface by which coprocessor 469 controls air flow through the module's venturi pump. An aspiration drive 485 receives the analog output of D/A converter 483 and drives an aspiration servo valve 487 in response thereto. The opening and closing of the aspiration servo valve 487 determines the air flow through the venturi and, thus, determines the vacuum level. Venturi IAV module 321 preferably supports operation of a single aspiration port driven from the venturi pump located within the module. The venturi pump requires an external gas/air input with pressures between, for example, 80 to 100 pounds per square inch—gauge. Module 321 further includes a pressure relief valve (not shown) for preventing over-pressure conditions. Advantageously, the control circuitry of module 321 provides both fixed and linear control of the aspiration vacuum level. For example, the aspiration vacuum level may range from 0 mmHg to 550 mmHg and may be varied in 1 mmHg increments. The user sets all aspiration parameters via touch-responsive screen 255, remote control 39 or foot control assembly 15 and controls the aspiration function via foot control assembly 15.

The irrigation portion of venturi IAV module 321 supports gravity fed irrigation. For example, IV pole assembly 17 supports a bag of sterile saline solution which the surgeon uses to irrigate the patient's eye during surgery. Module 321 includes a set of solenoid valves 493, one of which is a pinch valve 495 that prevents all fluid ingress to system 1 when it is closed. Either touch-responsive screen 255 or foot control assembly 15 provides the user with fixed and on/off (open/close) control the irrigation function of venturi IAV module 321. Neuron processor 225 cooperates with coprocessor 469 and a control register 496 of EPLD 467 to generate drive signals for commanding a set of solenoid drivers 497. In turn, the solenoid drivers 497 cause the solenoid valves 493 to open and close by the desired amount.

Preferably, IAV module 321 includes a set of pneumatic pressure transducers 501 which provide feedback regarding the actual aspiration or irrigation pressures. For example, an aspiration transducer 503 senses the aspiration pressure level and a line pressure transducer 505 senses the irrigation pressure level. An instrumentation amplifier circuit 507 associated with the line pressure transducer 505 amplifies its pressure signals before it is processed. Preferably, the aspiration transducer includes an internal amplifier. An analog-to-digital (A/D) converter 511 receives the amplified pressure signals and converts the analog pressure signals to digital values for processing by coprocessor circuit 465. In this manner, IAV module 321 provides closed loop control of the aspiration and irrigation functions.

Microsurgical ophthalmic systems typically employ a vacuum-operated aspiration system with a removable fluid collection cassette such as illustrated and described in commonly owned U.S. Pat. No. 4,773,897. The aspiration fluid is drawn into a cassette by connecting the aspirating instrument to the cassette which is under a vacuum or negative pressure. The surgeon carrying out the microsurgical ophthalmic procedure has control of the aspiration system by, for example, foot control assembly 15 which permits the surgeon to precisely control the suction by activating a wedge shaped solenoid plunger such as shown at reference number 182 in the aforesaid patent, or the aspiration servo valve 487 as shown in FIG. 32, to block or open the suction from the cassette to the microsurgical instrument.

The solenoids 493 of modules 321 also include a cassette capture valve 515 and a cassette pinch valve 517. The plunger (not shown) of the cassette capture valve 515 secures the cassette in position in module 321. The cassette pinch valve 517 closes the aspiration line when the aspiration function is not active to prevent backflow of fluid from the cassette or aspiration line to the patient's eye.

Additionally, one of the solenoids 493 in venturi IAV module 321 is a reflux solenoid valve 519 for driving a reflux plunger, such as shown at 184 in the aforesaid patent. When actuated, the reflux plunger squeezes a reflux chamber associated with the cassette to force a small amount of fluid in the aspiration tube back out the passage thereby assuring that the tube stays open and unblocked. Depending on the procedure being carried out, a different amount of reflux is required, for example, if an anterior or posterior procedure is being carried out. It is important that a cassette being used for a posterior procedure use a cassette which provides much less of an amount of reflux than is the case with a cassette used for an anterior procedure. An advantageous feature of system 1 automatically detects and differentiates between a posterior, or micro-reflux, cassette and an anterior cassette. This feature prevents the user from inadvertently installing and using the wrong reflux cassette for a given procedure.

In accordance with this invention, if a cassette designed for use during an anterior procedure is inserted into IAV module 321 which is to be used for a posterior procedure, the user interface indicates this error visually and/or audibly and prevents system 1 from being activated with an incorrect cassette installed.

Figure 61:
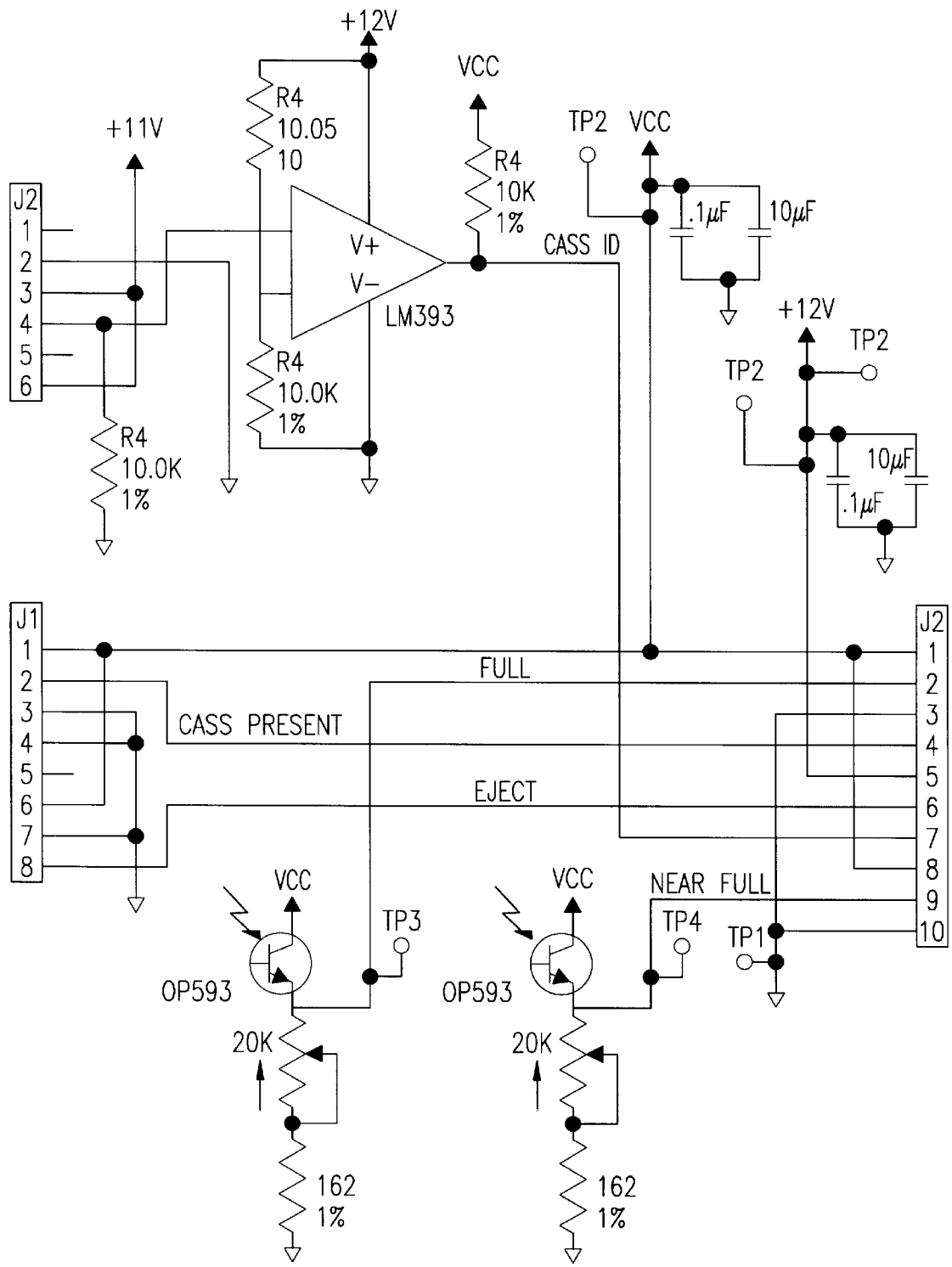
FIG. 61 is a schematic diagram illustrating a cassette detector for use with the irrigation, aspiration and/or vitrectomy module of FIGS. 32 and 43–60.
Figure 62:
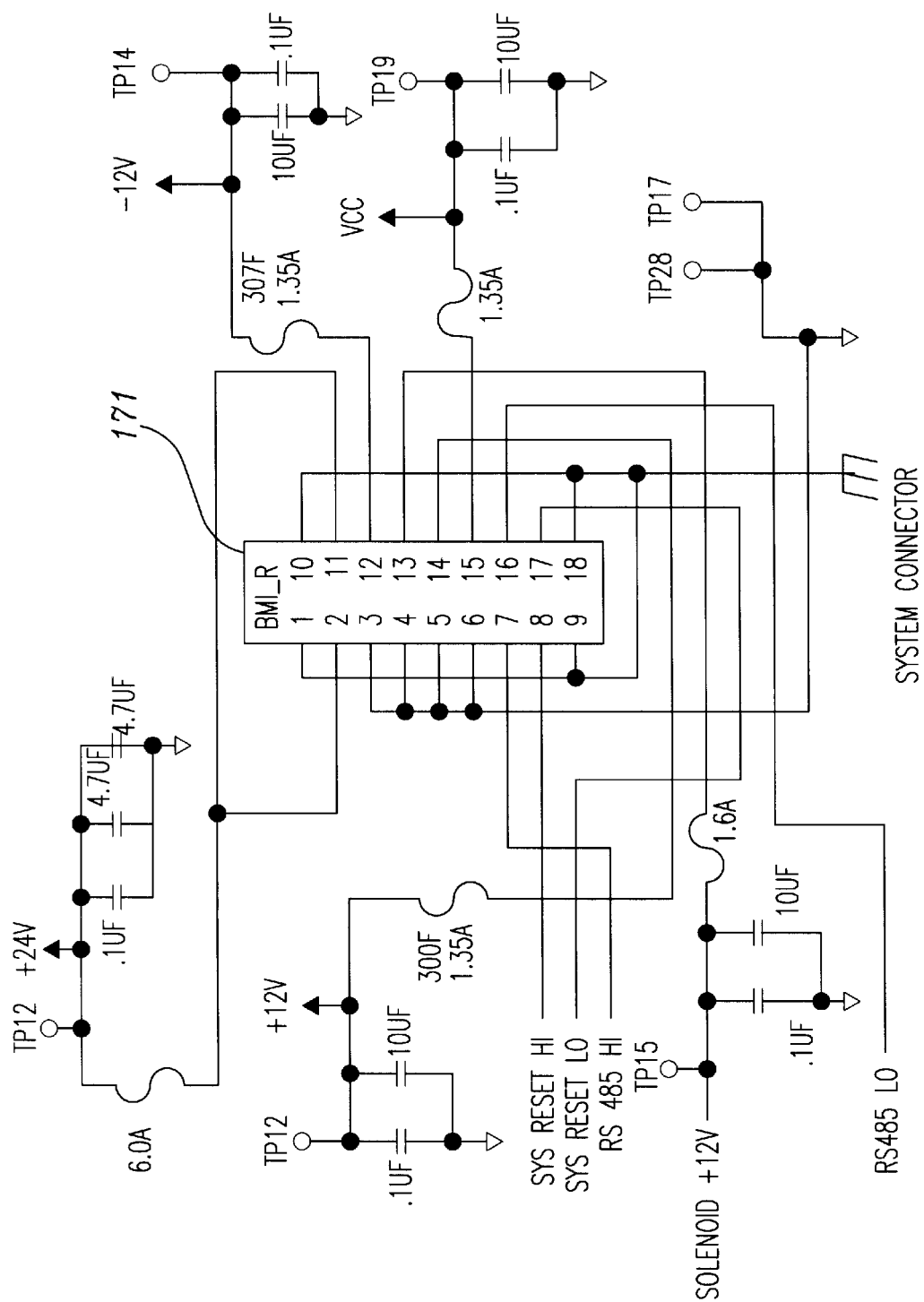
FIGS. 62–88 are schematic diagrams illustrating the phacoemulsification and/or phacofragmentation module of FIG. 33.
Figure 63:
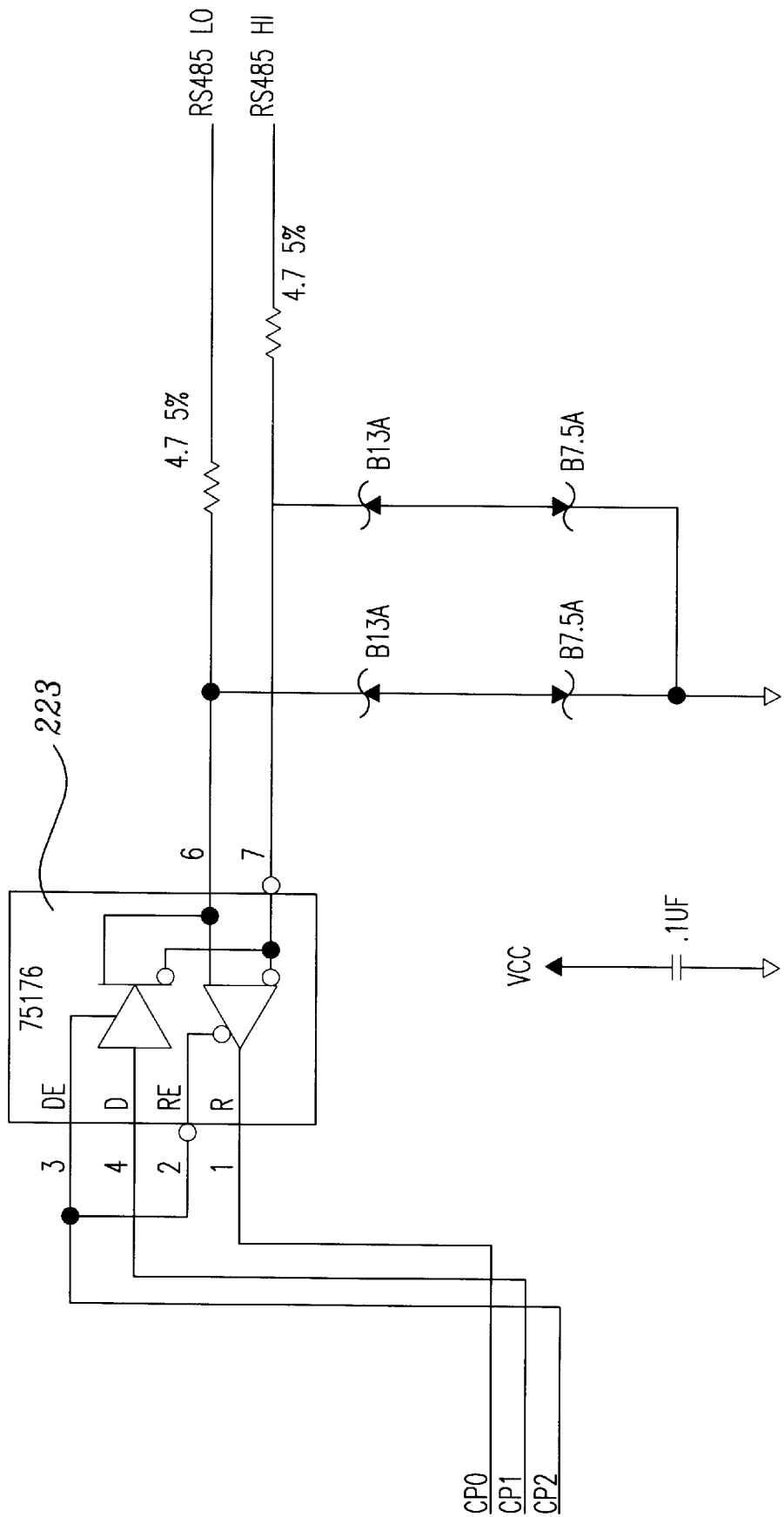
Figure 64:
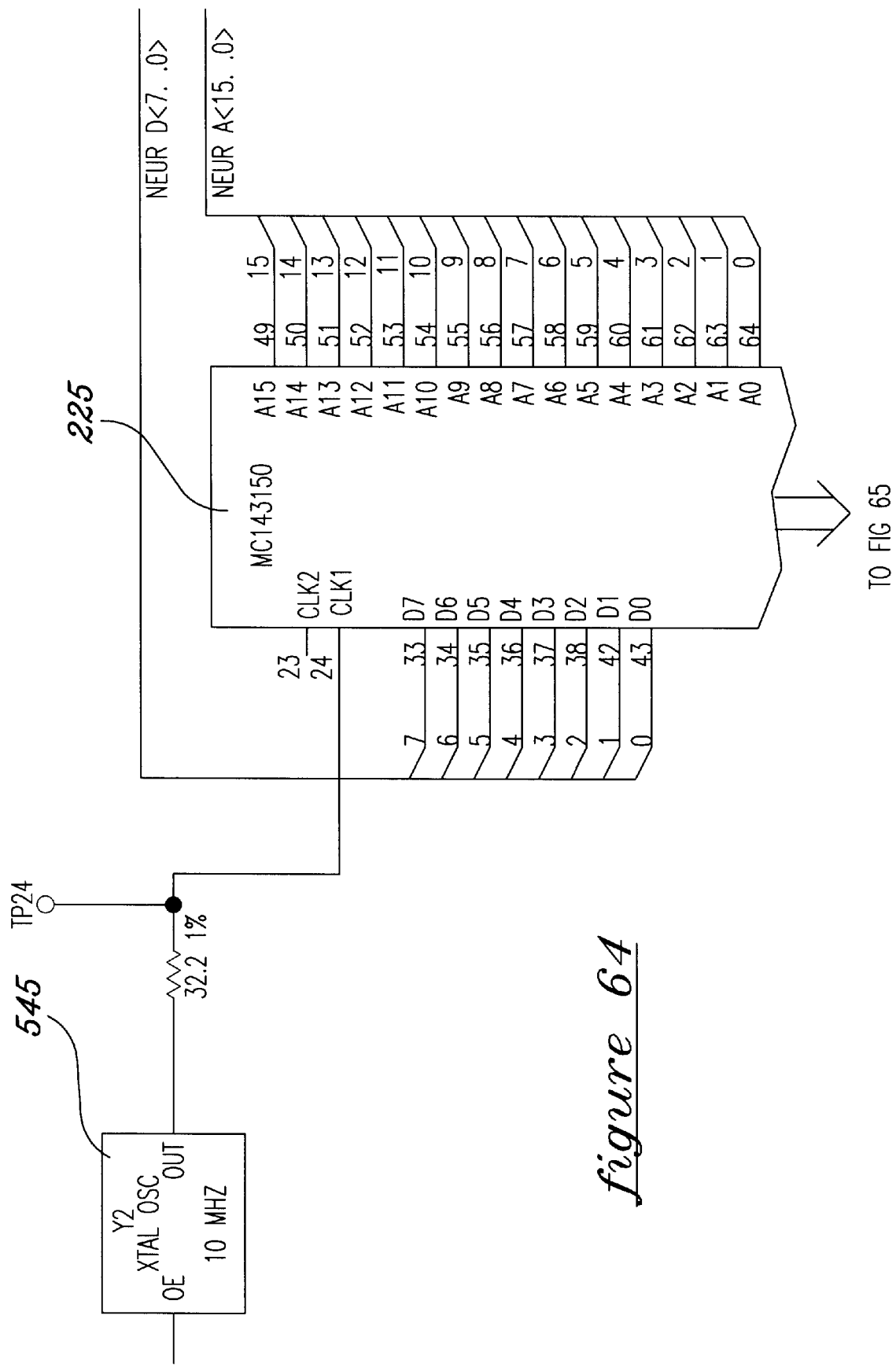
Figure 65:
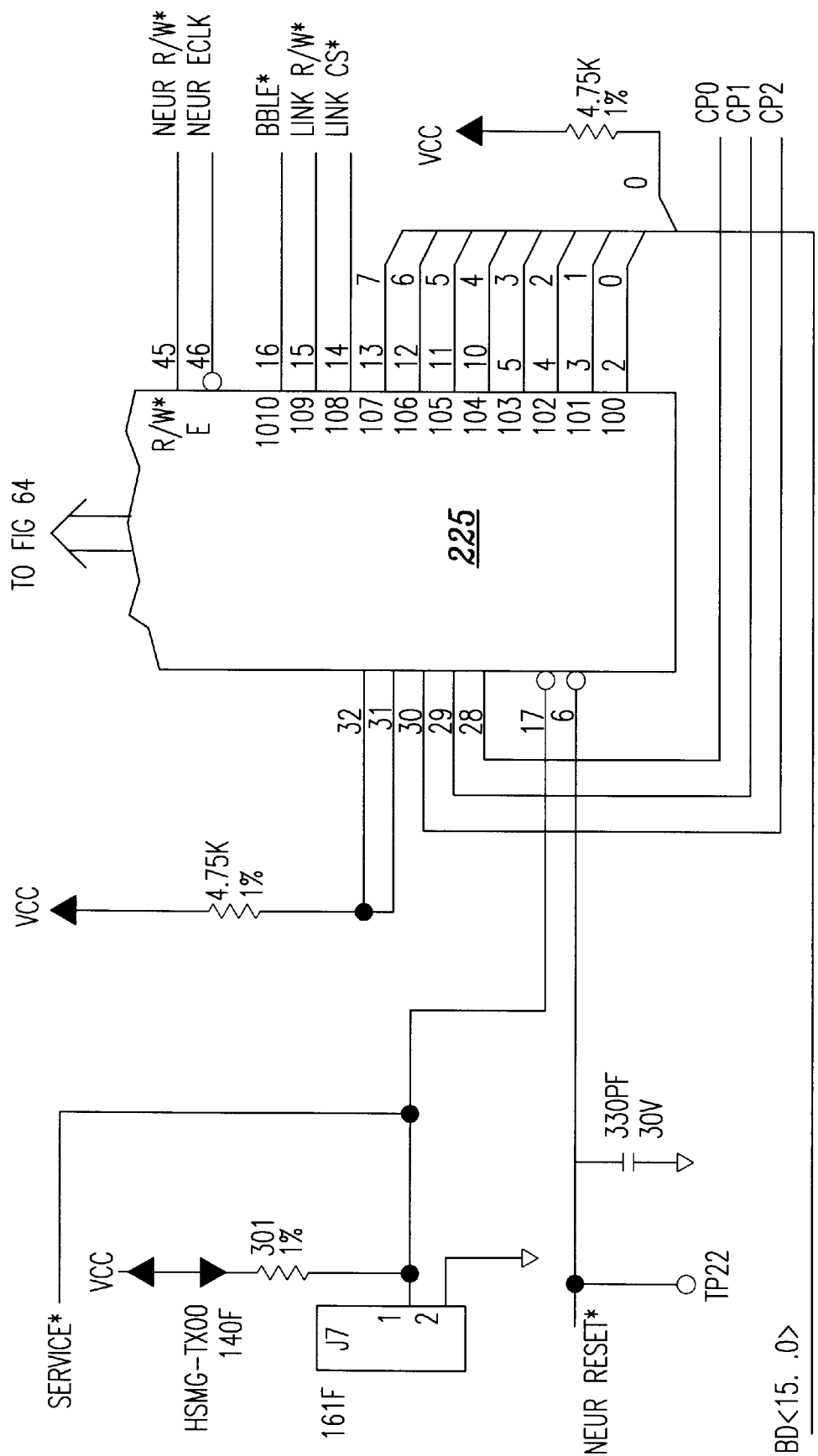
Figure 66:
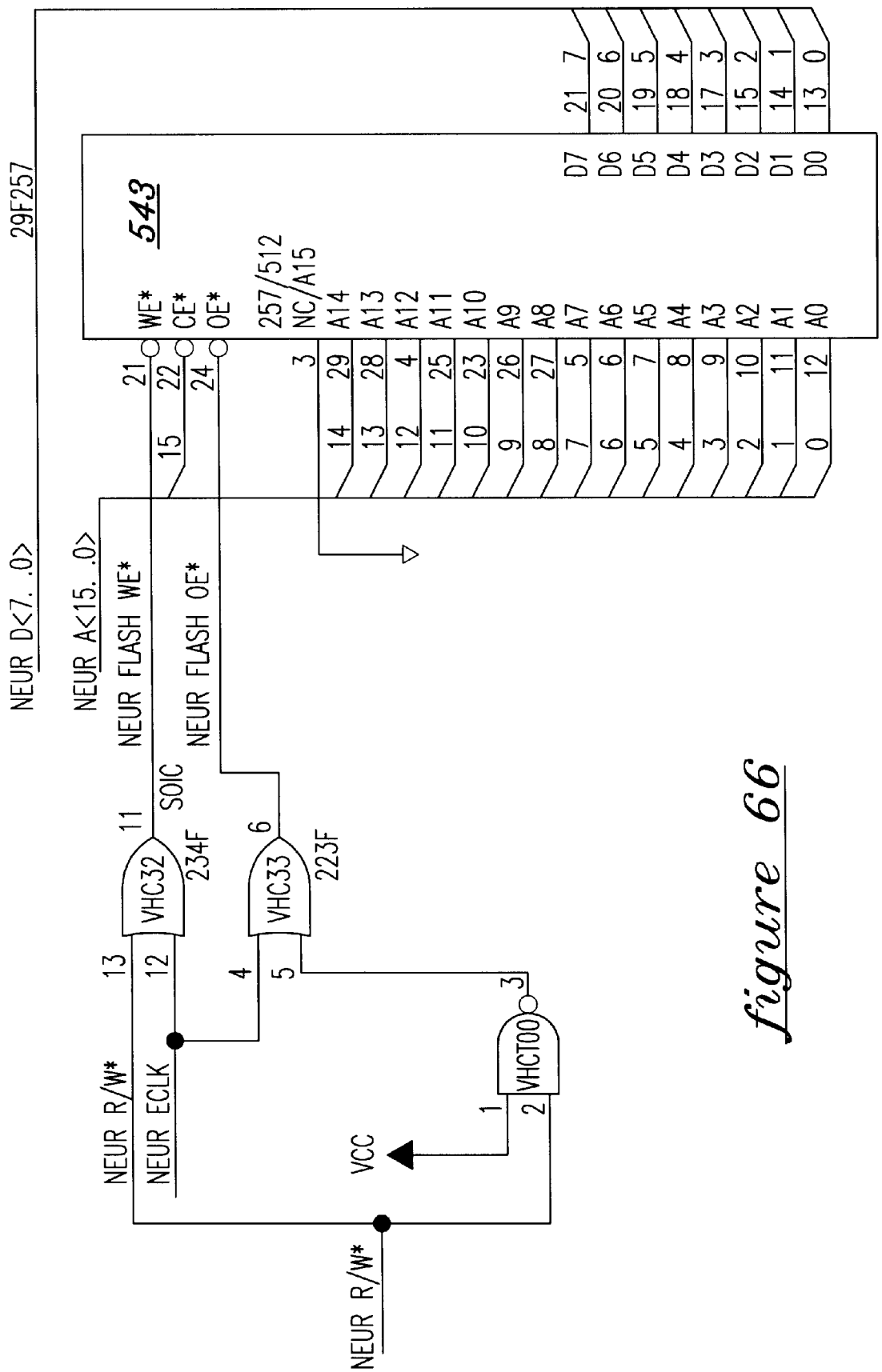
Figure 67:
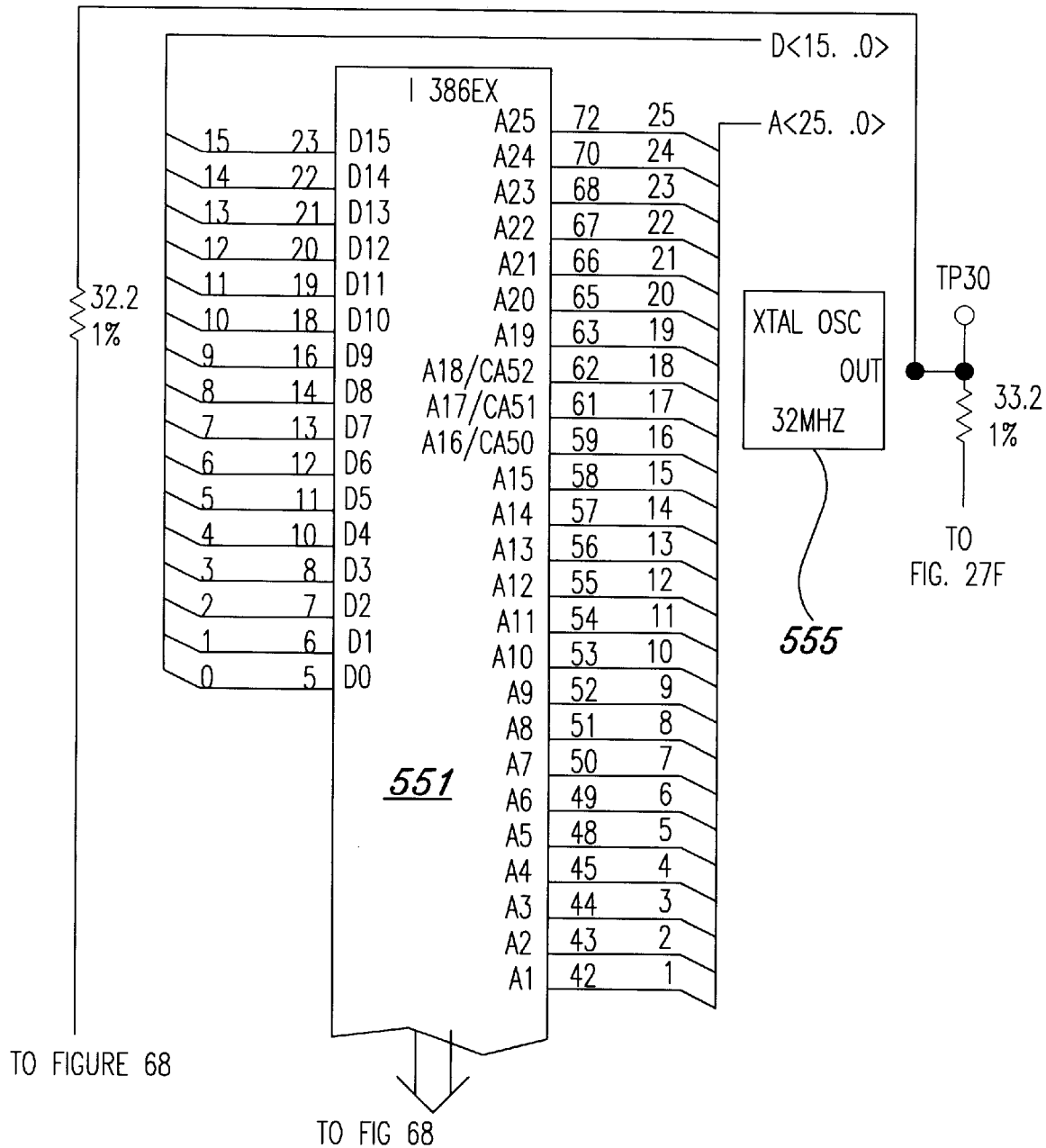
Figure 68:
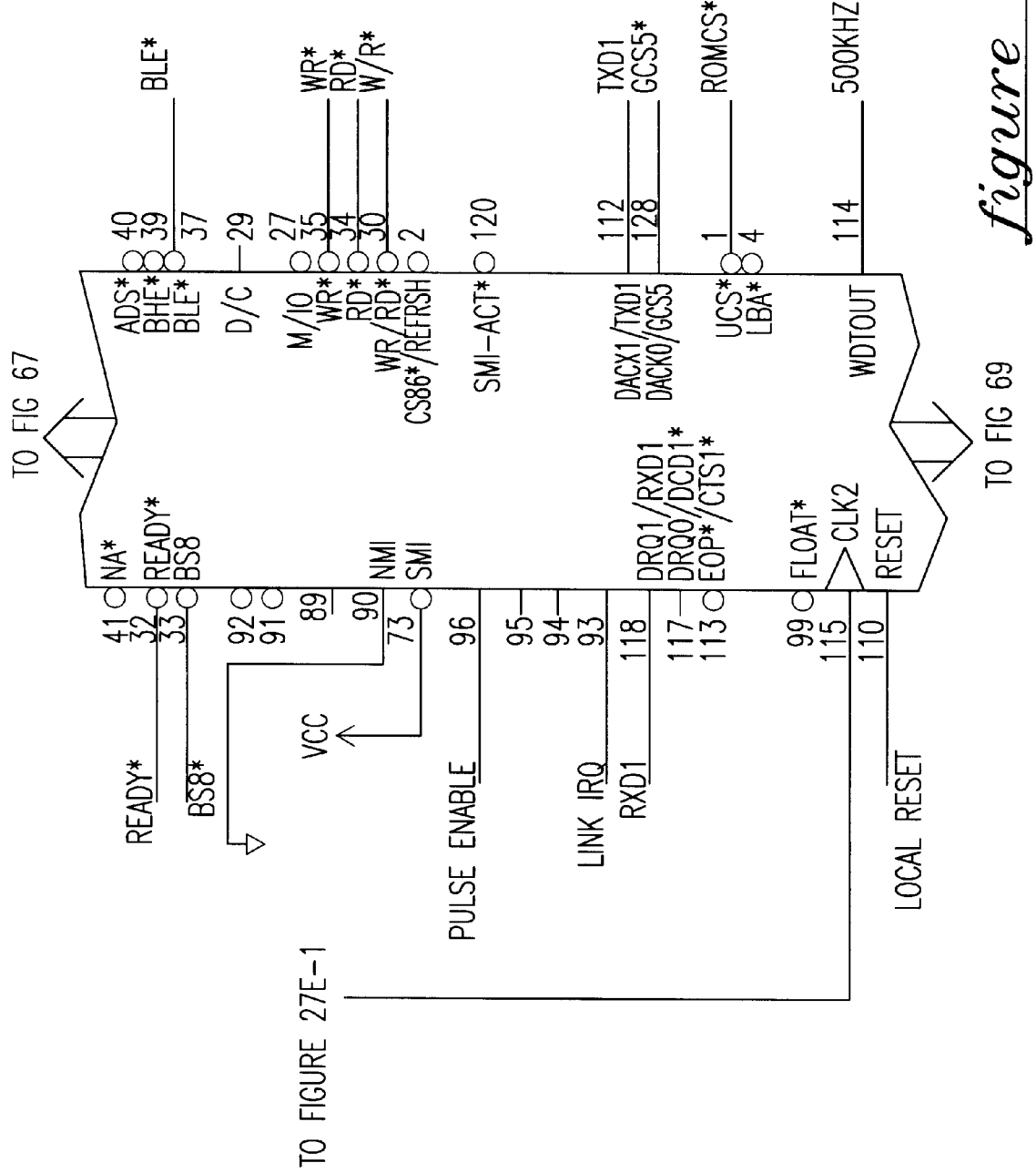
Figure 69:
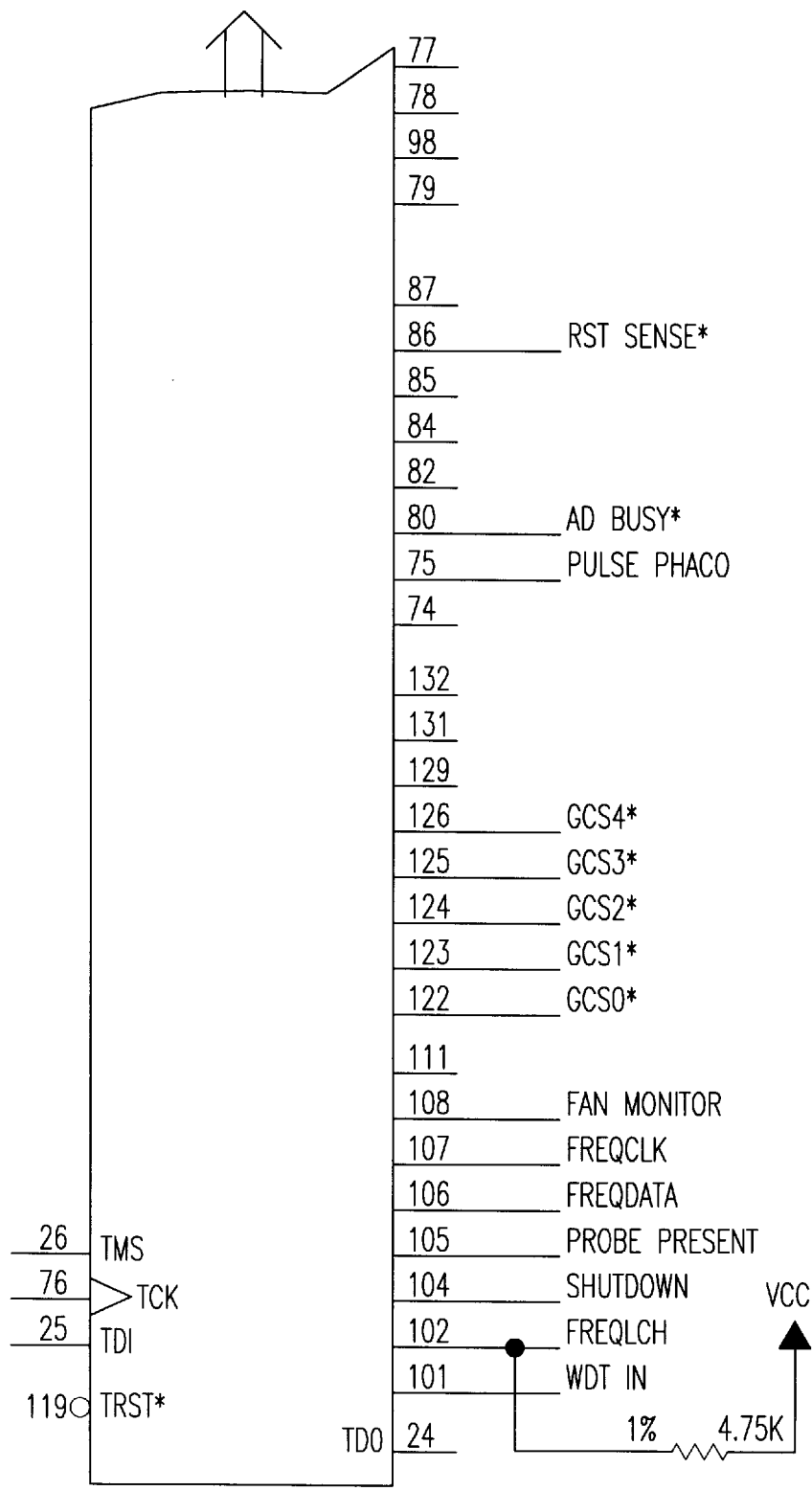
Figure 70:
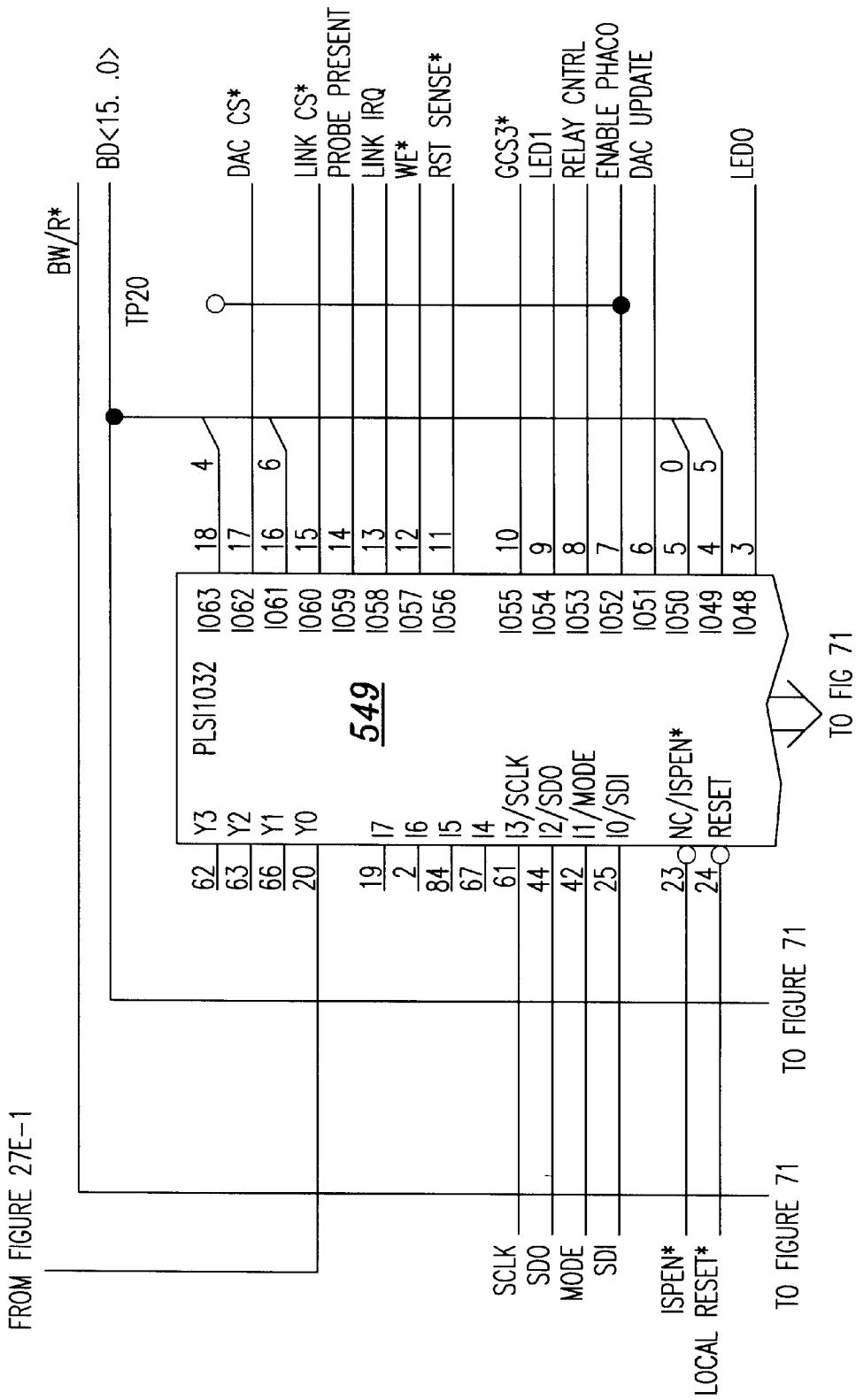
Figure 71:
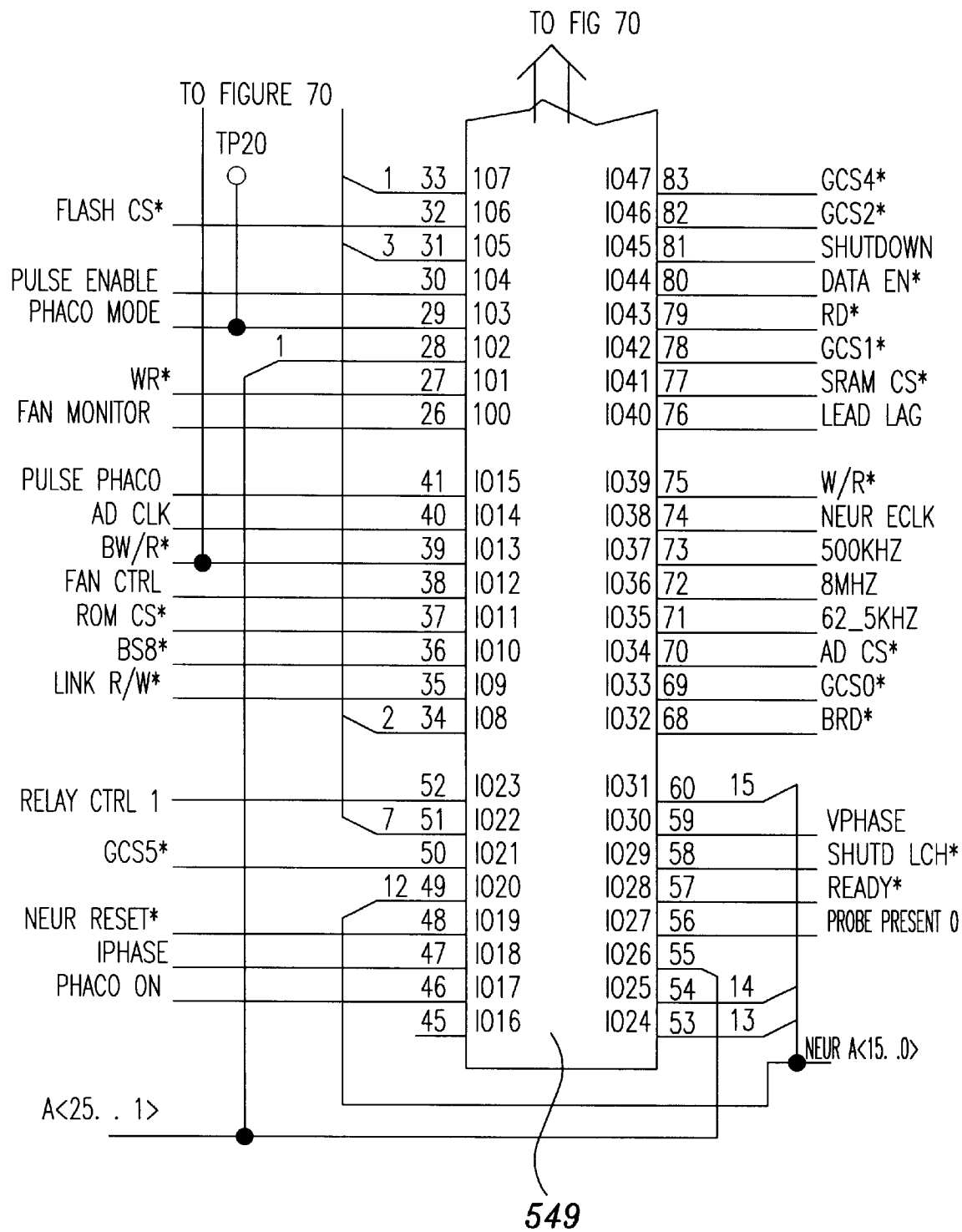
Figure 72:
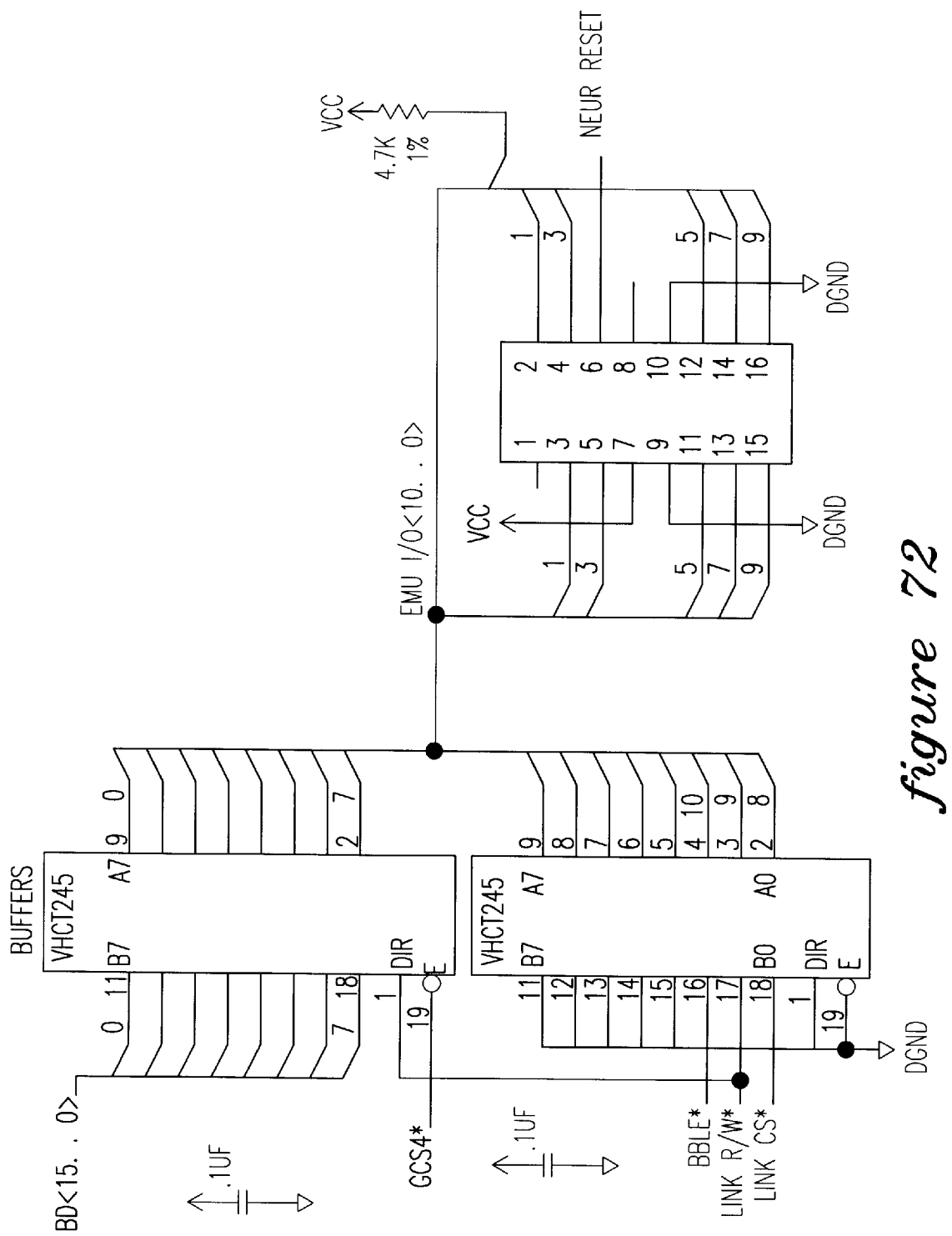
Figure 73:
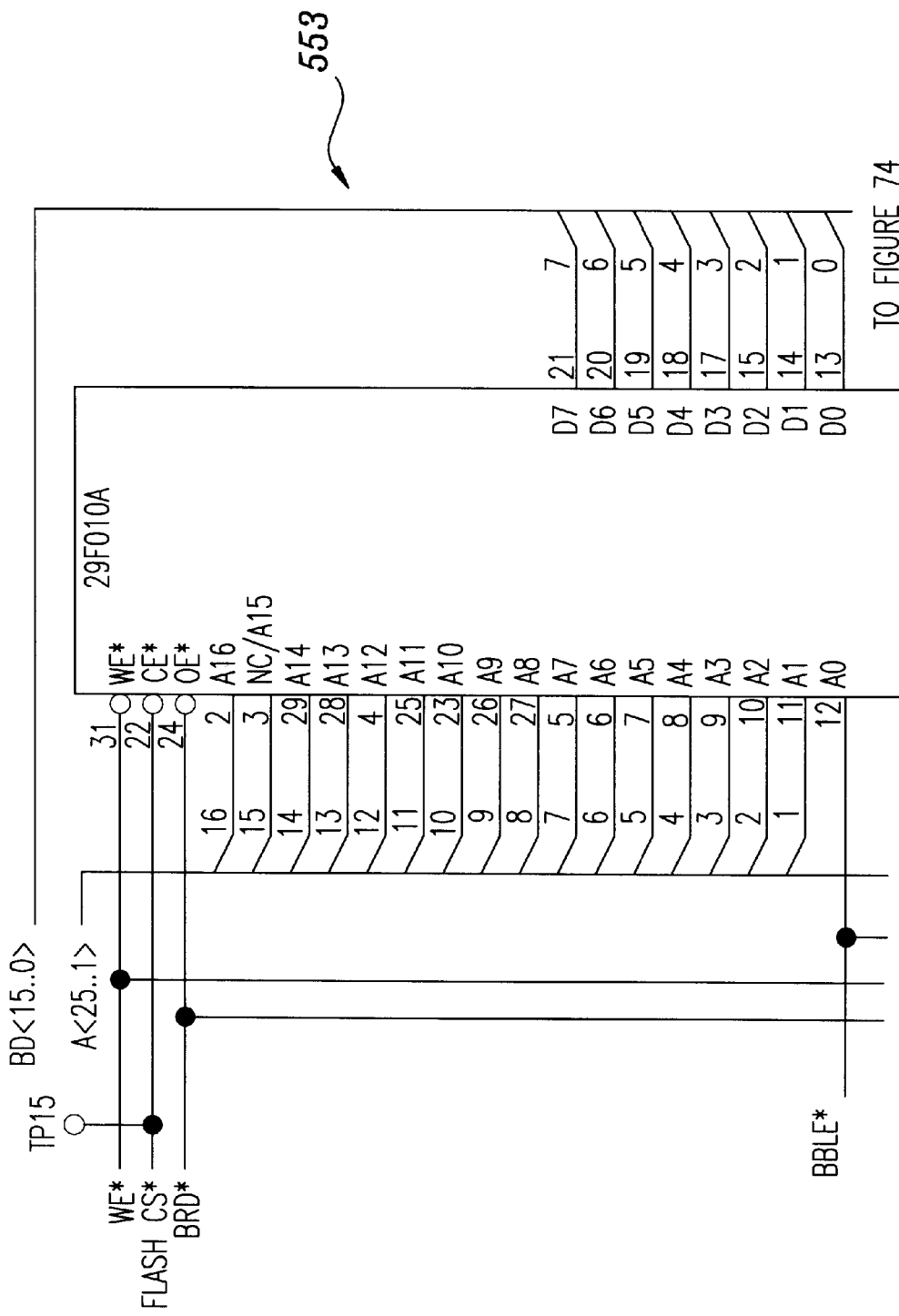
Figure 74:
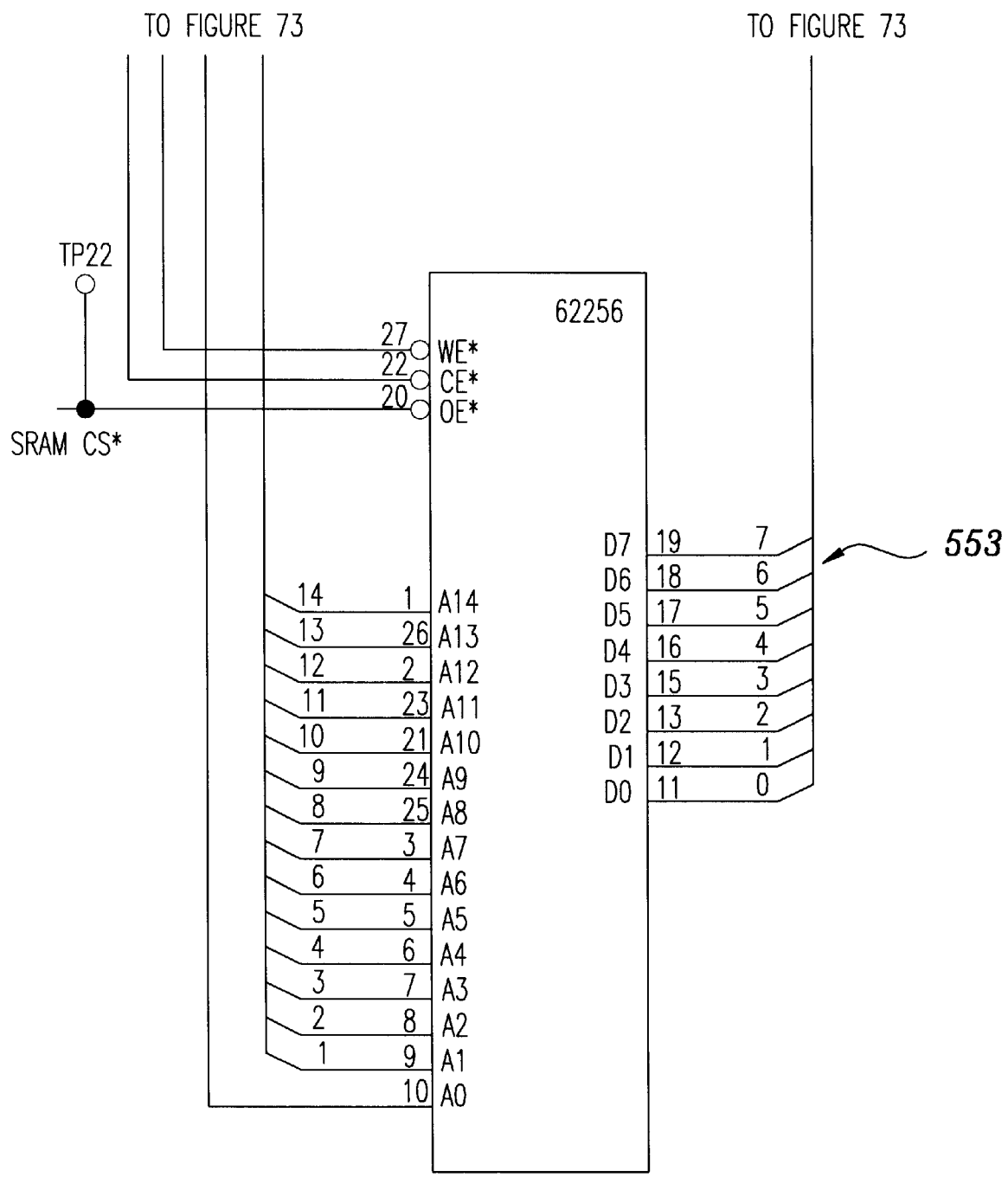
Figure 75:
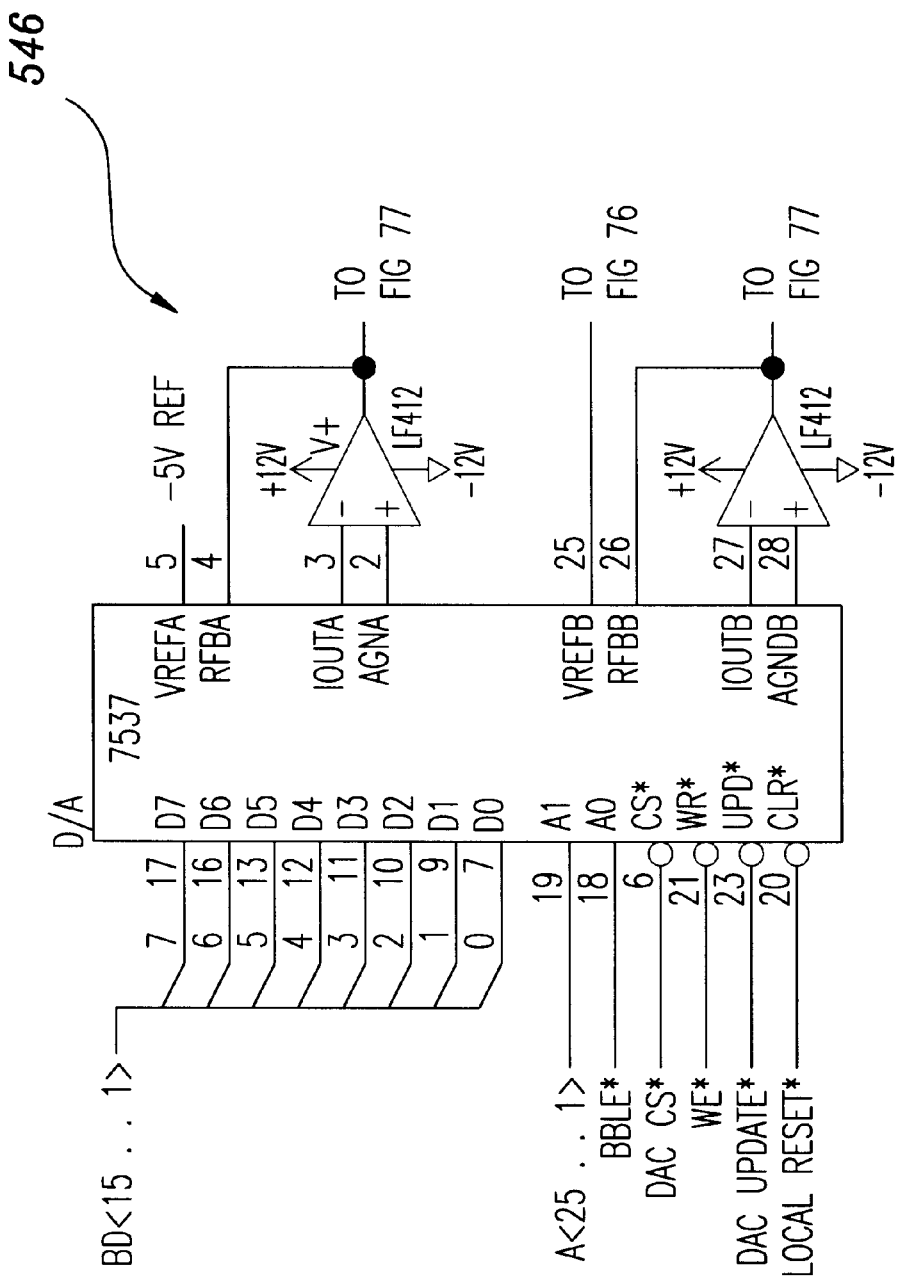
Figure 76:
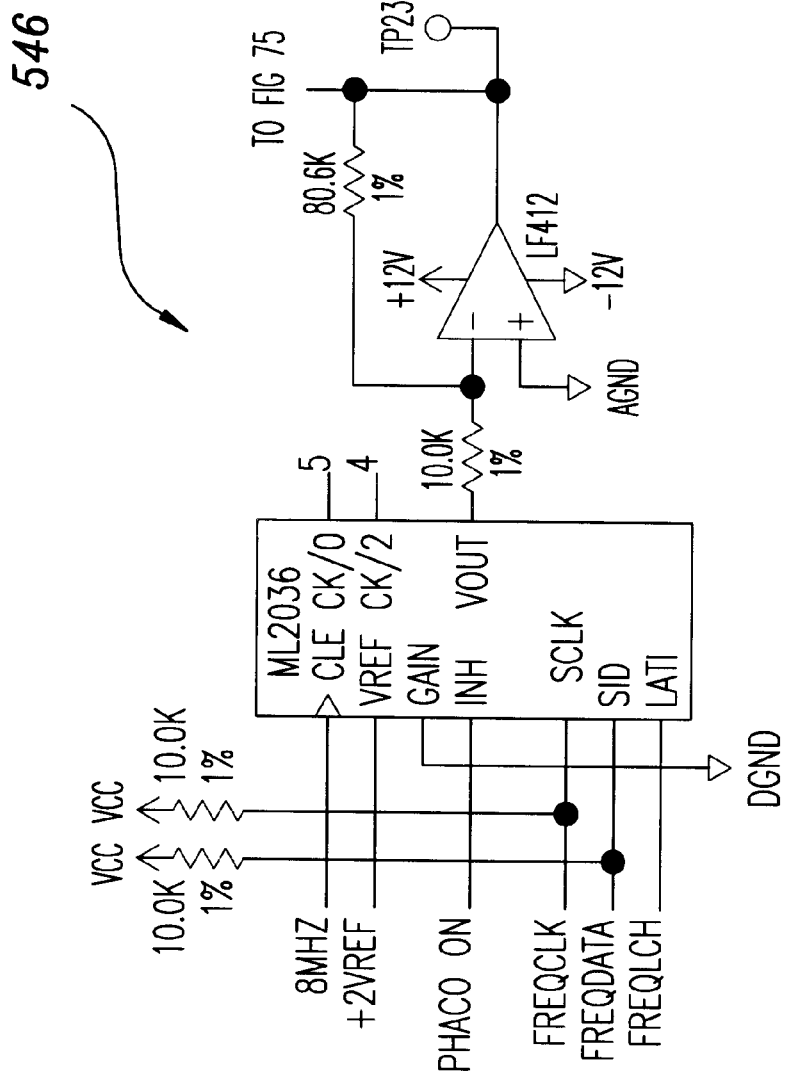
Figure 77:
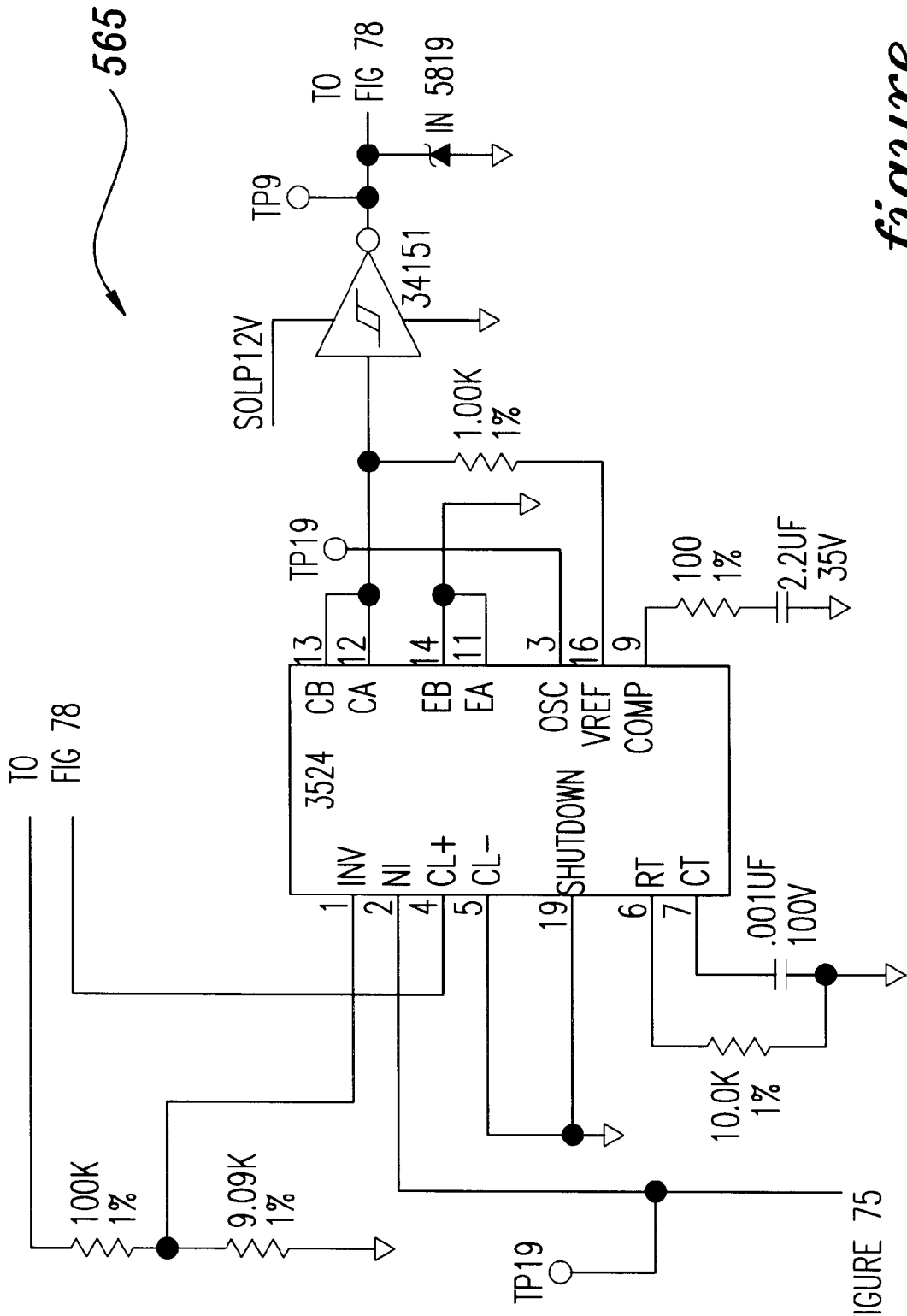
Figure 78:
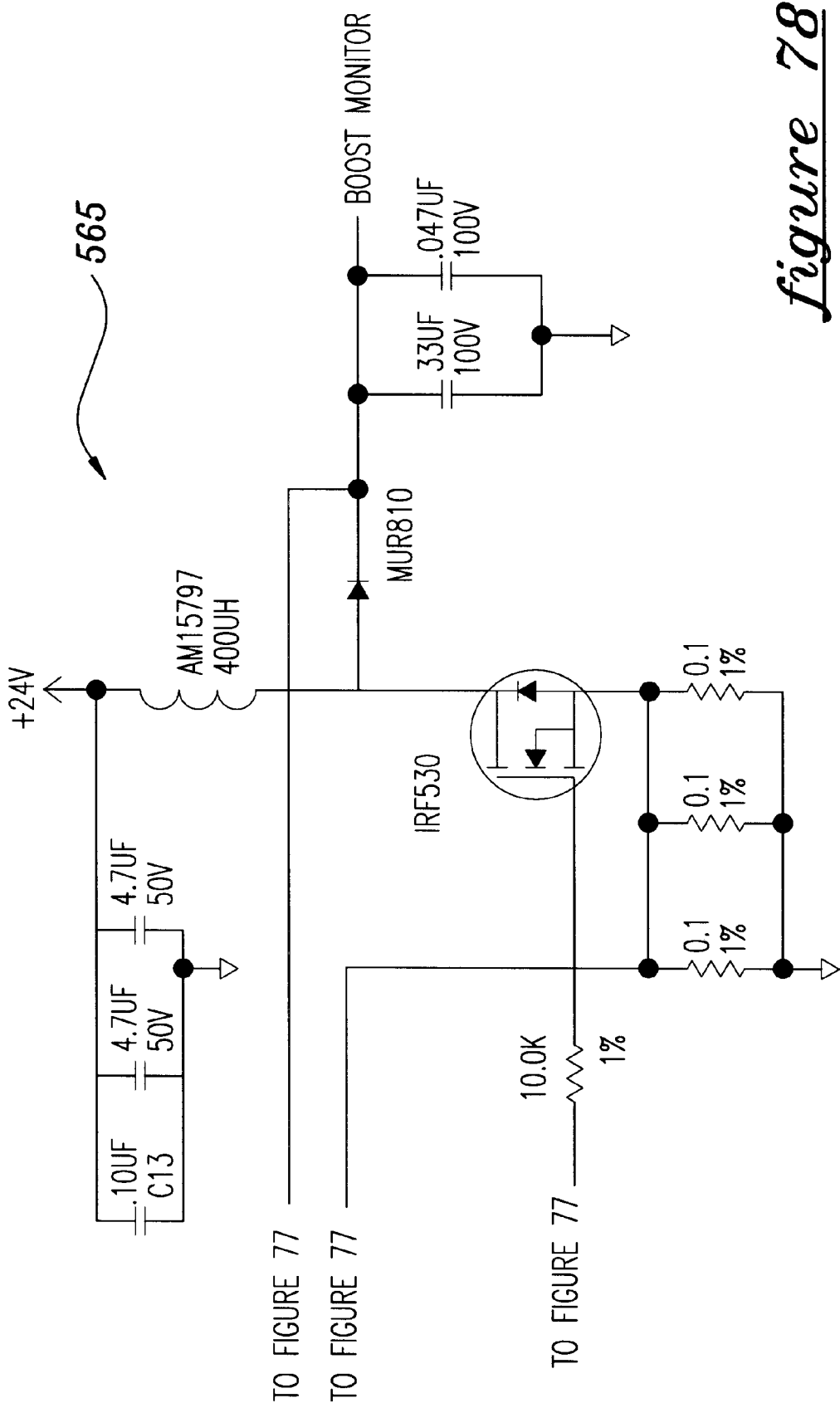
Figure 79:
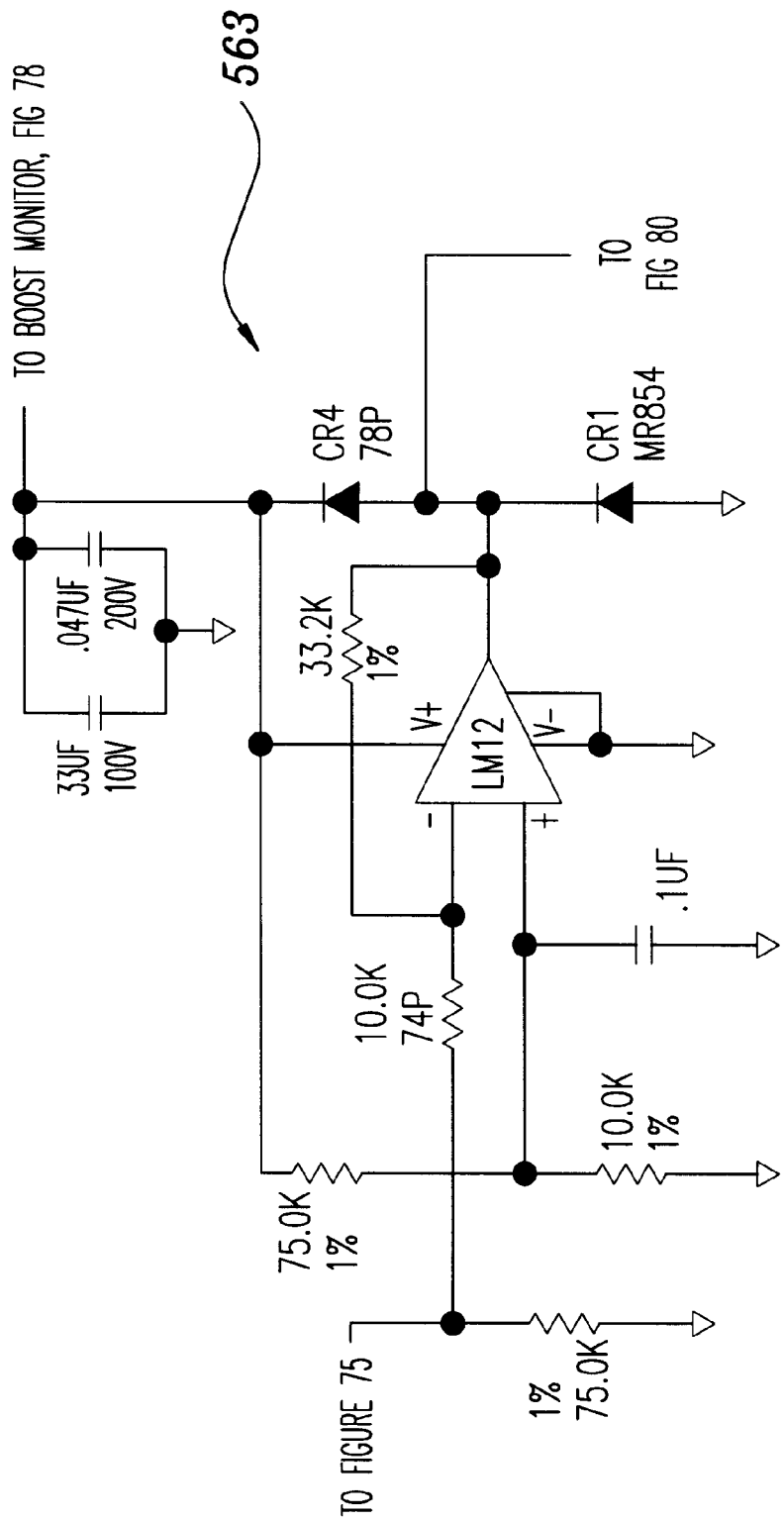
Figure 80:
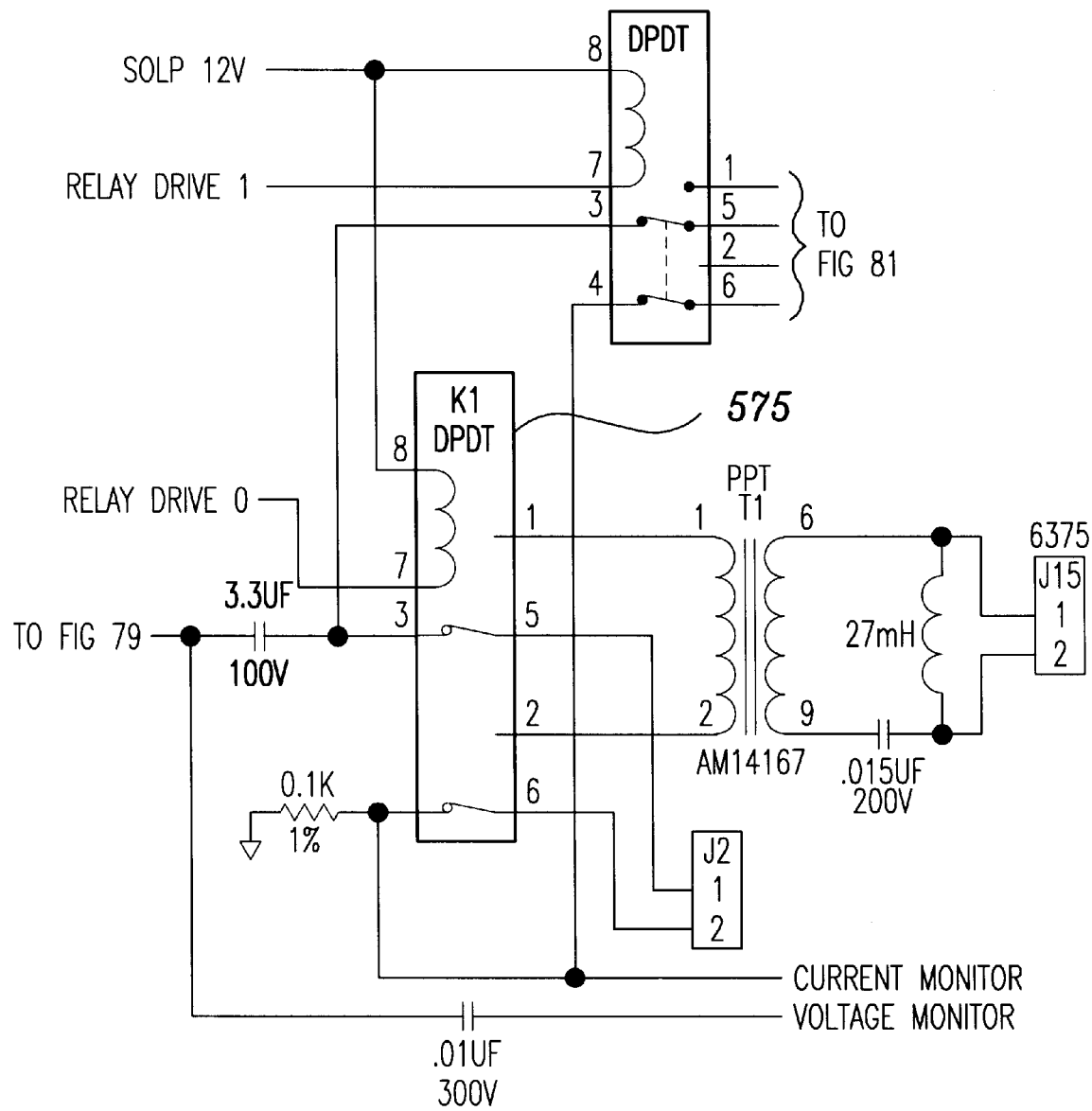
Figure 81:
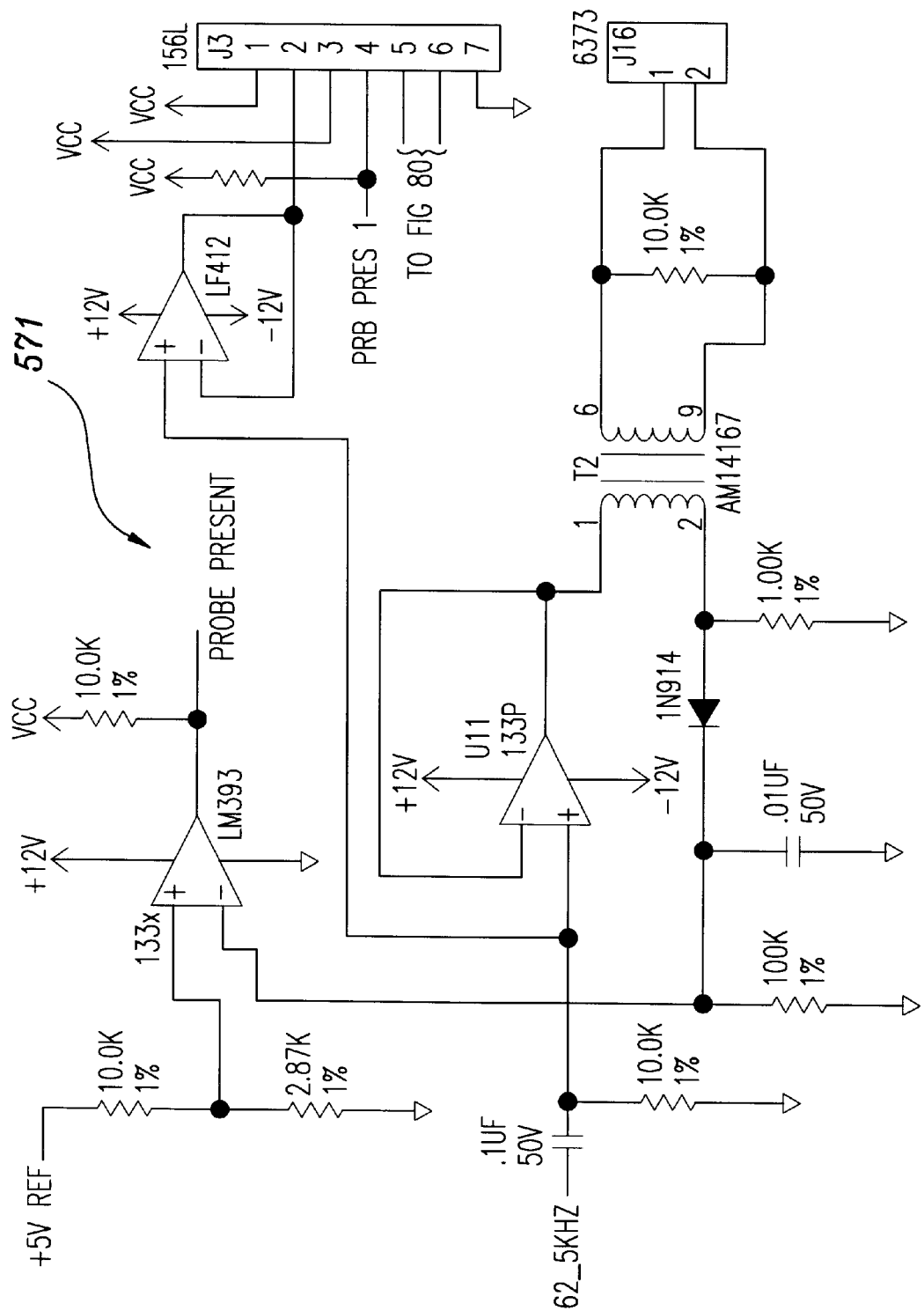
Figure 82:
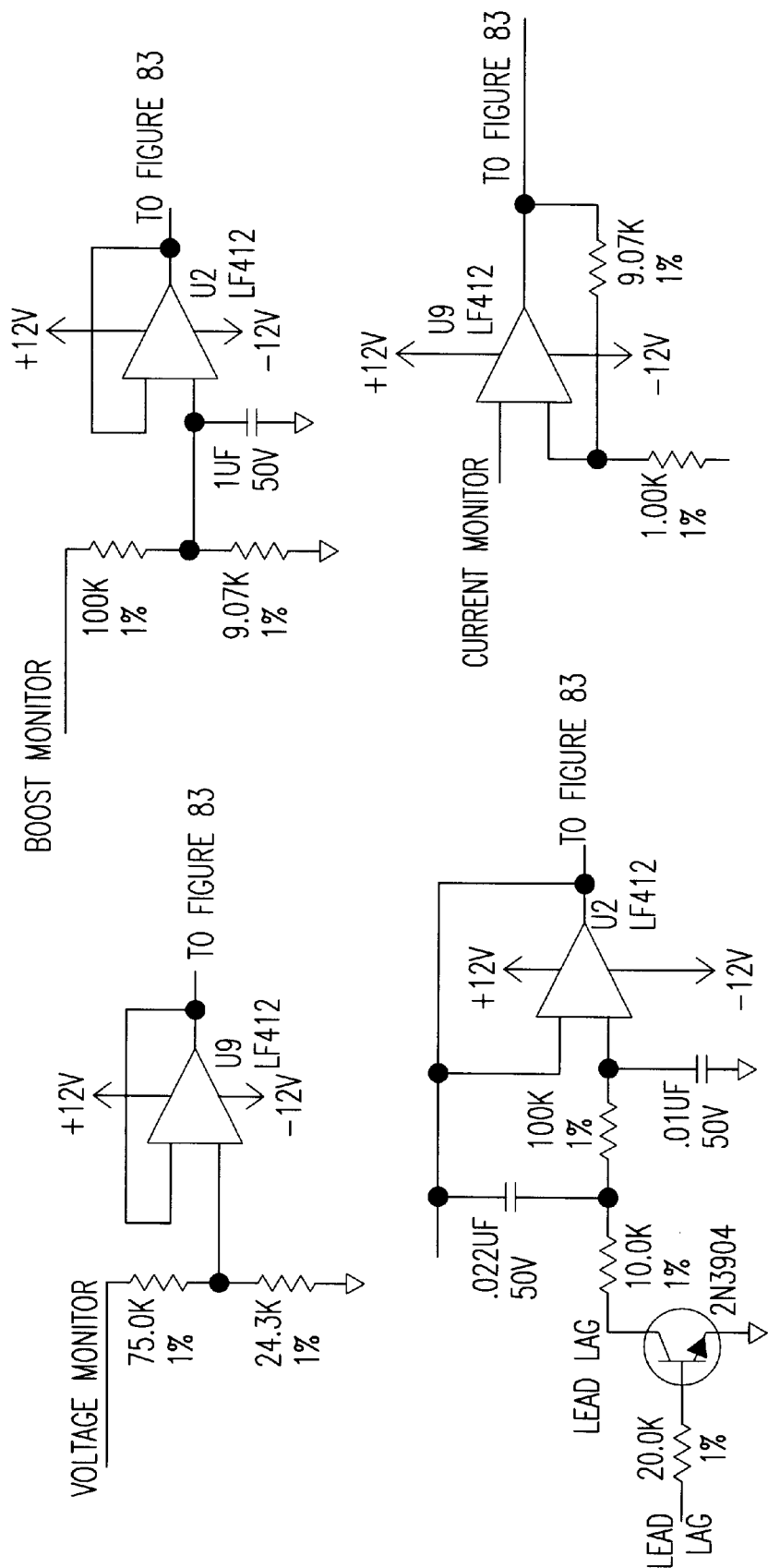
Figure 83:
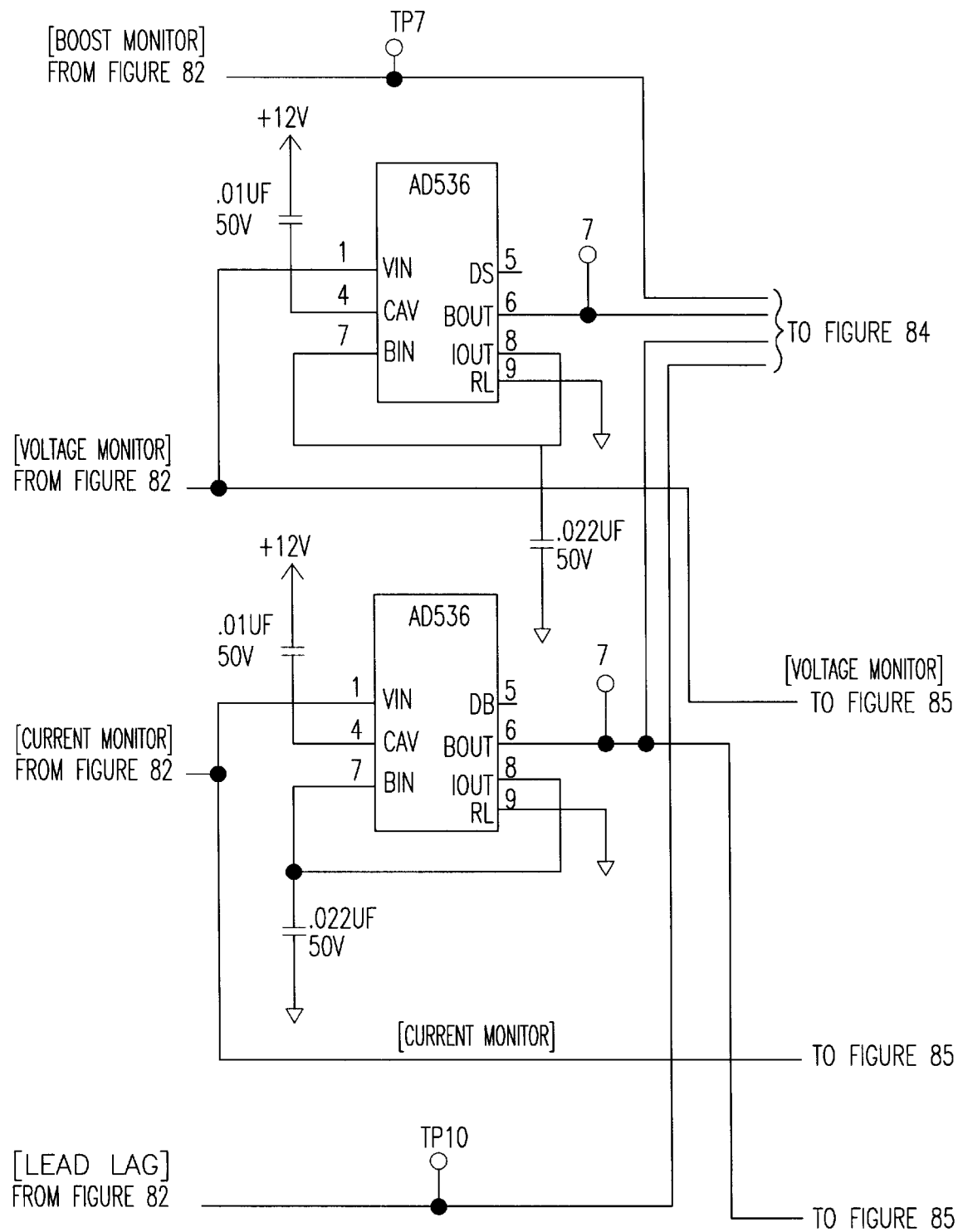
Figure 84:
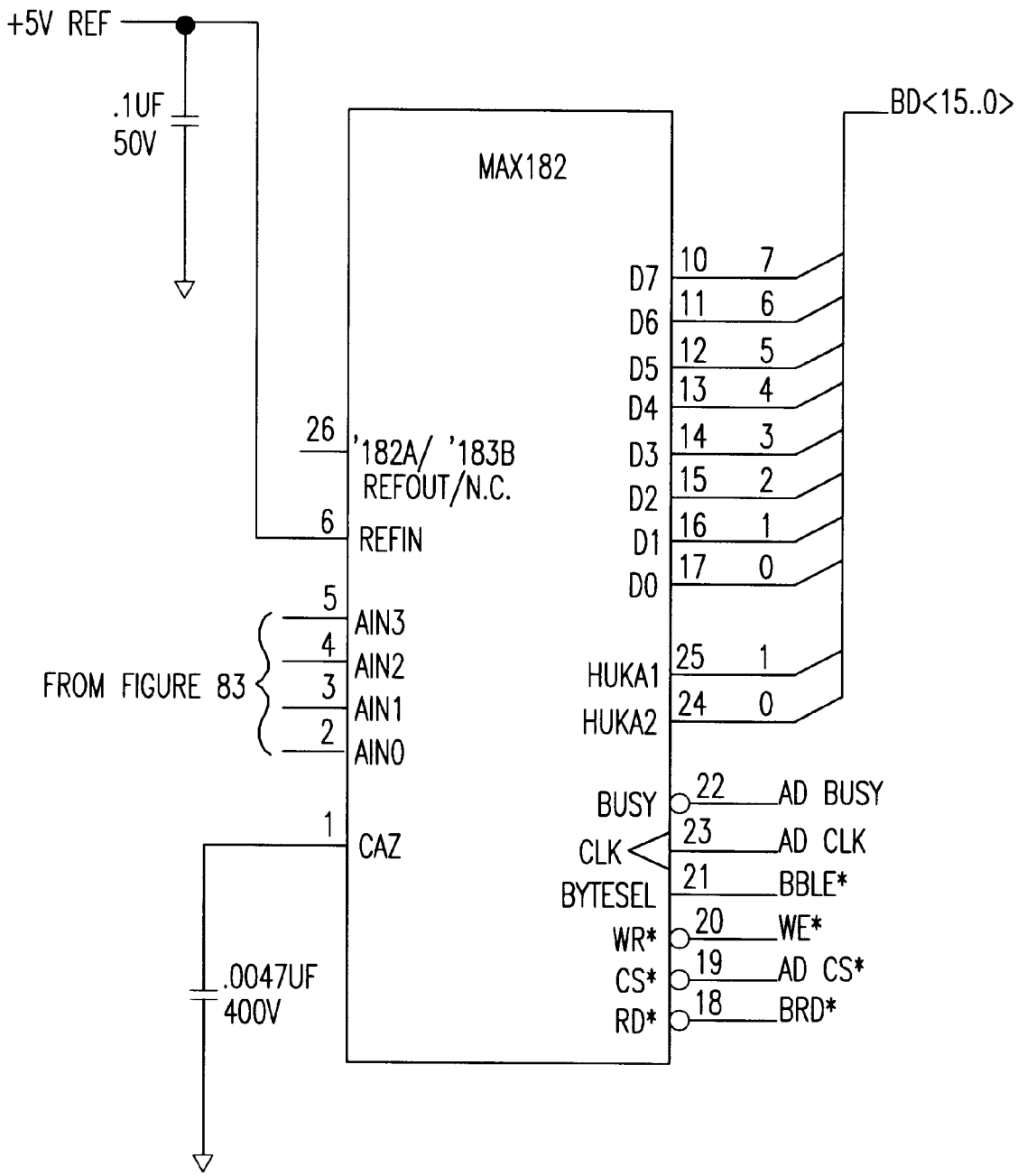
Figure 85:
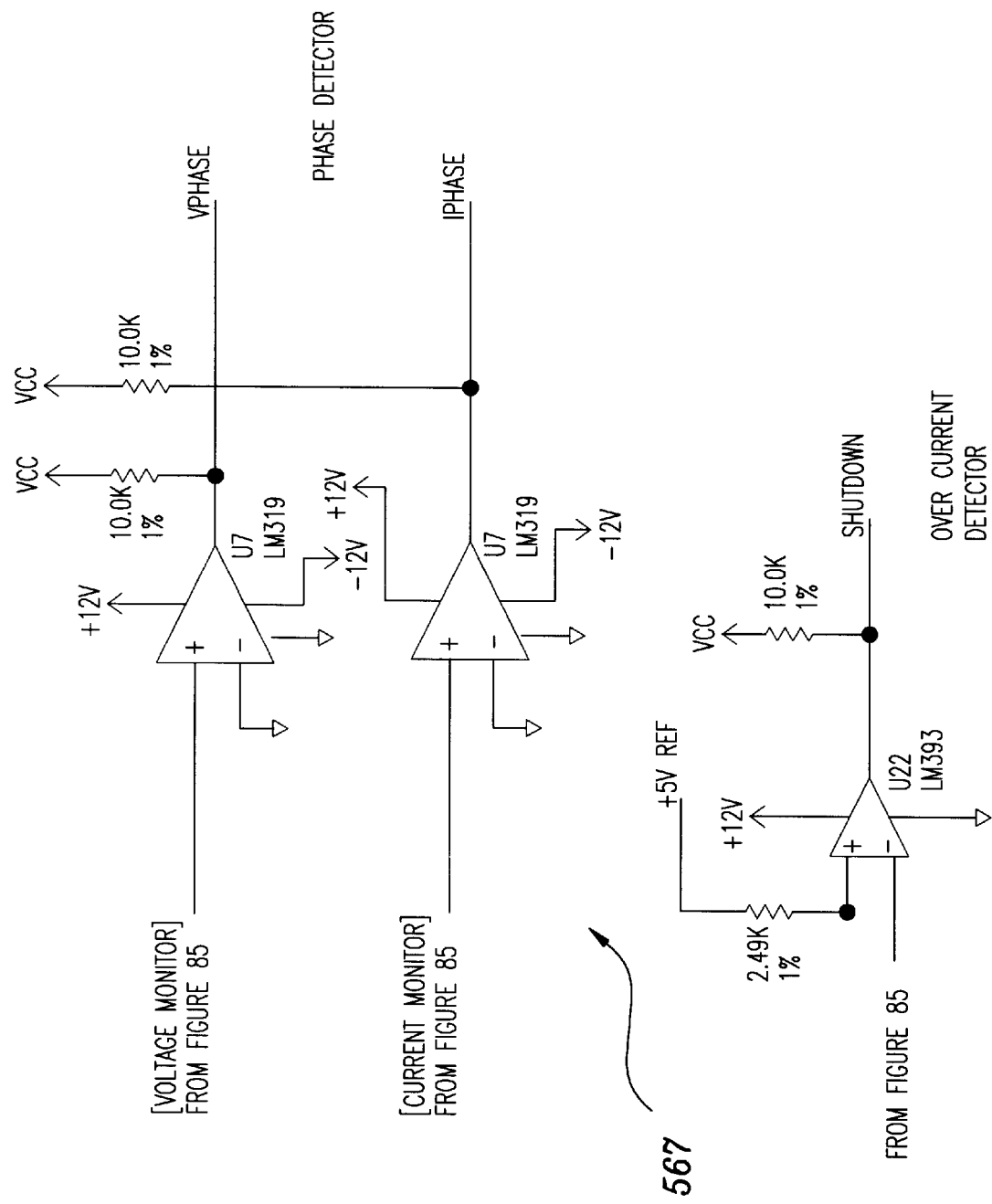
Figure 86:
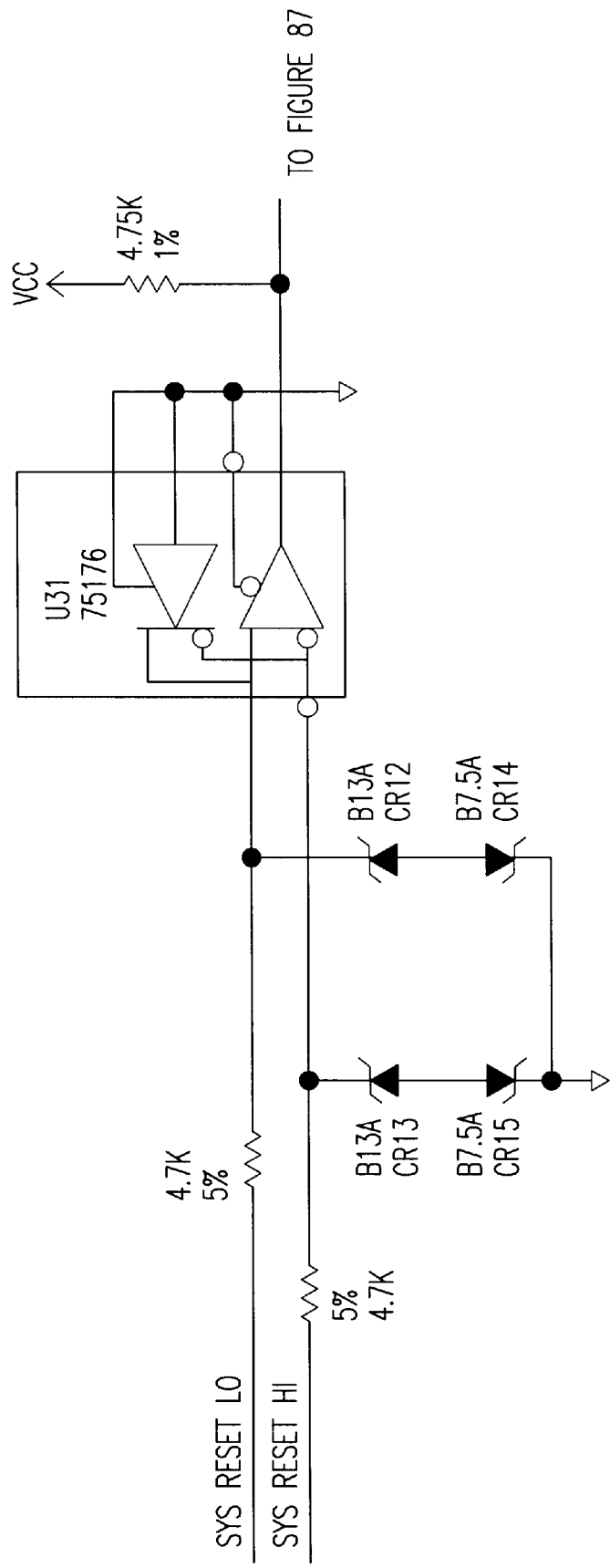
Figure 87:
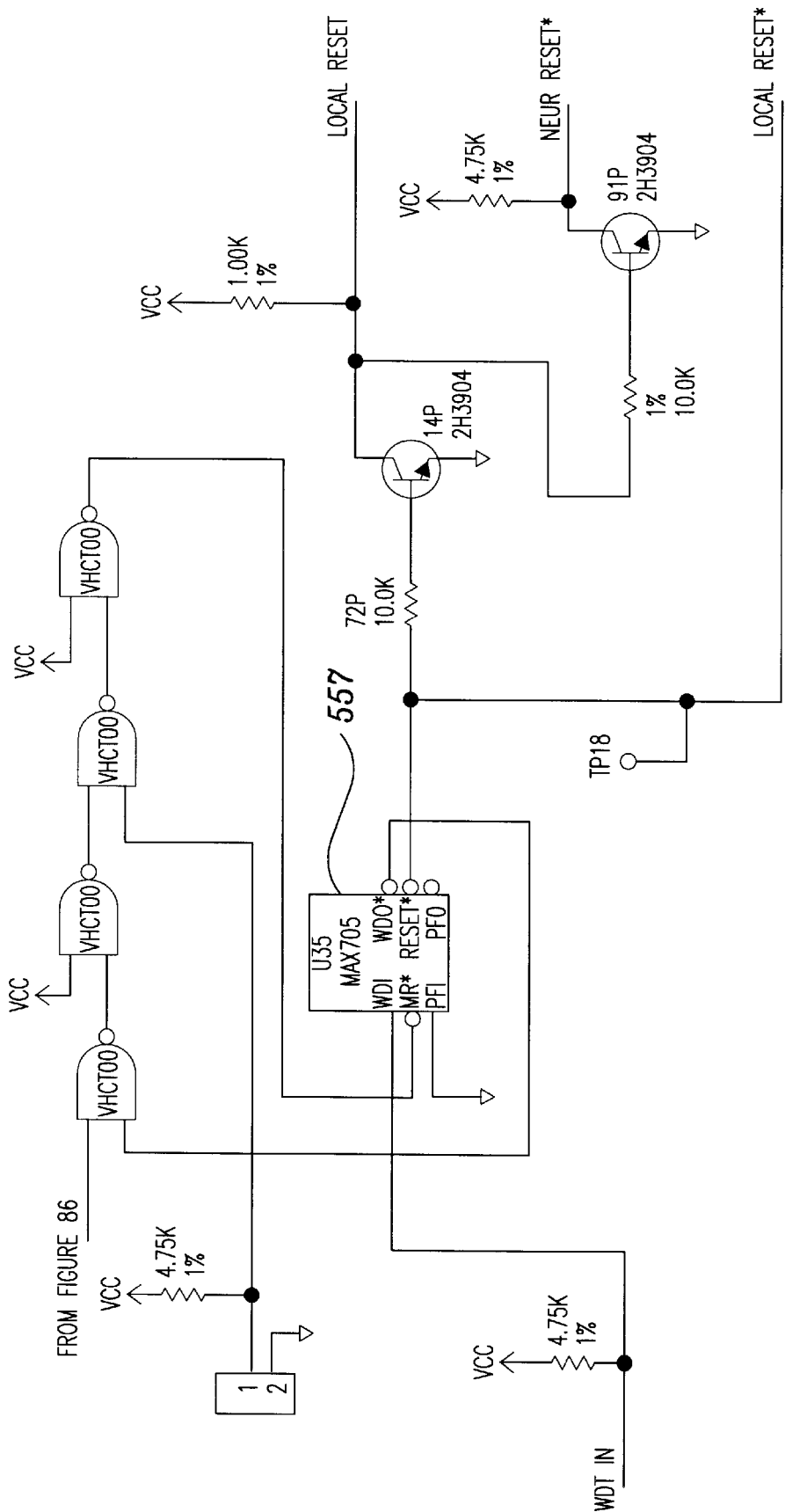
Figure 88:
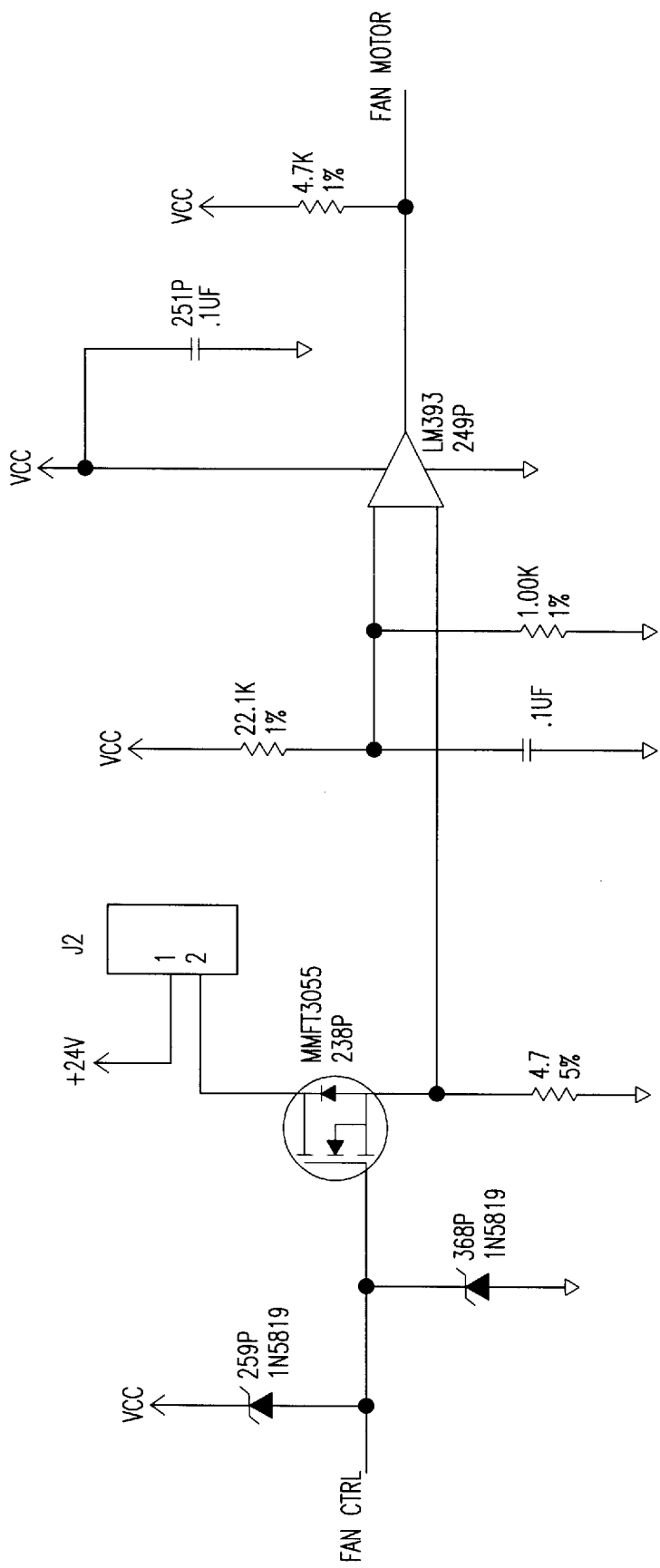
Figure 89:
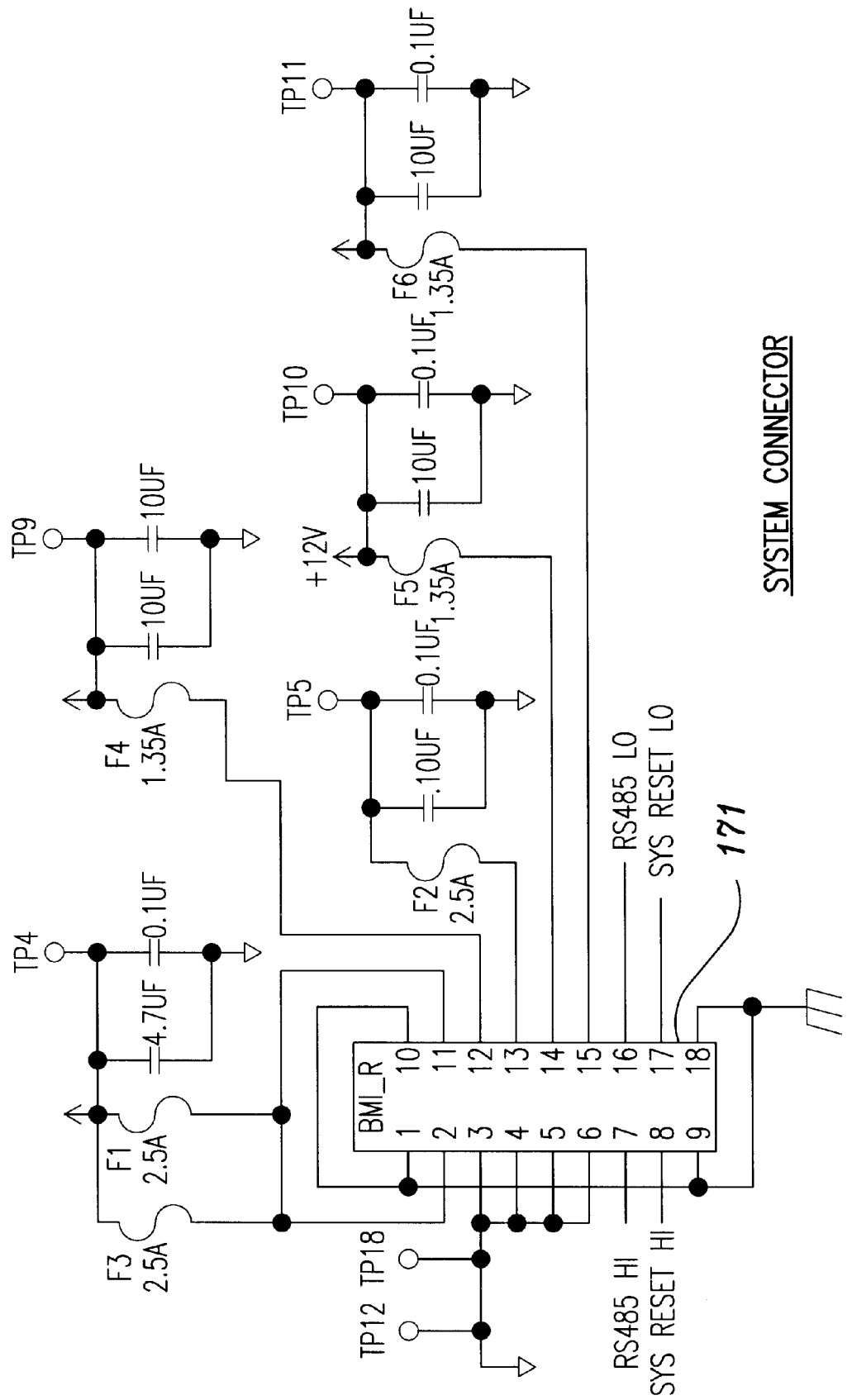
Figure 90:
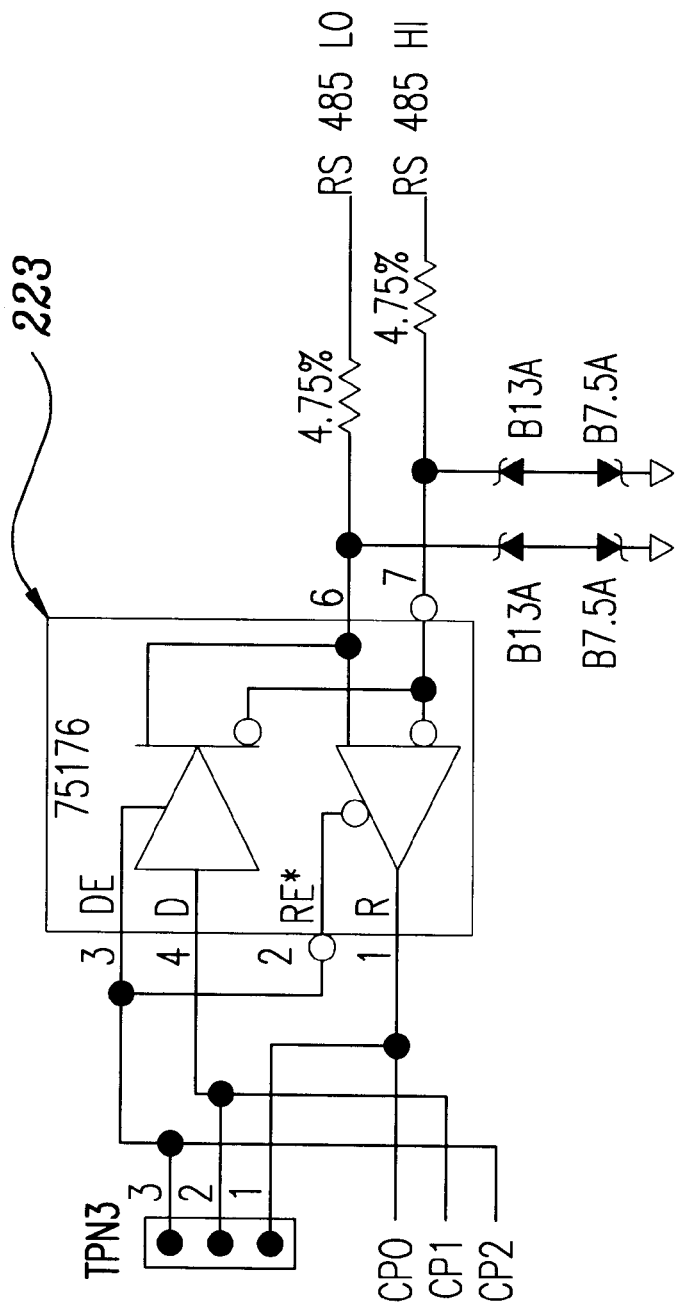
Figure 91:
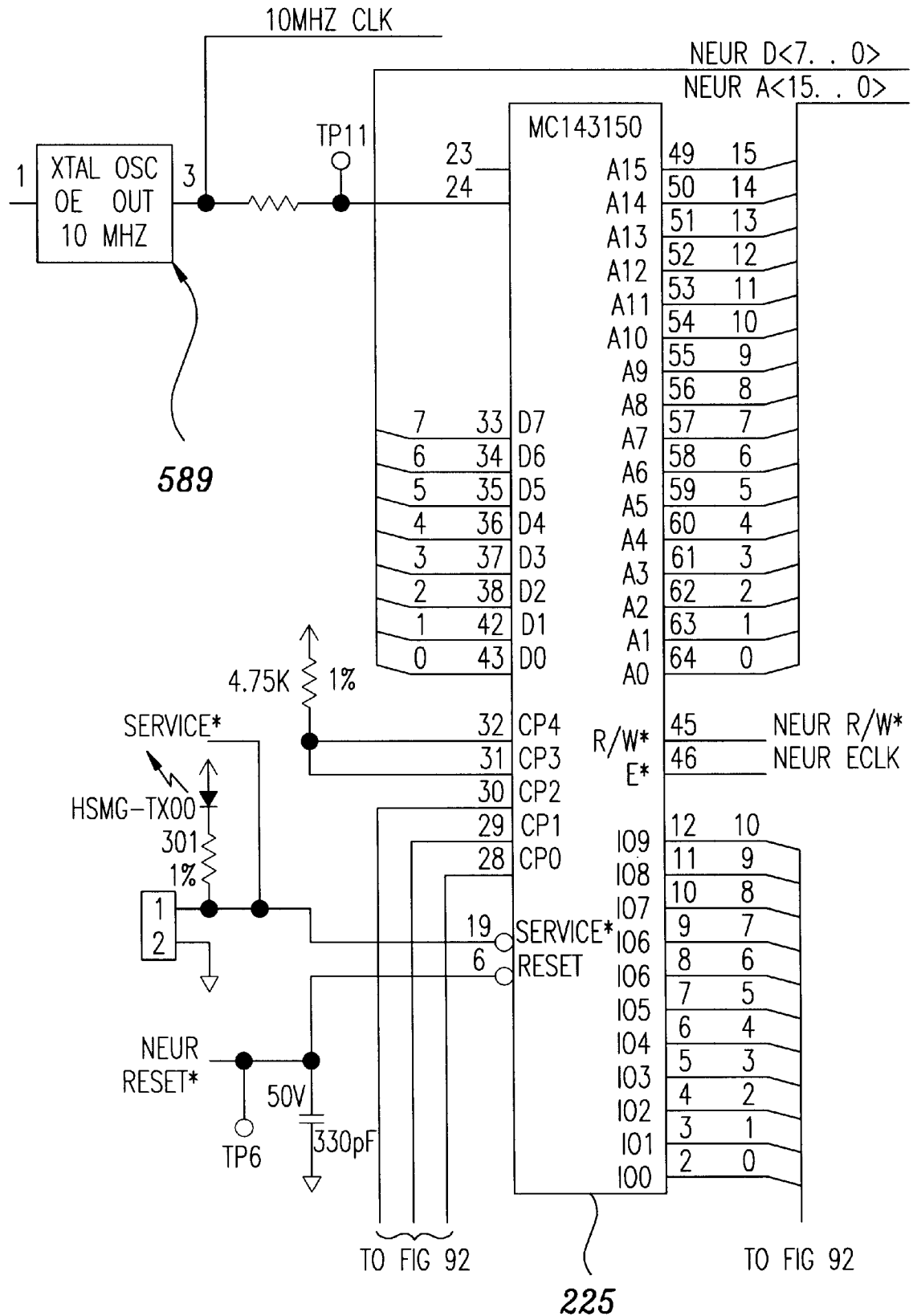
Figure 93:
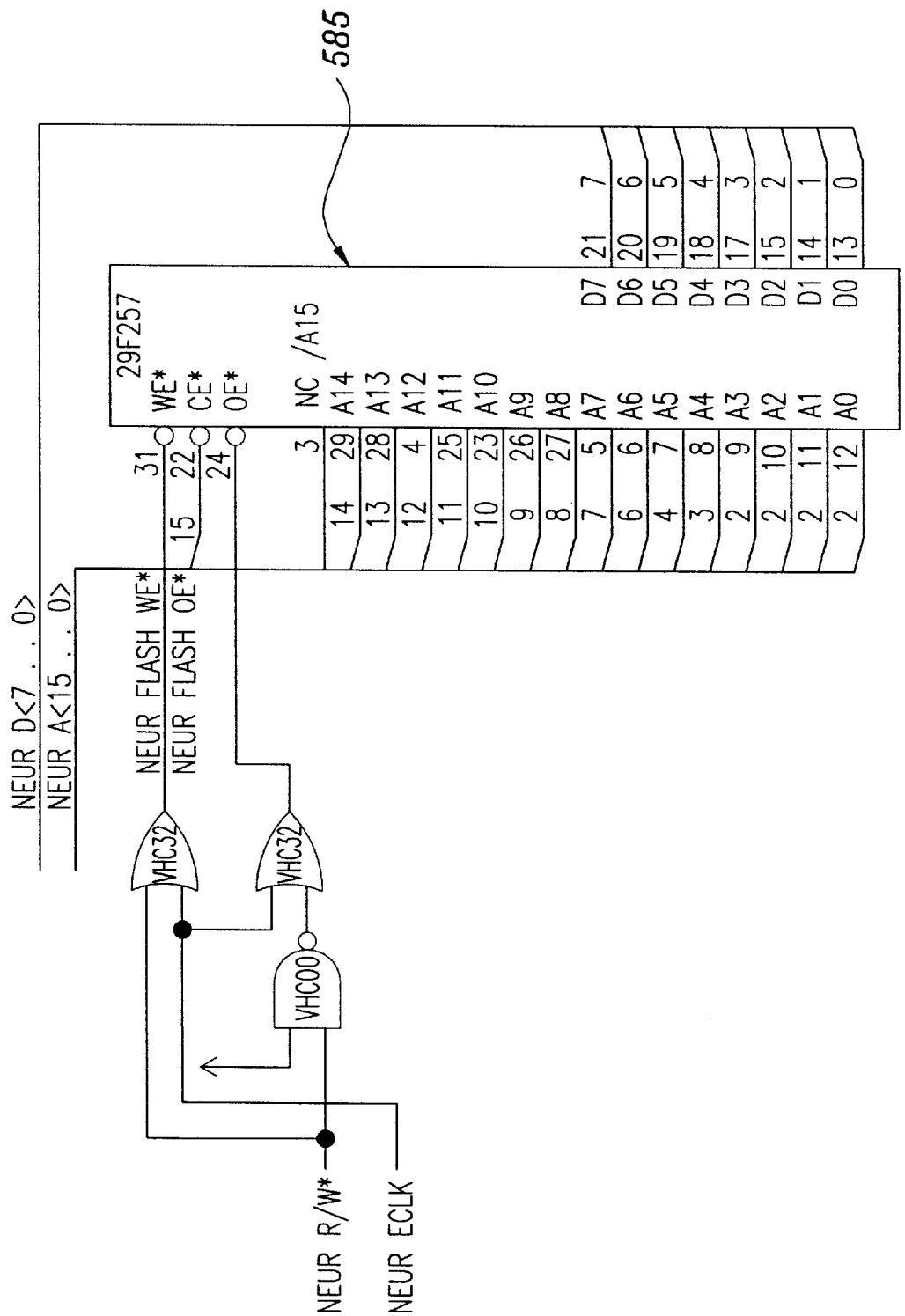
Figure 94:
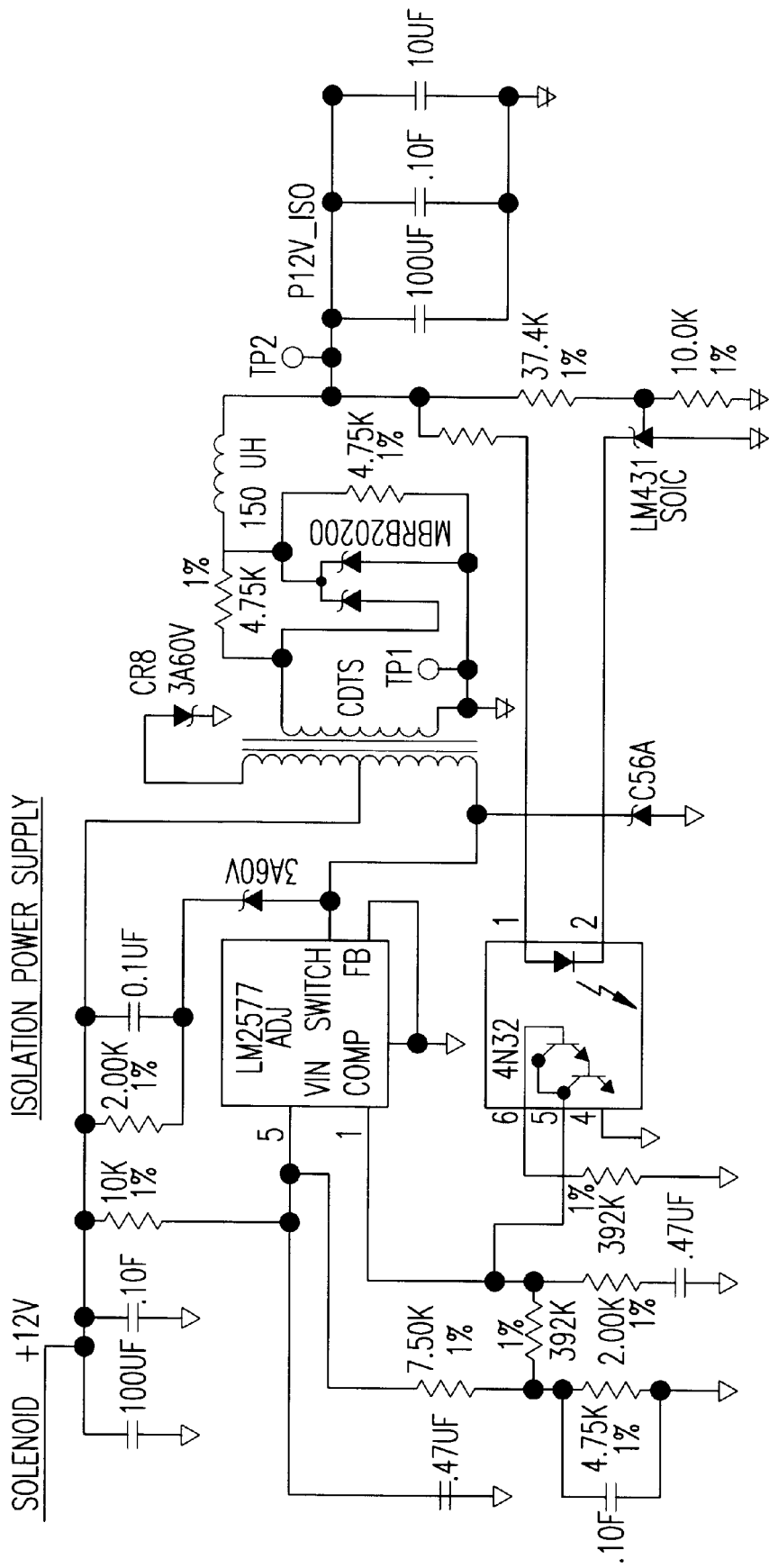
Figure 95:
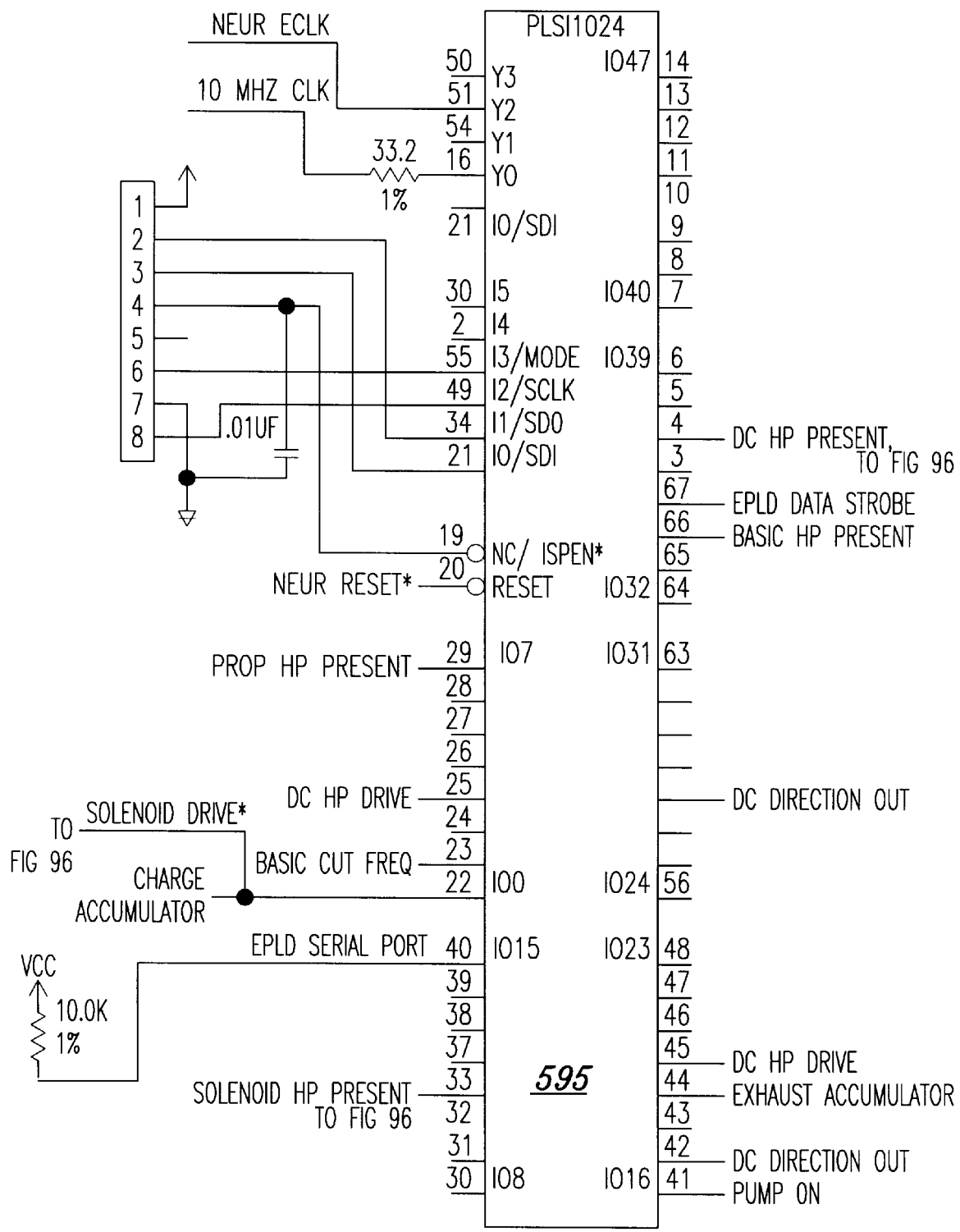
Figure 96:
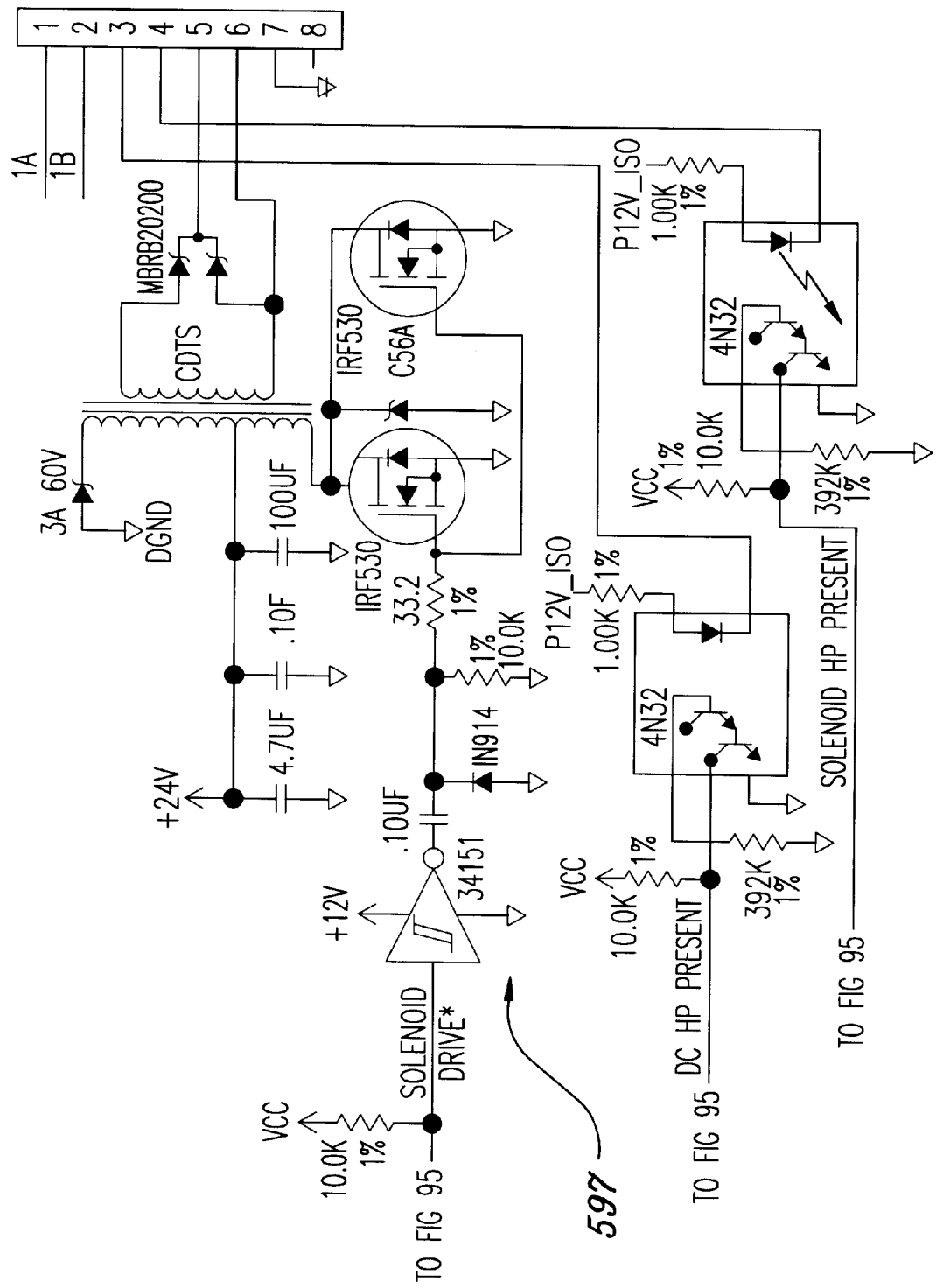
Figure 97:
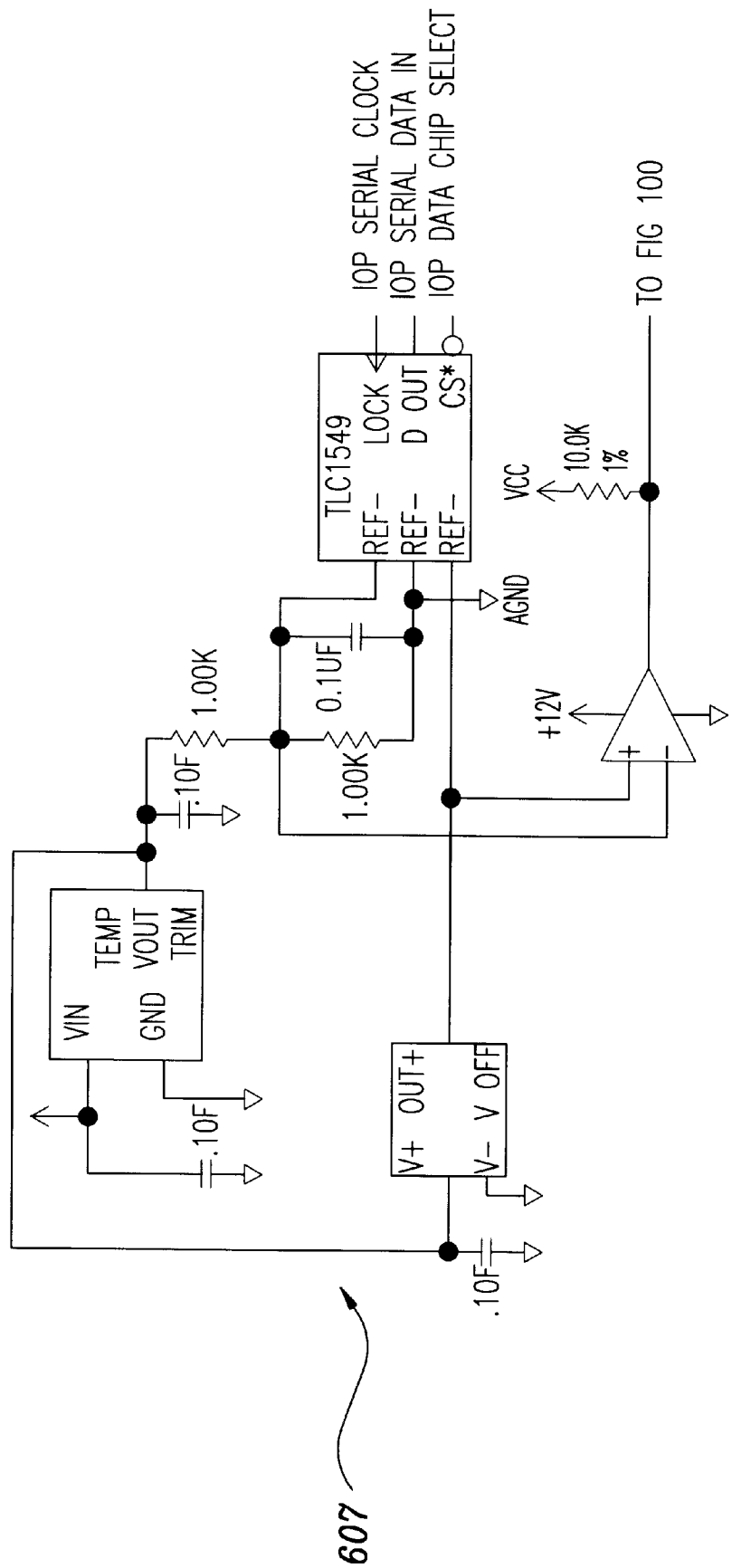
Figure 98:
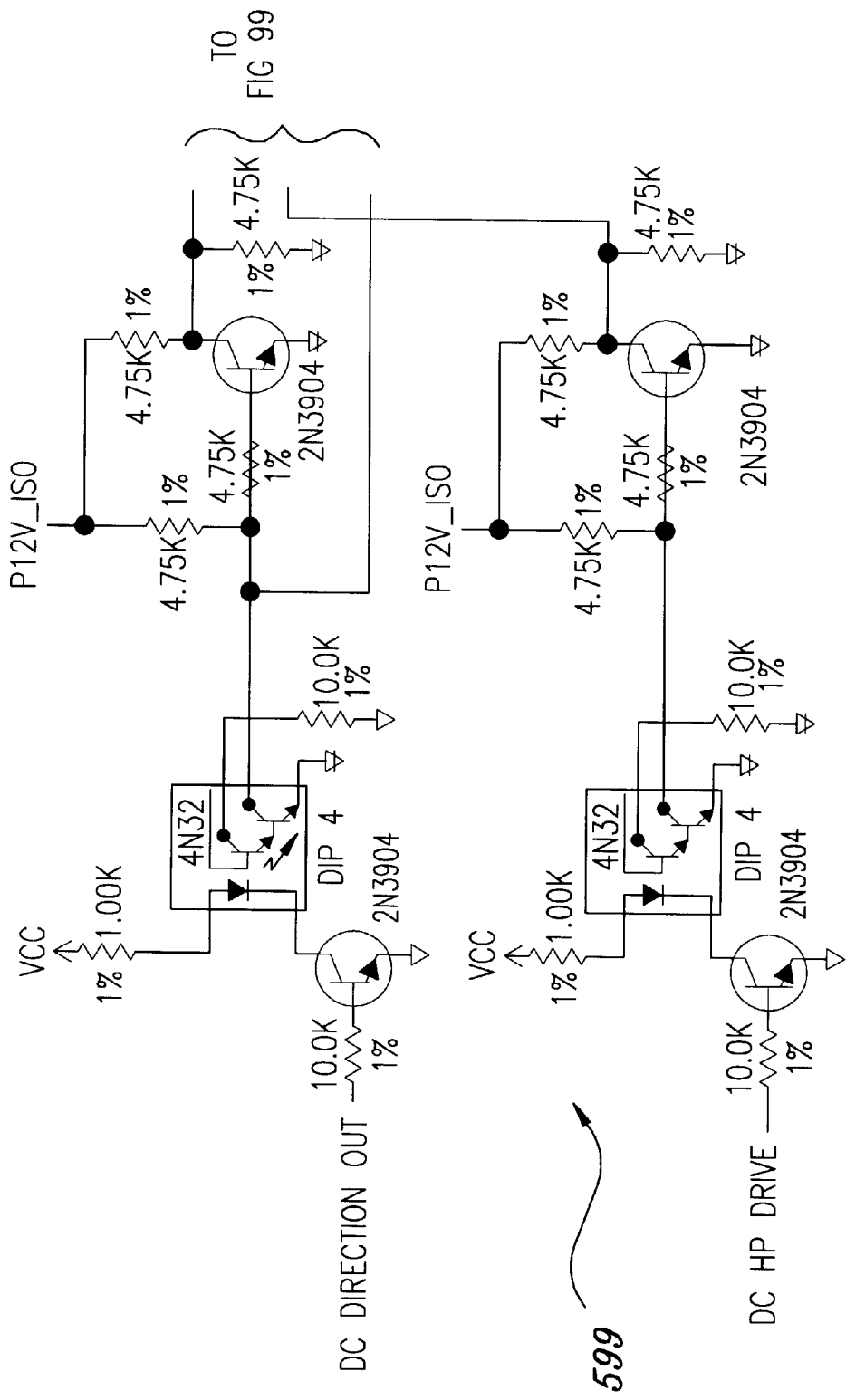
Figure 99:
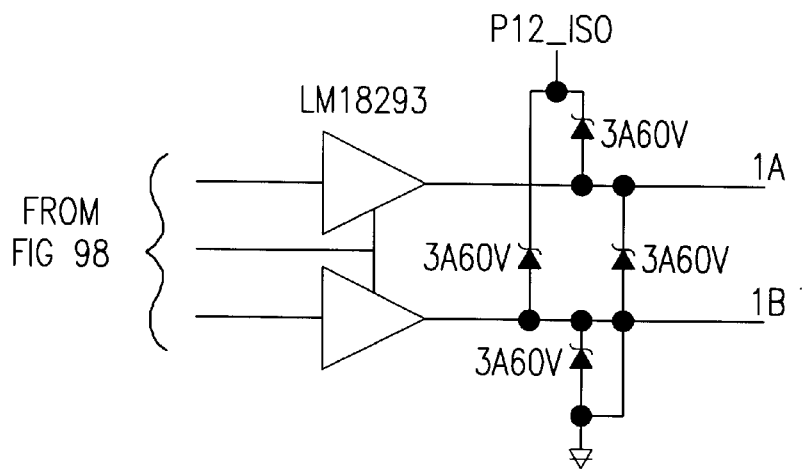
Figure 100:
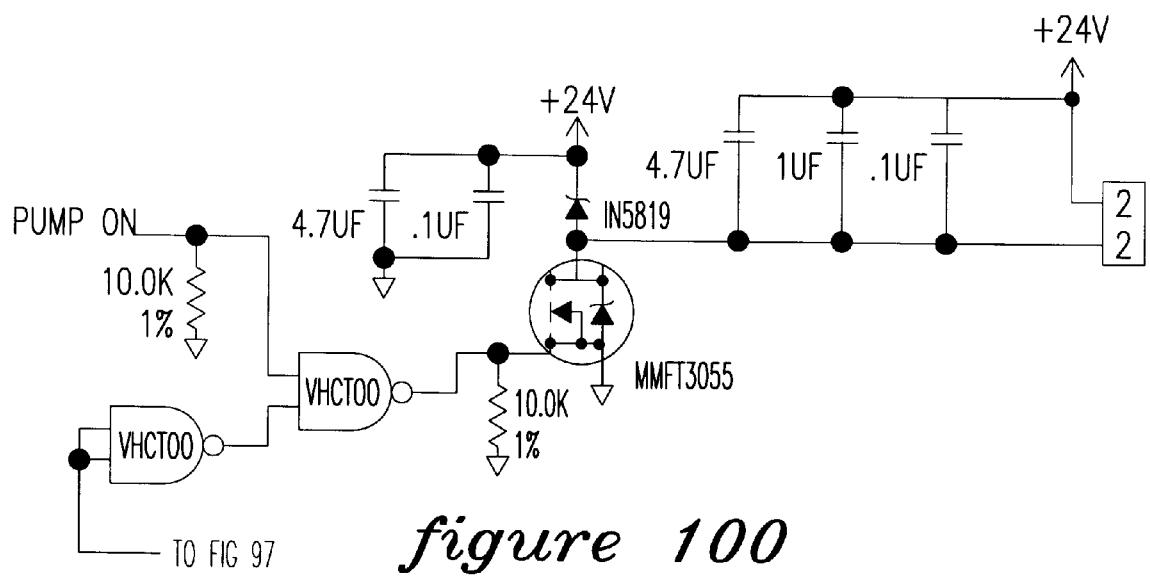
Figure 101:
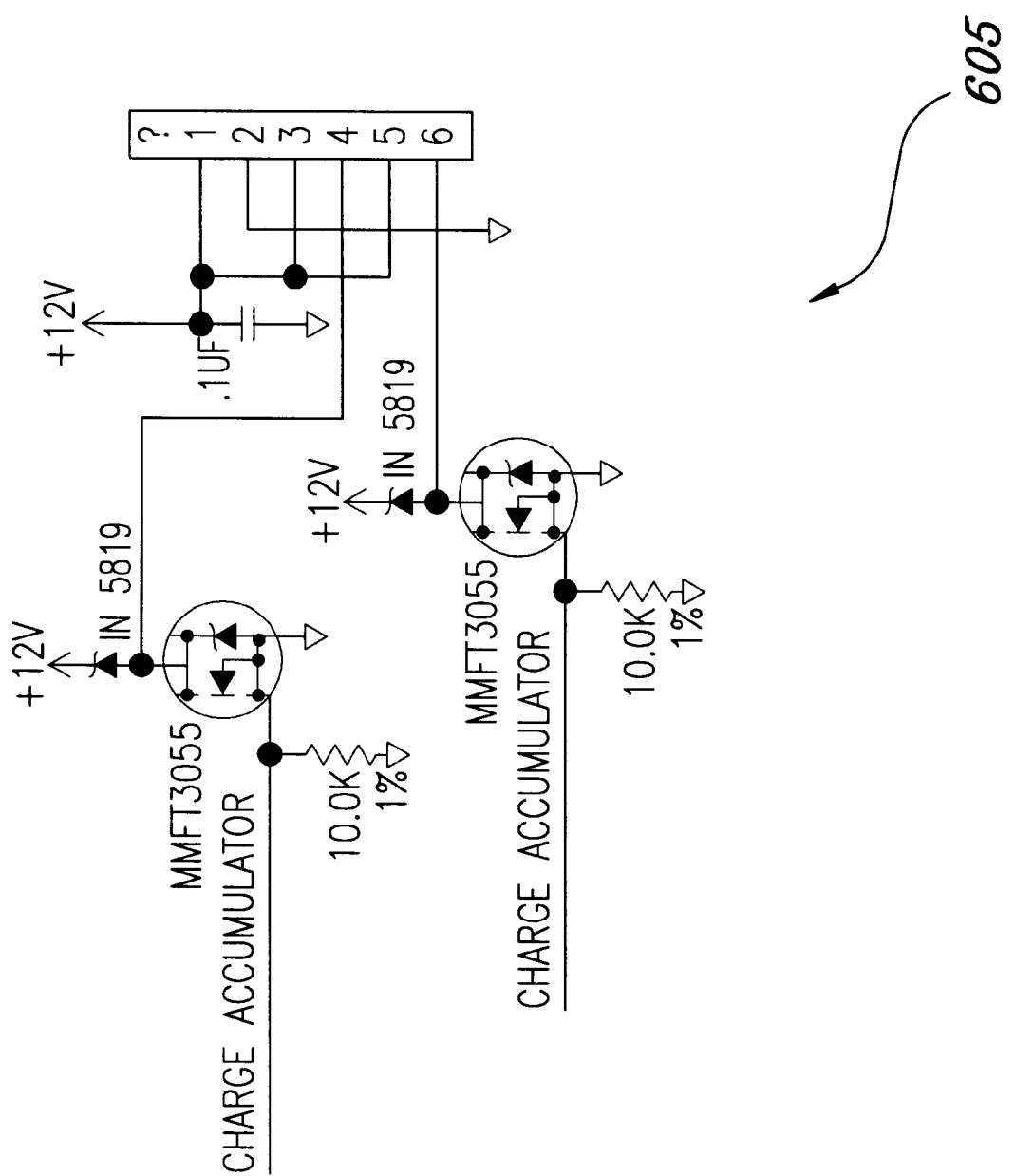
Figure 102:
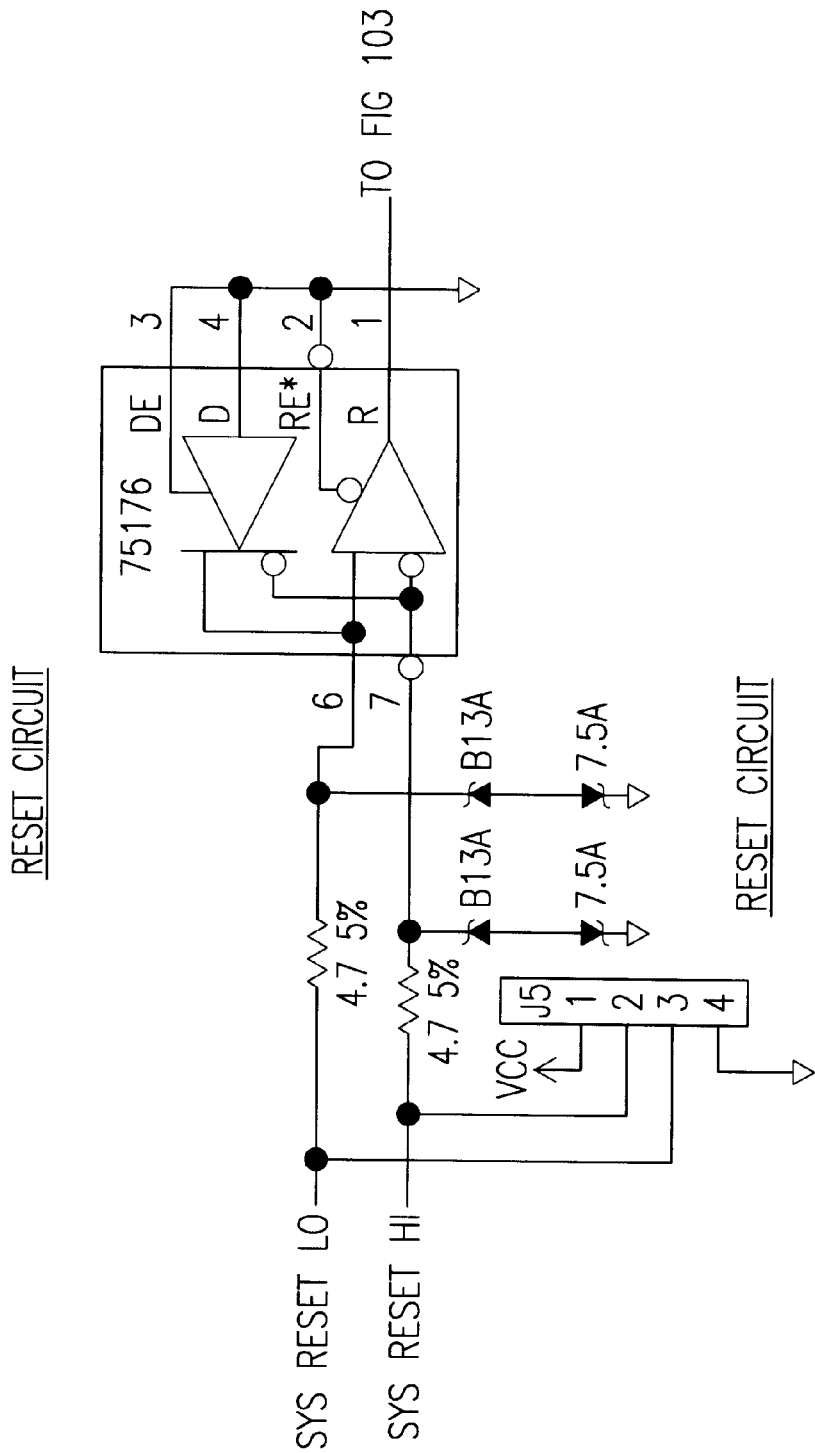
Figure 103:
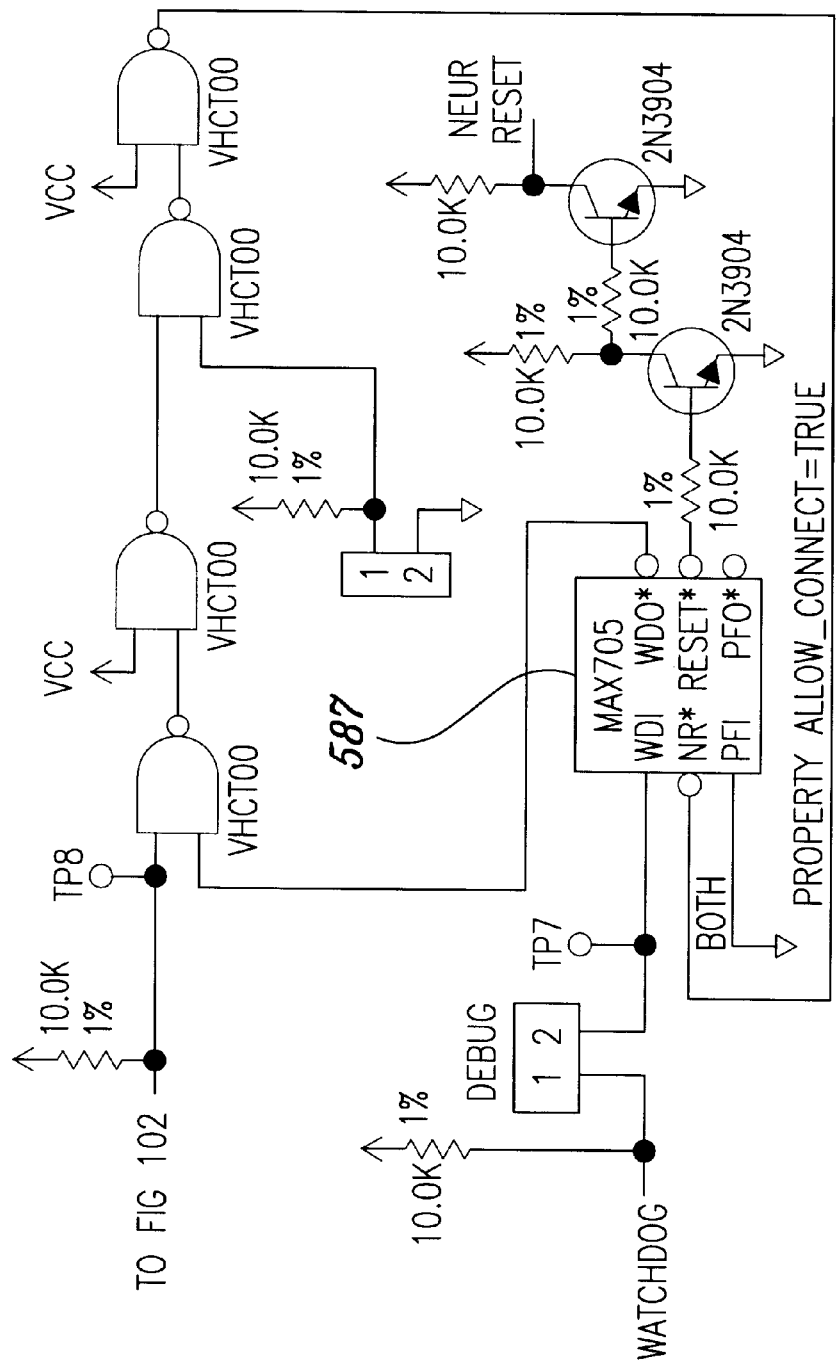
Figure 104:
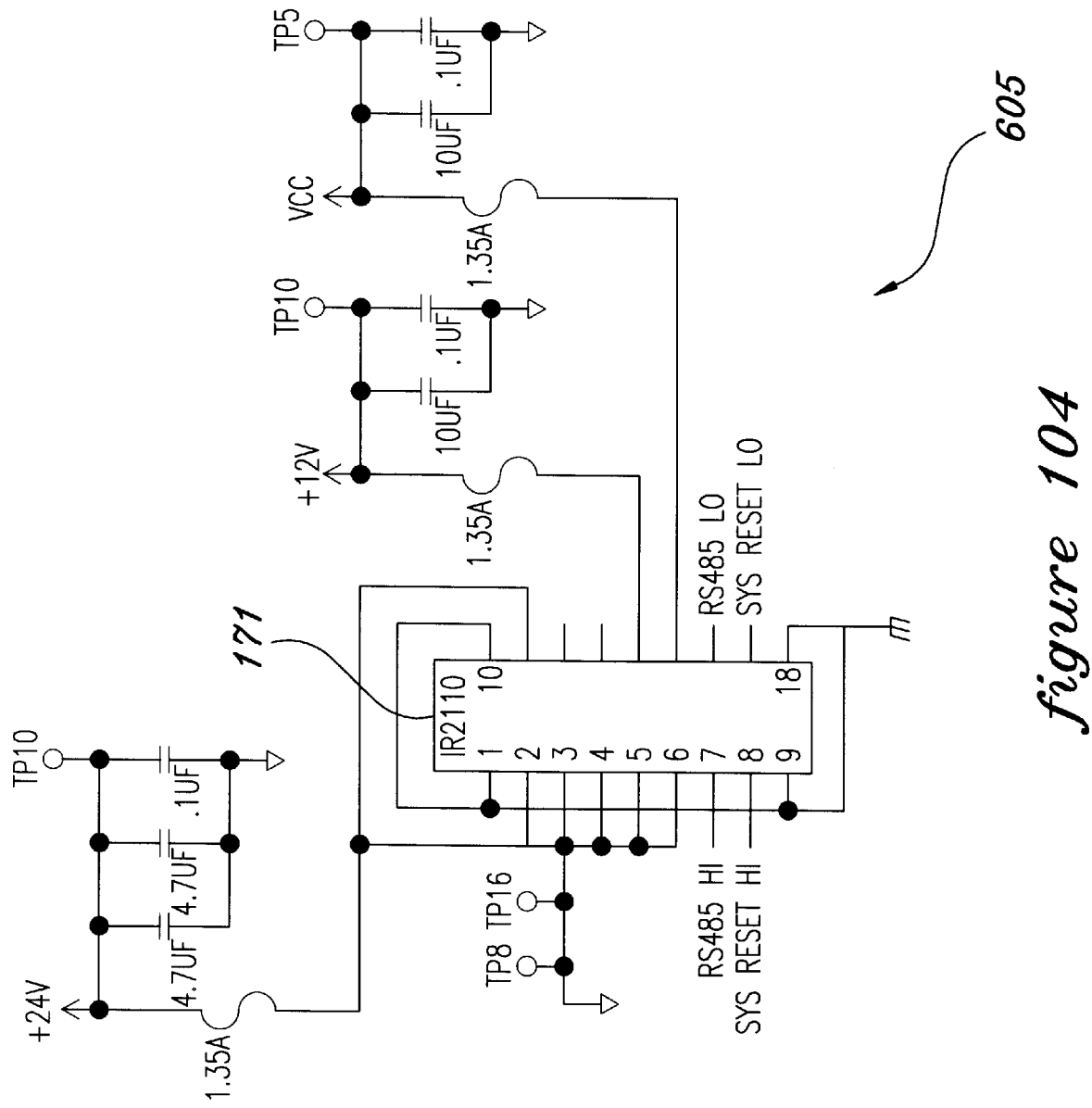
FIGS. 104–113 are schematic diagrams illustrating the bipolar coagulation module of FIG. 19.
Figure 105:
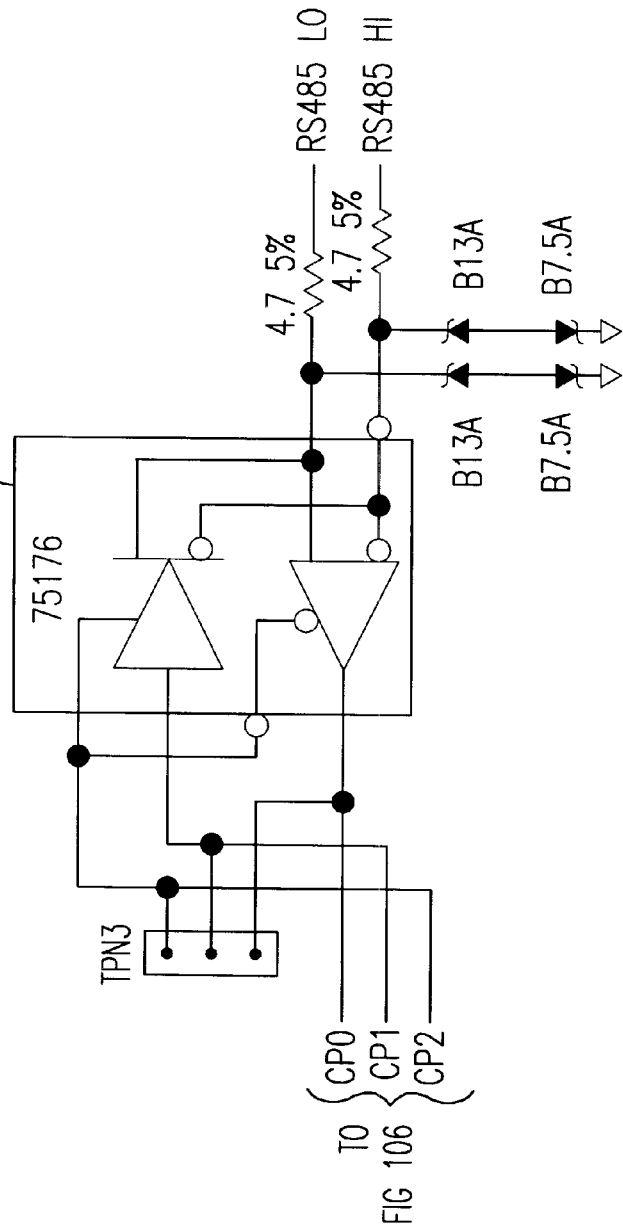
Figure 106:
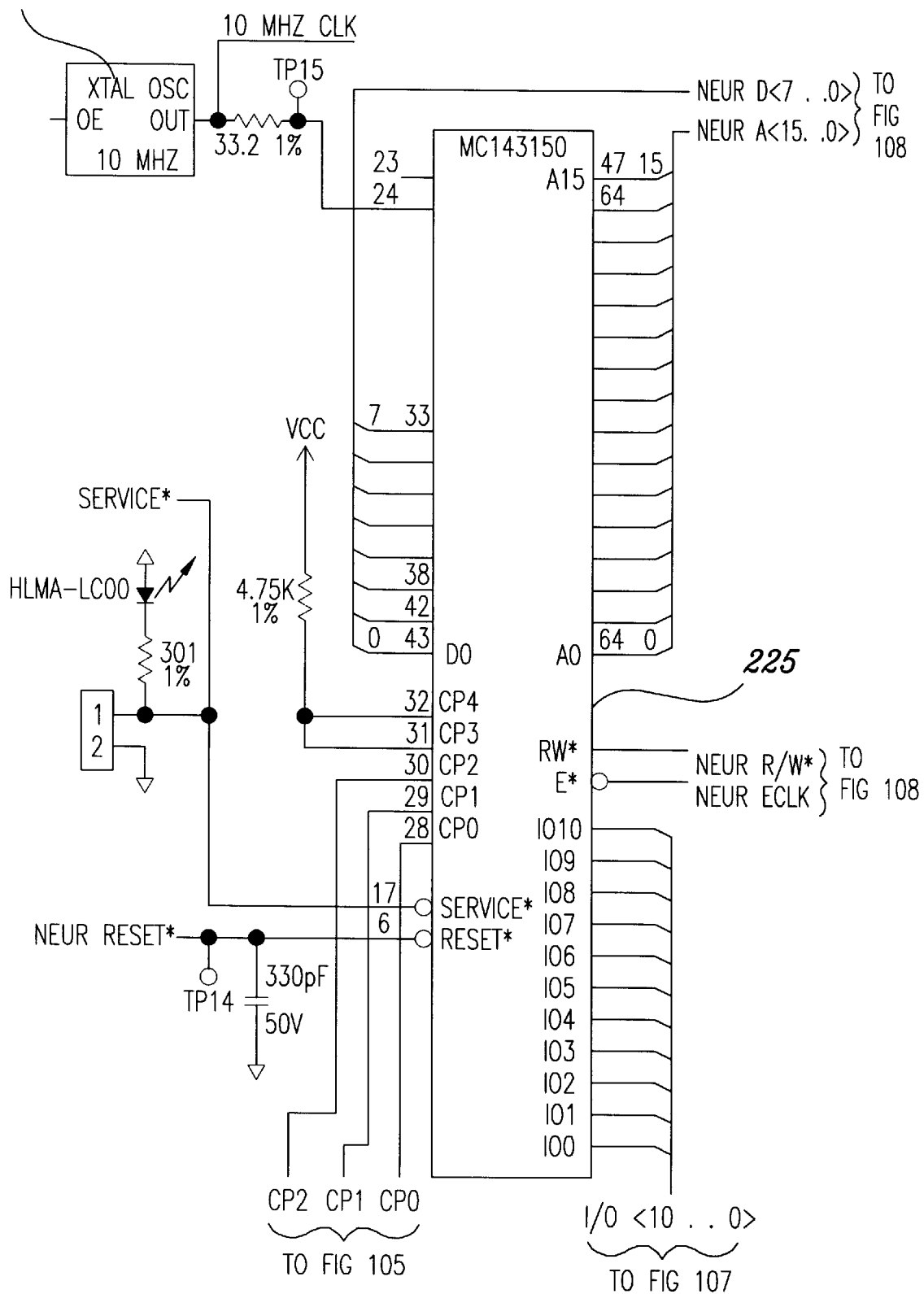
Figure 107:
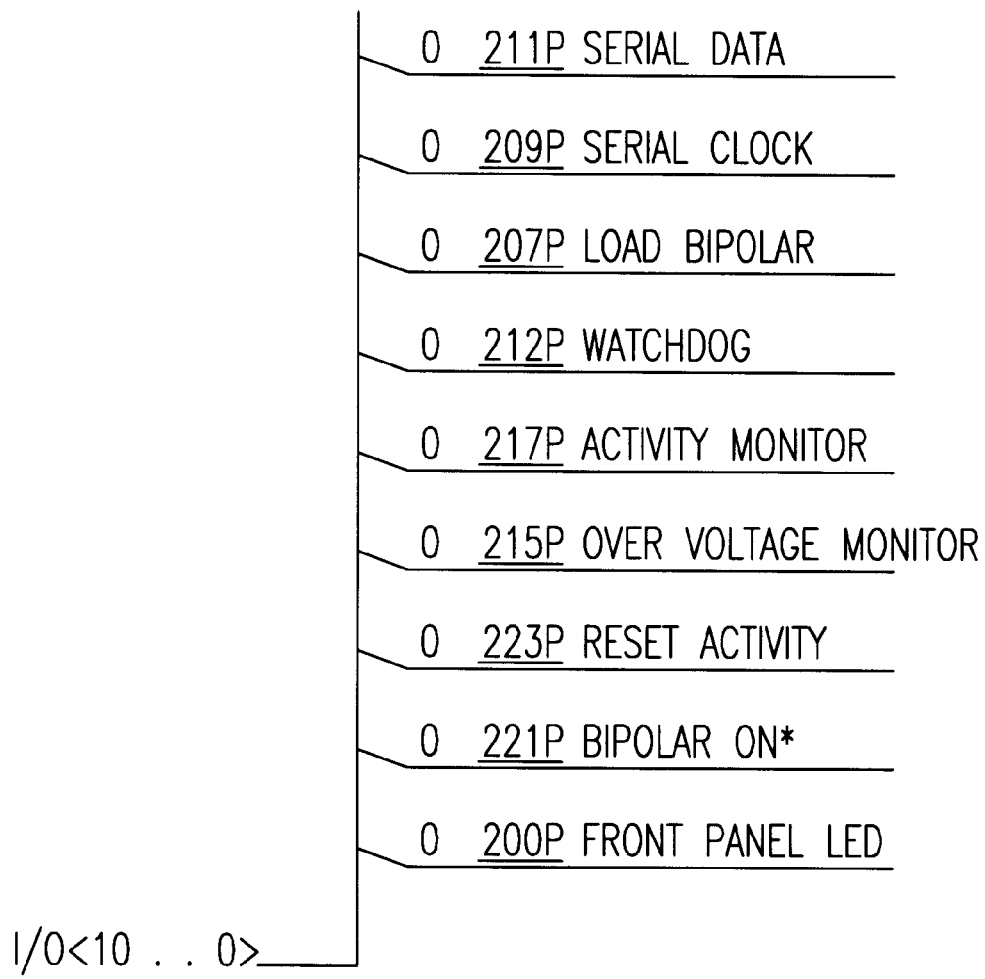
Figure 108:
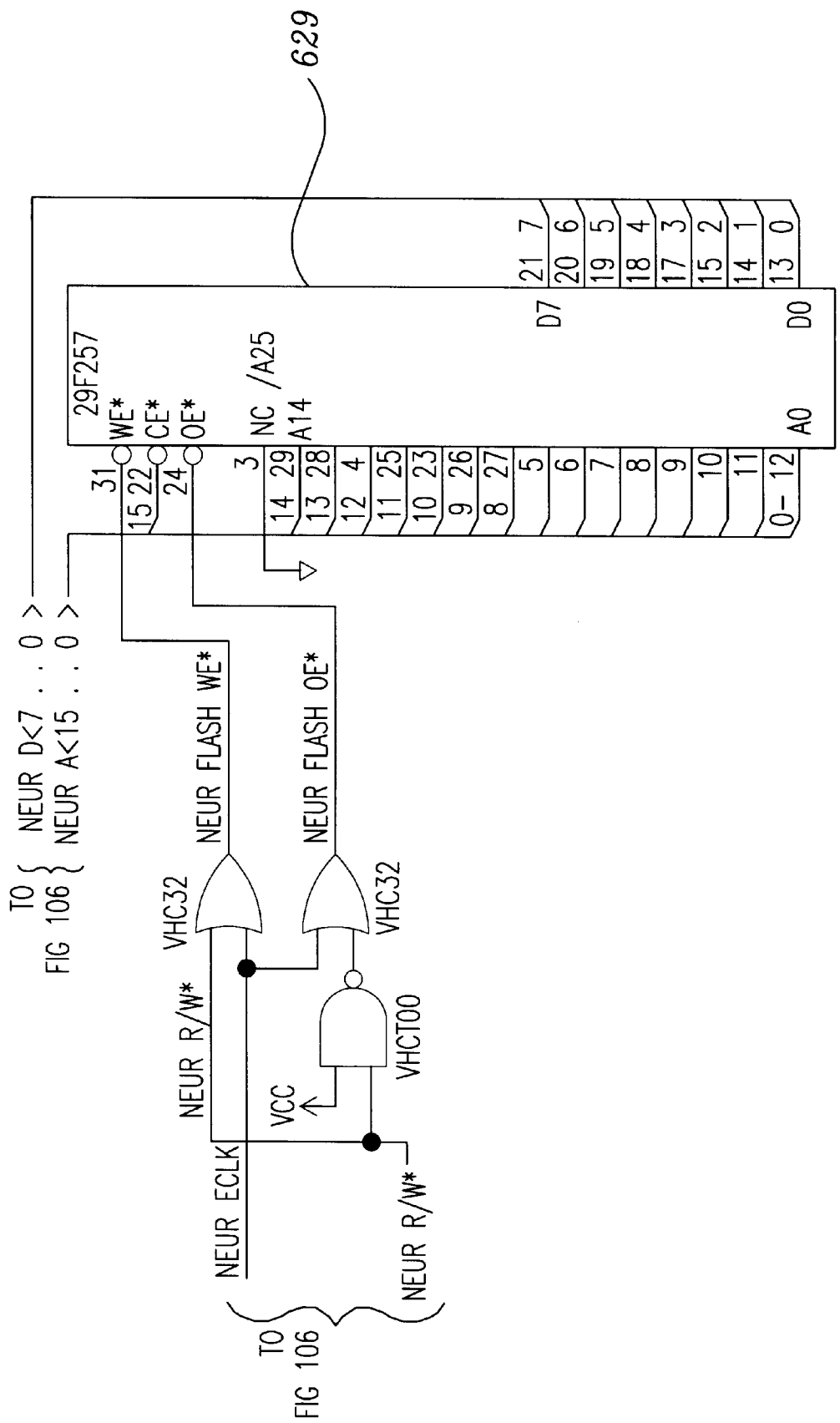
Figure 109:
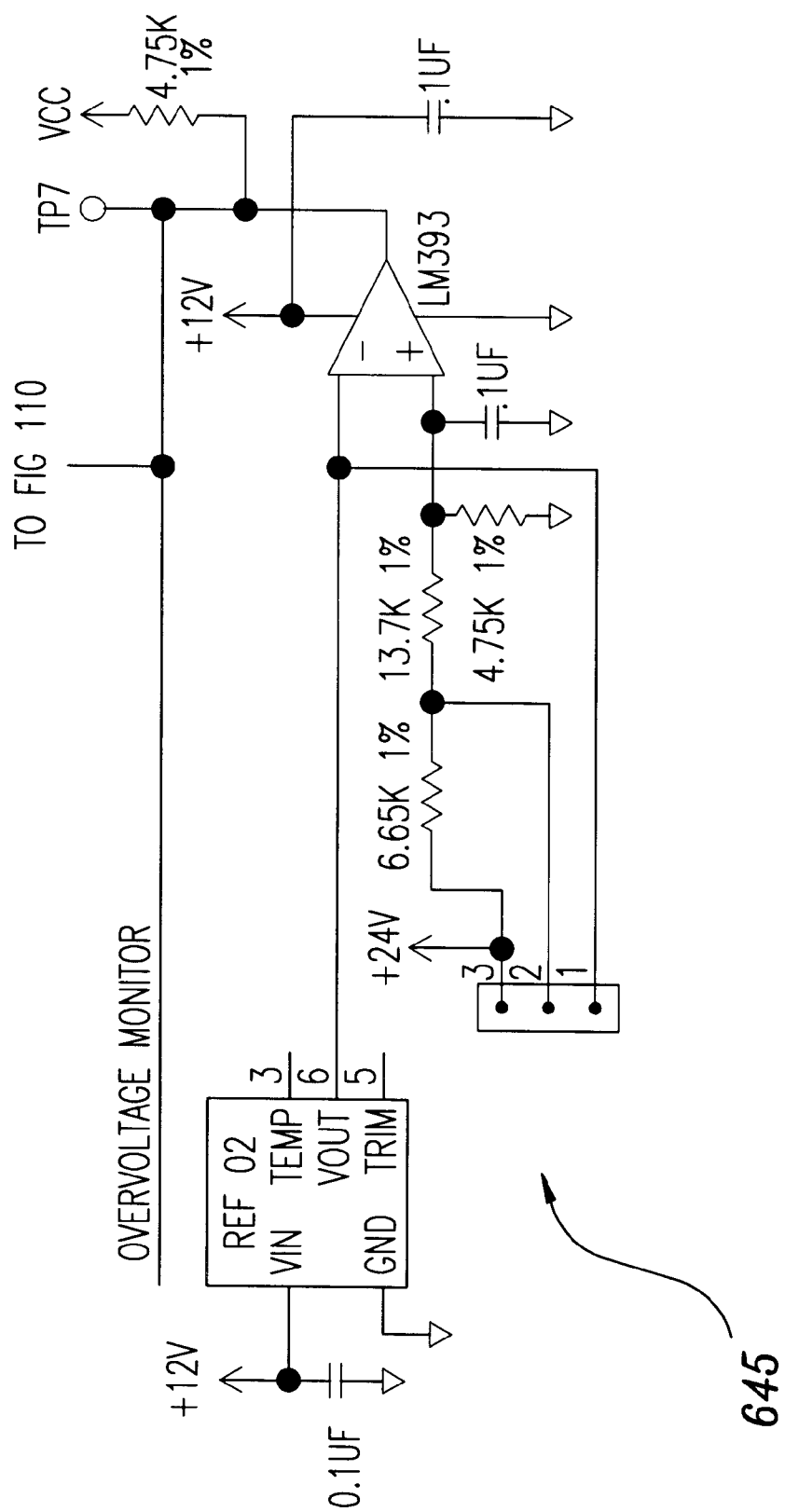
Figure 110:
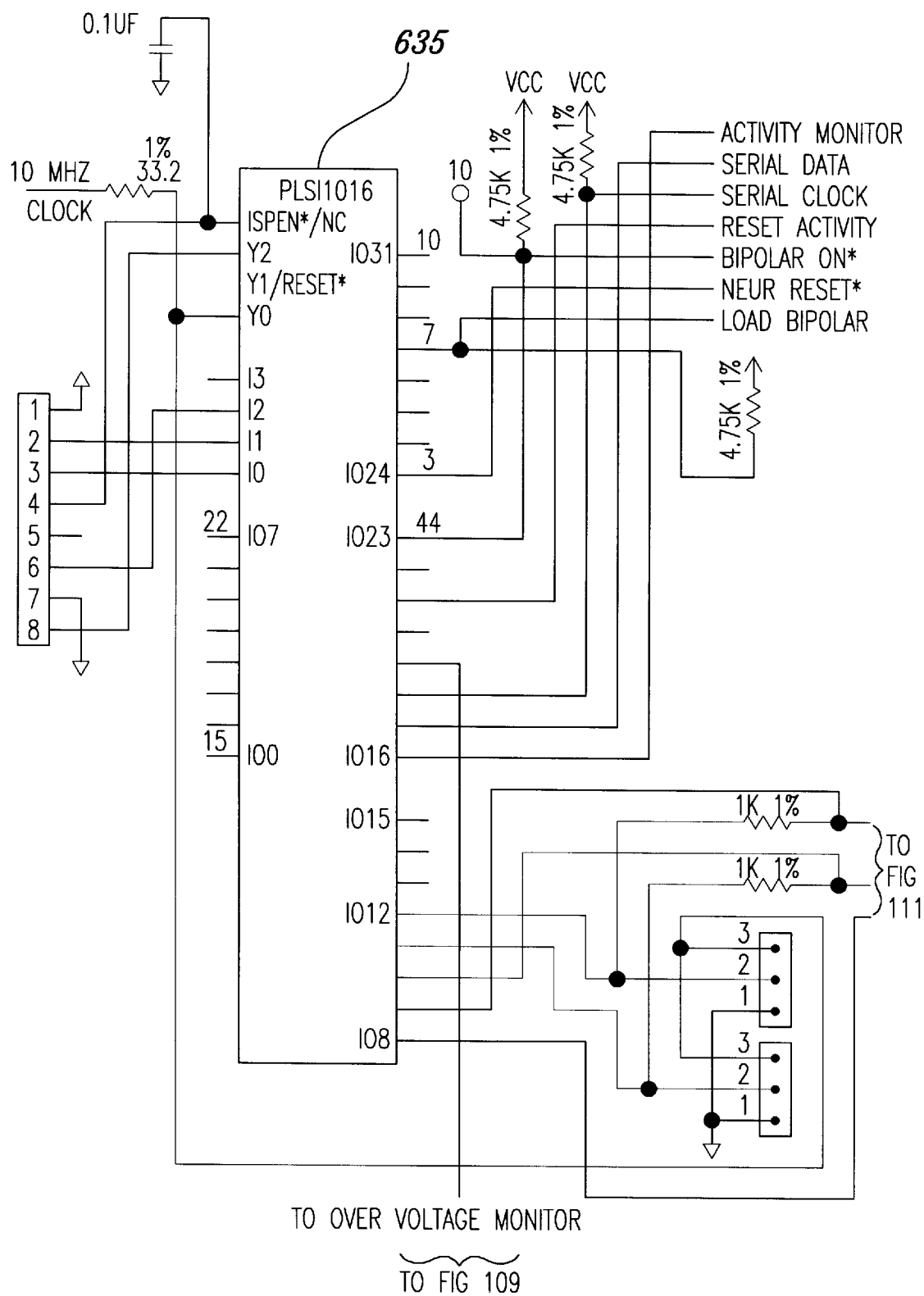
Figure 111:
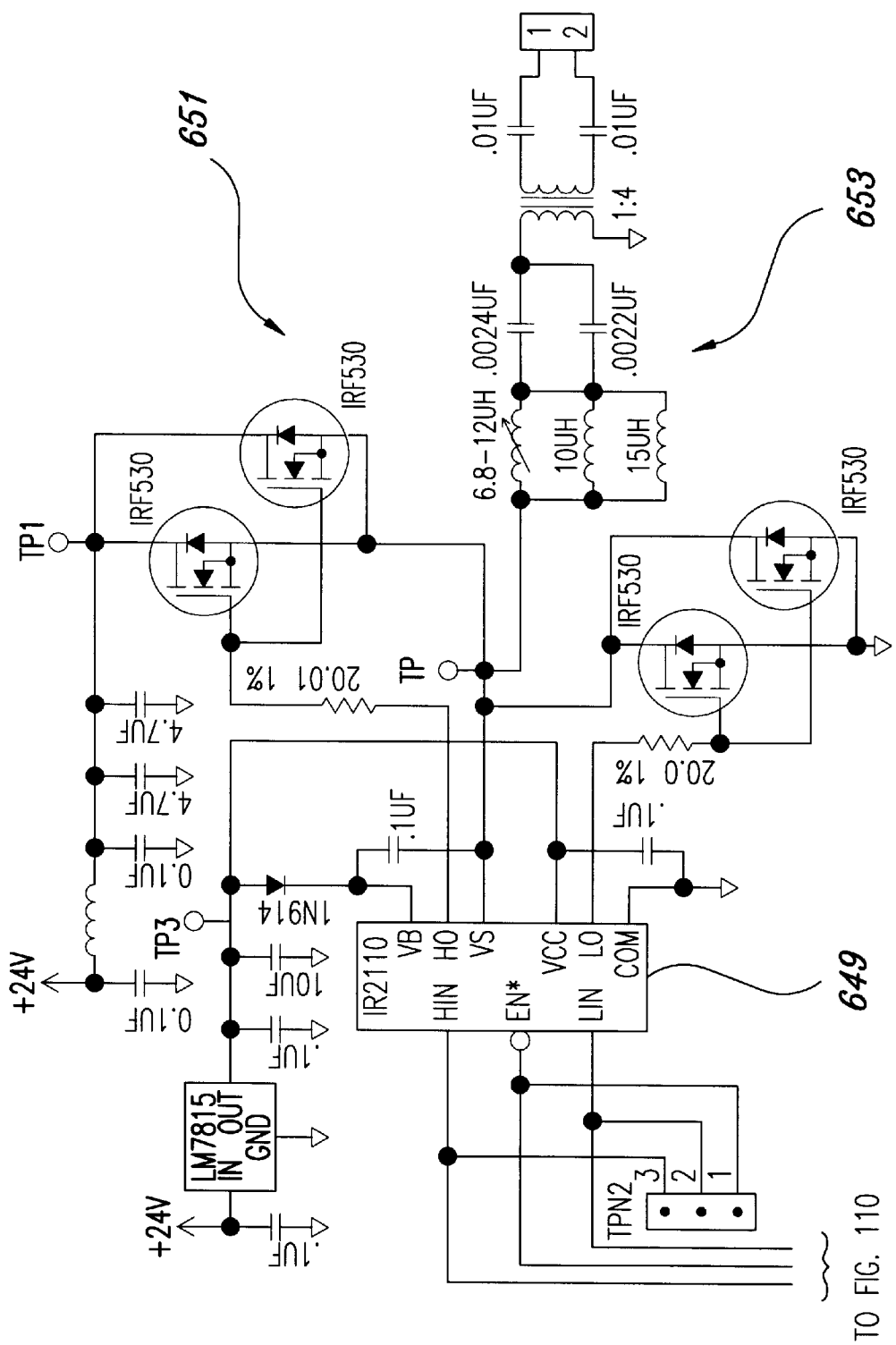
Figure 112:
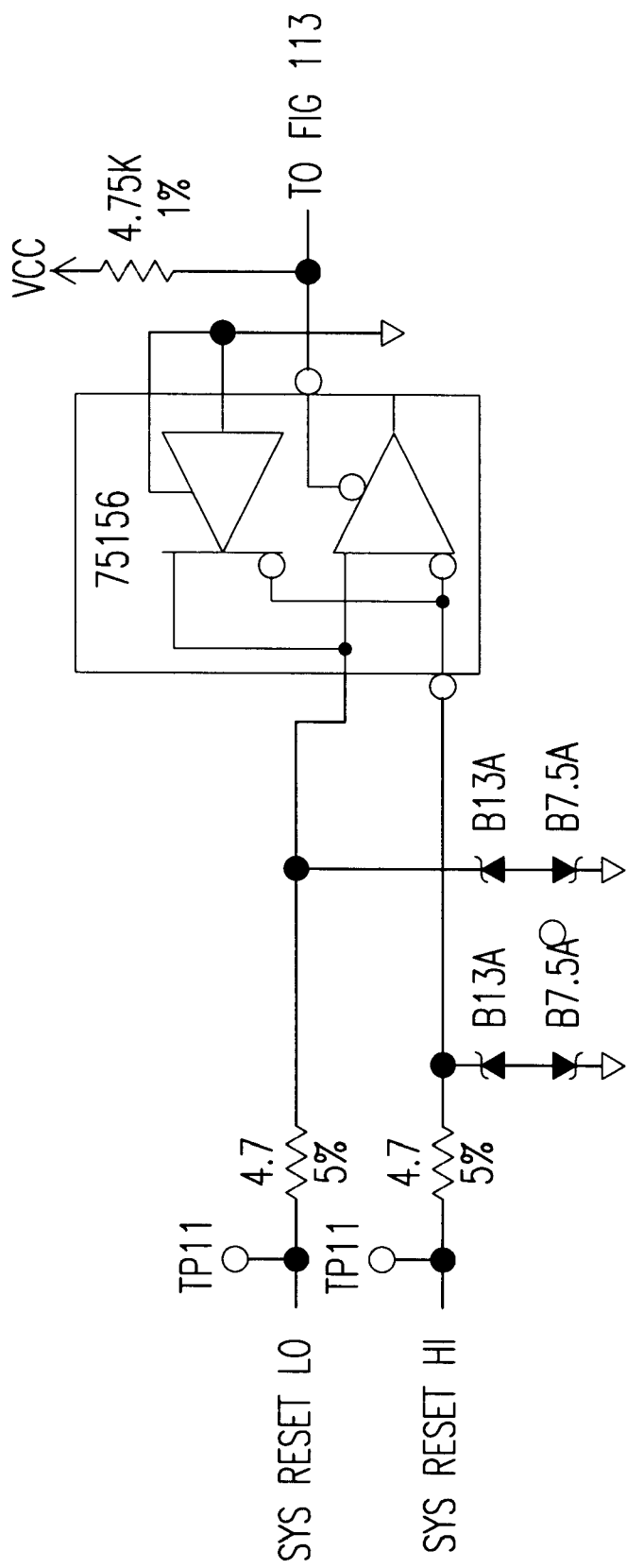
Figure 113:
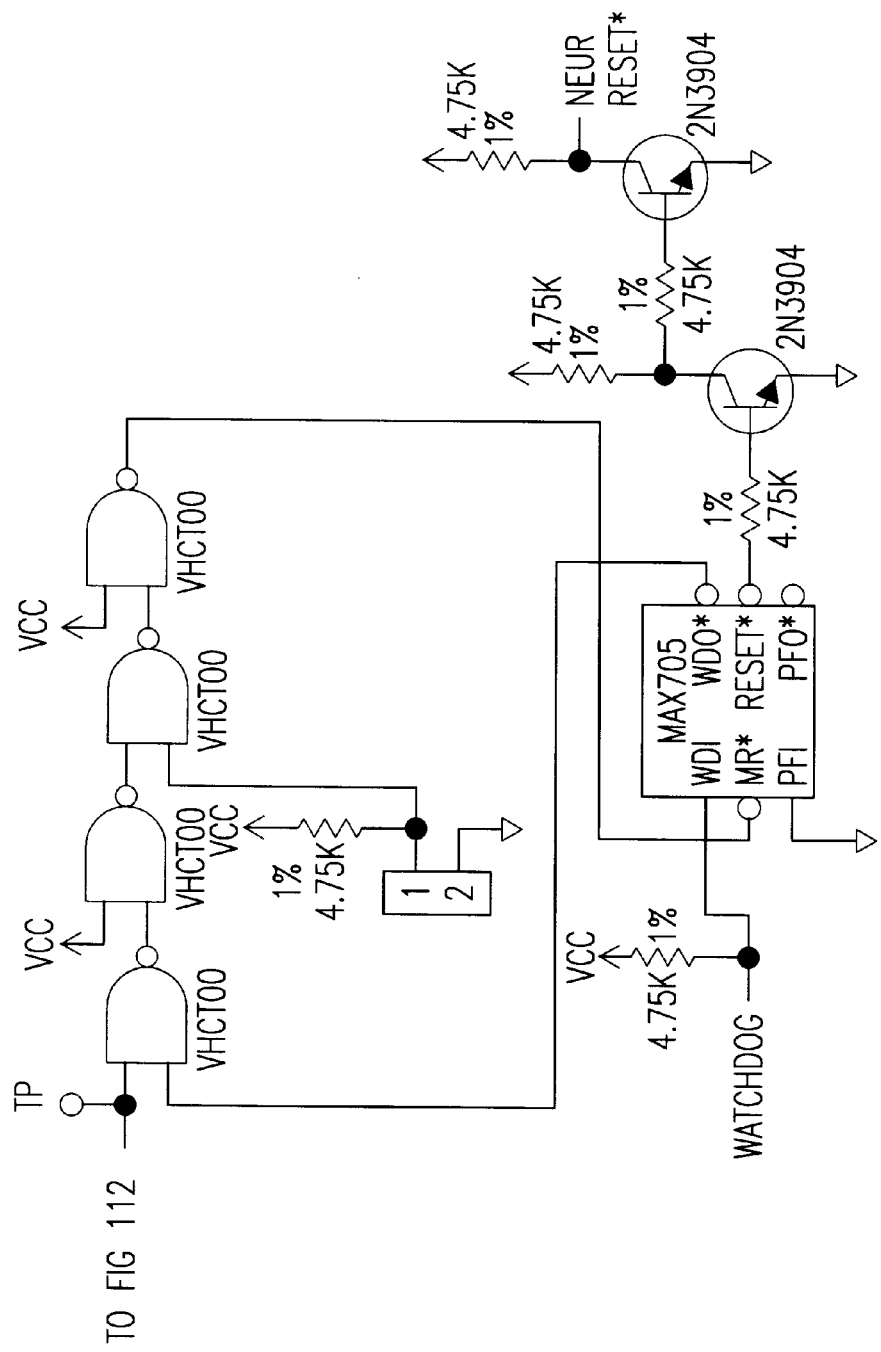
Figure 114:
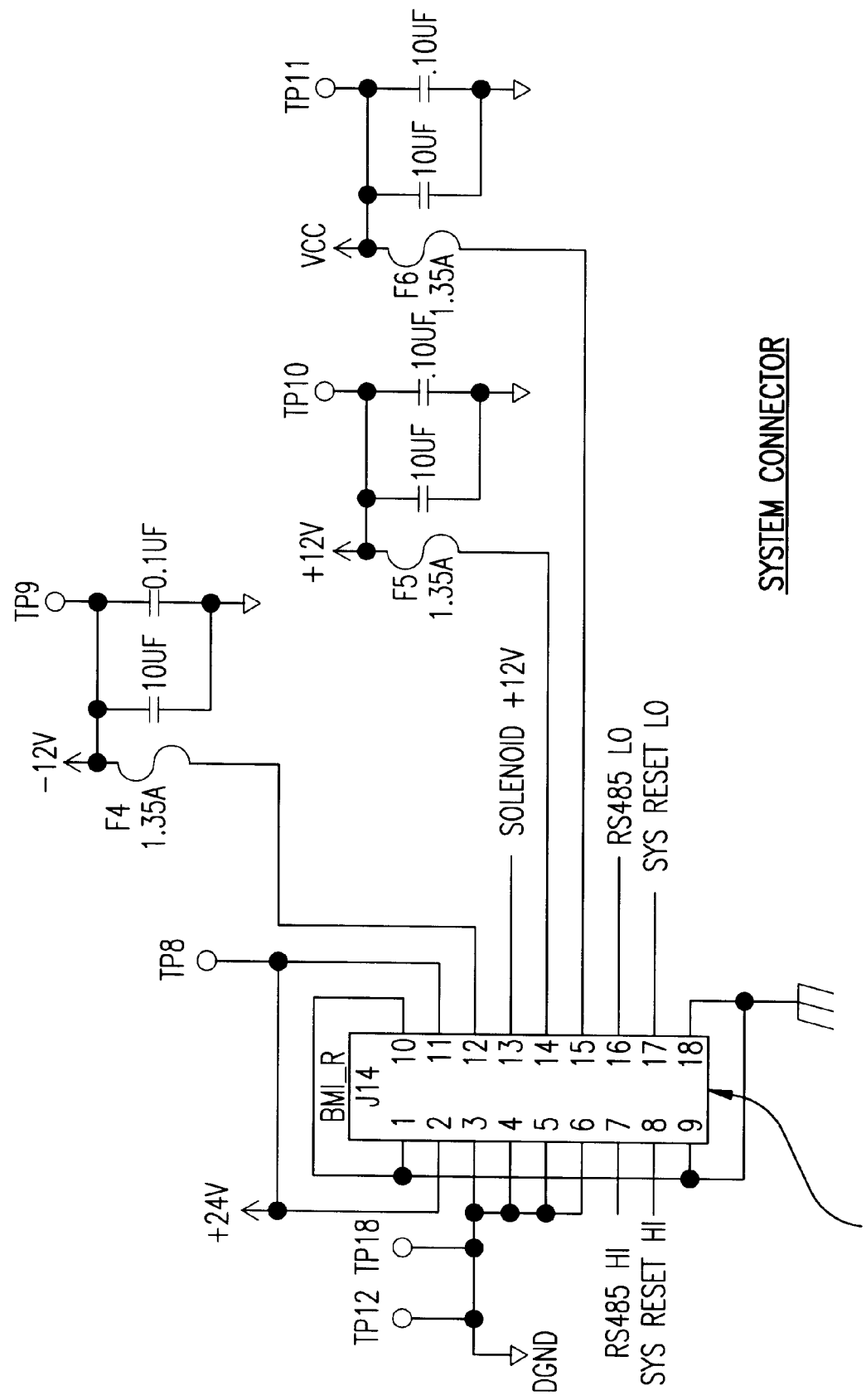
FIGS. 114–125 are schematic diagrams illustrating the illumination module of FIG. 36.
Figure 115:
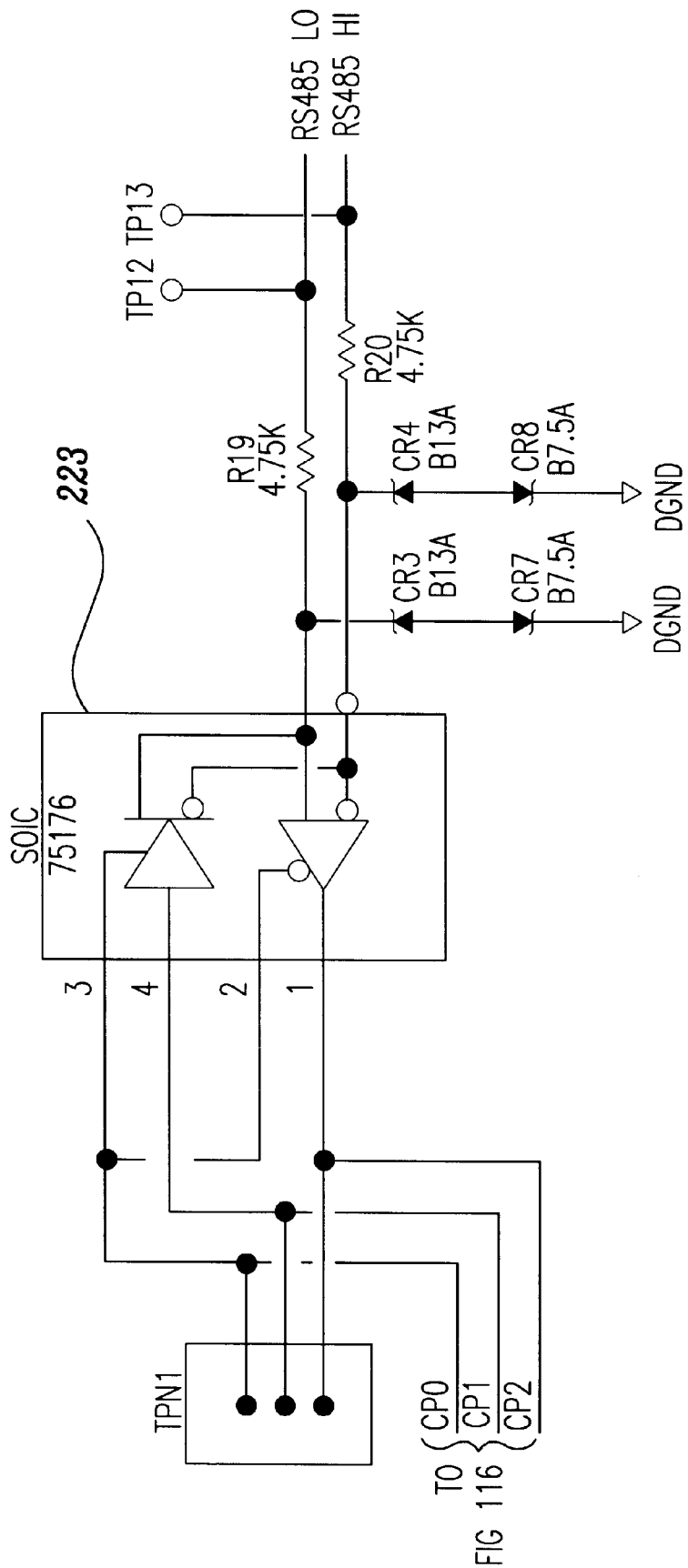
Figure 116:
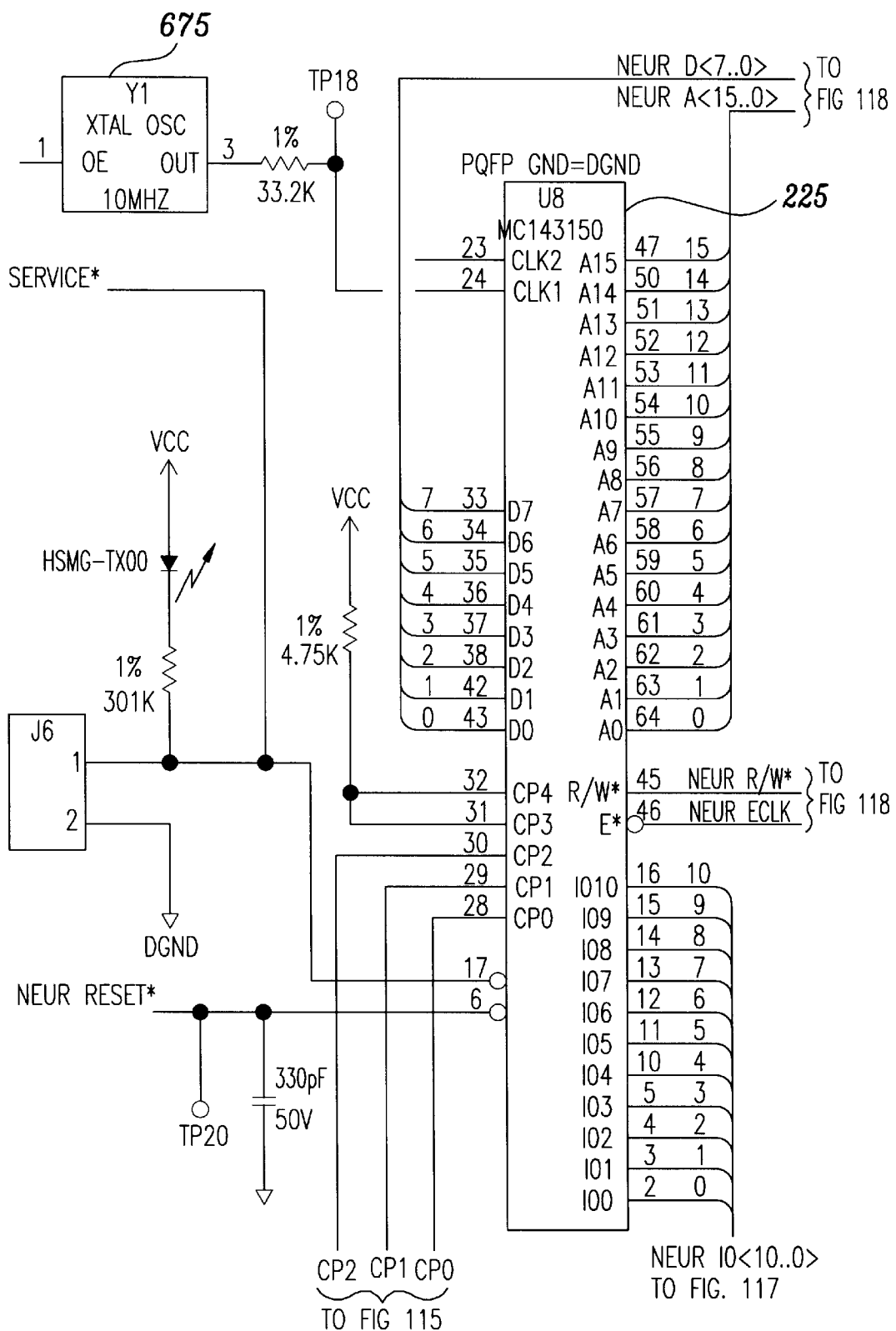
Figure 117:
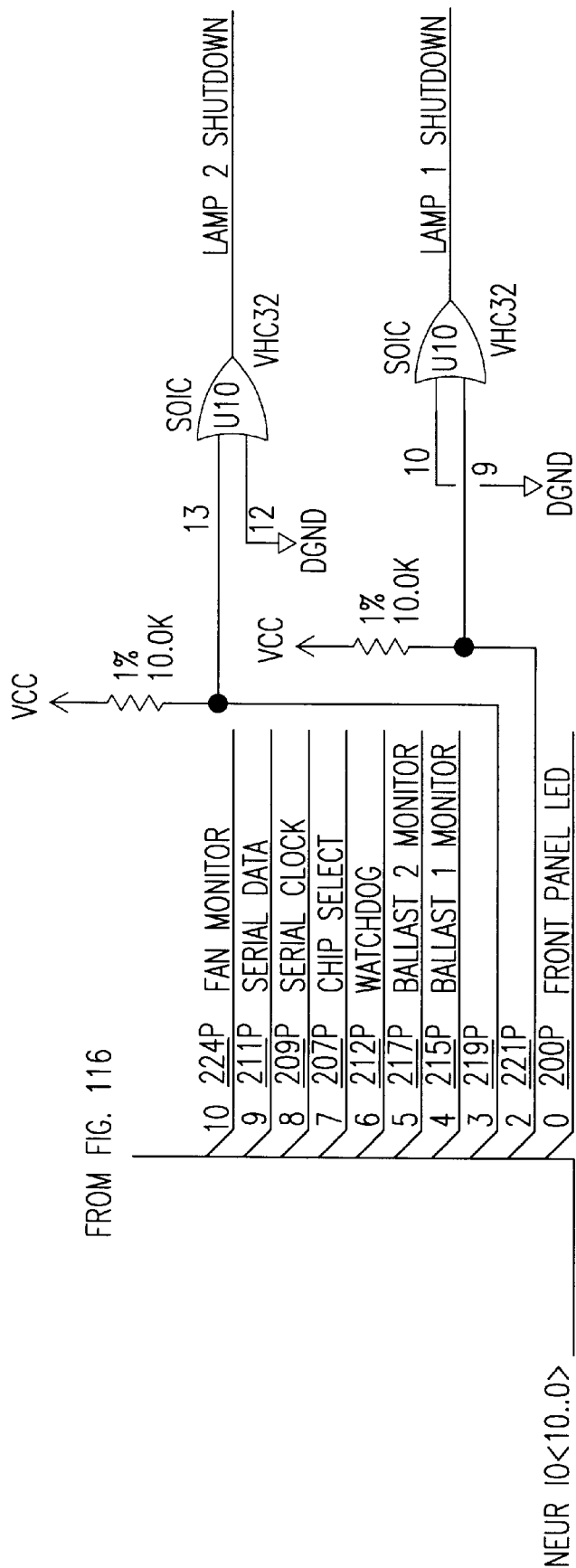
Figure 118:
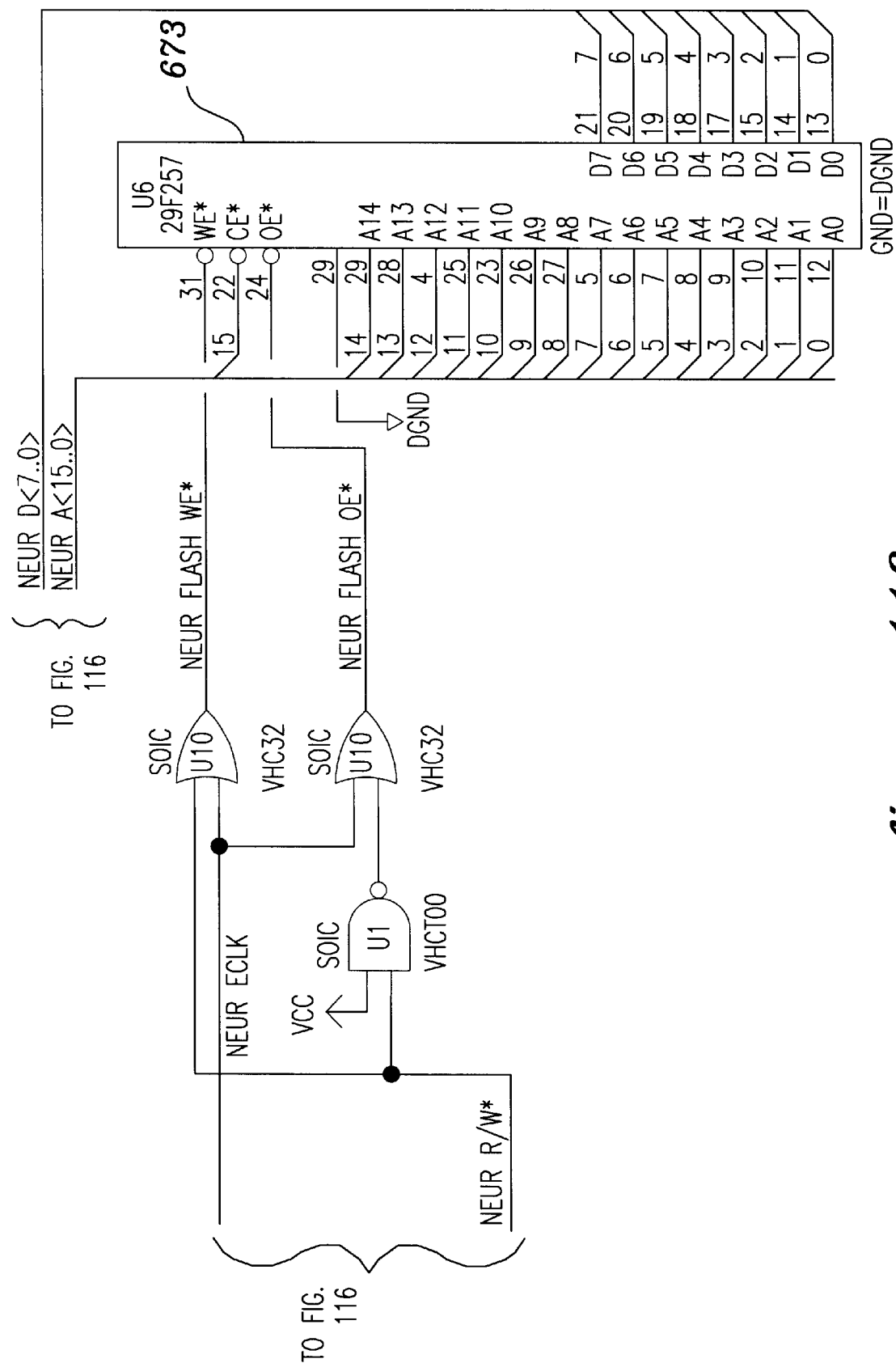
Figure 119:
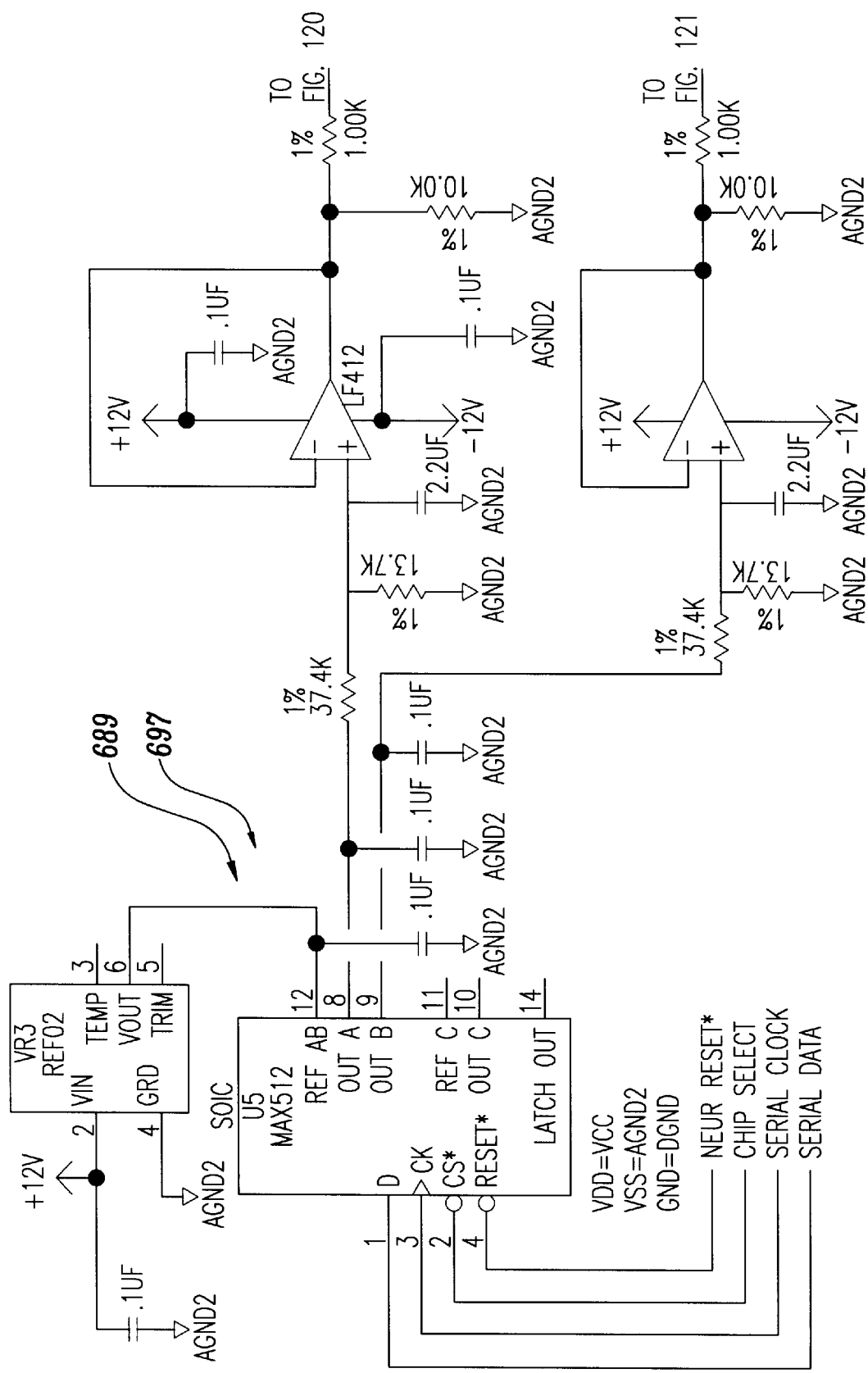
Figure 120:
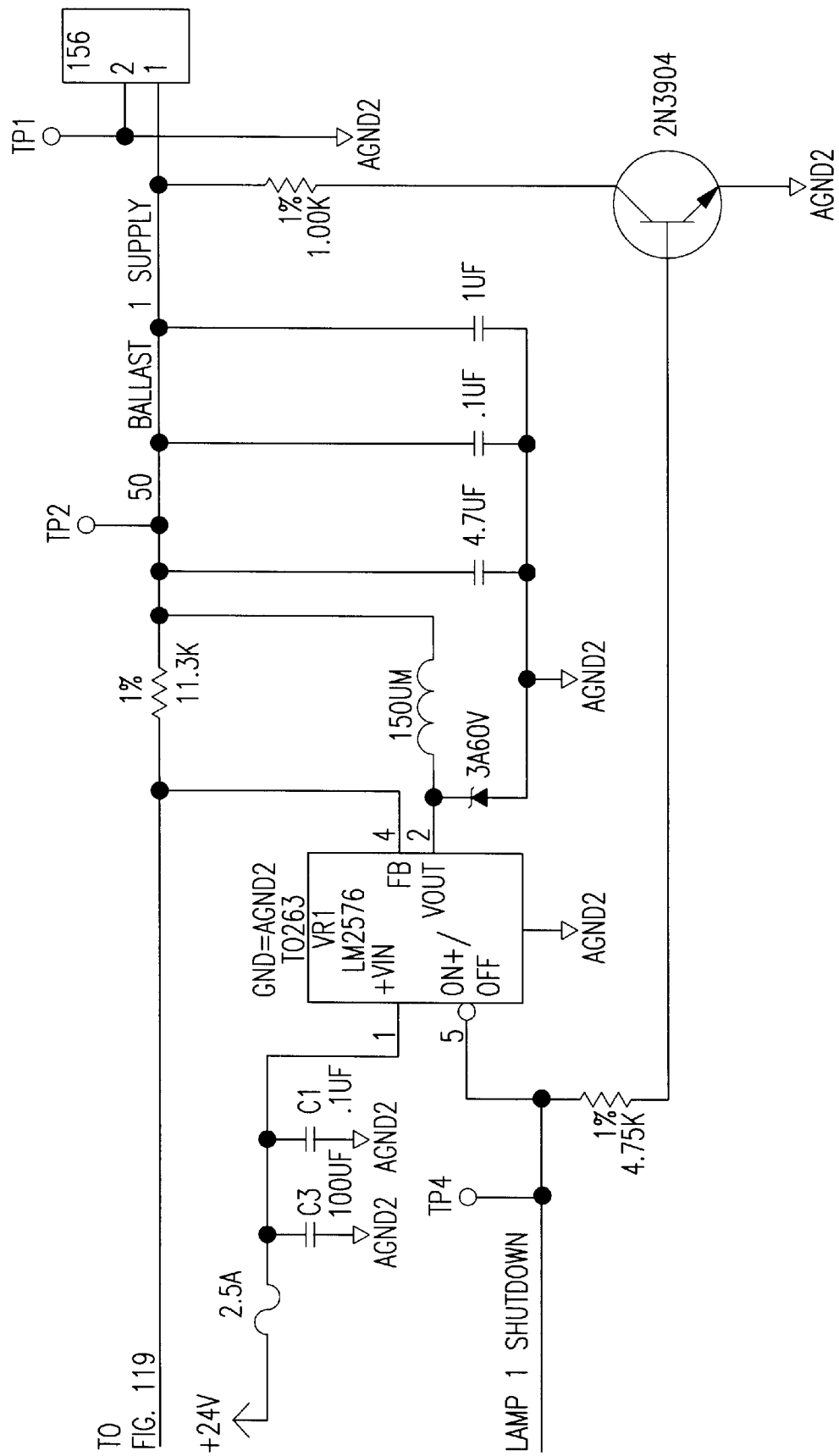
Figure 121:
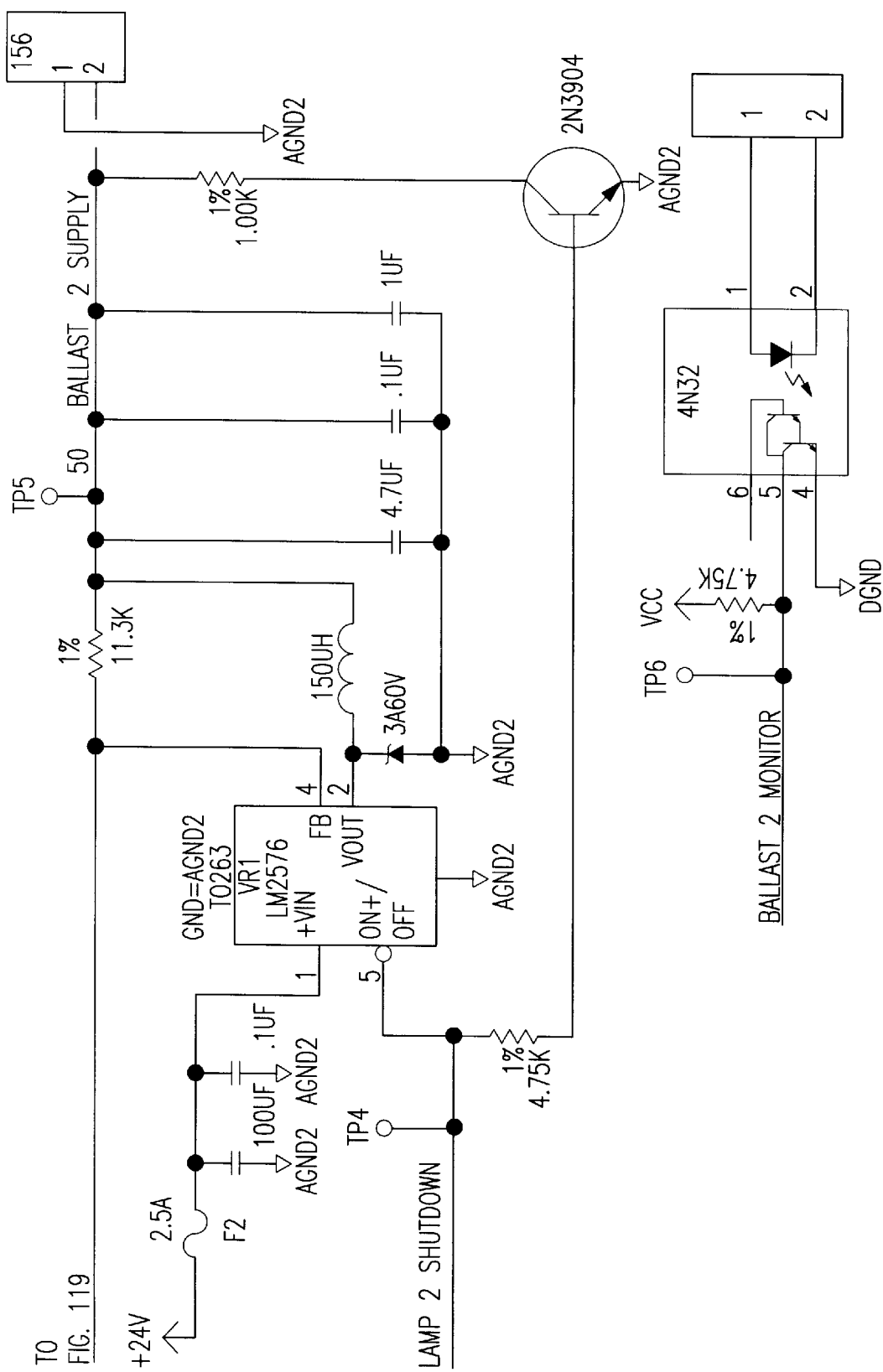
Figure 122:
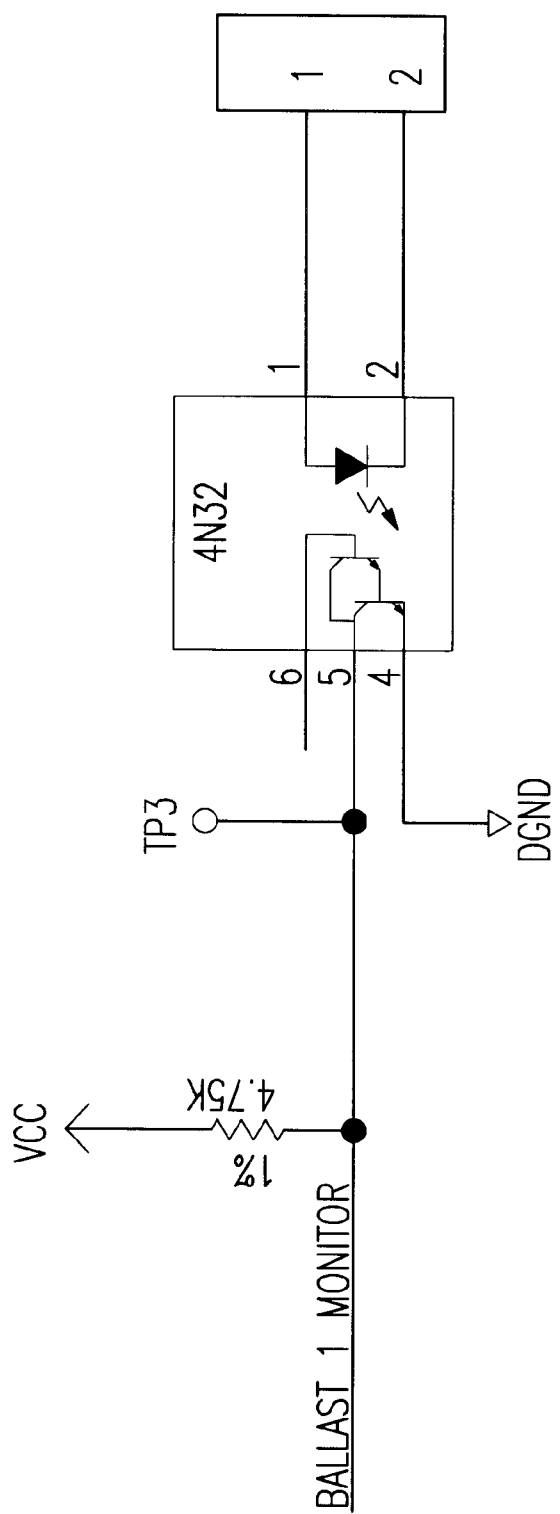
Figure 123:
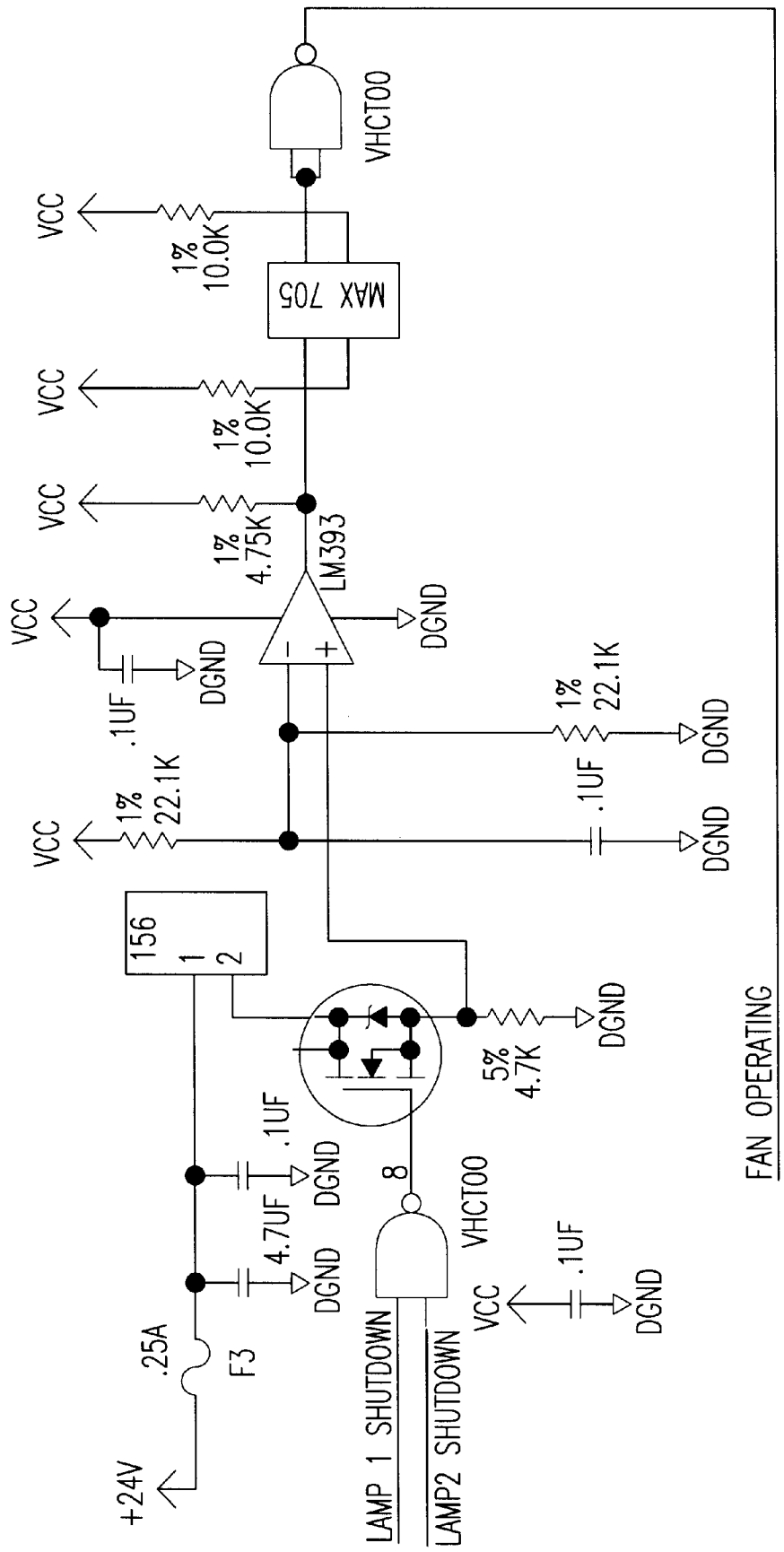
Figure 124:
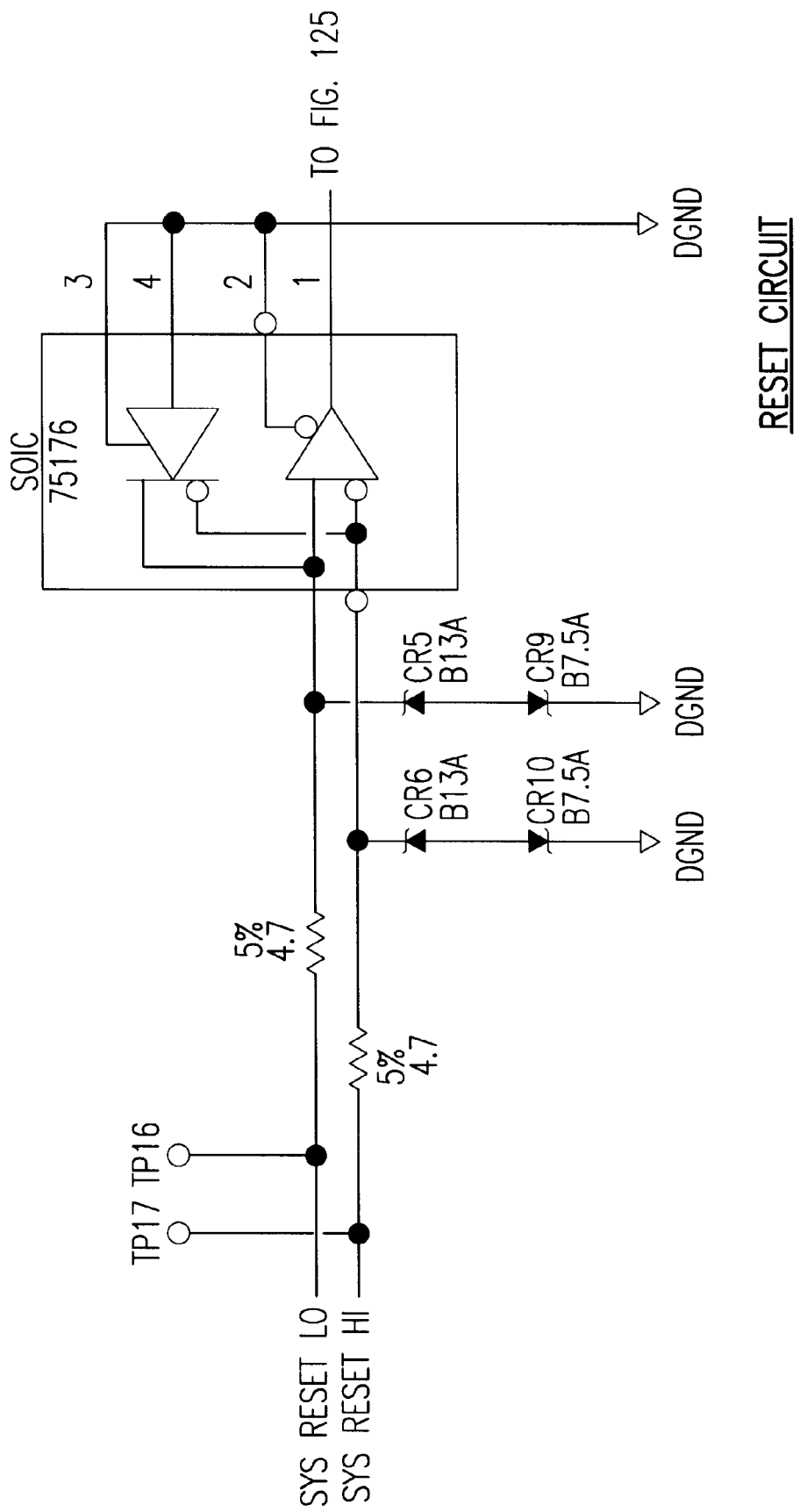
Figure 125:
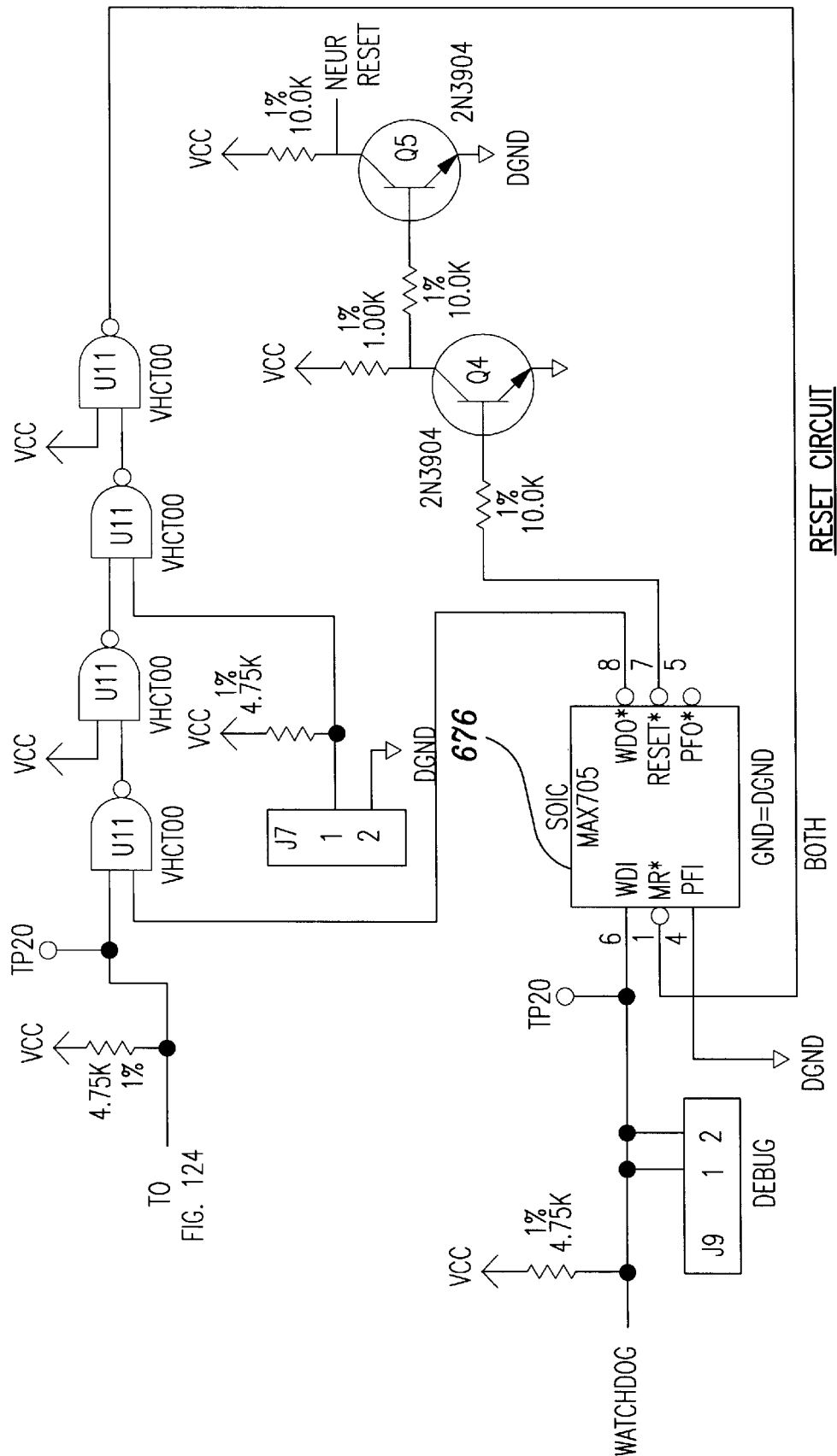
Figure 126:
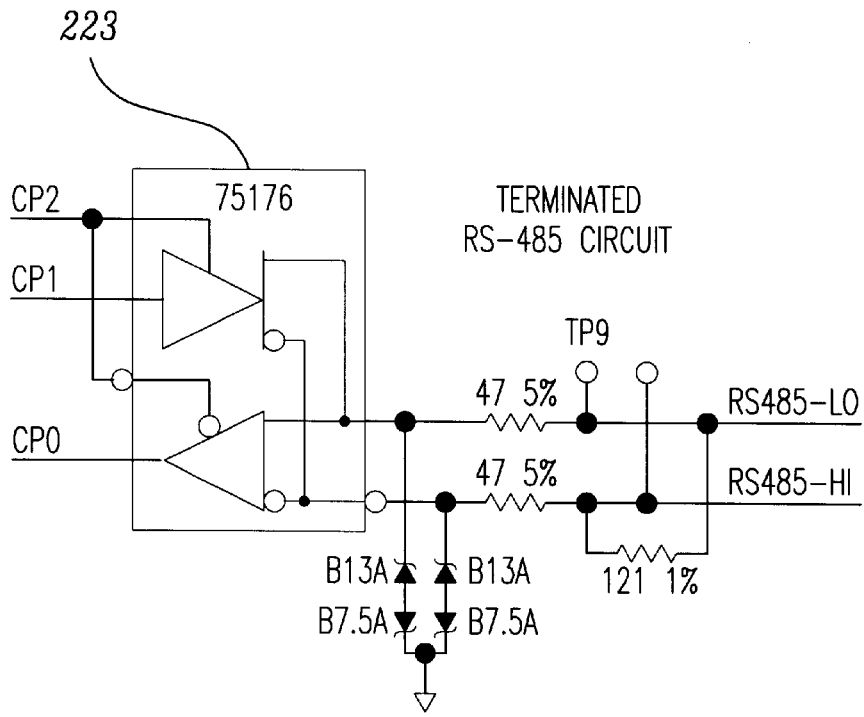
FIGS. 126–136 are schematic diagrams illustrating the foot control circuit of FIG. 37.
Figure 127:
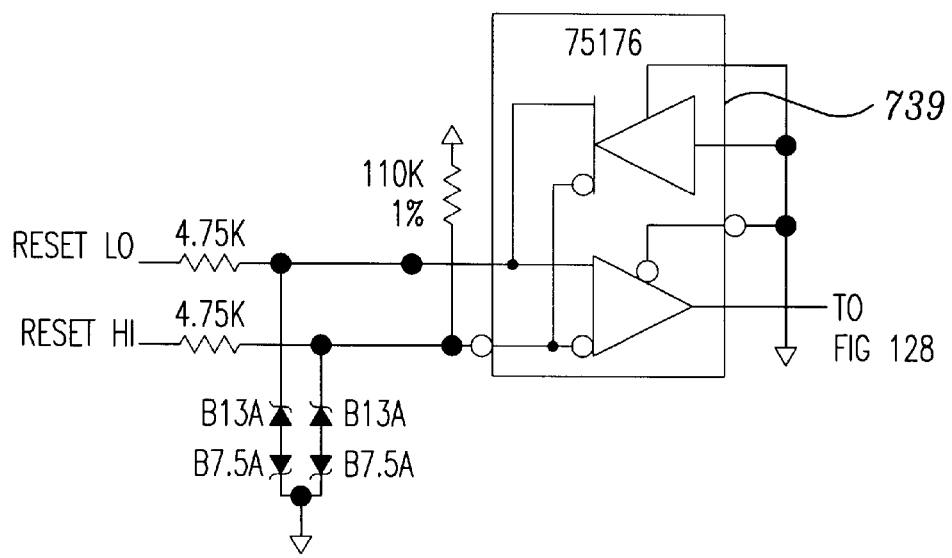
Figure 128:
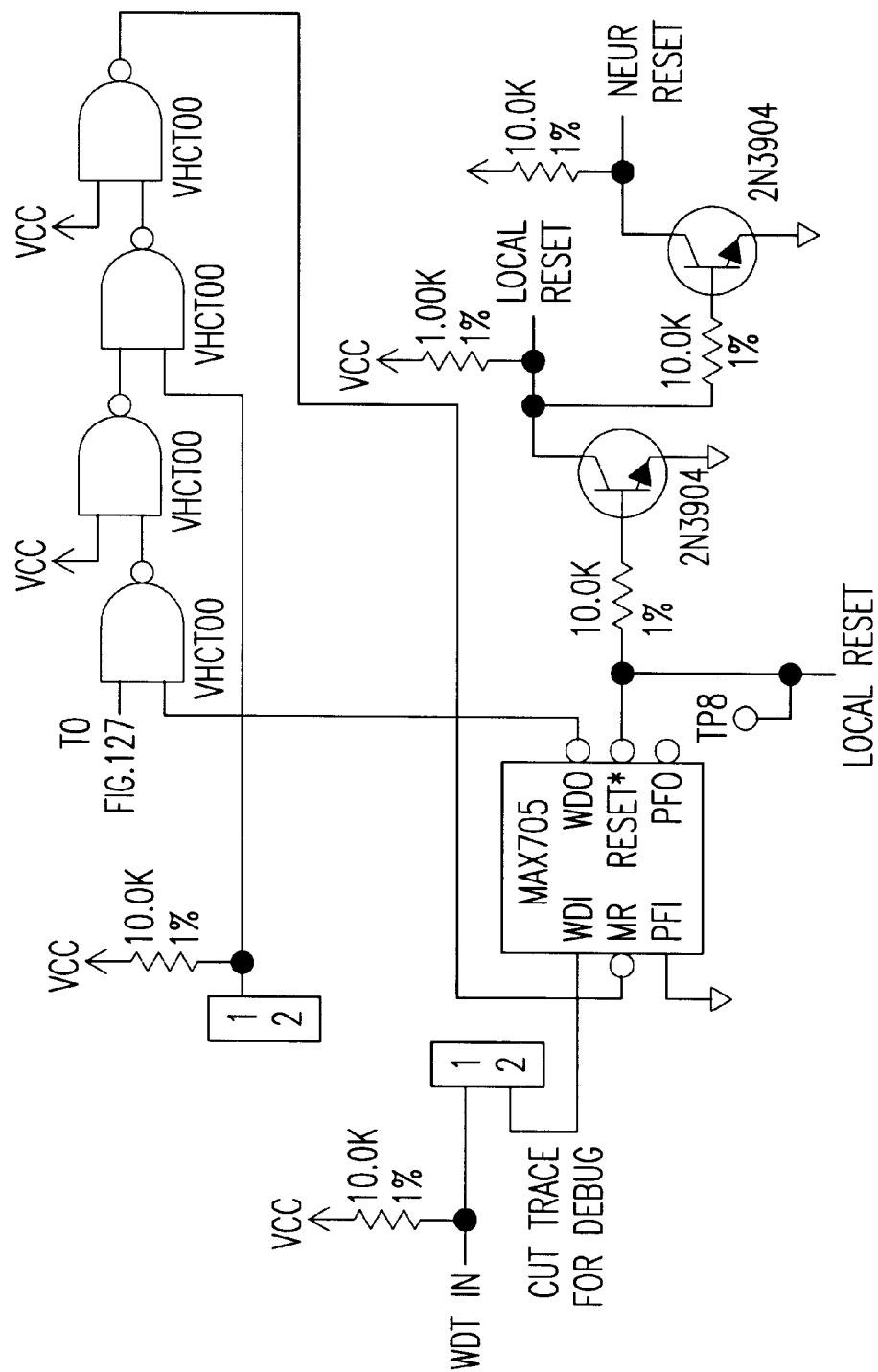
Figure 129:
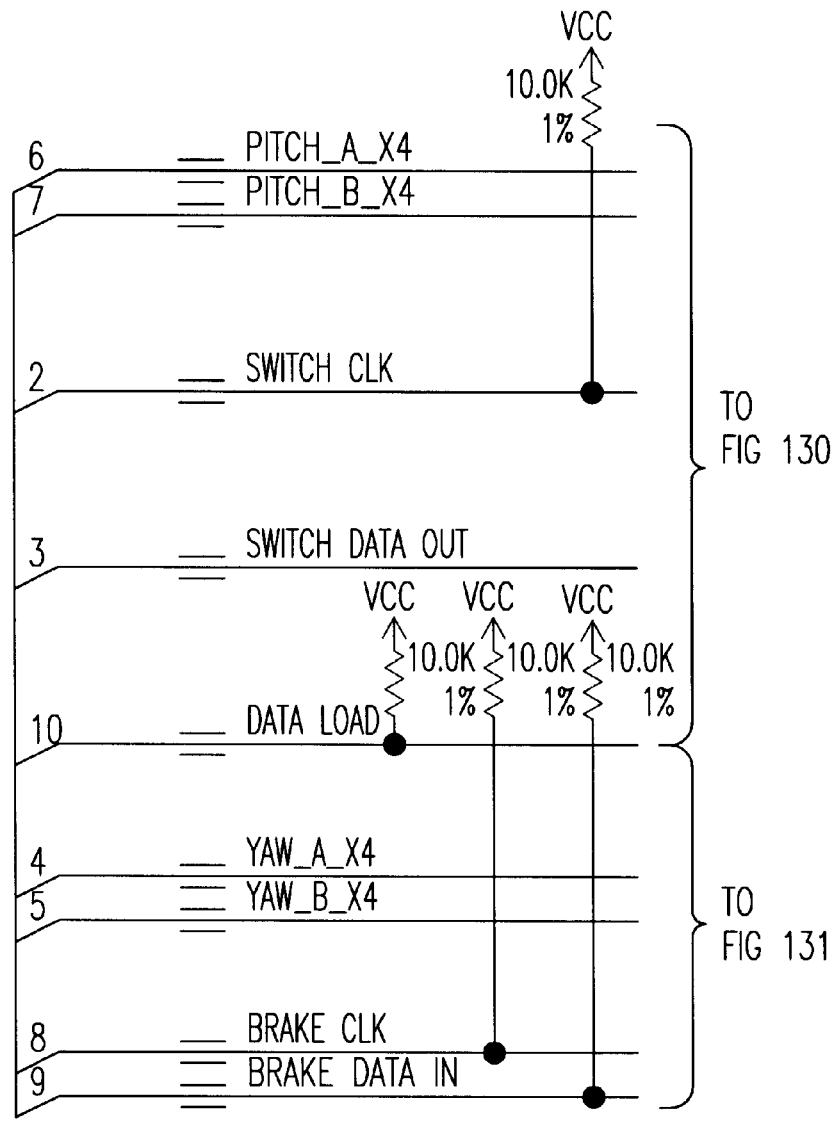
Figure 130:
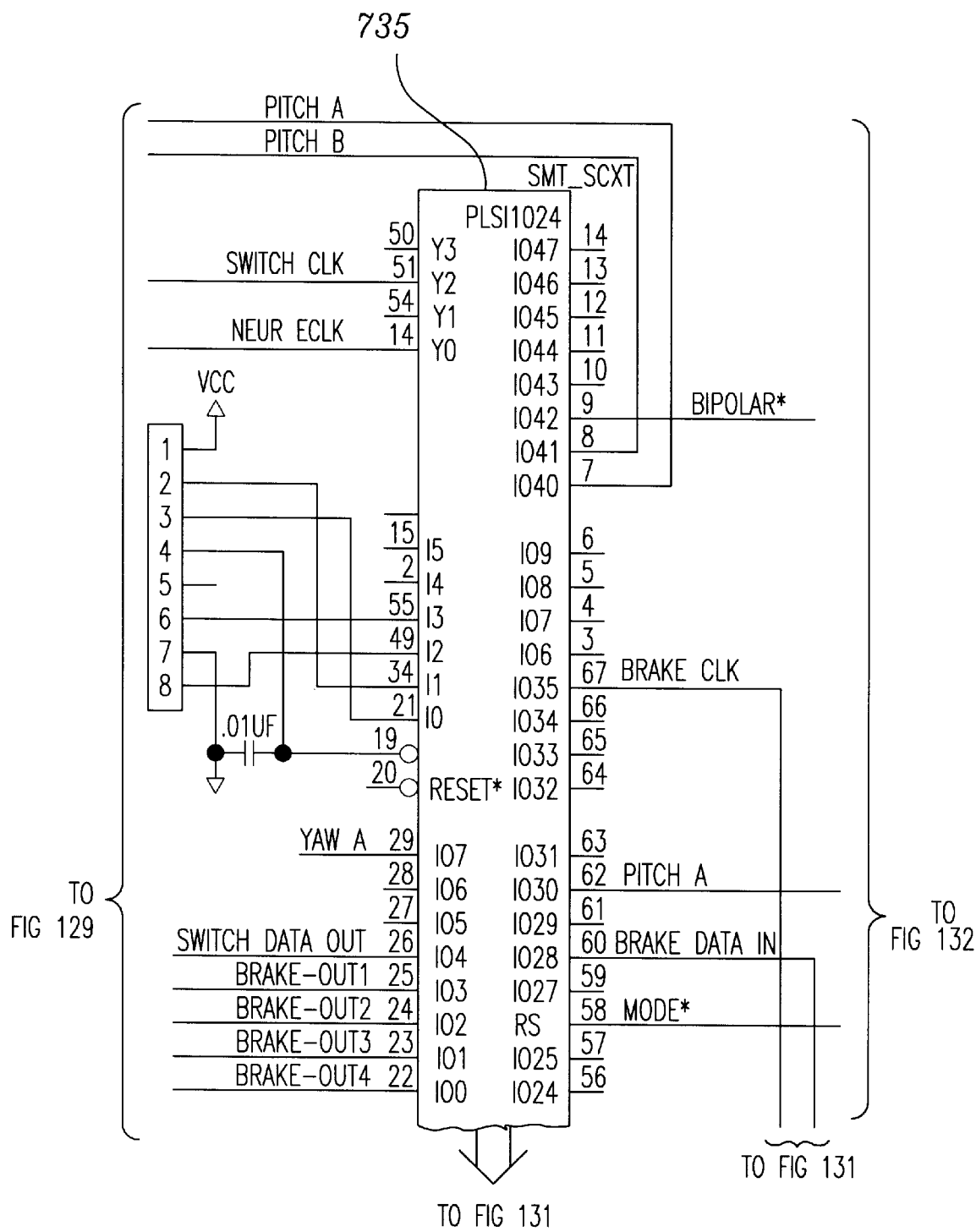
Figure 131:
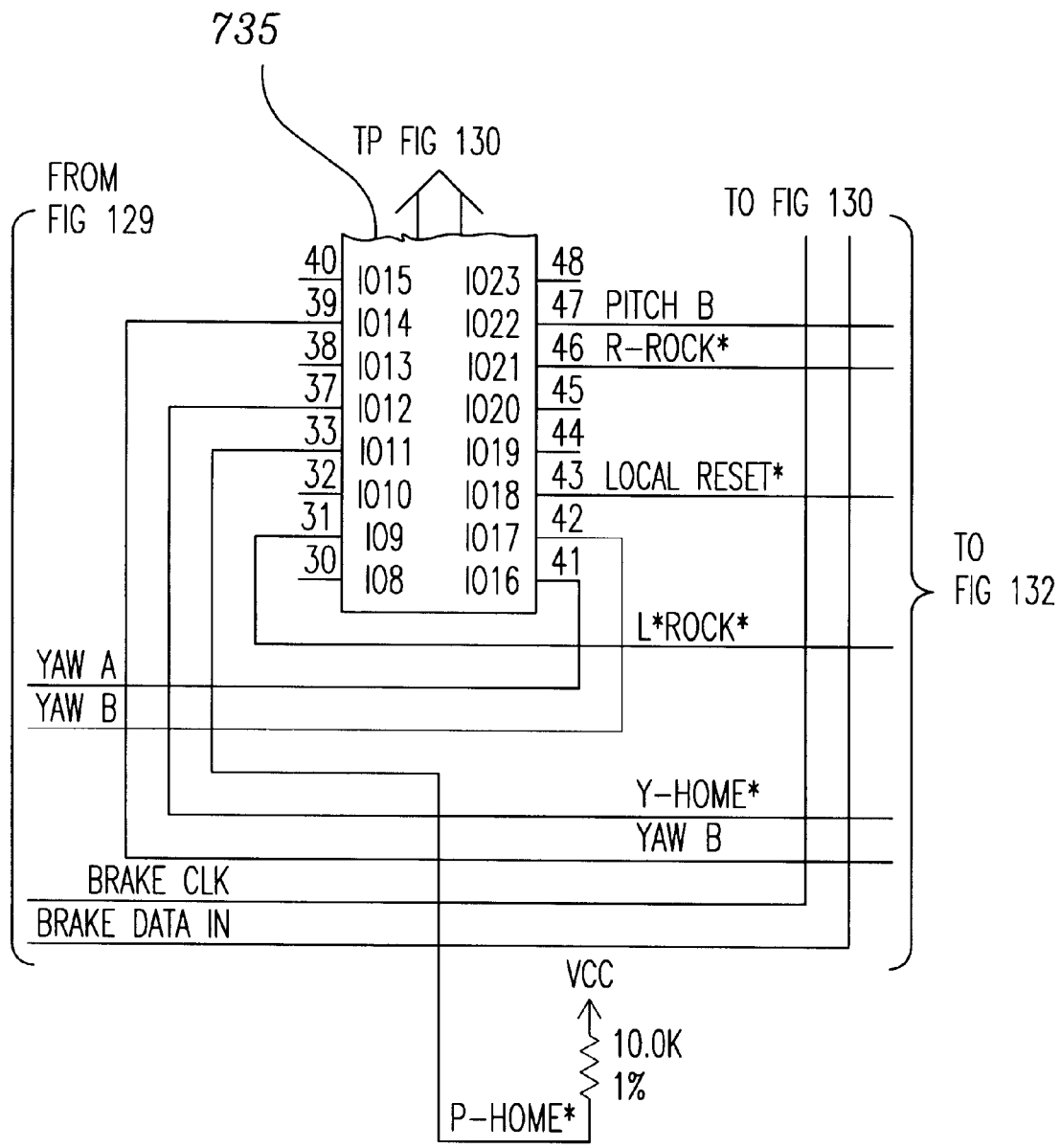
Figure 132:
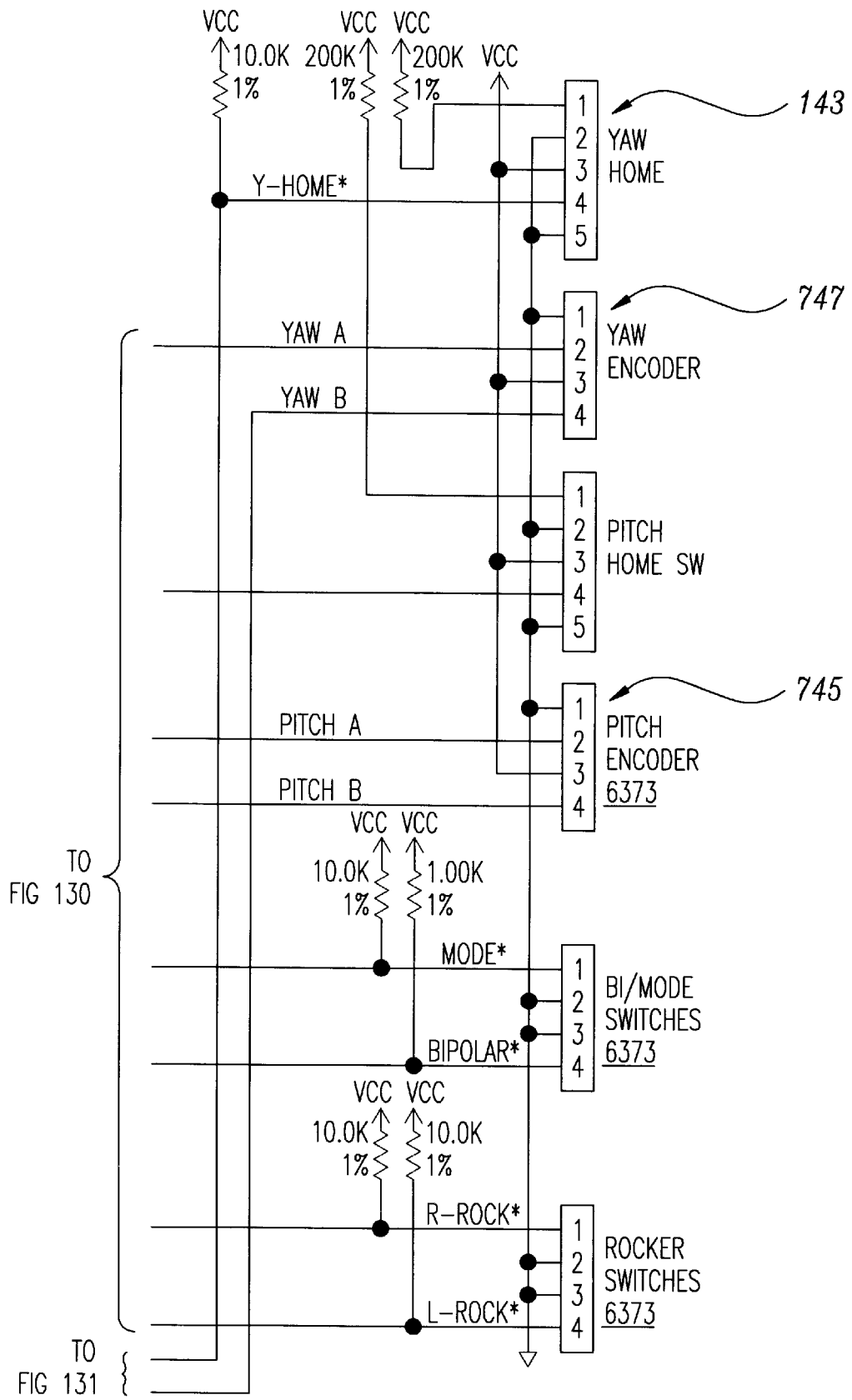
Figure 133:
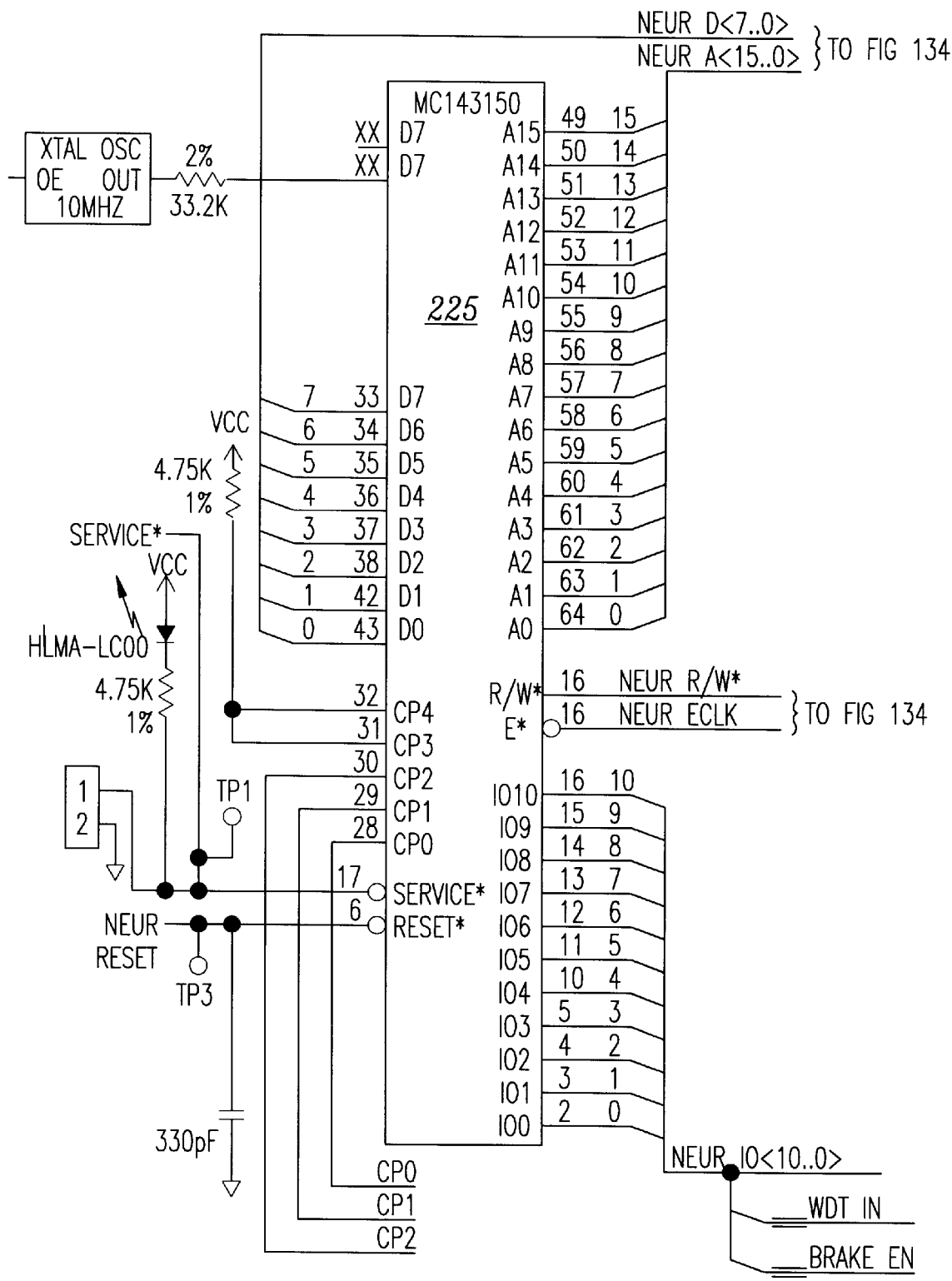
Figure 134:
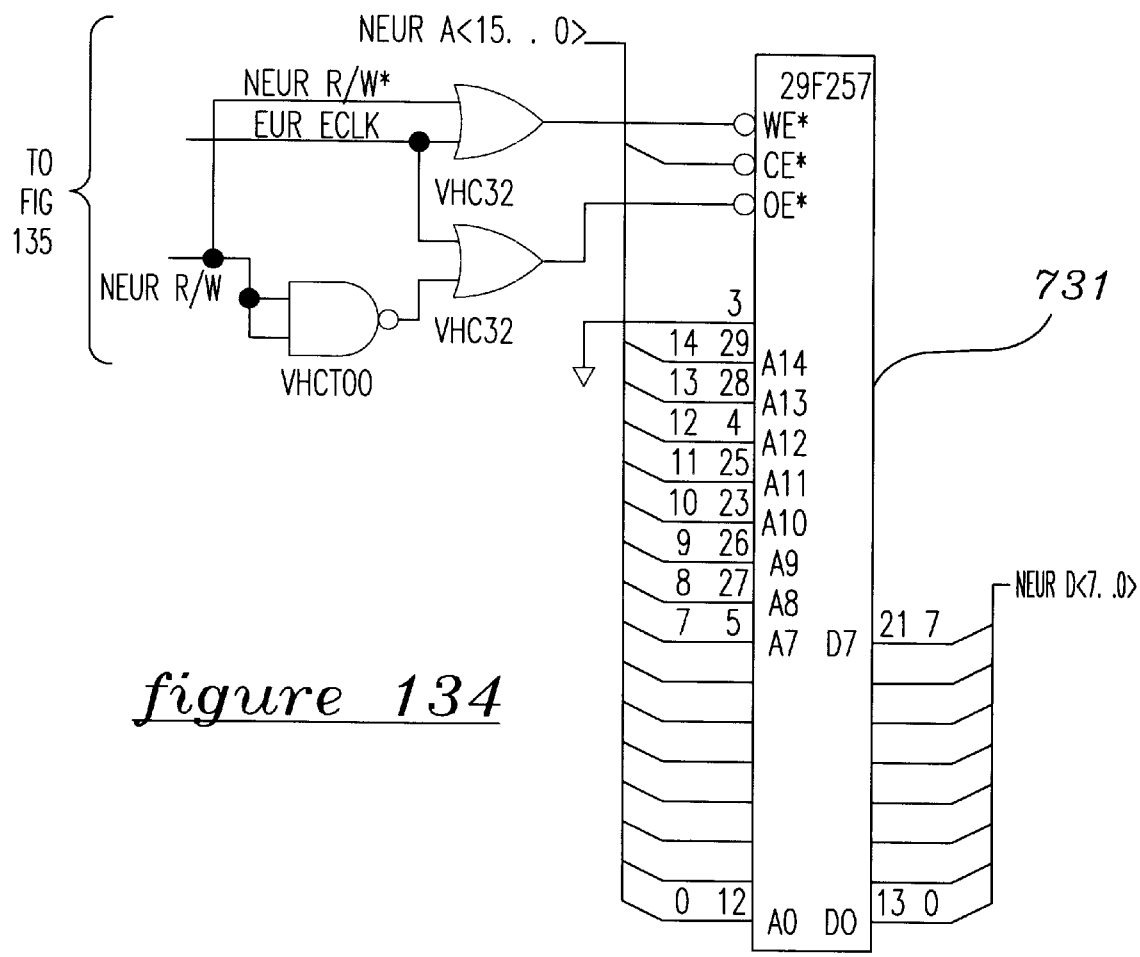
Figure 136:
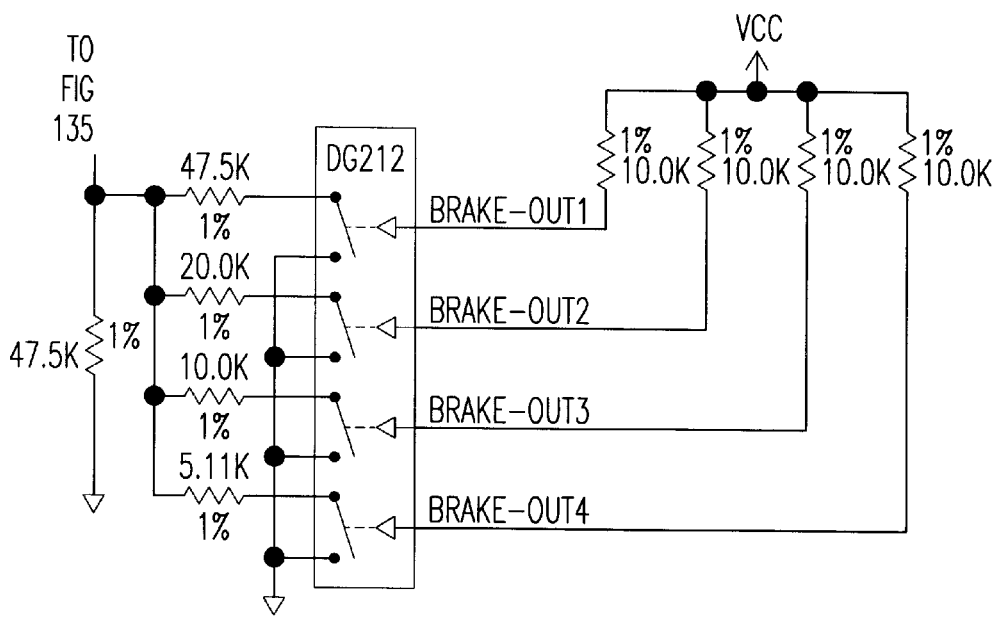
Figure 135:
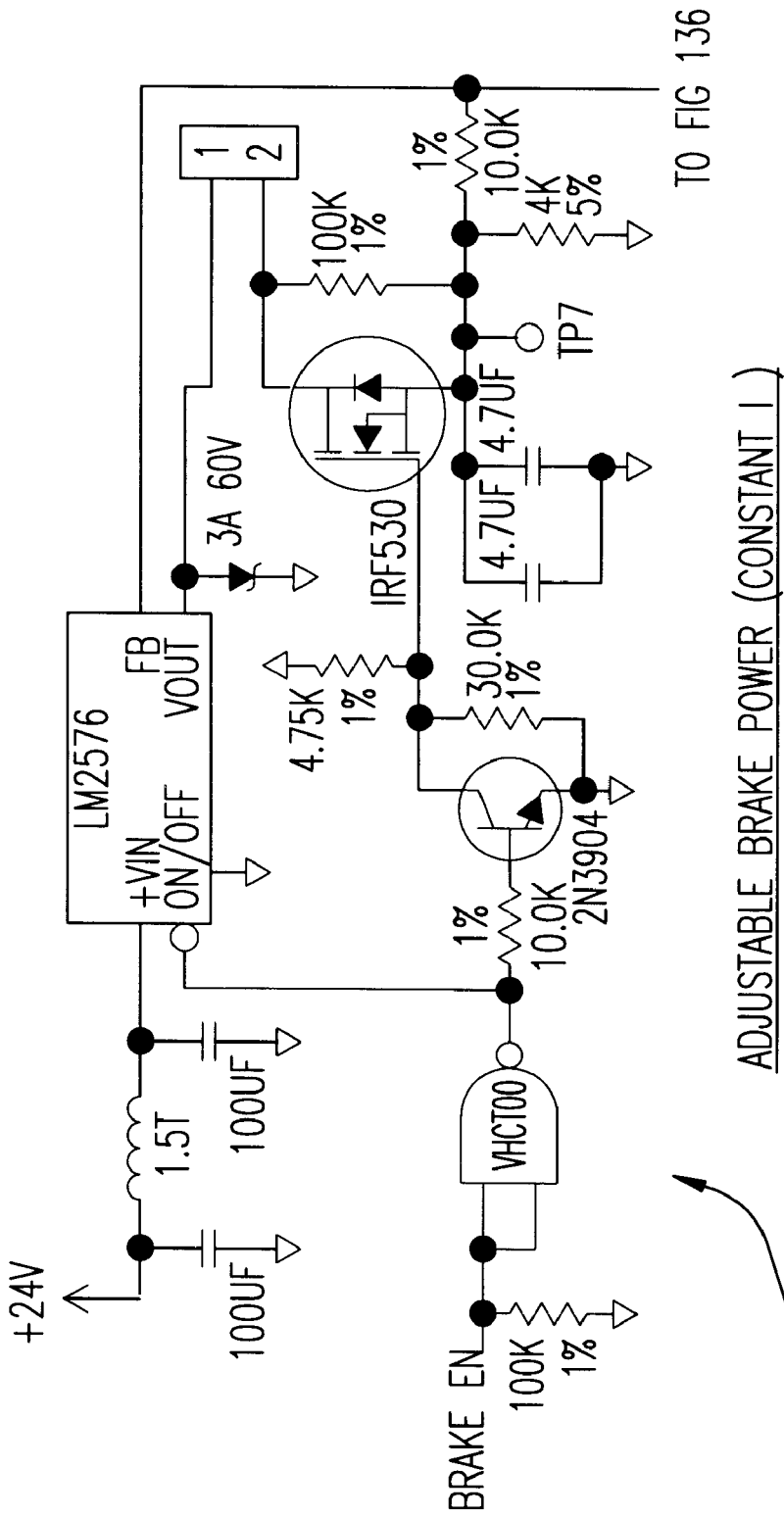
Figure 137:
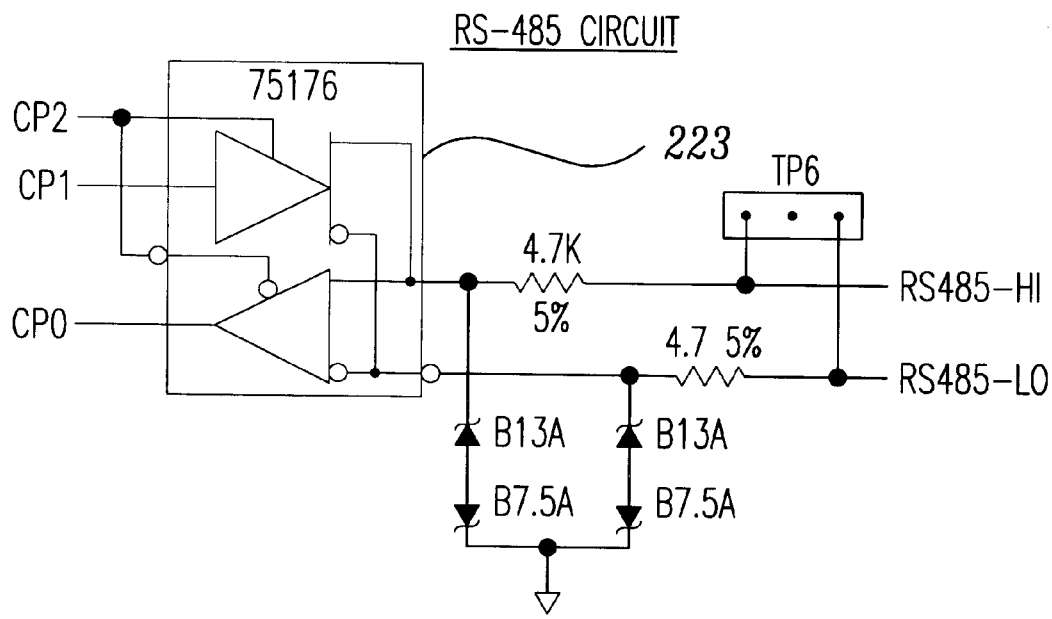
FIGS. 137–146 are schematic diagrams illustrating the intravenous pole control circuit of FIG. 38.
Figure 138:
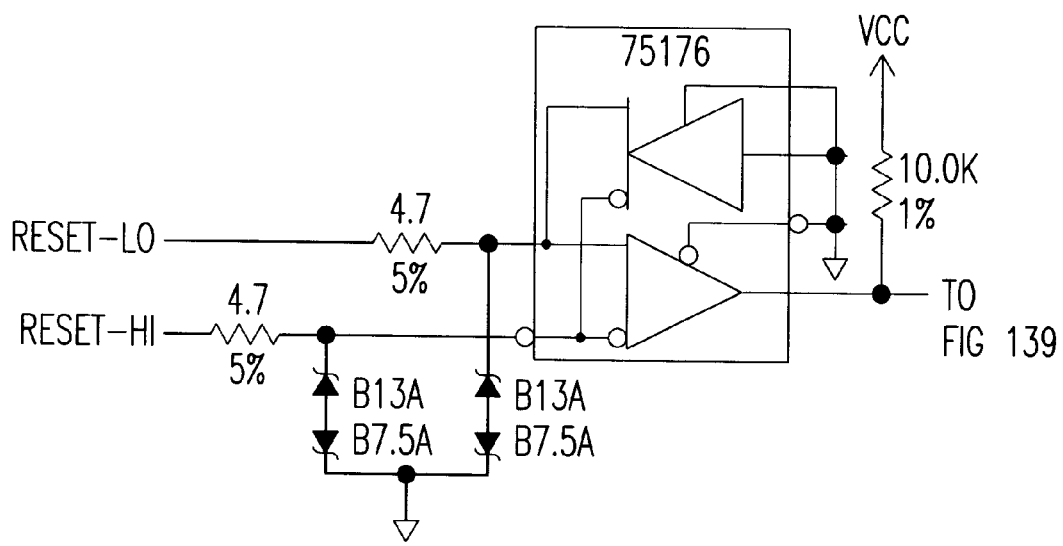
Figure 139:
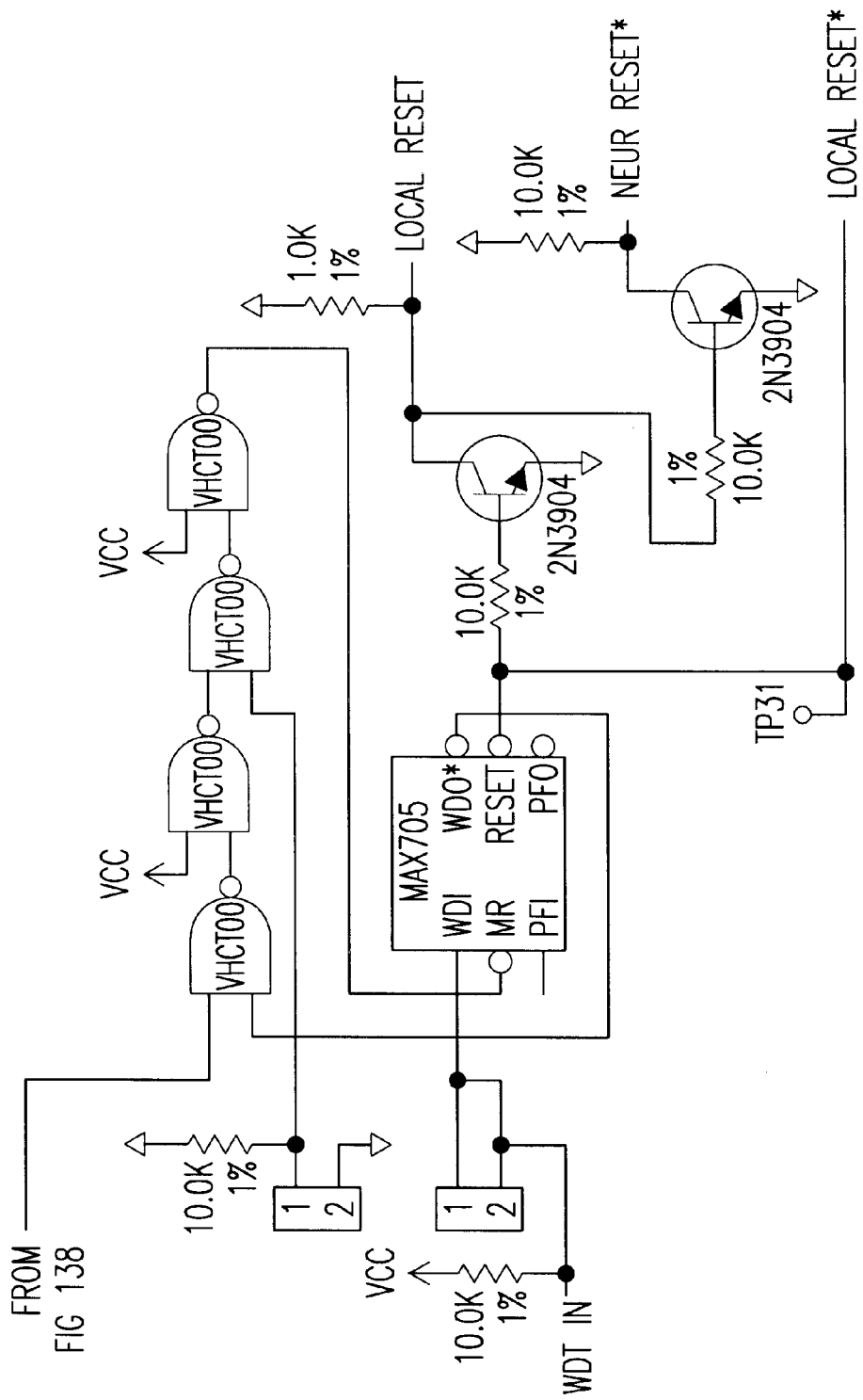
Figure 140:
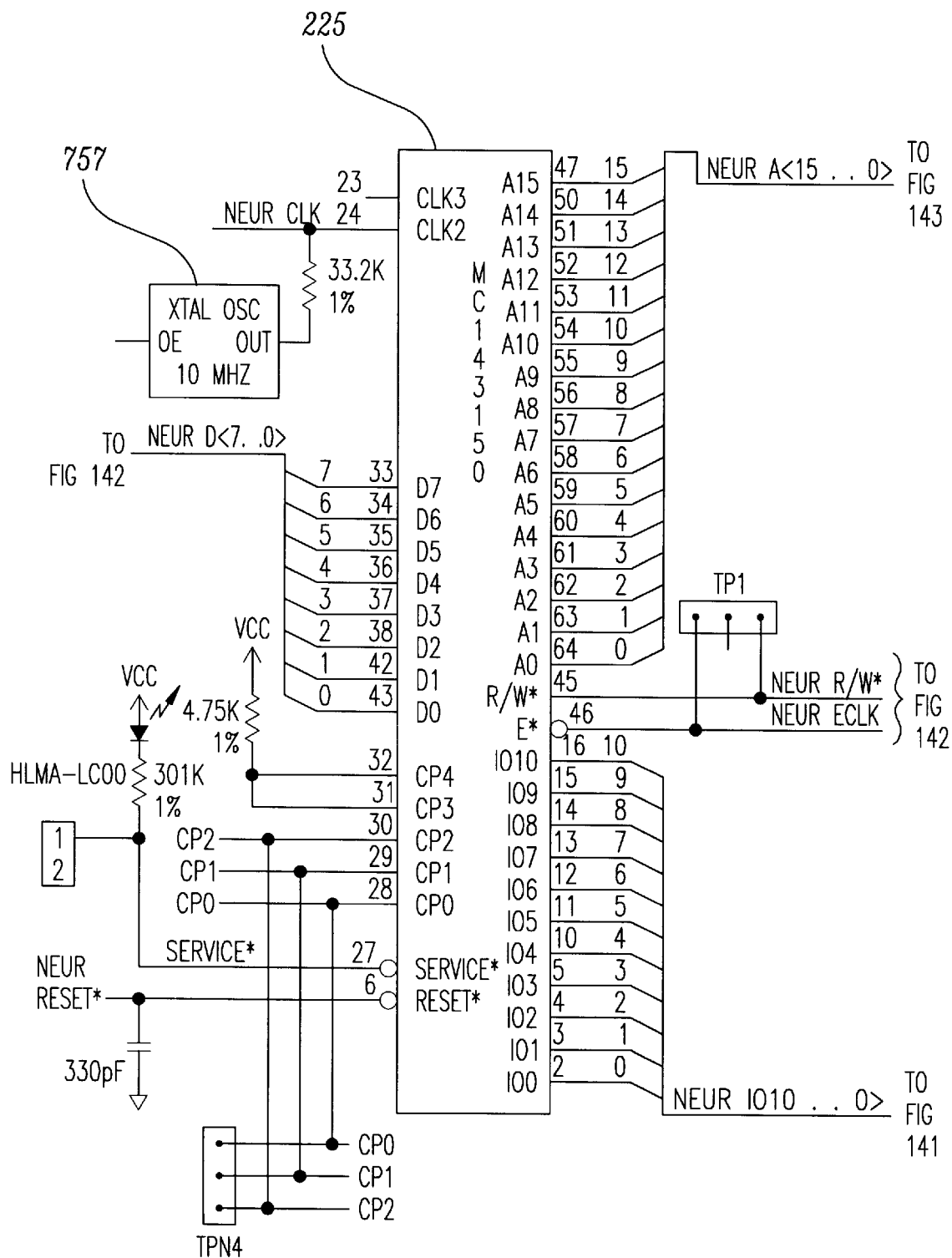
Figure 141:
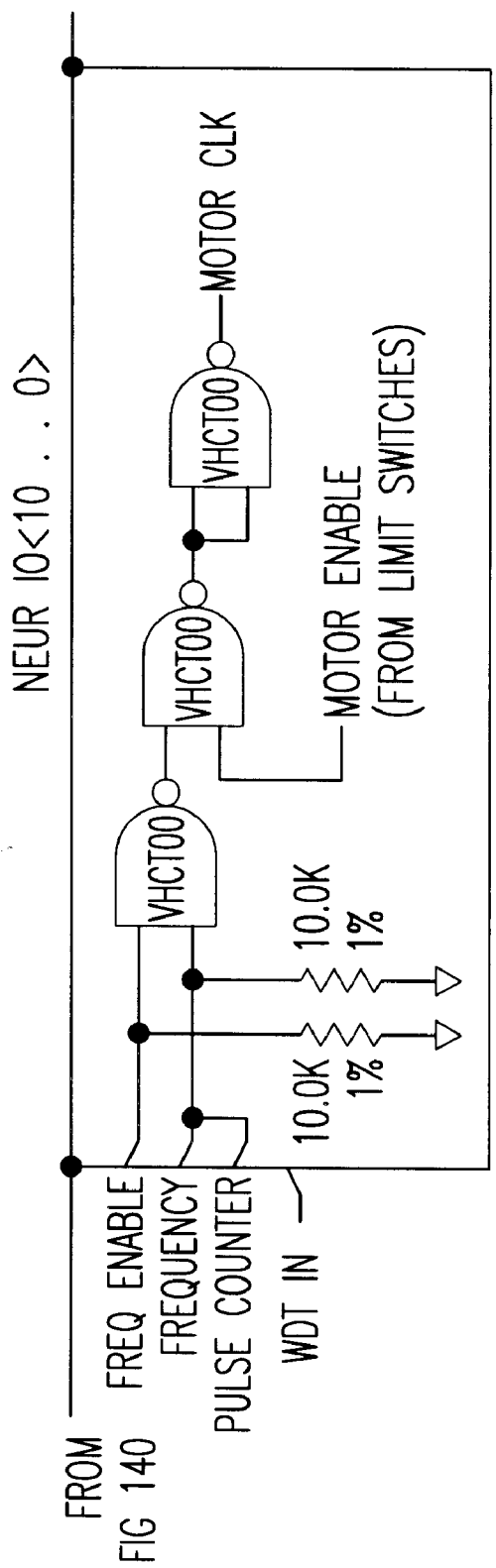
Figure 142:
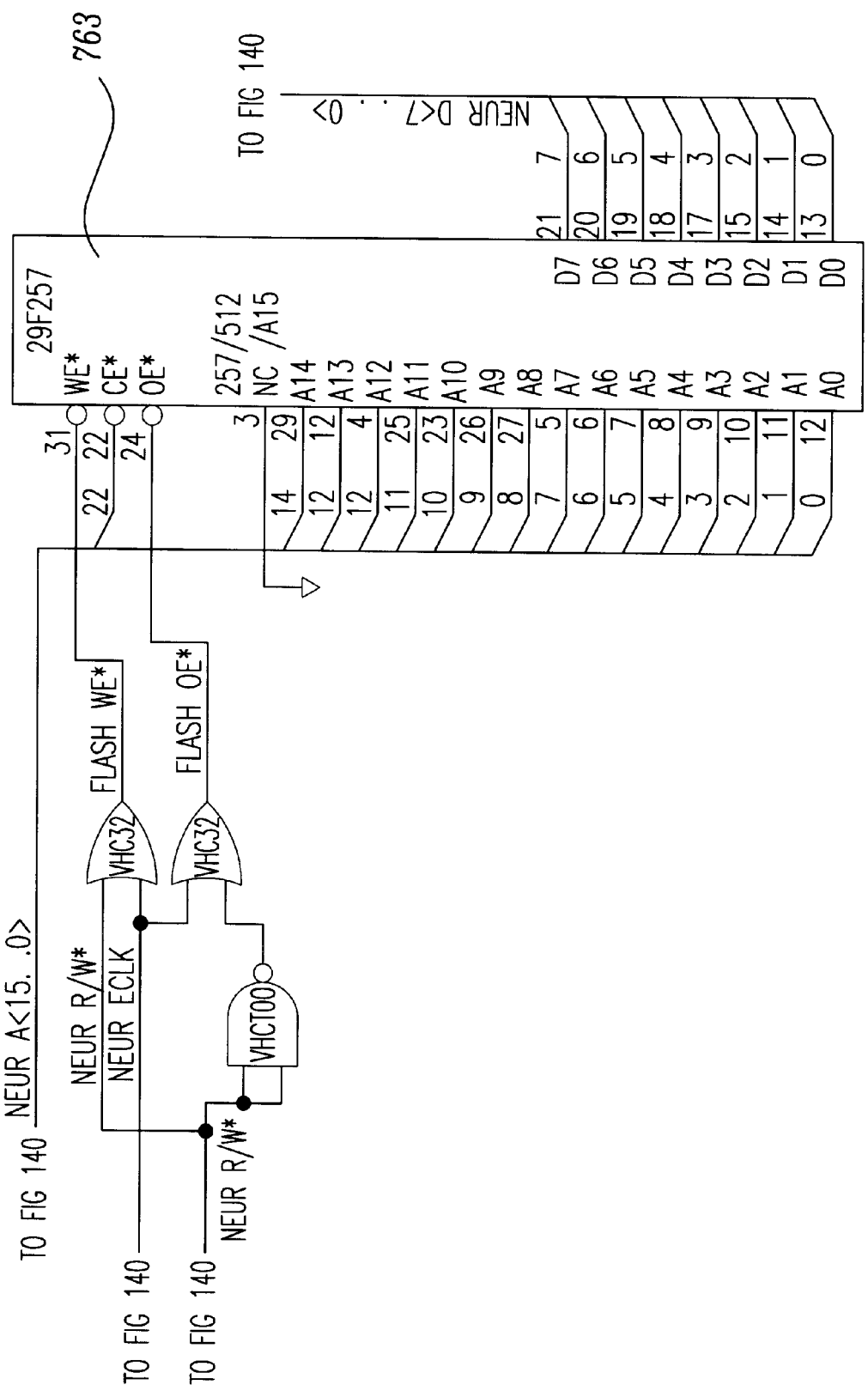
Figure 143:
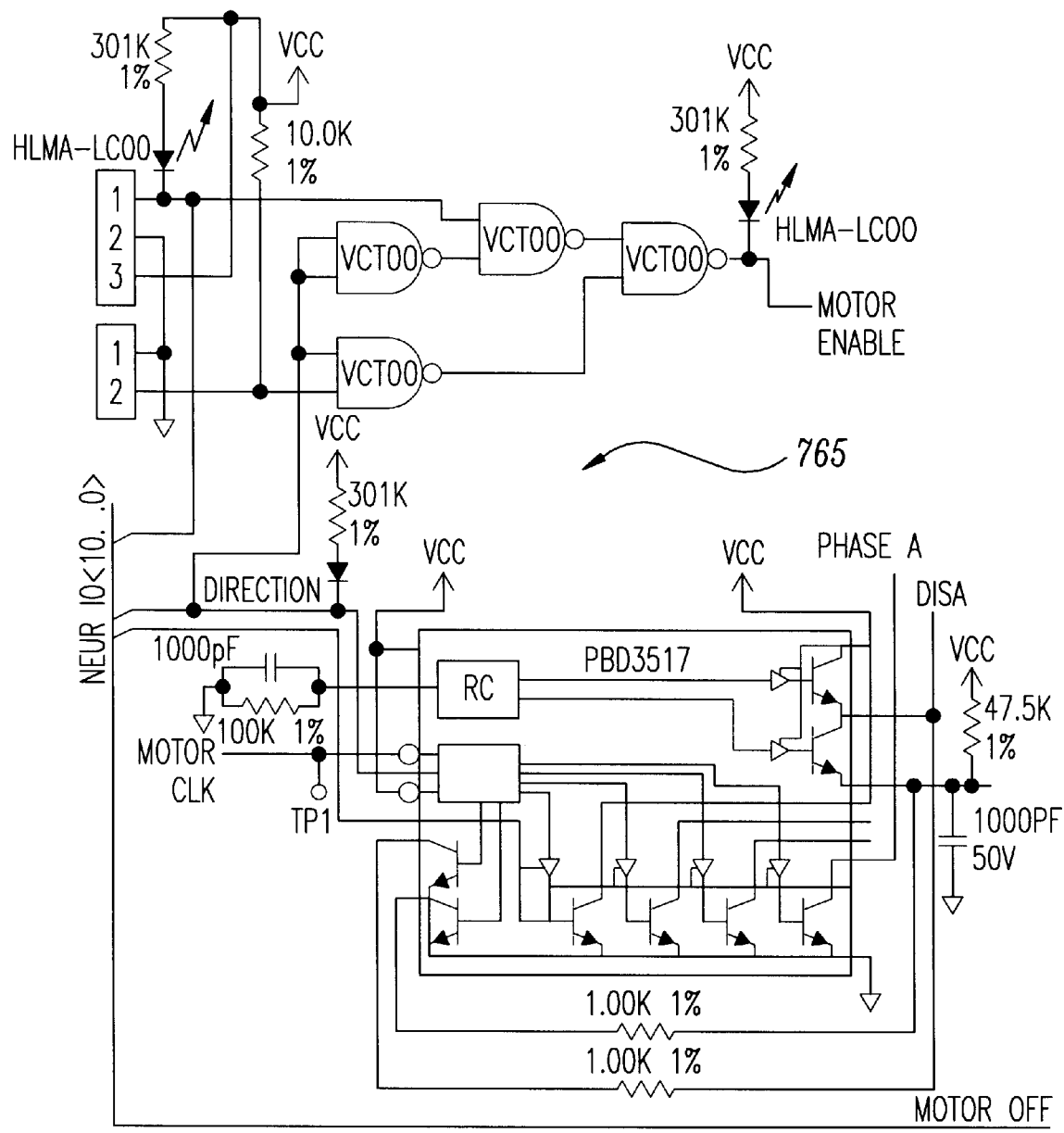
Figure 144:
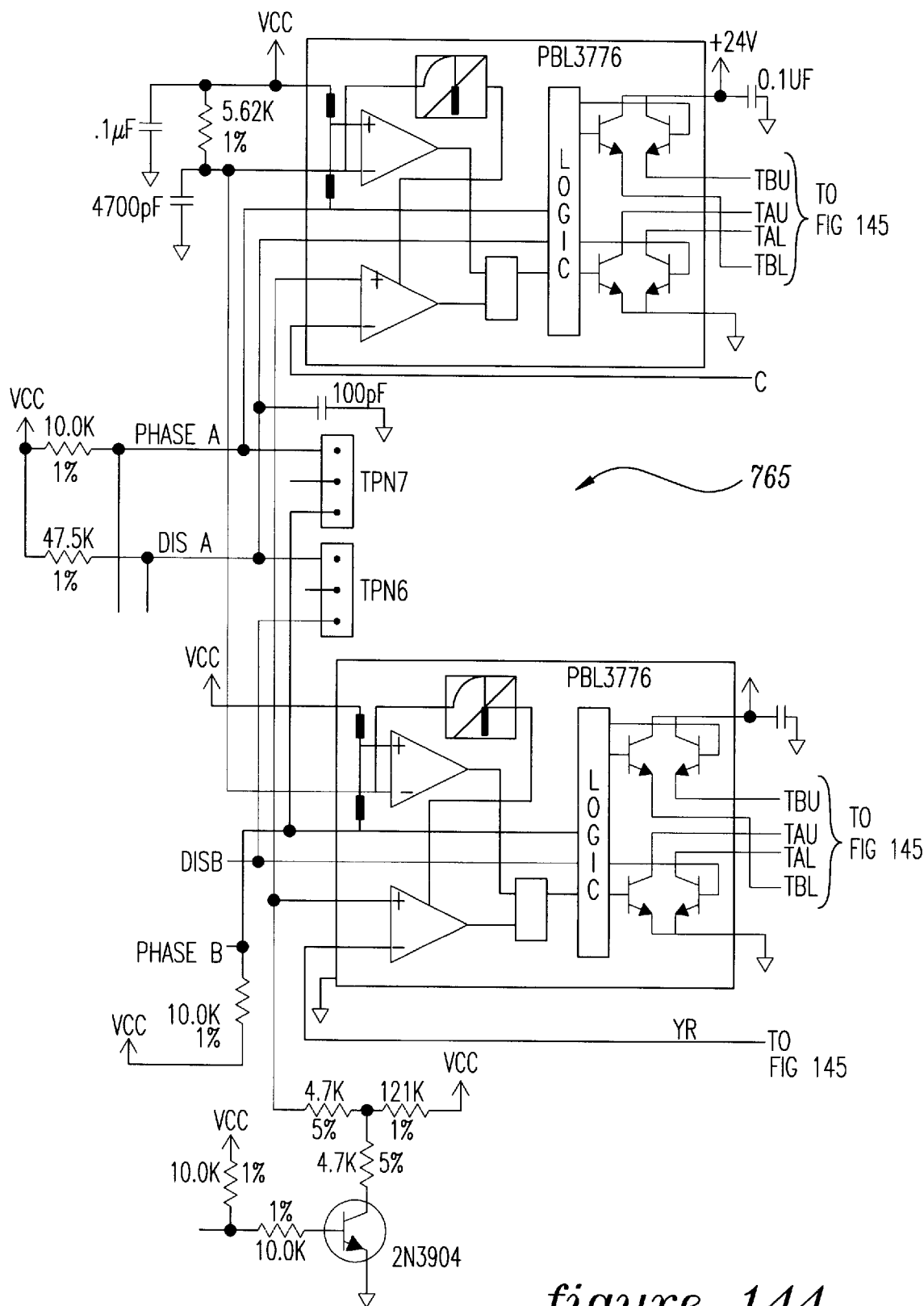
Figure 145:
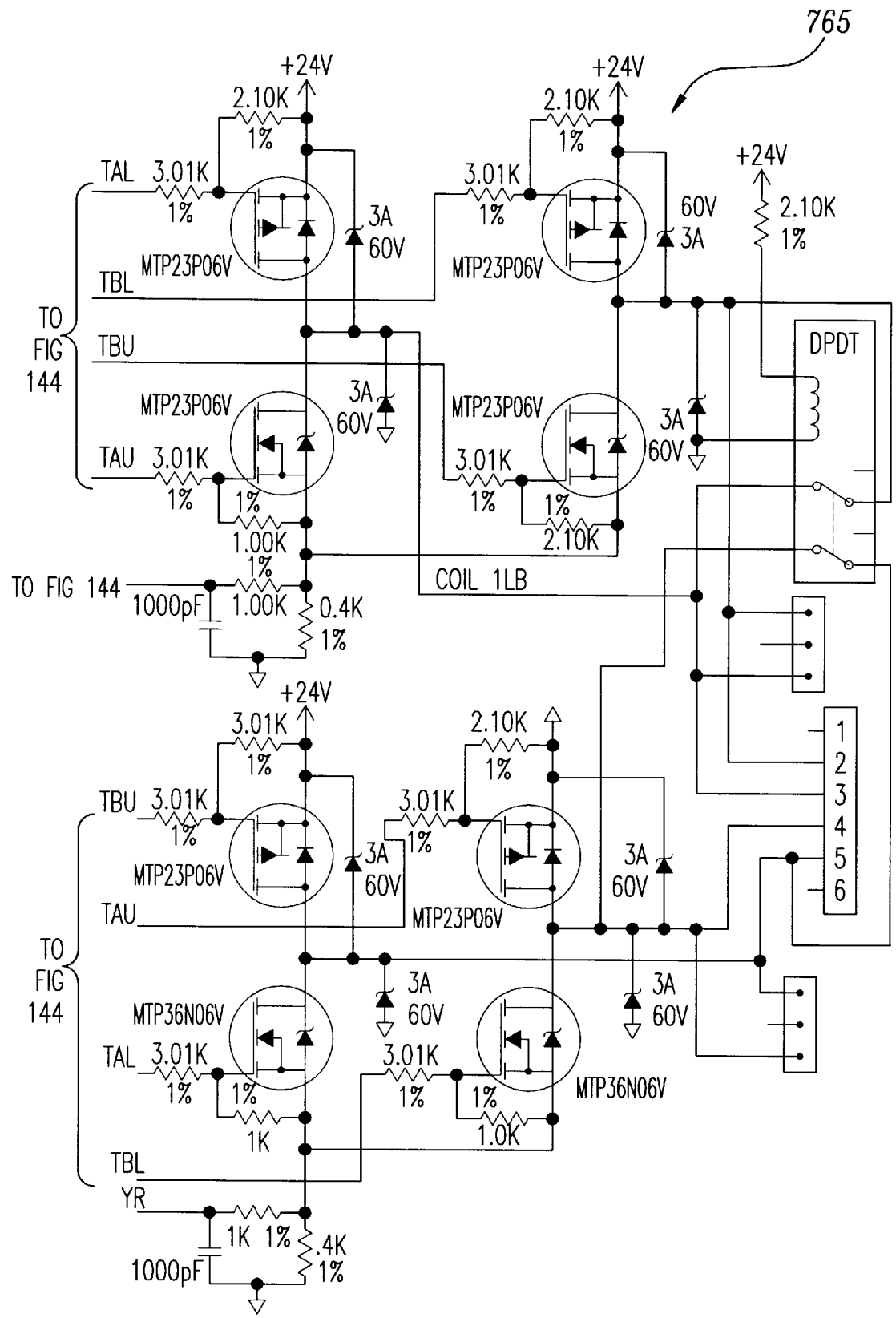
Figure 146:
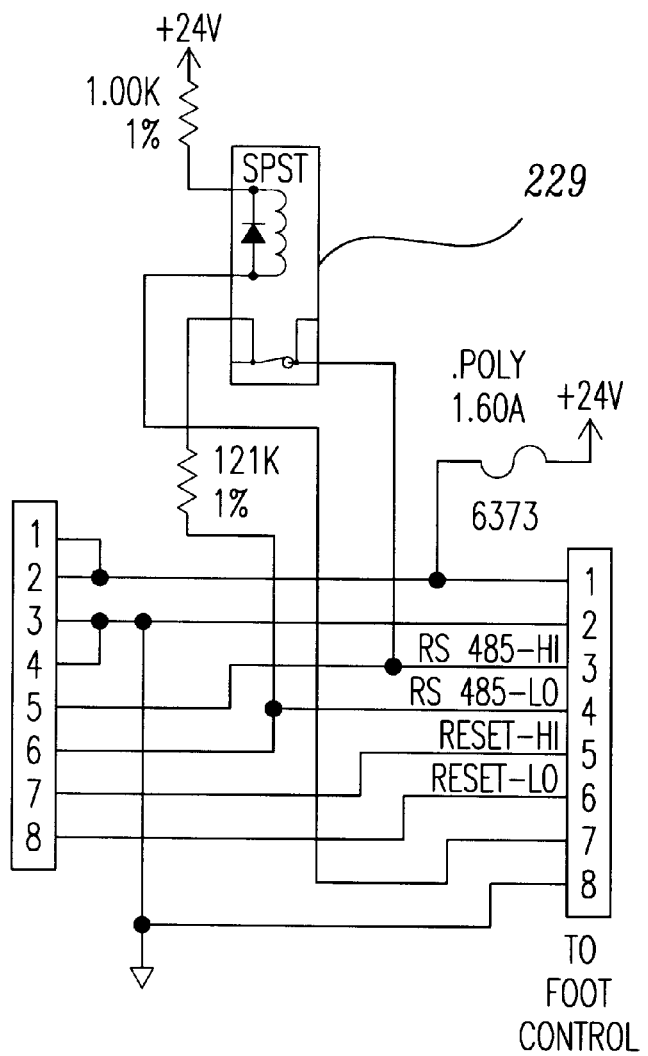

In order to identify the cassettes corresponding to the procedure with which they are to be used, each cassette carries a particular color. Preferably the color-bearing means carried by each cassette is a coupler member, or insert, such as illustrated at 150 in the aforesaid patent. It is generally I-shaped and frictionally fits in a recess in the cassette such as shown at 130 in the aforesaid patent. These removable color-bearing means, for example, one yellow and the other blue, may be easily applied to and removed from the cassettes which may be otherwise identical. When a cassette is inserted into module 321, the color-bearing means is positioned adjacent a cassette present sensor 525 which generates a signal indicating the presence of the cassette. Preferably, the cassette present sensor 525 is embodied by a photoelectric color sensor, e.g., an infrared light source in a photoelectric circuit, such as that sold by Tri-Tronics Co., Inc. of Tampa, Fla. under its model number F4. The yellow color will reflect the infrared light and the blue will absorb it thus differentiating a cassette for one particular procedure from another for a different procedure. Thus, cassette present sensor detects the presence of the cassette as a function of the color of the color-bearing means. FIG. 61 illustrates a preferred circuit which receives the signal generated by cassette present sensor 525 for communication to computer unit 3. If the cassette color does not correspond to the particular procedure selected by the surgeon, an audible and/or visible signal indicates this to the user via the user interface. Also, computer unit 3, in response to this information, prevents any ophthalmic procedure from being carried out until the user installs the correct cassette. In the embodiment of FIG. 32, cassette present sensor 525 provides a signal to computer unit 3 for informing the user of the incorrect cassette by first providing a signal to a status register 527 of EPLD 467. In turn, EPLD 467 and coprocessor circuit 465 provide the signal to neuron circuit 455 for communication back to computer unit 3.

In addition to feedback regarding the particular aspiration and irrigation levels, module 321 also includes cassette level sensors 529 for generating an almost full and a full signal for notifying the user via the user interface that the cassette should be changed.

A priming function available to the user via the user interface allows the user to prime the surgical handpieces by opening and closing the irrigation pinch valve 495 and by removing air from the aspiration line. This function also allows the user to eject the aspiration collection cassette by selecting an ejection option.

As described above, venturi IAV module 321 also supports the vitrectomy function of system 1. In a preferred embodiment, venturi IAV module 321 includes a vitrectomy port to which a vitrectomy cutter is connected. Preferably, module 321 controls the vitrectomy cutter so that it provides three types of cutting action: linear cut rate; fixed cut rate; and single cut. Preferably, the linear cut rate may range from 30 to 750 cuts per minute and may vary in 1 cut per minute increments. The user sets the cut rate via touch-responsive screen 255, remote control 39 or foot control assembly 15 and controls the cut rate via foot control assembly 15. The user may also program the fixed cut rate to provide 30 to 750 cuts per minute in 1 cut per minute increments. In this instance, the user sets the fixed cut rate via touch-responsive screen 255, remote control 39 or foot control assembly 15 and changes the fixed cut rate via foot control assembly 15. The single cut is provided with fixed, on/off control. When a single cut is enabled (on), the vitrectomy cutter will close/open one time with a single activation. The user selects the single cut via touch-responsive screen 255, remote control 39, or foot control assembly 15 and activates the cut via foot control assembly 15. The vitrectomy cutter attached to venturi IAV module 321 is driven from the external air/gas input which is also used to drive the venturi pump.

As shown in FIG. 32, EPLD 467 preferably includes a vitrectomy timer 533 for performing the timing functions necessary for setting the vitrectomy cutter's cut rate. Solenoid drivers 497 drive a vitrectomy solenoid 535 as a function of the timing signal from the vitrectomy timer 533 for controlling vitrectomy cutting.

Preferably, system 1 includes scroll IAV module 323 in addition to or instead of IAV module 321. Although similar to venturi IAV module 321, scroll IAV module 323 uses a scroll pump (not shown), rather than a venturi pump, to provide the irrigation and aspiration functions. According to the invention, the scroll pump of scroll IAV module 323 can function as a venturi aspiration system (i.e., vacuum control) or as a scroll aspiration system (i.e., flow control).

In this instance, module 323 operates in conjunction with a disposable scroll cassette which includes the scroll pump, pinch valve openings for controlling irrigation, aspiration, venting and calibration, a transducer diaphragm, and a collection reservoir. The scroll cassette also includes the irrigation line, the aspiration line, and the collection reservoir at the front of the cassette housing. The user loads the scroll cassette into a retractable drawer located on the front of module 323. Once loaded, the scroll cassette is engaged and disengaged to the drive and control systems of module 323 via touch-responsive screen 255. In other words, scroll IAV module 323 retracts, or engages, the cassette or extends, or disengages, the cassette when commanded via an entry to touch-responsive screen 255.

The aspiration portion of scroll IAV module 323 drives a single aspiration port which provides either vacuum or flow control of aspiration. Preferably, the vacuum aspiration function provides vacuum levels from 0 mmHg to 550 mmHg in 1 mmHg increments and the flow aspiration function provides flow rates from 1 cc/min to 60 cc/min in 1 cc/min increments. The user sets the aspiration operating parameters via touch-responsive screen 255, remote control 39 or foot control assembly 15 and changes them via foot control assembly 15.

The irrigation portion of scroll IAV module 323 also supports gravity-fed irrigation similar to venturi IAV module 321. In contrast to venturi IAV module 321, though, module 323 does not include pinch valve 495. Rather, scroll IAV module 323 provides irrigation control via the disposable scroll cassette in combination with a solenoid plunger inside module 323. As with module 321, the user has fixed, on/off (open/close) control of the irrigation function of scroll IAV module 323 via touch-responsive screen 255 or foot control assembly 15.

Similar to venturi IAV module 321, scroll IAV module 323 also supports the vitrectomy function of system 1. However, a pneumatic pump located inside module 323 drives the vitrectomy cutter attached to scroll IAV module 323 instead of the external air/gas input to venturi IAV module 321.

Figure 147:
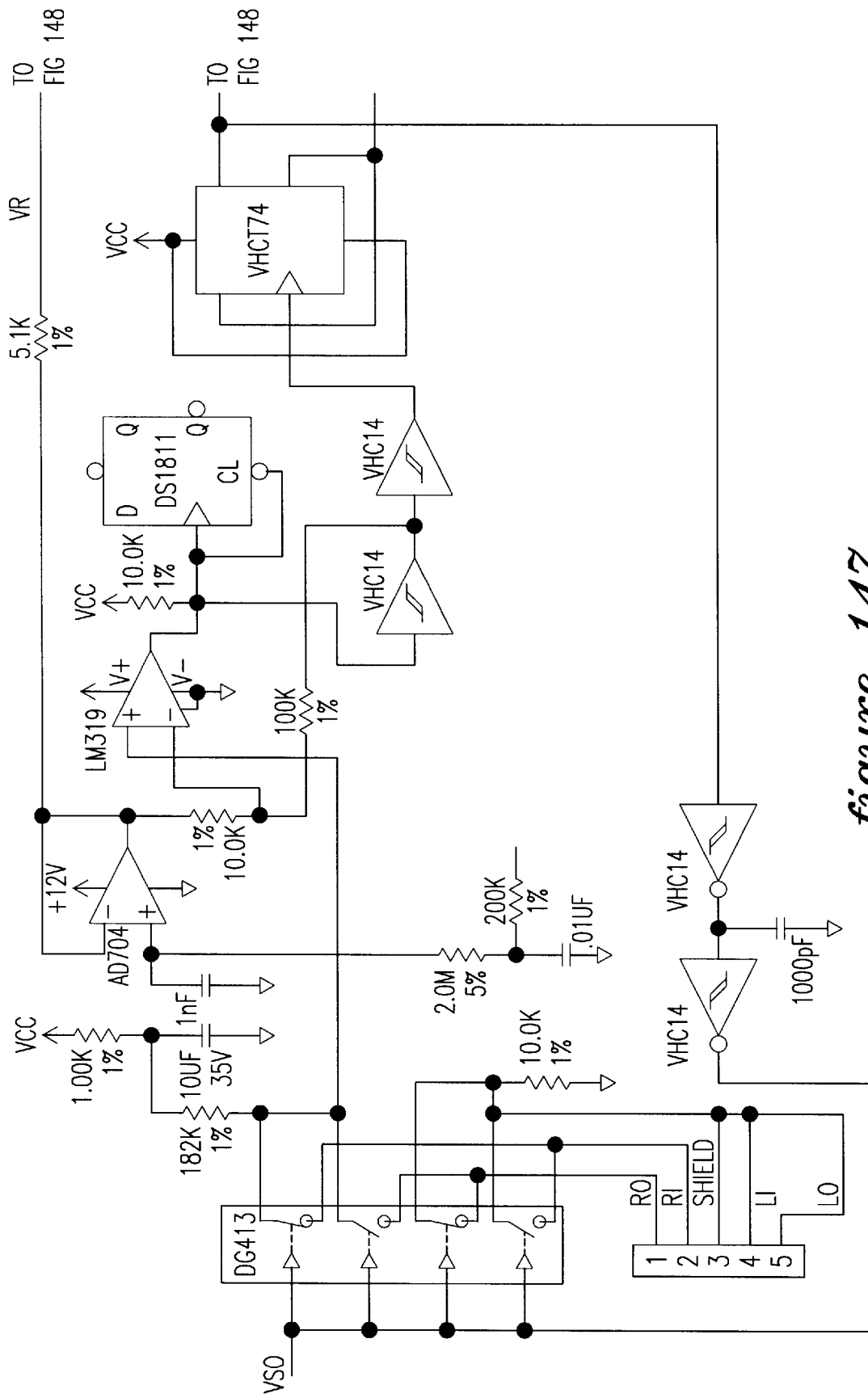
FIGS. 147 and 148 are schematic diagrams illustrating a pressure sensing circuit for use with a scroll pump according to an alternative embodiment of the irrigation, aspiration and/or vitrectomy module of FIGS. 32 and 43–60.
Figure 148:
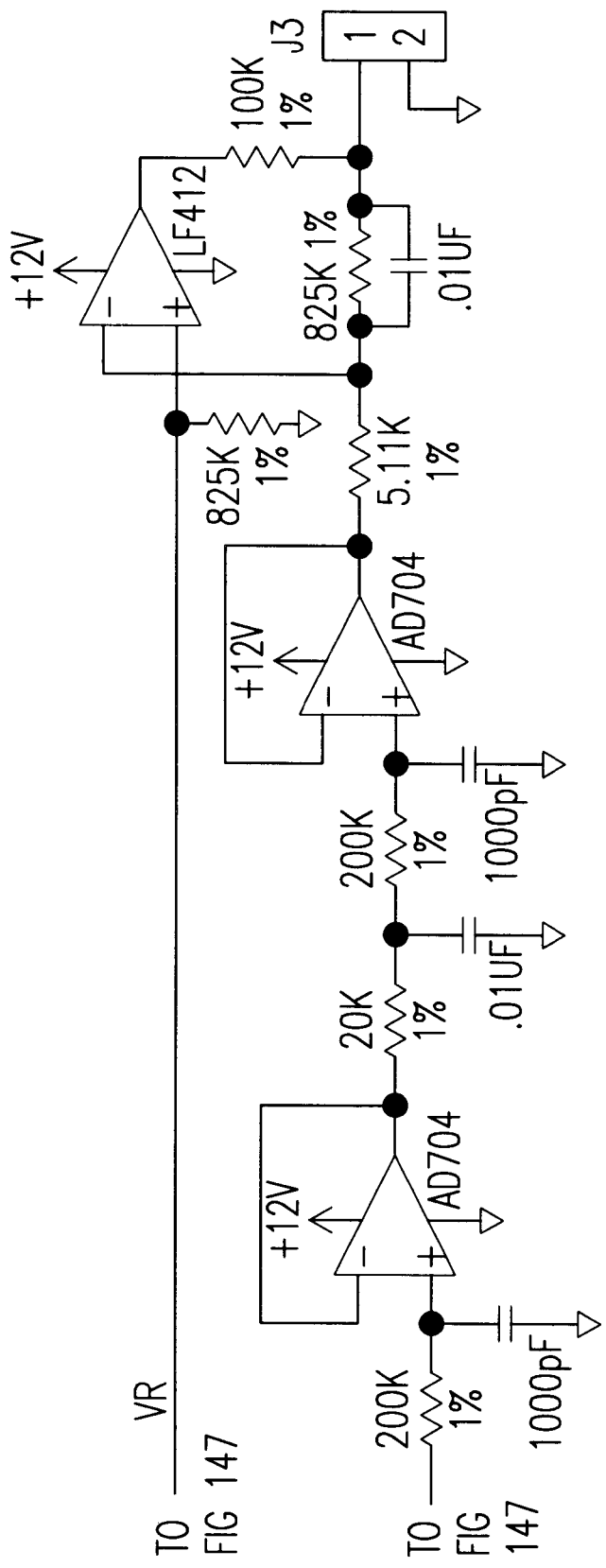
Figure 149:
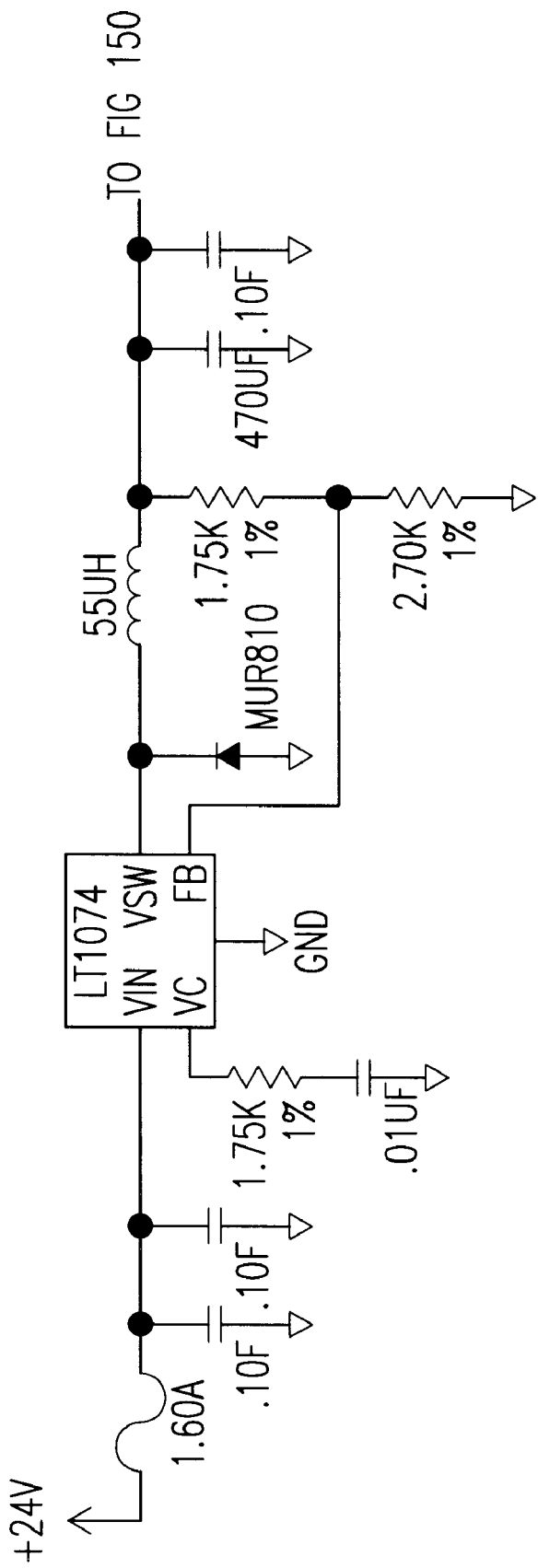
FIGS. 149 and 150 are schematic diagrams illustrating the power module of FIG. 39 for providing power to the backplane of FIGS. 40–42.
Figure 150:
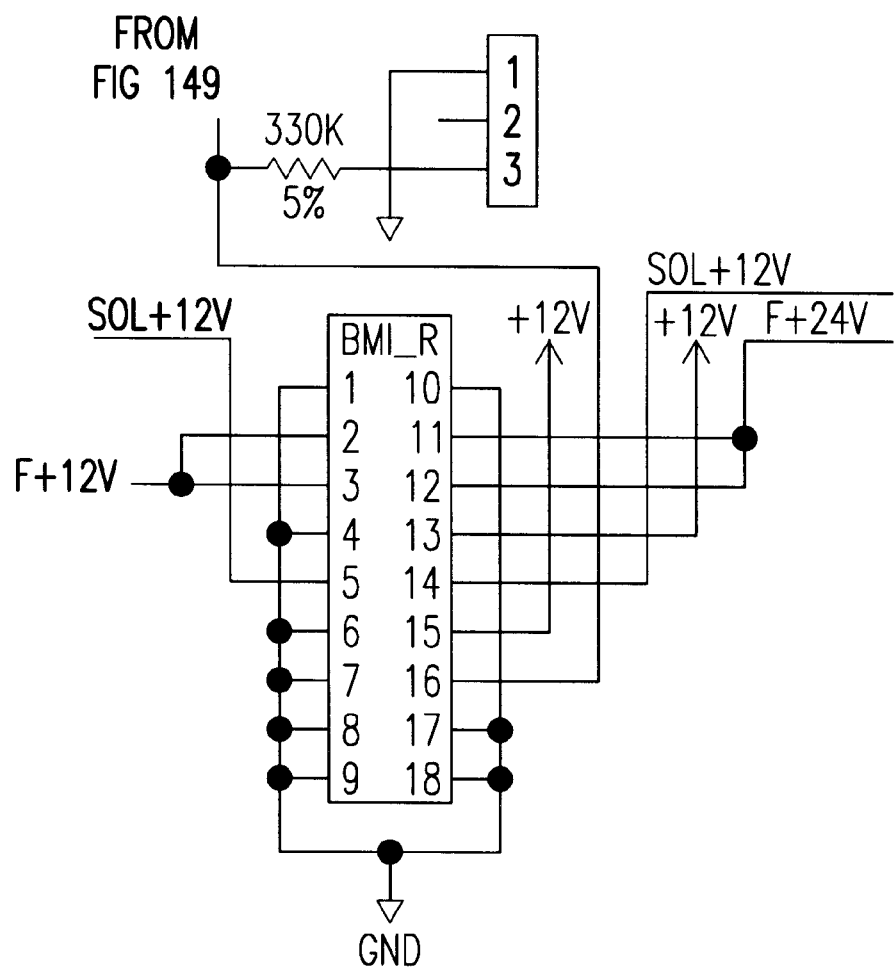

FIGS. 147 and 148 illustrate a preferred pressure sensing circuit for use with scroll IAV module 323 in schematic diagram form.

Figure 33:
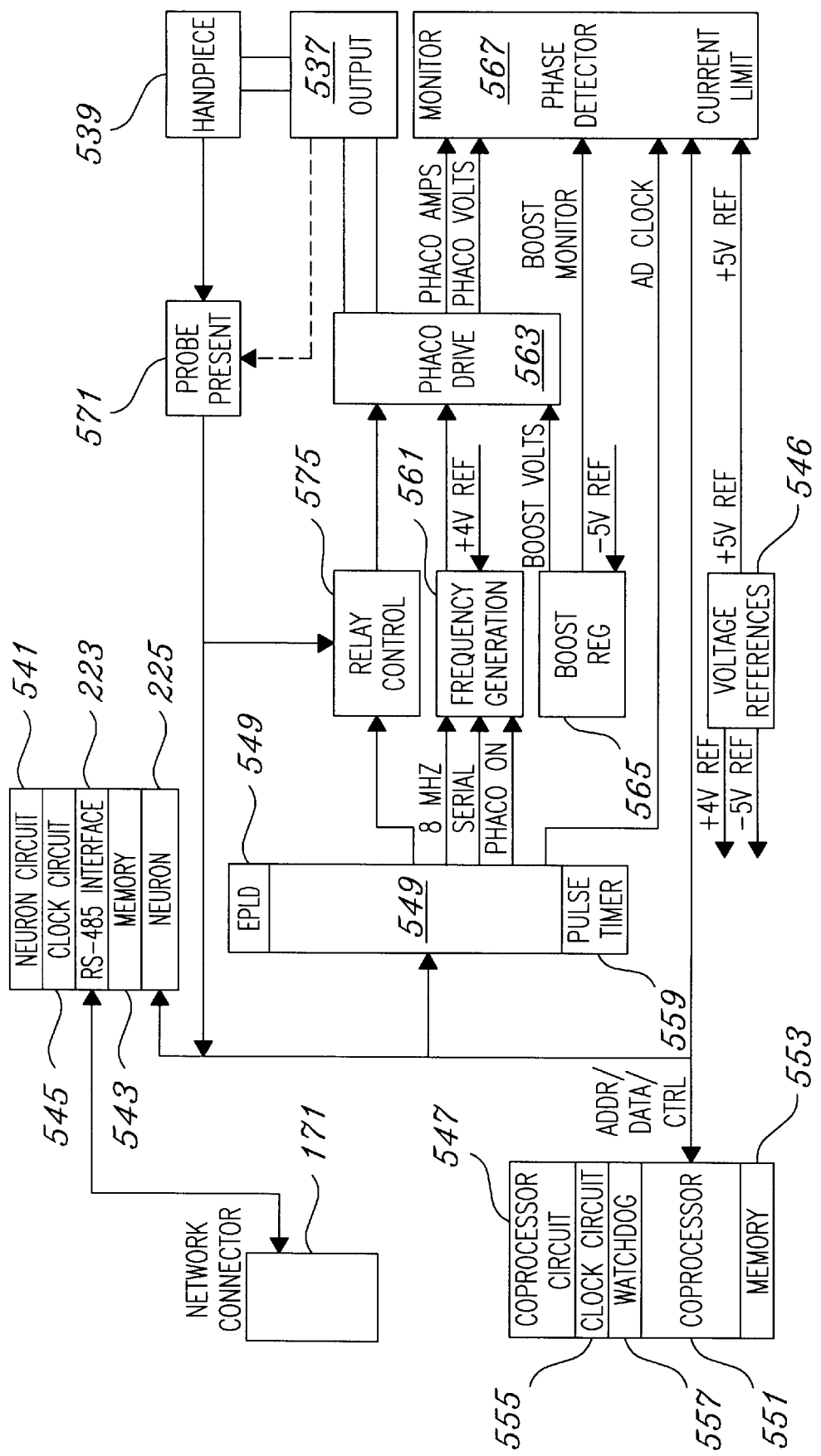
FIG. 33 is a block diagram of a phacoemulsification and/or phacofragmentation module according to a preferred embodiment of the system of FIG. 1.

Turning now to FIG. 33, phacoemulsification and phacofragmentation module (phaco) 325 (shown in detail in FIGS. 26A–26T) is a self-contained module which delivers, for example, up to 35 watts of phaco power into 5000 ohms at a frequency of 29±2 kHz to a phaco output port 537 to which a phacoemulsification and/or phacofragmentation handpiece 539 is connected. In one preferred embodiment, phaco module 325 supports both linear and pulsed operation. The linear phaco function provides continuous phaco power which the user may program to range from 0% to 100% of maximum 1% increments. The surgeon activates the linear phaco output at the minimum programmed phaco power level by depressing the center foot pedal of foot control assembly 15 and then increases it to the maximum programmed output level as a function of linear foot pedal travel. In this instance, linear phaco power ramps up from zero at a fixed linear rate. Preferably, the user sets the output levels via touch-responsive screen 255, remote control 39, or foot control assembly 15 and controls the linear phaco function via foot control assembly 15. In contrast to linear operation, the pulsed phaco function provides phaco power for programmed, finite time durations (e.g., periodic). Module 325 provides the user with fixed, on/off power control which the user may set at 1% to 100% of maximum in 1% increments. The user then may program the pulsed output control to provide between 1 to 20 pulses per second in 1 pulse per second increments. The user sets the output power level and pulse rate via touch-responsive screen 255 and controls them via foot control assembly 15.

In a preferred embodiment, phaco module 325 has a neuron circuit 541 connected to the network via the network connector 171 at the rear of module 325 which connects to backplane 101. The neuron circuit 541 includes RS485 transceiver 223 for receiving and transmitting data over the data communications bus. Neuron processor 225, coupled to transceiver 223, provides network communications control for module 325. Neuron processor 225 also executes embedded application programs stored in a memory 543 (e.g., a flash EEPROM) for controlling the phacoemulsification and phacofragmentation functions of system 1. The memory 543 also stores the configuration and identification data for use in initializing module 325 on the network. Advantageously, central processor 245 is able to reprogram memory 543 via the data communications bus in response to the information provided by the user. Neuron circuit 541 also includes a clock circuit 545 (e.g., a crystal oscillator) providing a time base for neuron 225 to operate. Phaco module 325, similar to IAV module 321, includes a power regulation or voltage reference circuit 546 for generating a ±5 volts and 4 volts supplies for use by the circuitry. Although not shown in FIG. 33, neuron circuit 541 also includes another RS485 transceiver for receiving a reset signal from computer unit 3 and a status LED for indicating that module 325 is active.

As shown in FIG. 33, phaco module 325 also includes a coprocessor circuit 547 which cooperates with an EPLD 549. The coprocessor circuit 547 preferably includes a coprocessor 551 (e.g., an Intel 386EX processor) and an associated memory 553 (e.g., a flash EEPROM and a static RAM), a clock circuit 555 (e.g., a crystal oscillator) and a watchdog 557. The EPLD 549 has a pulse timer 559 for providing clock signals used to a frequency generator 561 (e.g., sine wave generator). The coprocessor 551 of coprocessor circuit 545 cooperates with EPLD 547 to provide control signals to the frequency generator 561 for generating a programmable frequency for the pulsed phaco output. A phaco drive circuit 563 uses the programmable frequency generated by frequency generator 561 to drive the phaco output 537. Advantageously, phaco module 325 includes a boost regulator 565 for maintaining the rail voltage provided to the phaco drive 563 at 3 volts, for example, greater than the commanded phaco voltage level. This prevents excessive power dissipation in phaco drive 563. Phaco module 325 also includes a monitor circuit 567 for monitoring not only the boost voltage but also the phase of the phaco power. For optimum phaco functions, it is desired that the phase of the current and voltage remain on the resonant frequency of the handpiece 539 even as its load changes. The monitor circuit 567 also provides an overcurrent detector for preventing overcurrent conditions in phaco module 325.

According to the invention, phaco module 325 also includes a probe present circuit 571 for detecting the presence of handpiece 539 connected to phaco output 537. Coprocessor circuit 547 and EPLD 549 combine the output of the probe present circuit with shutdown signals generated by monitor circuit 567 to drive a relay control 575. In turn, the relay control 575 disables the phaco drive 563 in the event of undesirable operating conditions.

Figure 34:
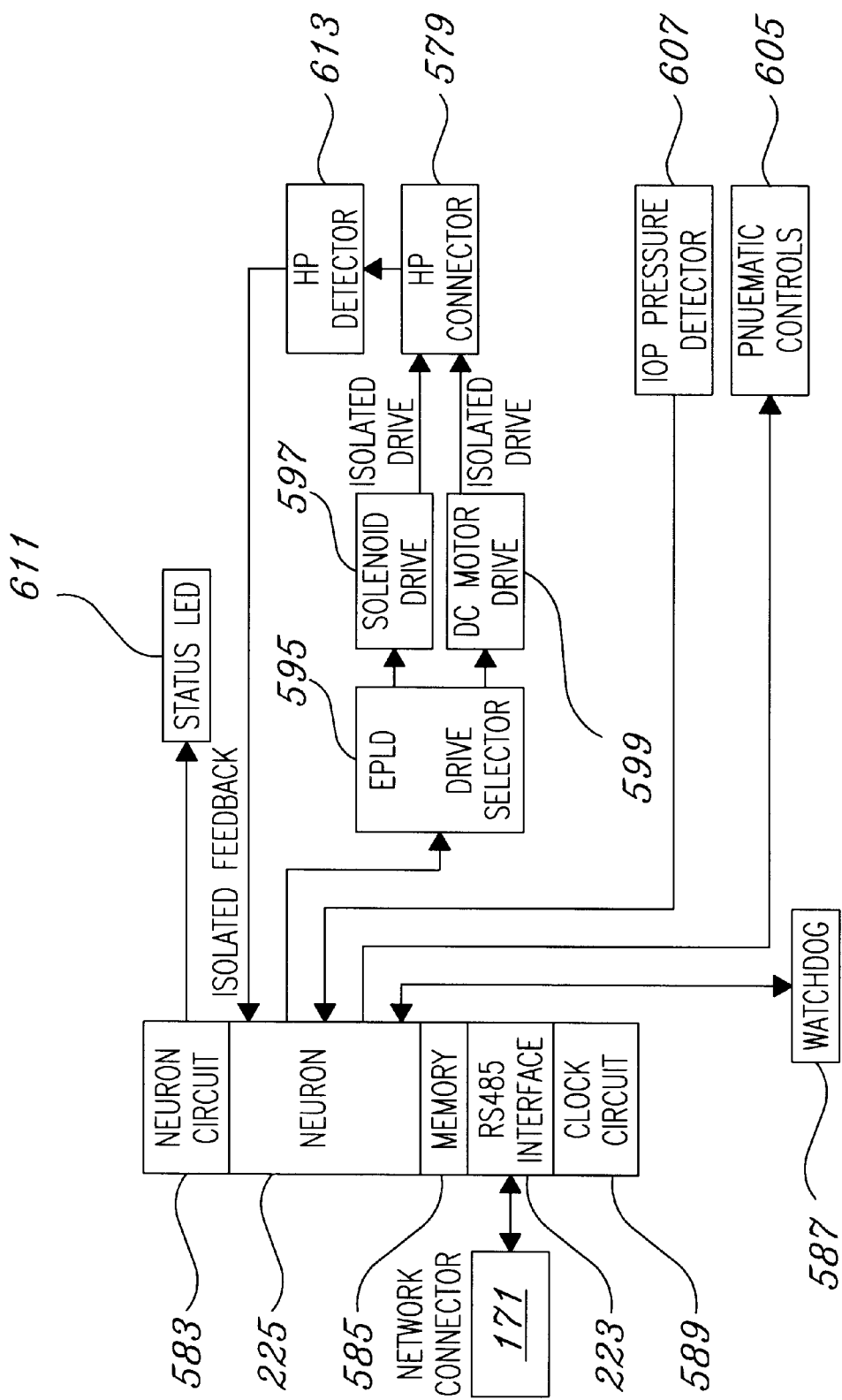
FIG. 34 is a block diagram of an air/fluid exchange, electric scissors and/or forceps module according to a preferred embodiment of the system of FIG. 1.

With respect to FIG. 34, scissors module 327 (shown in detail in FIGS. 89–103) preferably provides system 1 with not only a scissors function but also air/fluid exchange and forceps functions. In a preferred embodiment, module 327 supports an electrically driven port 579 which module 327 controls with respect to the user-selected operating mode and the operating parameters of a scissor/forceps handpiece connected to the port 579.

Scissors module 327 preferably provides the scissors/forceps function with a linear cut rate, a fixed cut rate, a single actuation and a proportional actuation. For example, the user may program scissors module 327 to provide a linear cut rate between 30 and 300 cuts per minute in one cut per minute increments via touch-responsive screen 255 or foot control assembly 15. In this instance, the surgeon controls the actual cutter rate via foot control assembly 15. The user may also program module 327 to provide a fixed cut rate between 30 and 300 cuts per minute in one cut per minute increments via touch-responsive screen 255 or foot control assembly 15 with foot control assembly 15 providing on/off control. As with the other operating parameters, the user may also program module 327 to provide a single cut, or an individual scissors/forceps cycle. The surgeon preferably activates the single cut via foot control assembly 15. The proportional actuation function closes the scissors handpiece by a certain percentage. For example, the user may program scissors module 327 to provide proportional actuation from 0% to 100% of closure in 25% closure increments wherein touch-responsive screen 255 and foot control assembly 15 provide the user with linear control.

As with the other modules 13, scissors module 327 has a neuron circuit 583 connected to the network via the network connector 171 at the rear of module 327 which connects to backplane 101. The neuron circuit 583 includes RS485 transceiver 223 for receiving and transmitting data over the data communications bus coupled to neuron processor 225. In addition to network communications control, neuron processor 225 also executes an embedded application program stored in a memory 585 (e.g., a flash EEPROM) for controlling the scissors/forceps and air/fluid exchange functions of system 1. The memory 585 also stores the configuration and identification data for use in initializing module 327 on the network. Advantageously, central processor 245 is able to reprogram memory 585 via the data communication bus in response to the information provided by the user. Neuron circuit 583 also includes a watchdog timer circuit 587 and a clock circuit 589. Although not shown in FIG. 34, neuron circuit 585 also includes another RS485 transceiver for receiving a reset signal from computer unit 3.

Similar to some of the other modules 13, scissors module 327 includes an EPLD 595 for use with the neuron processor 225 of neuron circuit 585 for controlling the scissor/forceps handpiece as a function of the user-entered operating parameters. In particular, the EPLD 595 is a drive selector for selecting either a solenoid drive 597 or a DC motor drive 599 for driving handpiece port 579. In this manner, scissors module 327 is able to drive two types of scissors instruments.

As shown in FIG. 34, scissors module 327 also includes pneumatic controls 605 for providing the air/fluid exchange function. For example, the pneumatic controls drive three solenoid valves for controlling charging, exhausting and holding of the IOP. Preferably, the air/fluid exchange portion of module 327 supports a single air port (not shown) driven by a pneumatic pump which is part of the pneumatic controls 605. As an example, the pump supports air pressures up to 100 mmHg in 1 mmHg increments at flow rates up to five standard cubic feet per hour. The user controls the air/fluid exchange port via touch-responsive screen 255 or foot control assembly 15. FIG. 34 also shows an IOP detector 607 (e.g., a pressure transducer) for providing feedback to neuron circuit 583. In response to the IOP detector 607 detecting either an over-pressure or under-pressure condition, the user interface provides an audible warning. Scissors module 327 further includes a status LED 611, such as a green LED on the front panel of module 327, for indicating that the module is active and a handpiece detector circuit 613 for detecting the presence of a scissors handpiece connected to port 579. Although not shown in FIG. 34, neuron circuit also includes another RS485 transceiver for receiving a reset signal from computer unit 3.

In the event of power loss or module failure, module 327 is equipped with a pneumatic receiver and shut-off valve to give the user adequate time to respond to the failure condition.

Figure 35:
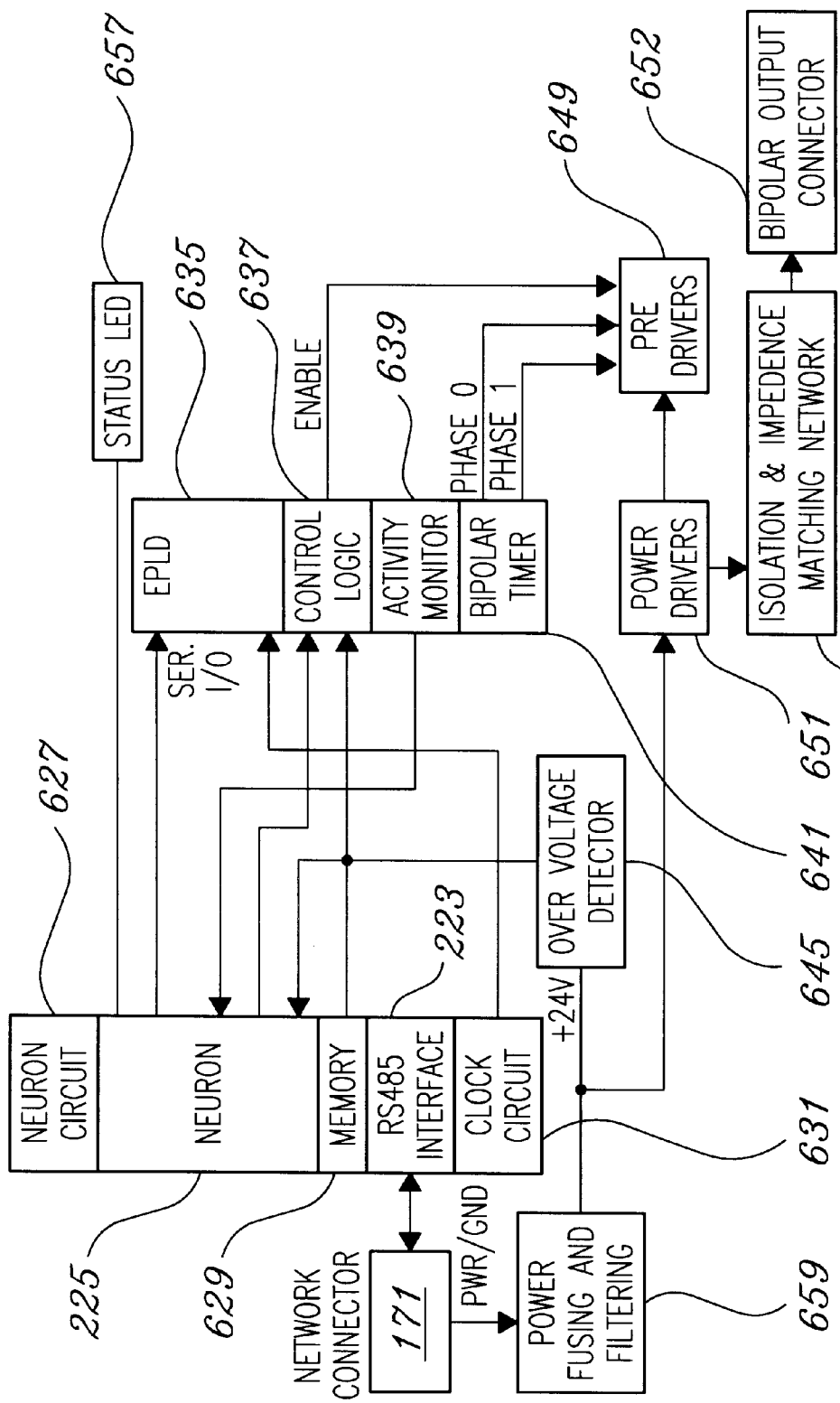
FIG. 35 is a block diagram of a bipolar coagulation module according to a preferred embodiment of the system of FIG. 1.

As shown in FIG. 35, bipolar coagulation module 329 (shown in detail in FIGS. 104–113) is a self-contained module which supports a single bipolar output 625. In a preferred embodiment, the bipolar output delivers up to 7.5 watts of bipolar power into 100 ohms. Preferably, module 329 controls the port to provide either a fixed bipolar function or a linear bipolar function. The user may program bipolar coagulation module 329 to provide fixed bipolar power between 2% to 100% of maximum in 1% increments. The bipolar output is preferably activated at the programmed output power level via a momentary contact (push-button) switch on foot control assembly 15. The bipolar output remains activated as long as the push-button remains depressed. The user sets the output level via touch-responsive screen 255, remote control 39 or foot control assembly 15 and changes the setting via a push-button on foot control assembly 15. The user may program module 329 to provide linear bipolar power between 2% to 100% of maximum and may vary the power level in 1% increments. The bipolar output is preferably activated at the minimum programmed output power level when the surgeon depresses the center foot pedal of foot control assembly 15 and then increases to the maximum programmed output power level as a function of linear foot pedal travel. The user sets the output level via touch-responsive screen 255, remote control 39 or foot control assembly 15 and controls the level via foot control assembly 15.

As with the other modules 13, coagulation module 329 has a neuron circuit 627 connected to the network via the network connector 171 at the rear of module 329 which connects to backplane 101. The neuron circuit 627 includes RS485 transceiver 223 for receiving and transmitting data over the data communications bus. Neuron processor 225, coupled to transceiver 223, provides network communications control for module 329. Neuron processor 225 also executes an embedded application program for controlling the bipolar coagulation function of system 1. In this instance, neuron circuit 627 includes a memory 629 (e.g., a flash EEPROM), for storing the application program for coagulation module 329. In addition, the memory 629 stores the configuration and identification data for use in initializing module 329 on the network. Advantageously, central processor 245 is able to reprogram memory 629 via the data communication bus in response to the information provided by the user. Neuron circuit 627 also includes a clock circuit 631 (e.g., a crystal oscillator) providing a time base for neuron 225 to operate. Although not shown in FIG. 35, neuron circuit 627 also includes another RS485 transceiver for receiving a reset signal from computer unit 3.

Coagulation module 329 also includes an EPLD 635, for use with the neuron processor 225 of neuron circuit 627 for controlling the bipolar coagulation device as a function of the user-entered operating parameters. In particular, the EPLD 635 includes a control logic circuit 637 for generating an enable signal to enable coagulation, an activity monitor 639 to monitor bipolar output voltage and output activity (whether fixed or linear output) and a bipolar timer 641 for generating a pulse width modulation frequency.

Bipolar coagulation module 329 further includes an over-voltage detector 645 for interrupting power to the bipolar output 625 in the event of an excessive or unwanted output condition. Preferably, the overvoltage detector 645 also communicates with the network via neuron processor 225 and transceiver 223 for signaling an alarm to the user of the undesirable output condition.

According to the invention, the neuron processor 225 of neuron circuit 627 in combination with EPLD 635 enable a set of pre-drivers 649 in the proper phase sequence and, in turn, a set of power drivers 651 provide power to bipolar output 625. In one embodiment, coagulation module 329 also includes an isolation and impedance matching network 653 for conditioning the output of power drivers 651.

FIG. 35 also illustrates a status LED 657 which, as described above, is preferably a green LED positioned on the front panel of module 329 for indicating to the user that coagulation module 329 is active. Module 329 also includes power fusing and filtering circuitry 659 to prevent overcurrent conditions and to reduce noise.

Figure 36:
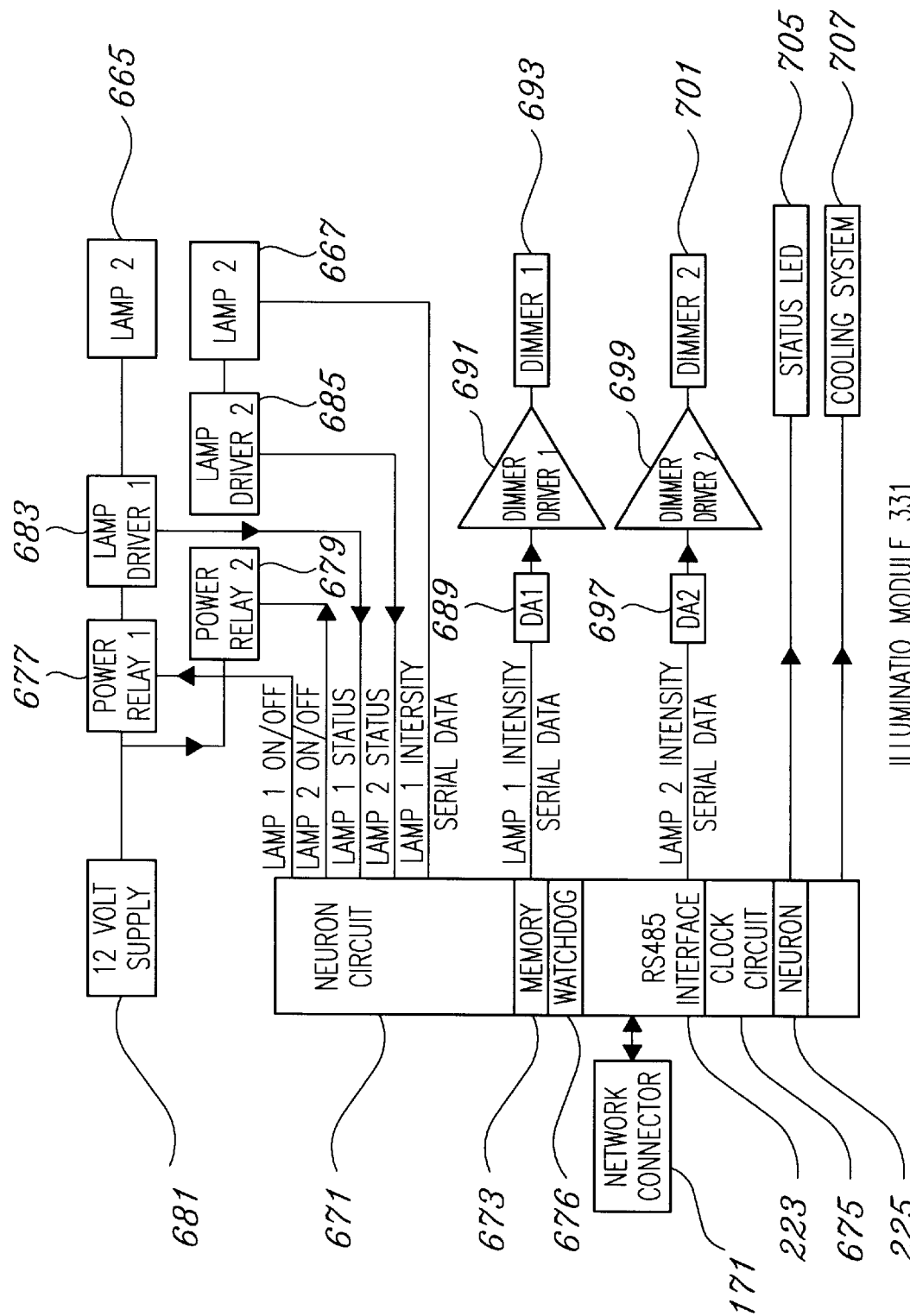
FIG. 36 is a block diagram of an illumination module according to a preferred embodiment of the system of FIG. 1.

Referring now to FIG. 36, illumination module 331 (shown in detail in FIGS. 114–125, is a self-contained module having at least two lamps, such as a first lamp 665 and a second lamp 667, for providing light to corresponding illumination ports at the front of module 331. According to the invention, the user connects a fiber optic illumination instrument, such as the endo-illuminator to one or both of the ports for use by the surgeon in illuminating the posterior portion of a patient's eye during surgery. Although module 331 provides individual control over the light supplied to each of the ports by lamps 665, 667, they may be used simultaneously if desired. Further, module 331 provides independent control of the intensity of the light provided at the ports. The user is able to select high (100%), medium (75%) or low (50%) output illumination levels via touch-responsive screen 255 or remote control 39.

In a preferred embodiment, illumination module 331 has a neuron circuit 671 connected to the network via the network connector 171 at the rear of module 331 which connects to backplane 101. The neuron circuit 671 includes RS485 transceiver 223 and neuron processor 225. Neuron processor 225 executes network communications control as well the application program for controlling the illumination function of system 1. In this instance, neuron circuit 671 includes a memory 673 (e.g., a flash EEPROM), for storing the application program for illumination module 331. In addition, the memory 673 stores the configuration and identification data for use in initializing module 331 on the network. Advantageously, central processor 245 is able to reprogram memory 673 via the data communication bus in response to the information provided by the user. Neuron circuit 671 also includes a clock circuit 675 (e.g., a crystal oscillator) for providing the clock signals used by neuron circuit 671, and a watchdog timer 676. Although not shown in FIG. 36, neuron circuit 671 also includes another RS485 transceiver for receiving a reset signal from computer unit 3.

As shown in FIG. 36, the neuron processor 225 of neuron circuit 671 provides an on/off signal to a first power relay 677 for lamp 665 and an on/off signal to a second power relay 679 for lamp 667. In turn, either or both of the relays 677, 679 connect a 12 volt supply 681 (provided via backplane 101 from power module 103) to a first lamp driver circuit 683 and/or a second lamp driver circuit 685, respectively, for firing either or both lamp 665 and lamp 667. In a preferred embodiment, lamp drivers 683, 685 provide feedback to neuron circuit 671 regarding the status of lamps 665, 667.

In order to vary the intensity of the light provided by lamp 665, the neuron circuit 671 of illumination module 331 first provides serial data representative of the desired intensity to a digital-to-analog (D/A) converter 689. In response to the output of the D/A converter 689, a dimmer driver circuit 691 drives a dimmer circuit 693. According to the invention, the dimmer circuit 693 adjusts the intensity of lamp 665. Thus, dimmer driver 691 controls the dimmer circuit 693 as a function of the serial data input to D/A converter 689 to set the intensity of lamp 665 at a desired level. In a similar manner, neuron circuit 671 also provides serial data representative of the desired intensity to a digital-to-analog (D/A) converter 697 to vary the intensity of the light provided by lamp 667. The D/A converter 697 then provides an analog intensity signal to a dimmer driver circuit 699 which in turn controls a dimmer circuit 701 as a function of the serial data input to D/A converter 697 for varying the intensity level of lamp 667.

Referring further to FIG. 36, illumination module 331 also includes a status LED 705, such as a green LED at the front of module 331 for indicating that module 331 is active. Module 331 also provides a cooling system 707, such as a fan, which is responsive to the neuron processor 225 of neuron circuit 671 for dissipating excessive heat inside module 331 which might damage its components.

In a preferred embodiment of the invention, system 1 also supports peripherals selected from the following: remote foot control assembly 15; instrument cart 21 with automated IV pole assembly 17; expansion base unit 207; and handheld IR remote control unit 39.

One of these peripherals, namely, foot control assembly 15, provides the surgeon with remote control of at least one microsurgical instrument 19 during performance of the surgical procedures. Although the user may be the surgeon, often a nurse or other person in the operating room provides input directly to the user interface of system 1. As such, foot control assembly 15 provides the primary interface between the surgeon and the microsurgical system 1. Advantageously, the surgeon can control a number of the functions provided by system 1 as well as change operating modes from foot control assembly 15.

Figure 37:
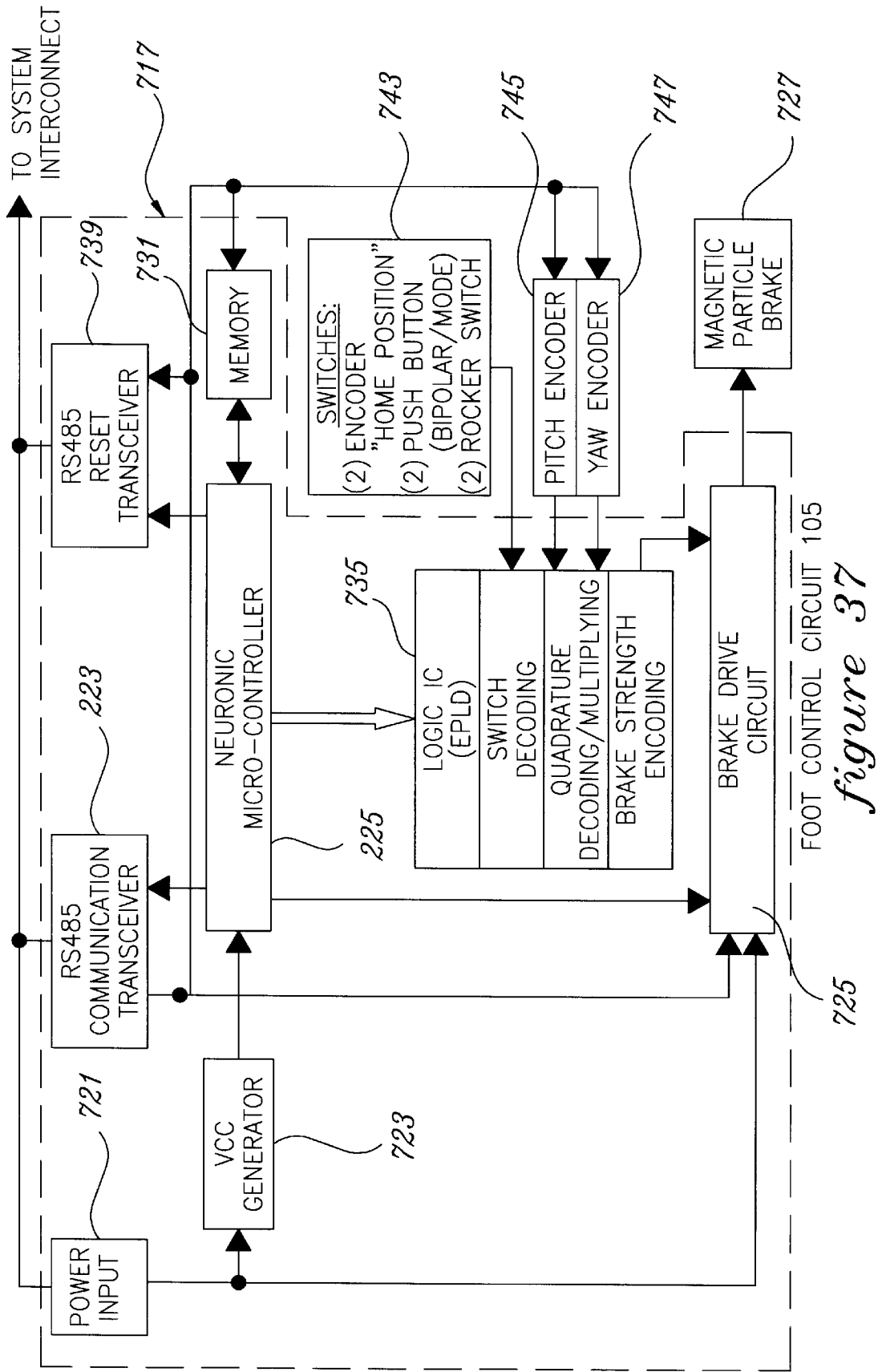
FIG. 37 is a block diagram of a peripheral foot control circuit according to a preferred embodiment of the system of FIG. 1.

FIG. 37 illustrates control circuit 105 according to one preferred embodiment of the invention for controlling foot control assembly 15. Preferably, the foot control circuit 105 (shown in detail in FIGS. 126–136) provides network communication and controls the operation of foot control assembly 15 as a function of at least one operating parameter.

Although not installed in base unit 7, foot control circuit 105 has a neuron circuit 717 that includes RS485 transceiver 223 for receiving and transmitting data over the data communications bus. Neuron processor 225, coupled to transceiver 223, provides network communications control for foot control circuit 105. Thus, with respect to the computer network, foot control assembly 15, as controlled by foot control circuit 105, is functionally equivalent to modules 13. In other words, foot control circuit 105 is also connected to the data communications bus which provides communication of data representative of the operating parameters between the user interface and foot control circuit 105. Thus, the data communications bus also provides peer-to-peer communication between foot control circuit 105 and surgical modules 13. Further, foot control circuit 105 is responsive to the surgeon's instructions via foot control assembly 15 for changing the operating parameters of microsurgical instruments 19 via the network.

In this instance, the transceiver 223 of neuron circuit 717 is connected to the data communications bus via a data cable (not shown) which connects to the connector 157 on the back of backplane 101. In the alternative, IV pole assembly 17 provides a jumper to which foot control circuit 105 connects. A power input 721 provides power to foot control circuit 105 and a voltage regulator, such as a VCC generator 723, provides the necessary logic voltages for the circuit. FIG. 37 further illustrates a brake drive circuit 725 connected to a magnetic particle brake 727 for providing detents in foot pedal travel.

The neuron circuit 717 also includes a memory 731 (e.g., a flash EEPROM) for storing an application program for foot control circuit 105. In this instance, neuron processor 225 cooperates with an EPLD 735, to execute the embedded application program for controlling foot control assembly 15. In addition, the memory 731 stores the configuration and identification data for use in initializing foot control circuit 105 on the network. Further, as with modules 13, central processor 245 is able to reprogram memory 731 via the data communication bus in response to the information provided by the user. As shown in FIG. 37, neuron circuit 717 also includes an RS485 transceiver 739 for receiving a reset signal from computer unit 3.

In one preferred embodiment, foot control assembly 15 comprises a center foot pedal, a single rocker switch, and two separate push-button switches (see FIG. 231). Pitch and yaw movements of the center pedal preferably provide system 1 with dual linear and on/off controls. Each of these controls are fully programmable with respect to function and control parameters (i.e., range, mode, and the like). According to the invention, the EPLD 735 receives information from the various switches 743 and receives information regarding the travel of the center pedal via a pitch encoder 745 and a yaw encoder 747. According to the invention, EPLD 735 provides switch decoding, quadrature decoding/multiplying and brake strength encoding. Due to the limited number of inputs available to neuron 225, EPLD 735 provides decoding of the switch signals provided by switches 743. Further, pitch and yaw encoders 745, 747 each provide two quadrature signals to represent the amount and direction of travel of the foot pedal. EPLD 735 decodes these signals for use by the neuron 225 of neuron circuit 717. Additionally, EPLD 735 encodes brake strength signals generated by neuron 225 for use by the brake drive circuit 725.

As an example, the center pedal of foot control assembly 15 provides approximately 15° of up and down movement in the pitch, or vertical, direction. Within this range of movement, the user may program two detent positions. Further, when the center pedal travels through either of these detent positions, the resistance offered by the pedal changes to provide tactile feedback to the surgeon. This resistance preferably remains the same so long as the center pedal is traveling within the programmed range of the detent. When released, the pedal returns to a home (up) position. Functionally, the user may also program pitch movement to provide linear or on/off control for all applicable surgical functions. For example, foot control assembly 15 provides linear control as a function of relative foot pedal displacement (e.g., 0° to 15° down corresponds to 0% to 100% output) and provides fixed control as a function of absolute foot pedal displacement (e.g., 0° to 10° down corresponds to off while 10° to 15° corresponds to on).

In the horizontal or yaw direction, the center foot pedal provides approximately ±10° of left/right movement. In this instance, the pedal has a center detent and, when released, returns to a home (center) position. Functionally, the user may program the yaw movement to provide linear or on/off control for all applicable surgical functions. For example, the pedal provides linear control as a function of relative foot pedal displacement (e.g., 0° to 10° left corresponds to 0% to 100% output) and provides fixed on/off control as a function of absolute foot pedal displacement (e.g., moving to the left (right) of the center detent corresponds to on (off)).

Preferably, the rocker switch is a two-position switch located to the right of the center foot pedal of foot control assembly 15. When released, the rocker switch returns to an off (center) position. Functionally, the user may program the rocker switch to provide up/down, increment/decrement, or on/off controls for all applicable surgical functions (e.g., phacoemulsification and phacofragmentation power levels, bipolar power levels, aspiration levels, and the like). The two push-button switches of foot control assembly are preferably located opposite the rocker switch to the left of the center foot pedal. In a preferred embodiment, one of the switches is dedicated to bipolar output control, while the user may program the other switch to control one of the surgical functions. When released, the push-button switches return to an off (up) position.

Figure 38:
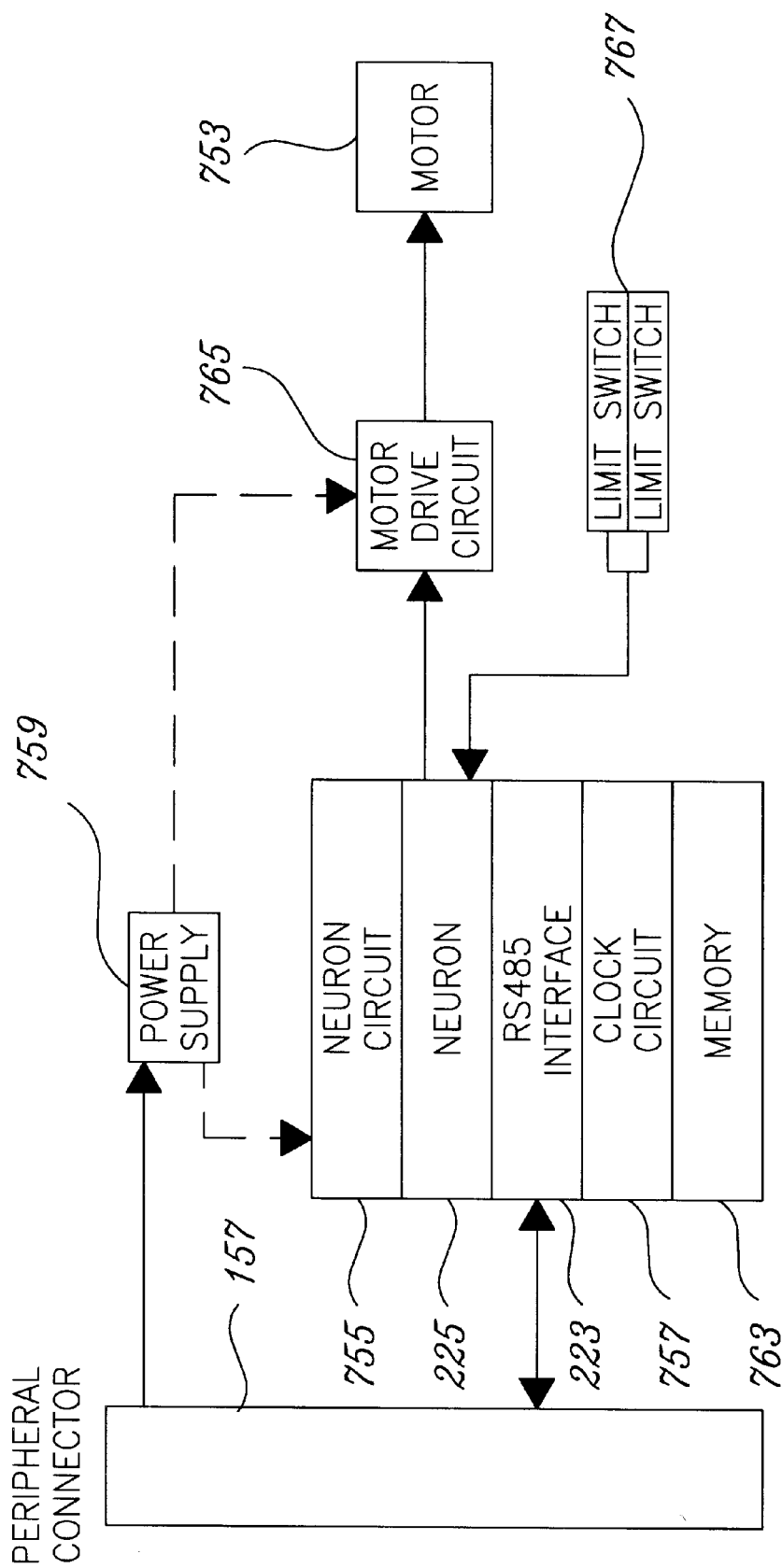
FIG. 38 is a block diagram of a peripheral intravenous pole control circuit according to a preferred embodiment of the system of FIG. 1.

Referring now to FIG. 38, system 1 also includes IV pole assembly 17 having the control circuit 107 (shown in detail in FIGS. 137–146) for controlling a motor 753 to raise and lower the IV pole of IV pole assembly 17. Preferably, the IV pole control circuit 107 provides network communication and controls the operation of IV pole assembly 17 as a function of at least one operating parameter. Although not installed in base unit 7, IV pole control circuit 107 has a neuron circuit 755 that includes RS485 transceiver 223 and neuron processor 225, coupled to transceiver 223. As such, the neuron circuit 755 provides network communications control for IV pole control circuit 107. Thus, with respect to the computer network, IV pole assembly 17, as controlled by IV pole control circuit 107, is functionally equivalent to modules 13. In other words, IV pole control circuit 107 is also connected to the data communications bus which provides communication of data representative of the operating parameters between the user interface and IV pole control circuit 107. Neuron circuit 755 also includes a clock circuit 757 (e.g., a crystal oscillator) providing a time base for neuron 225 to operate. A power input 759, preferably from base unit 7, provides power to IV pole control circuit 107.

Similar to foot control circuit 105, the transceiver 223 of IV pole control circuit 107 is connected to the data communications bus via a data cable (not shown) which connects to the connector 157 on the back of backplane 101. The neuron circuit 755 also includes a memory 763 (e.g., a flash EEPROM) for storing an application program for IV pole control circuit 107. In this instance, neuron processor 225 executes the embedded application program for controlling a motor drive circuit 765 as a function of the operating parameters of IV pole assembly 17. In addition, the memory 763 stores the configuration and identification data for use in initializing IV pole control circuit 107 on the network. Further, as with modules 13, central processor 245 is able to reprogram memory 763 via the data communication bus in response to the information provided by the user. Although not shown in FIG. 38, neuron circuit 755 also includes a watchdog timer and another RS485 transceiver for receiving a reset signal from computer unit 3.

Preferably, IV pole assembly 17 is an integrated part of instrumentation cart 21 and is used to position, for example, two 500 cc containers of fluid up to 100 cm above cart 21. In this regard, an IV pole of IV pole assembly 15 is able to travel up or down at a rate of 6 cm/sec and has a positioning resolution of 1 cm and a positioning repeatability of 2 cm. Functionally, the user sets the IV pole parameters via touch-responsive screen 255, remote control 39 or foot control assembly 15. A pair of limit switches 767 provide feedback to neuron circuit 755 regarding the height of the IV pole. For example, if the IV pole reaches its maximum allowed height, one limit switch 767 instructs neuron circuit 755 to discontinue causing motor 753 to drive the pole up. Likewise, if the pole reaches its minimum height, the other limit switch 767 instructs neuron circuit 755 to discontinue causing motor 753 to drive the pole down. In an alternative embodiment, a single limit switch 767 senses when the IV pole reaches its minimum height. In this embodiment, the motor 753 is a stepper motor and neuron 225 counts the number of steps to determine when the pole reaches its maximum height.

Figure 39:
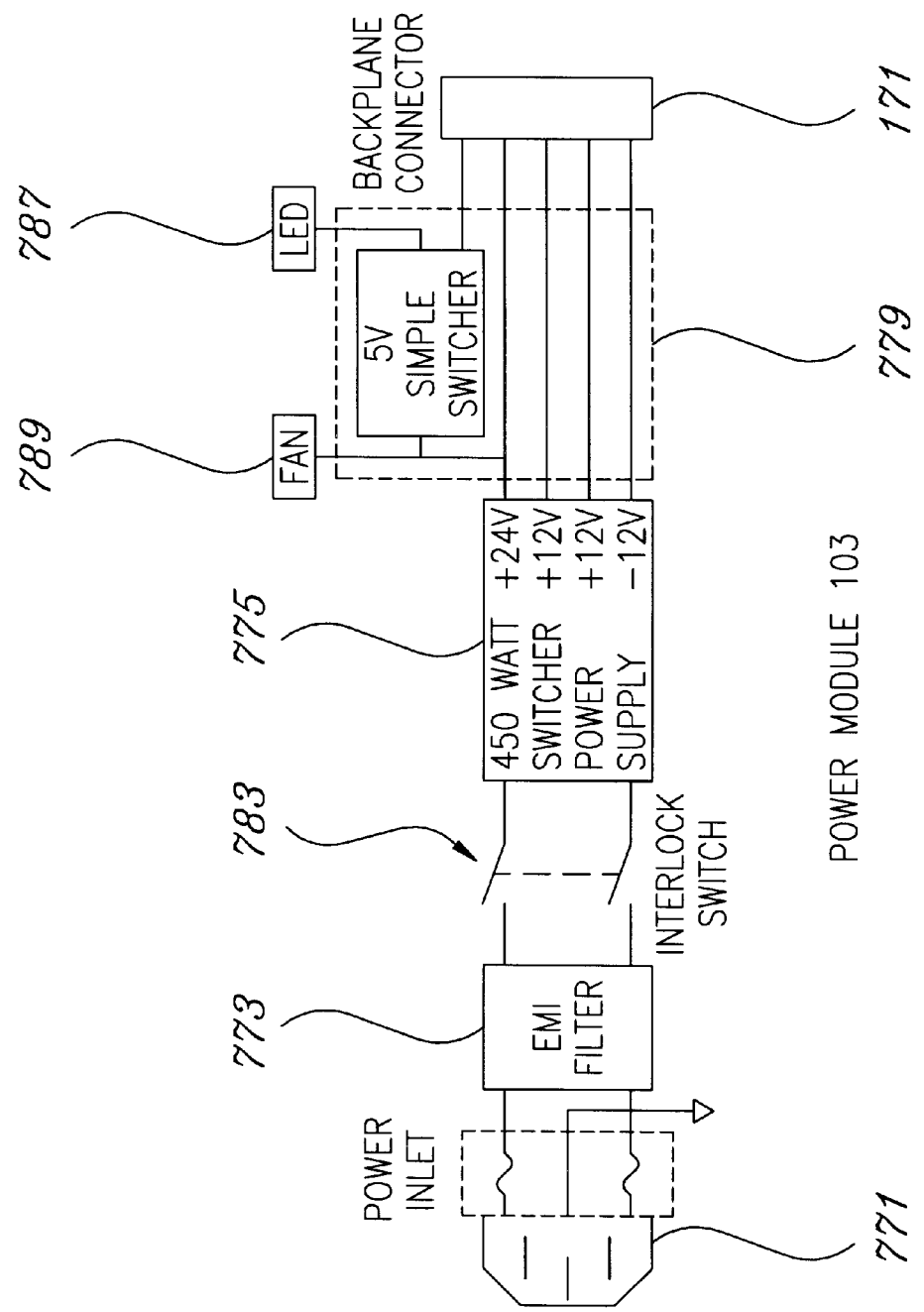
FIG. 39 is a block diagram of a power module according to a preferred embodiment of the system of FIG. 1.
Figure 40:
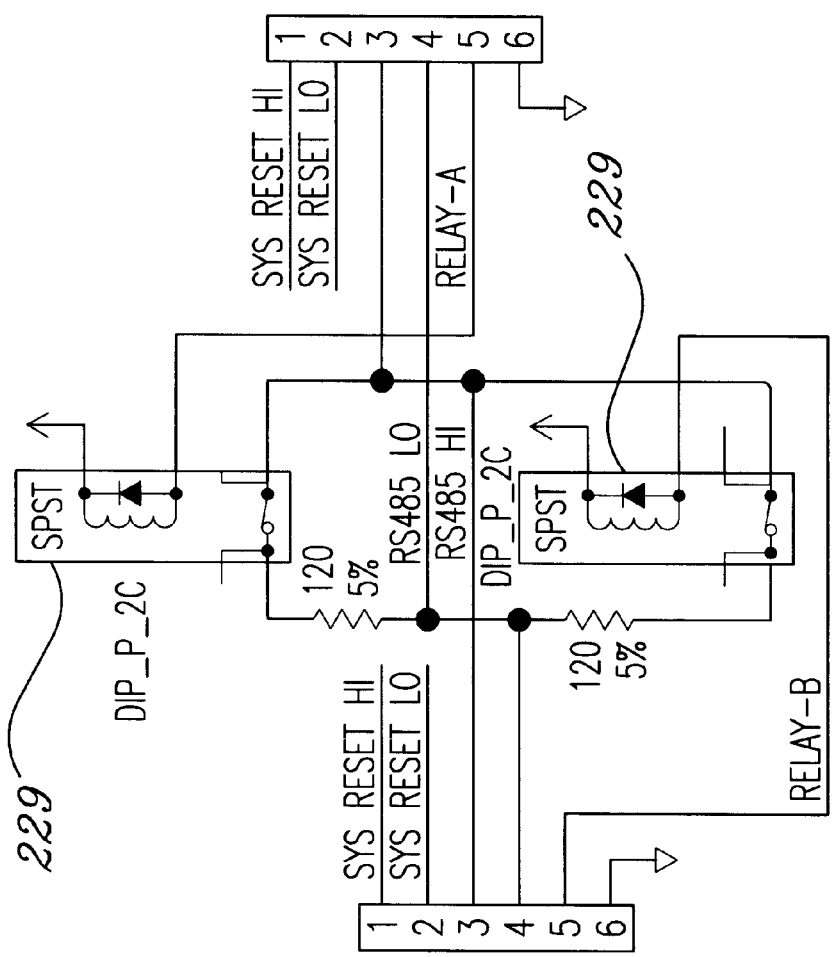
FIGS. 40–42 are schematic diagrams illustrating a communications and power backplane in the base unit of FIGS. 3–8.
Figures 41, 42:
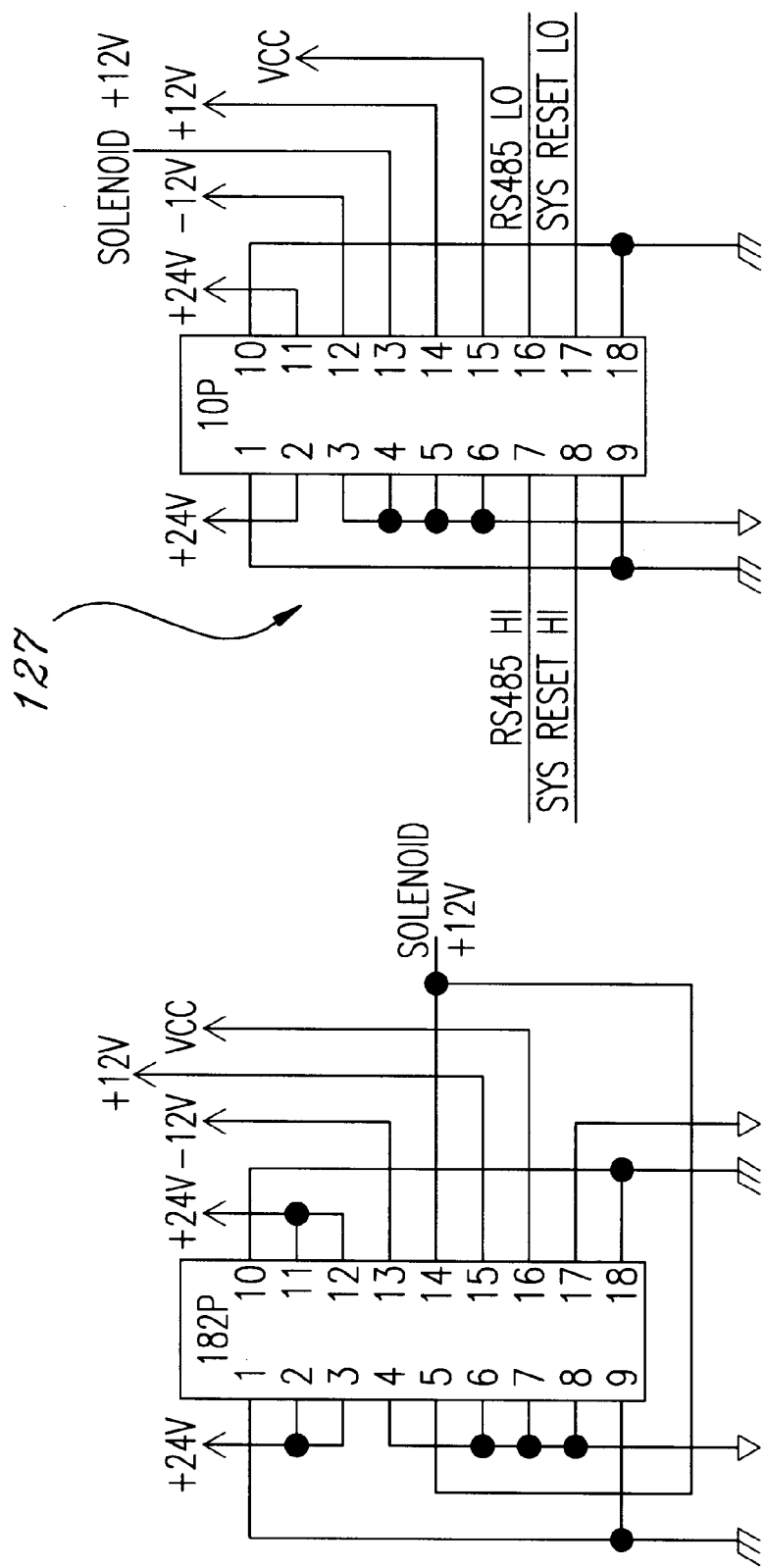
Figure 44:
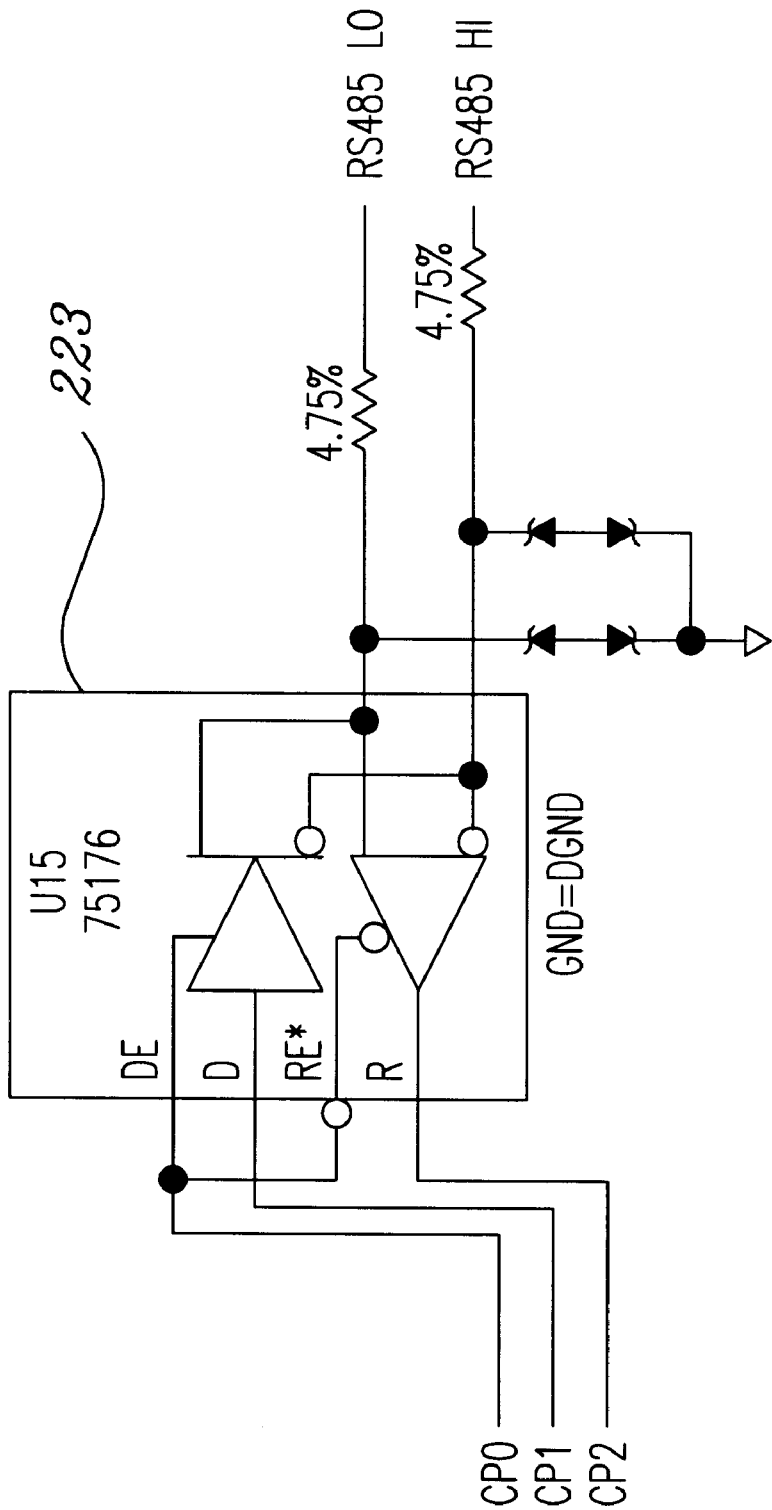
Figure 45:
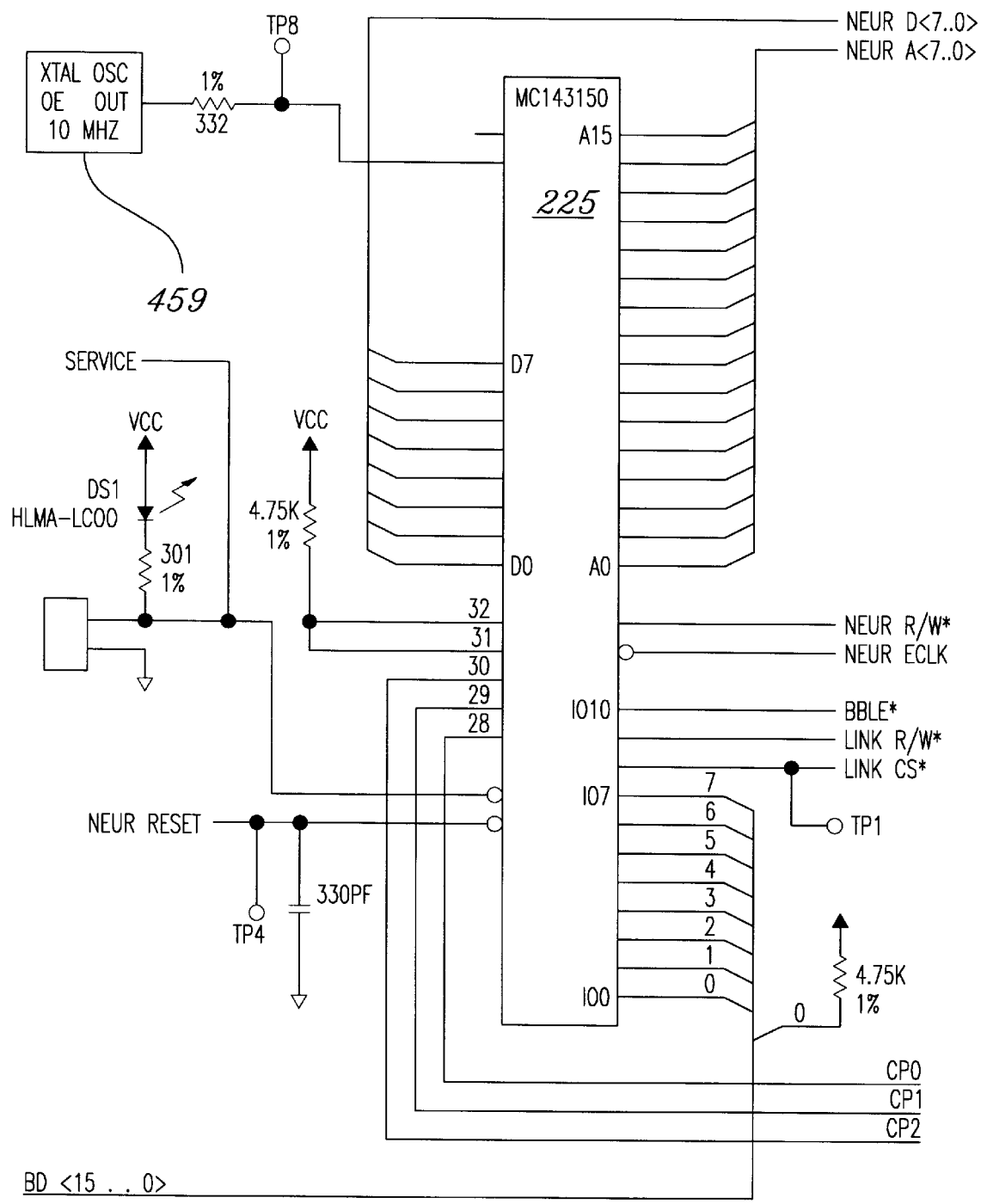
Figure 46:
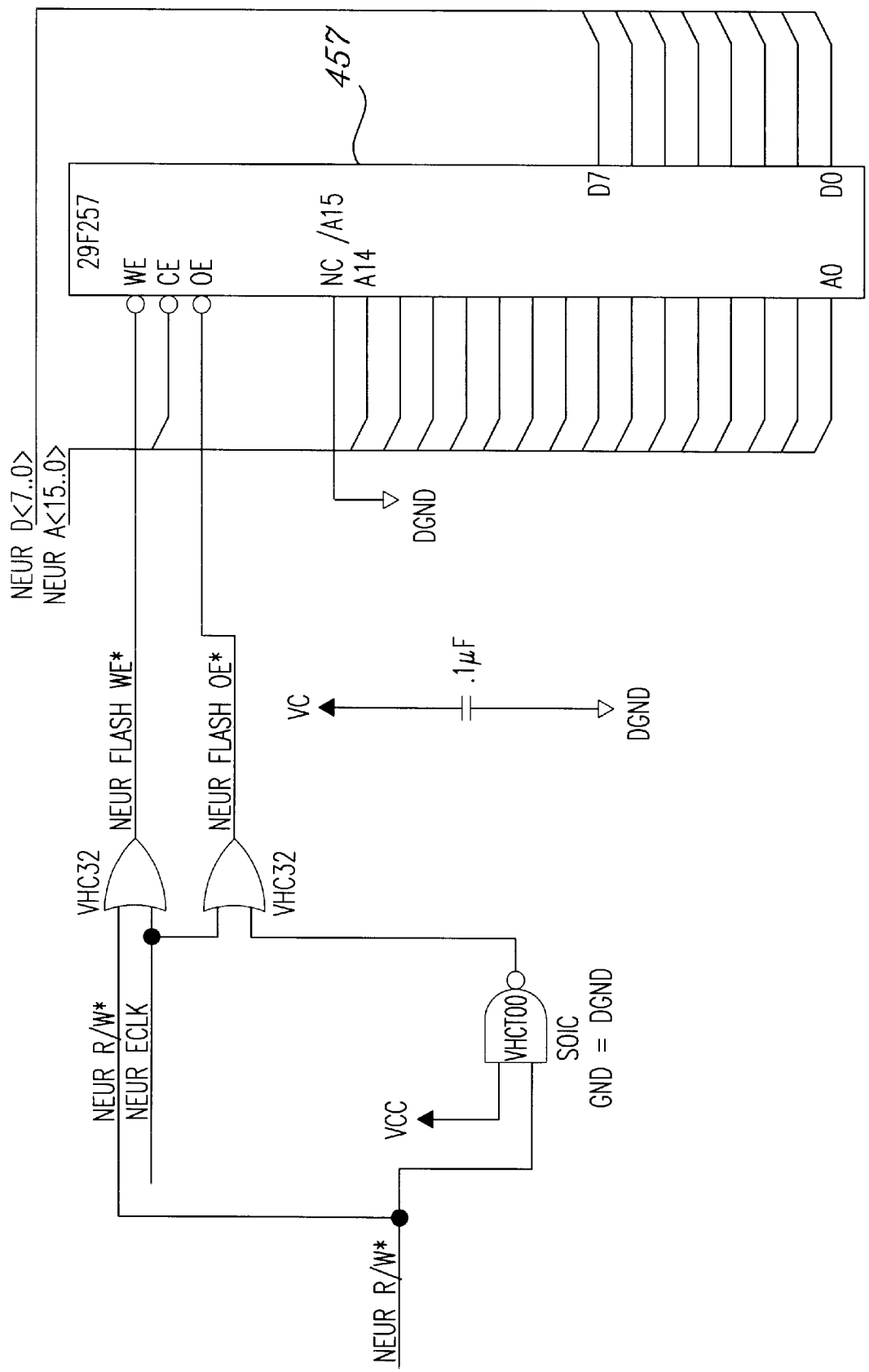
Figure 47:
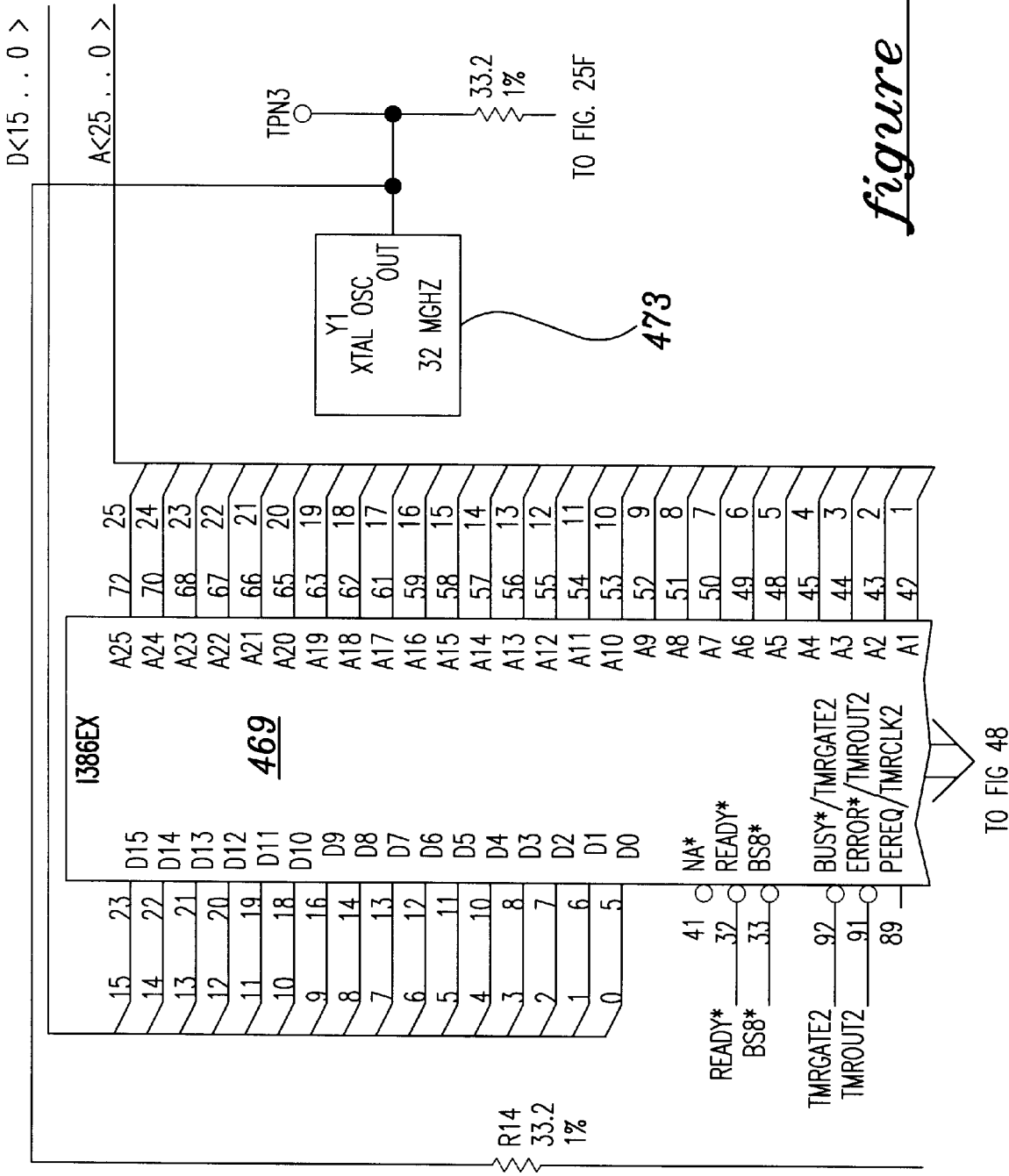
Figure 48:
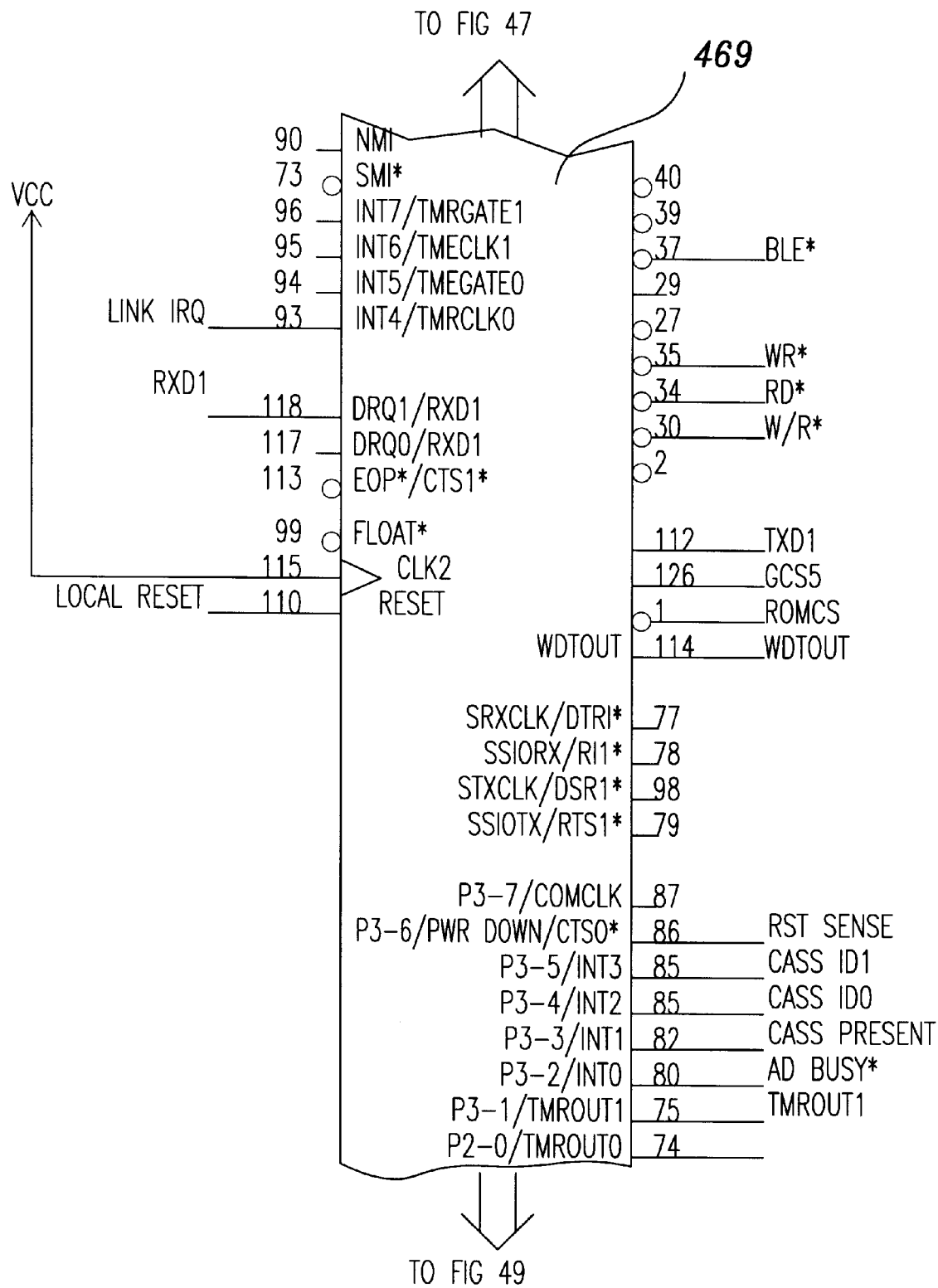
Figure 49:
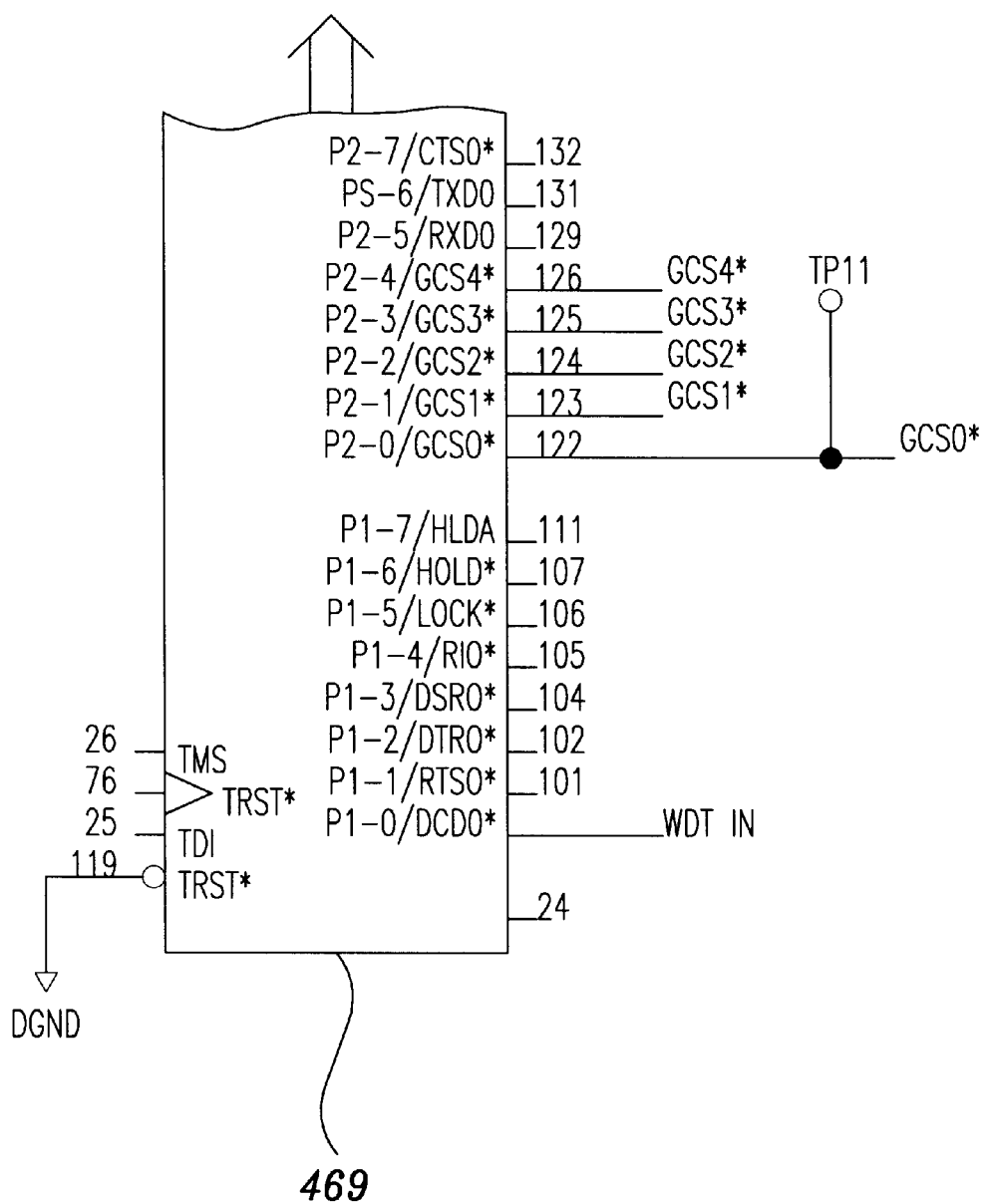
Figure 50:
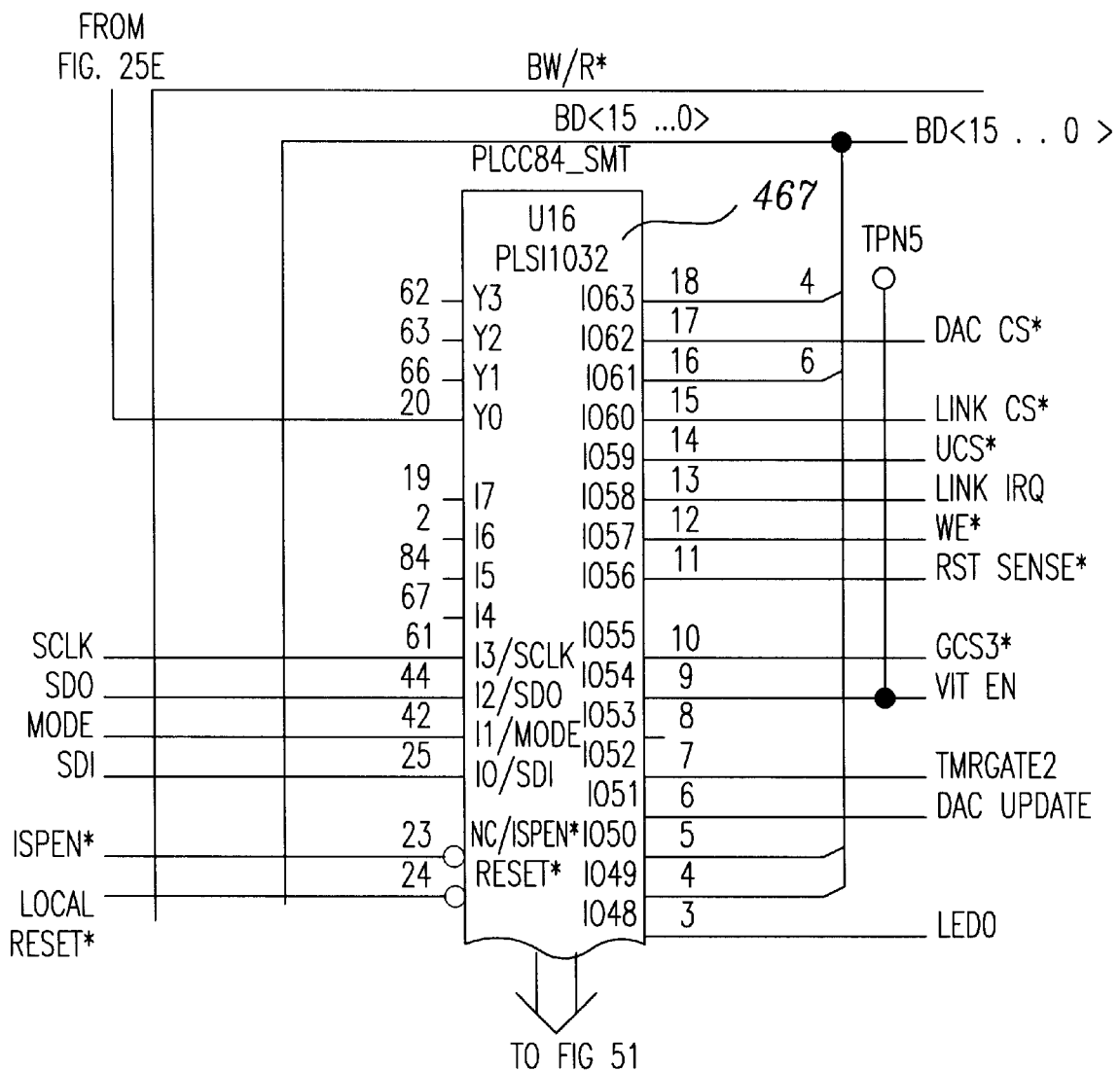
Figure 51:
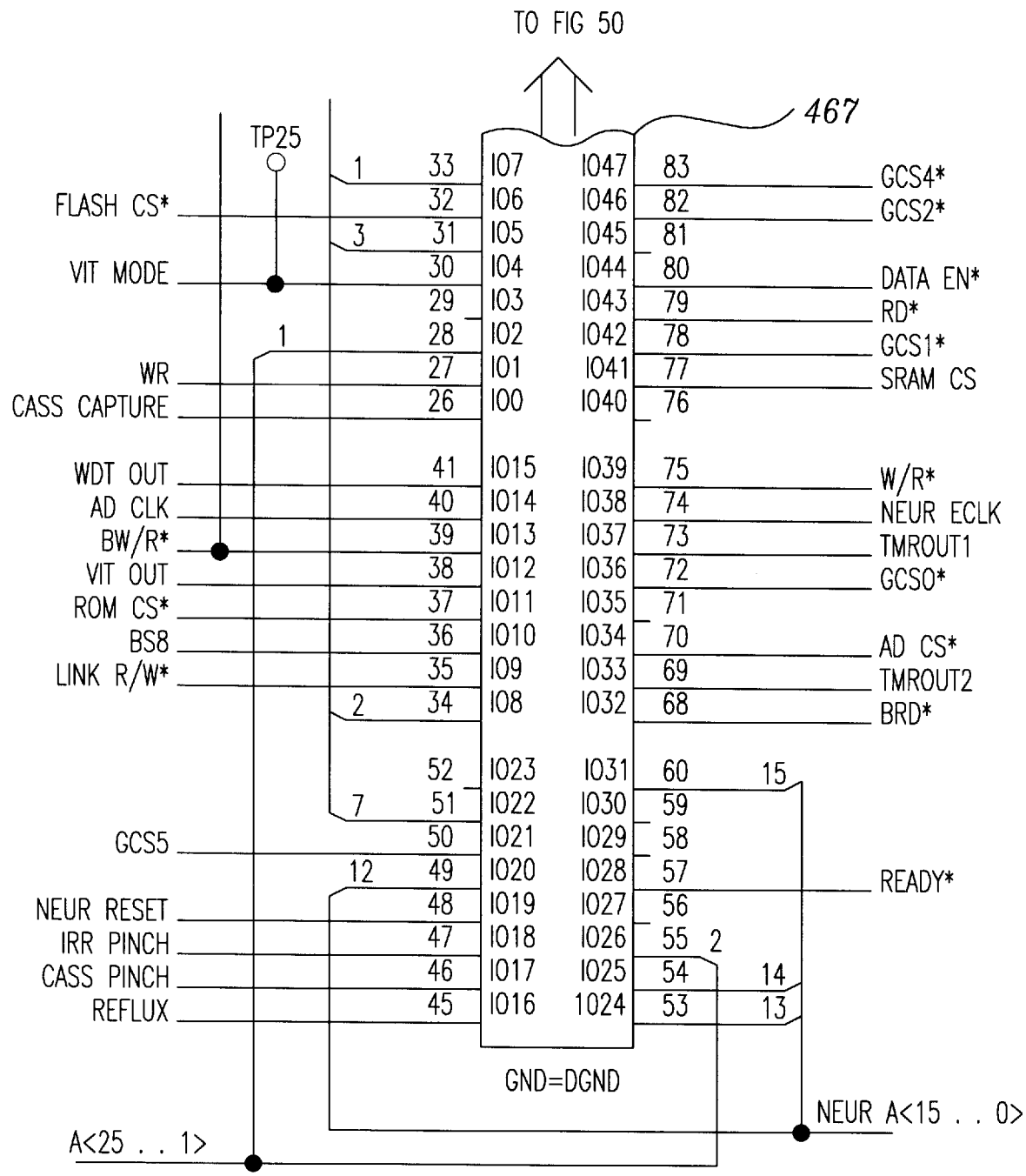
Figure 52:
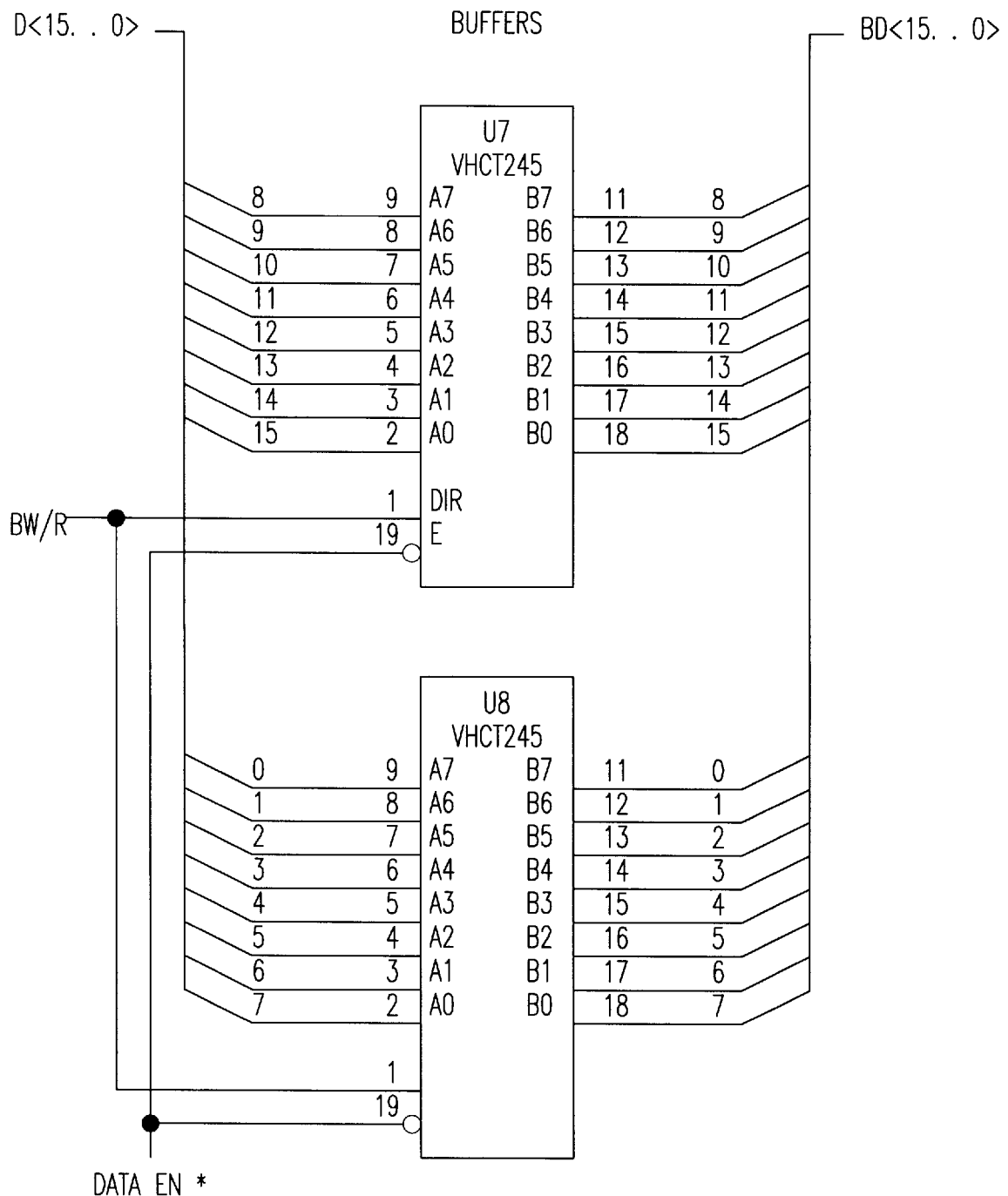
Figure 53:
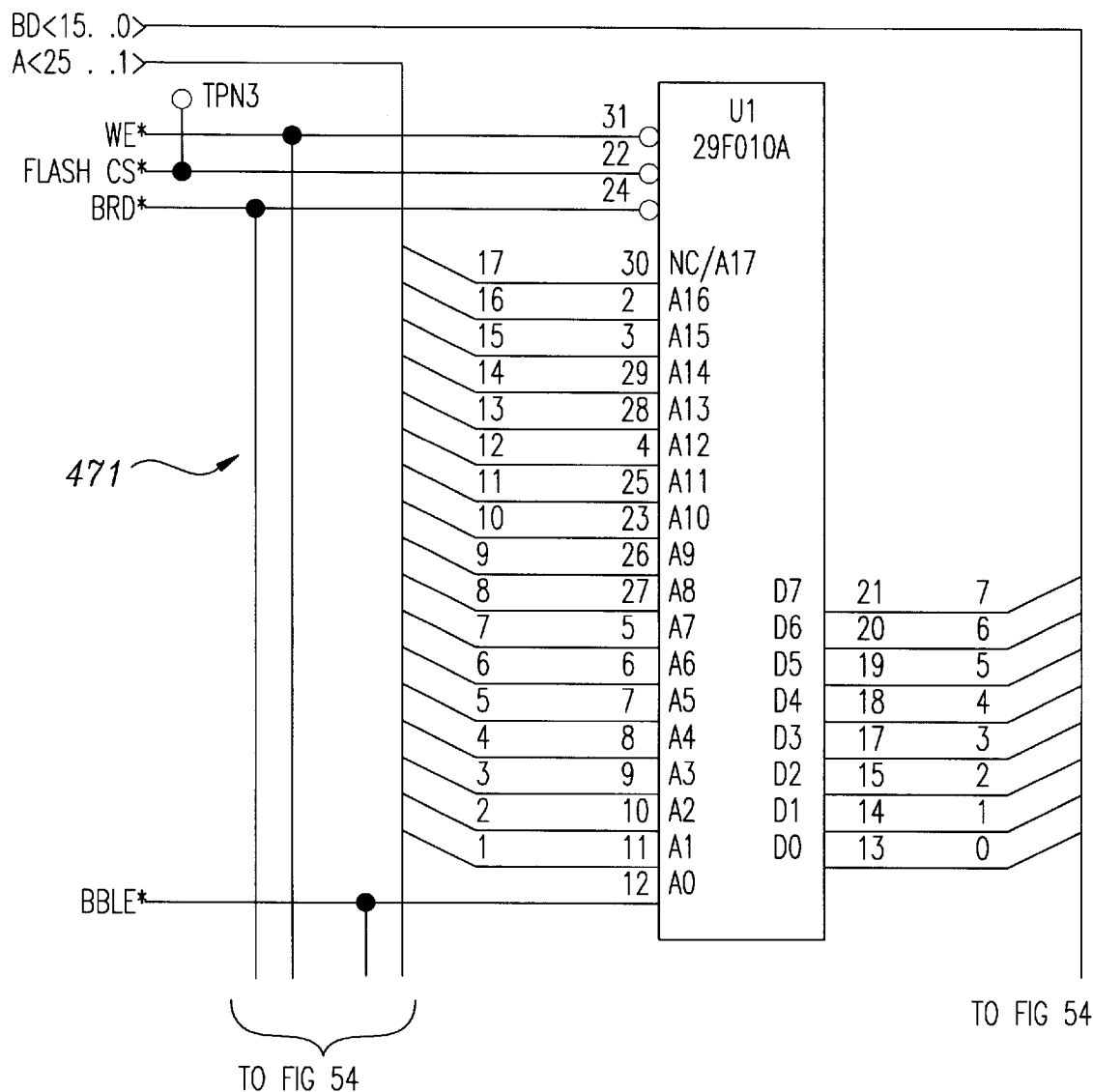
Figure 54:
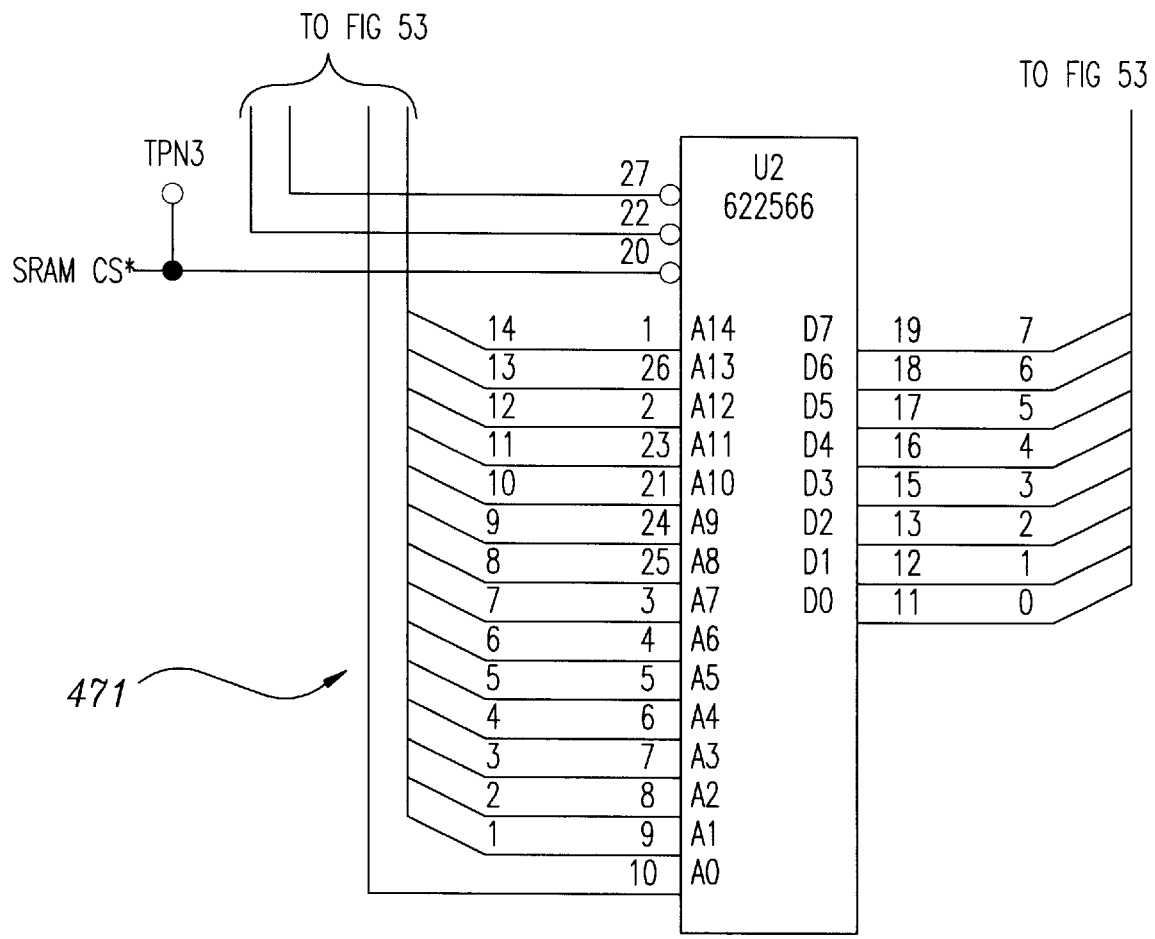
Figure 55:
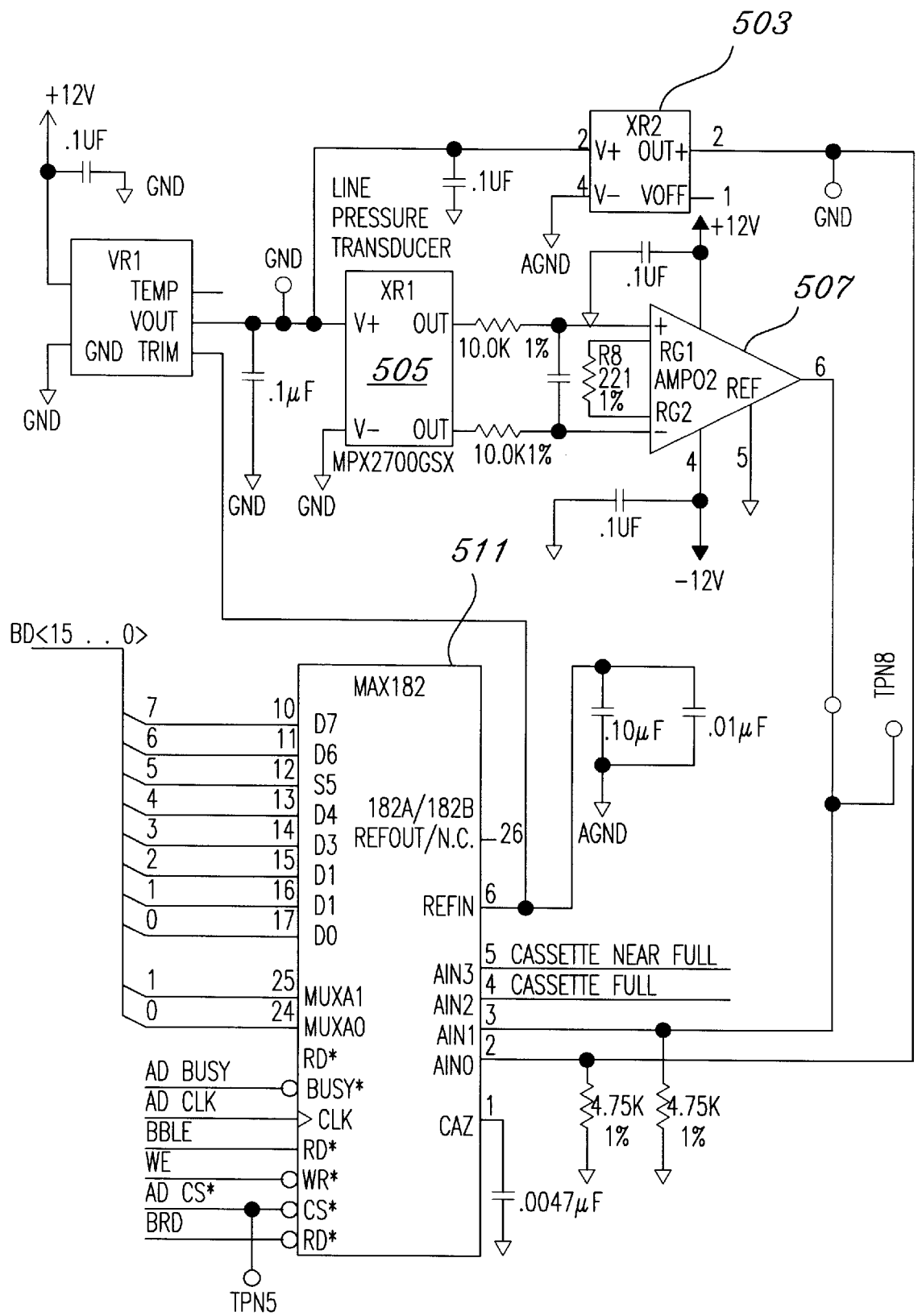
Figure 56:
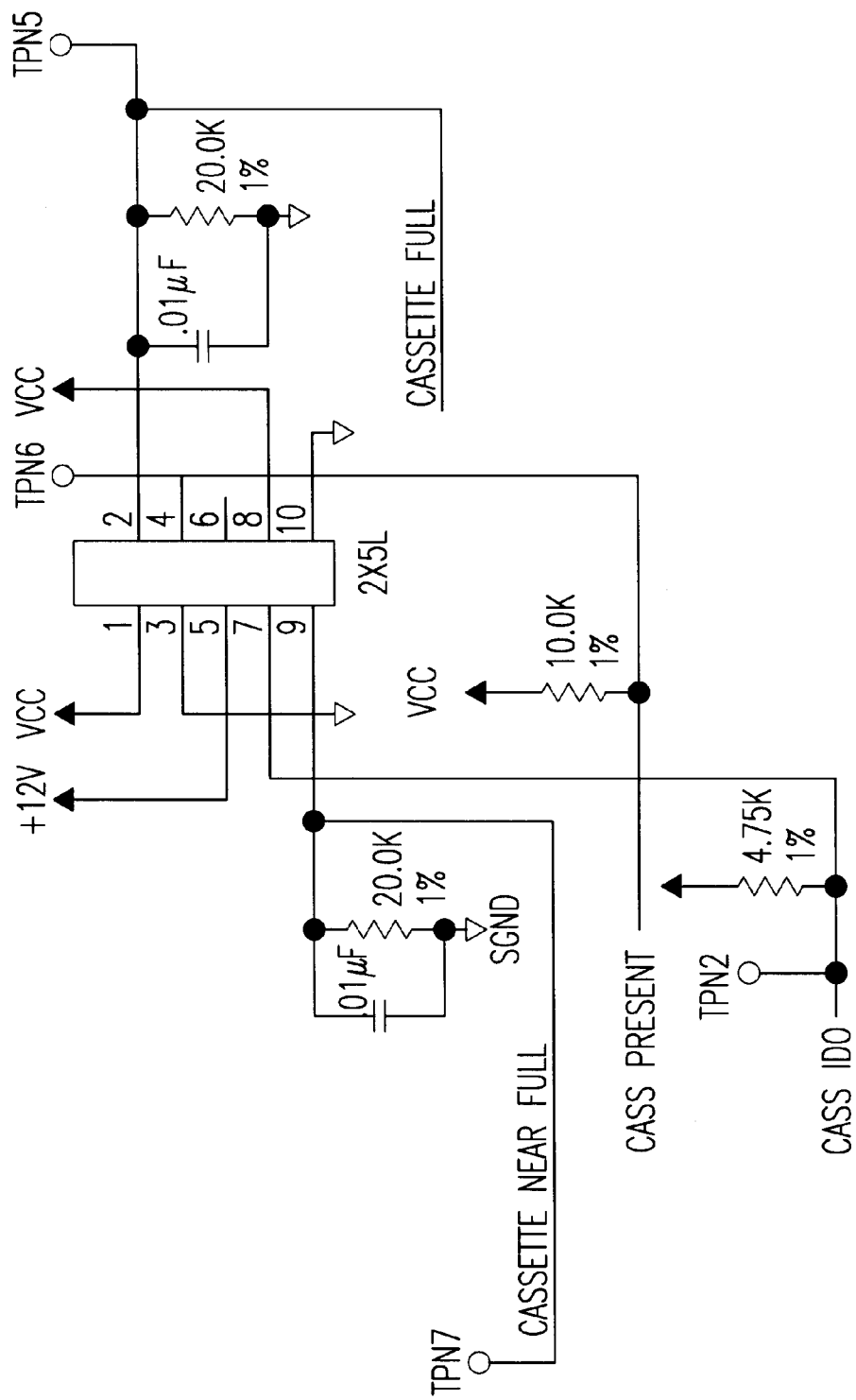
Figure 57:
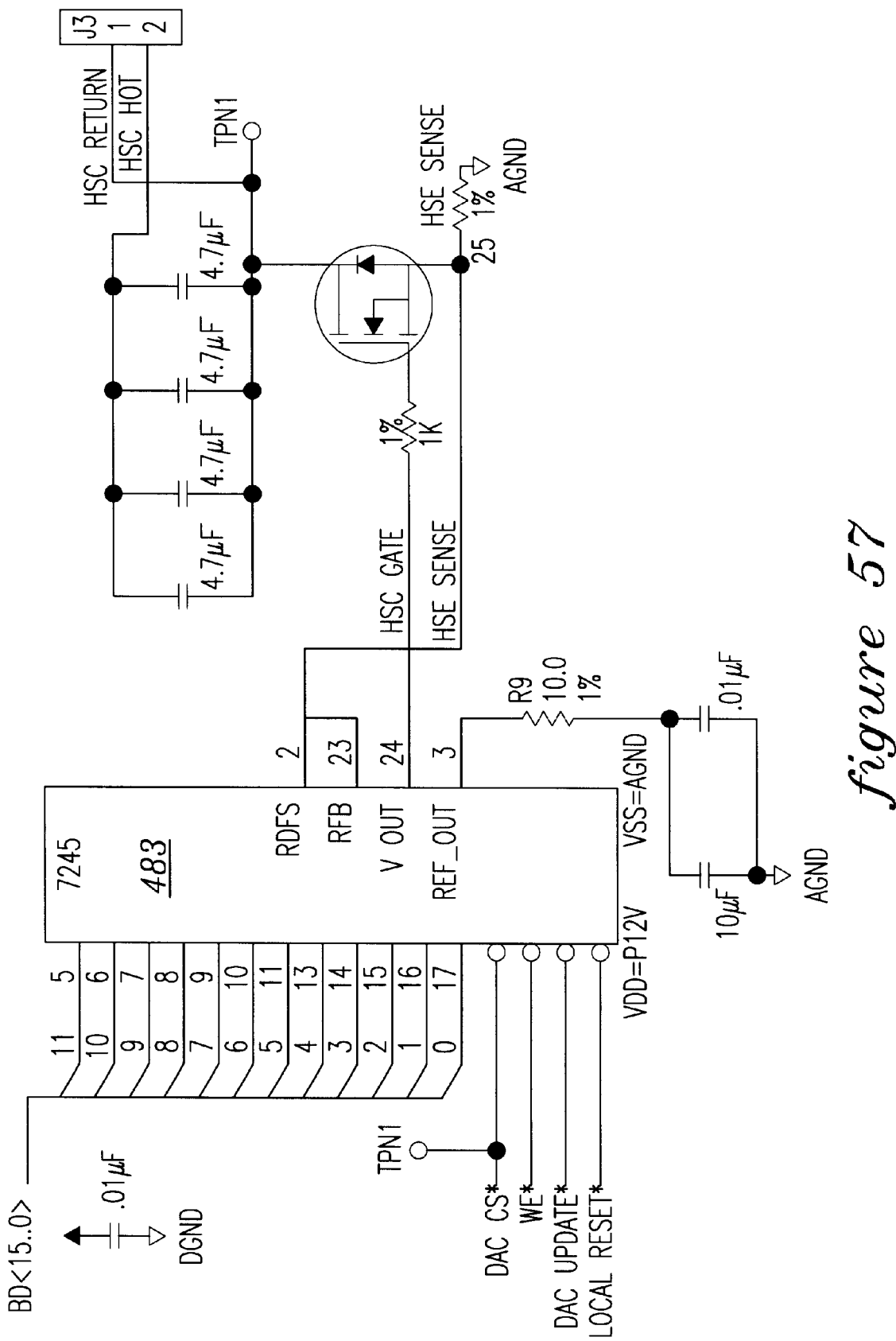
Figure 58:
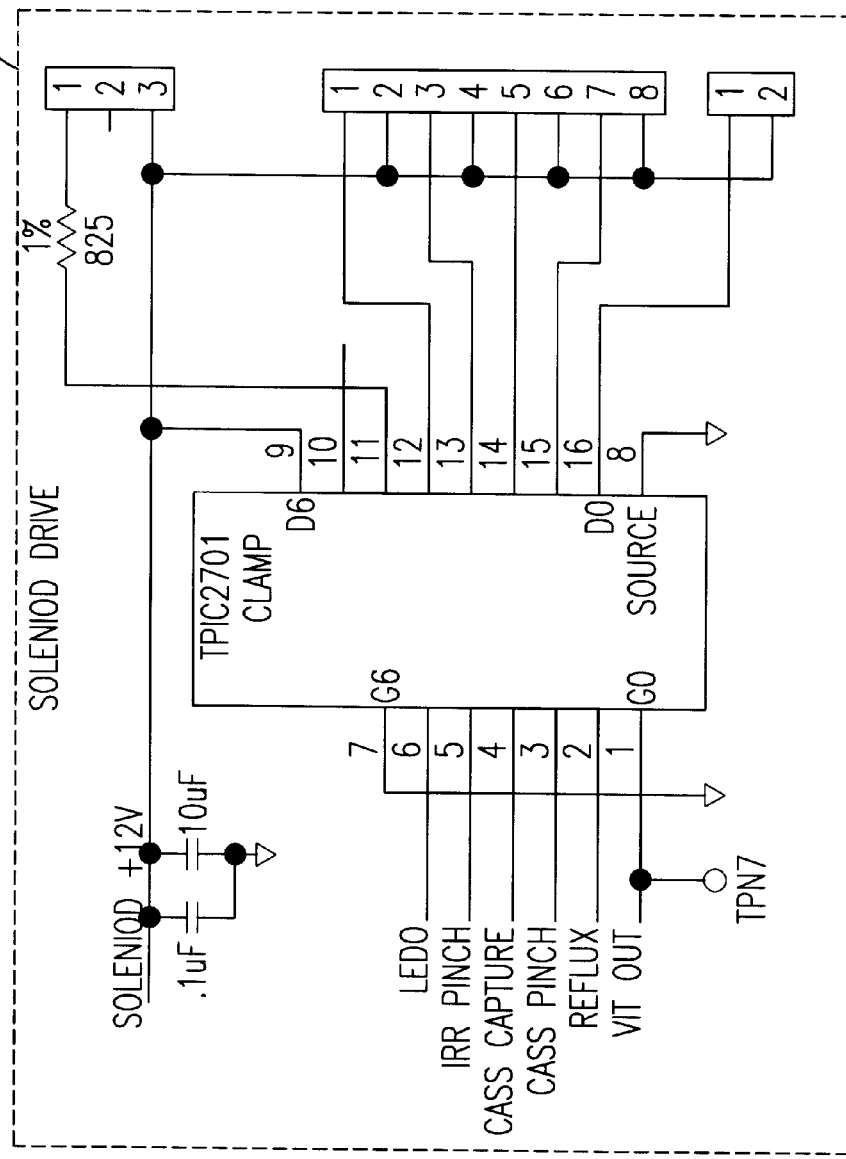
Figure 59:
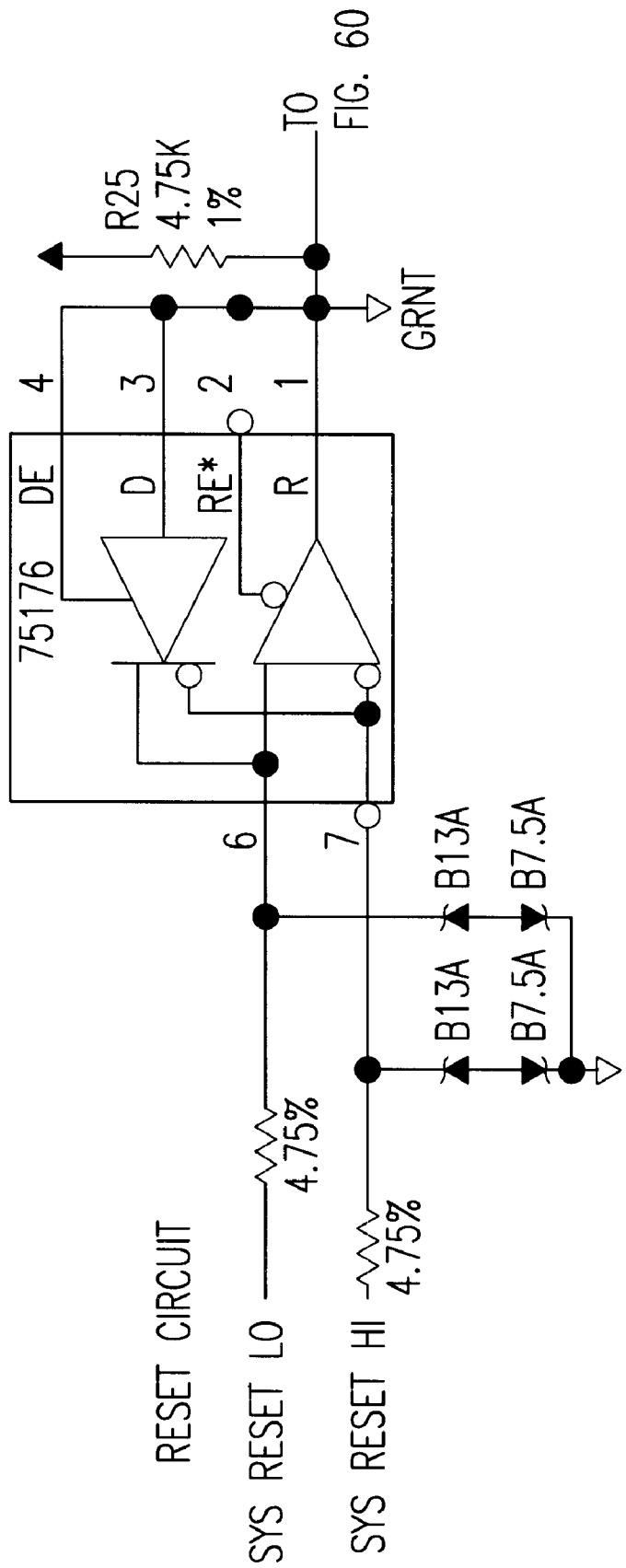
Figure 60:
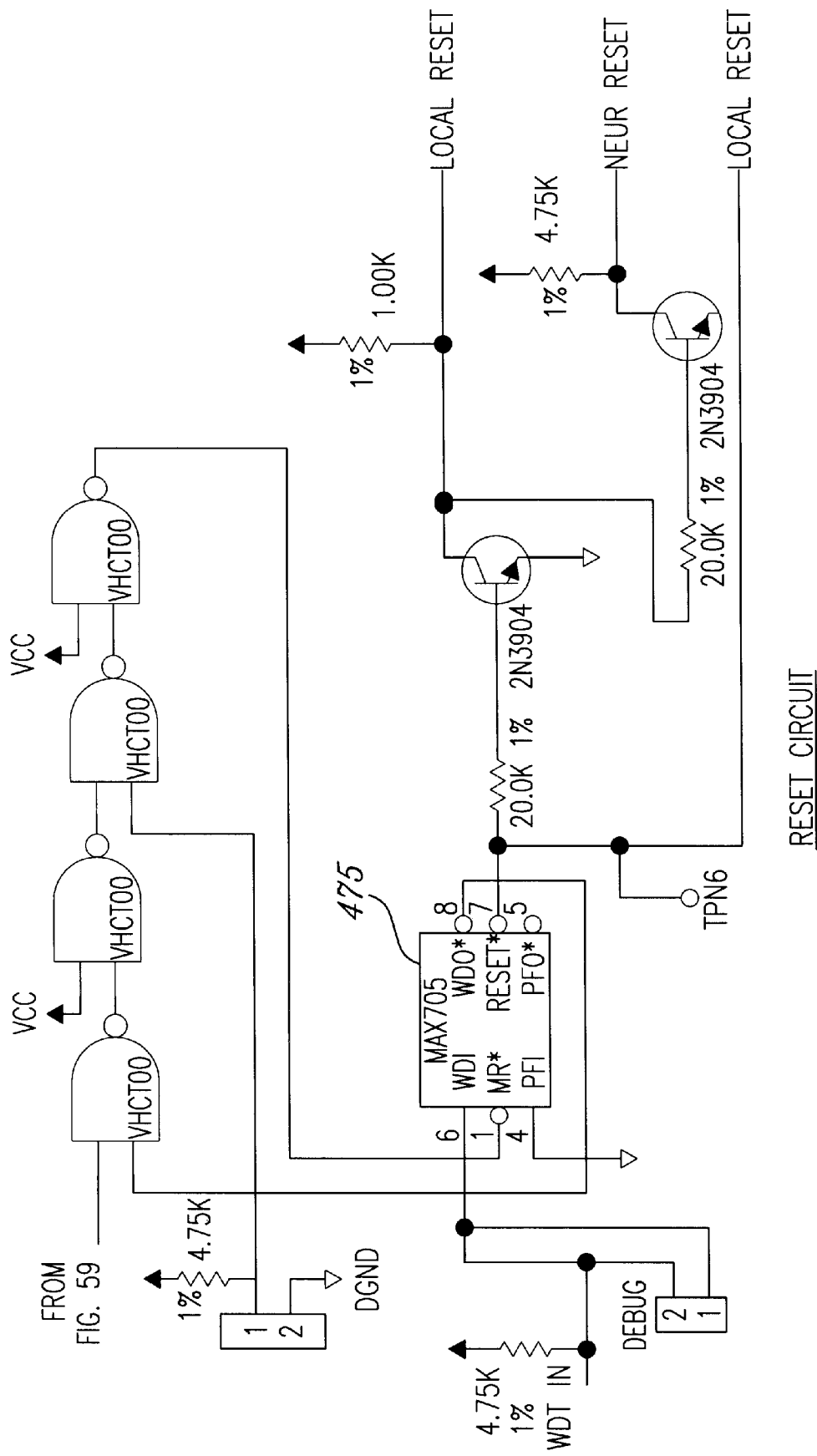

FIG. 39 illustrates power module 103 in block diagram form. As shown, power module 103 includes a power inlet 771 receiving AC power. Preferably, an electromagnetic interference (EMI) filter 773 conditions the power before a switchable power supply circuit 775 generates the DC voltages used by the various modules 13 installed in base unit 7. A switching circuit 779 then provides these voltages to backplane 101 via a backplane connector (such as connector 171). In a preferred embodiment, power module 103 includes an interlock switch 783, preferably located in the opening 197 shown in FIG. 9, which is normally open to interrupt power from being supplied to the power bus of backplane 101. When front cover 113 is installed on base unit 7, the post 195 extends into the opening 197 to close interlock switch 783. In this manner, system 1 provides a reset condition each time the modules 13 are changed and prevents the user from coming into contact with the backplane 101 when it is energized.

Power module 103 also includes a status LED 787 indicating its active status and a fan 789 for preventing overheating within the module.

The attached microfiche appendix is a program listing of the software for system 1. In accordance with the invention as described herein, computer unit 3 executes the software listed in the microfiche appendix for providing the user interface and network management features of the invention. Further, neuron processors 225 execute the software listed in the appendix for controlling the various microsurgical instruments 19 and peripherals.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A system for controlling a plurality of ophthalmic microsurgical instruments connected thereto, said microsurgical instruments for use by a user such as a surgeon in performing ophthalmic surgical procedures, said system comprising:

a data communications bus;

a user interface connected to the data communications bus, said user interface providing information to the user and receiving information from the user which information is representative of operating parameters of the microsurgical instruments;

a first surgical module connected to and controlling one of the microsurgical instruments as a function of at least one of the operating parameters, said first surgical module being connected to the data communications bus;

a second surgical module connected to and controlling another one of the microsurgical instruments as a function of at least one of the operating parameters, said second surgical module being connected to the data communications bus;

wherein the data communications bus provides communication of data representative of the operating parameters between the user interface and the first and second surgical modules;

a touch-responsive screen having a display responsive to the user interface for displaying information to the user; and wherein the display includes a representation of a numeric keypad and wherein the user interface is responsive to information provided by the user via the numeric keypad for changing the operating parameters of the microsurgical instruments.

2. A system for controlling a plurality of ophthalmic microsurgical instruments connected thereto, said microsurgical instruments for use by a user such as a surgeon in performing ophthalmic surgical procedures, said system comprising:

a data communications bus;

a user interface connected to the data communications bus, said user interface providing information to the user and receiving information from the user which information is representative of operating parameters;

a surgical module connected to and controlling one of the microsurgical instruments as a function of at least one of the operating parameters, said surgical module being connected to the data communications bus;

a remote control circuit connected to and controlling a remote control unit as a function of at least one of the operating parameters, said remote control circuit being connected to the data communications bus, said remote control unit operating to change the operating parameters of the microsurgical instruments during performance of the surgical procedures;

wherein the data communications bus provides communication of data representative of the operating parameters between the user interface and the surgical module and the remote control circuit;

a touch-responsive screen having a display responsive to the user interface for displaying information to the user; and wherein the display includes a representation of a numeric keypad and wherein the user interface is responsive to information provided by the user via the numeric keypad for changing the operating parameters.

* * * * *